United States Patent
He et al.

(10) Patent No.: US 11,891,398 B2
(45) Date of Patent: Feb. 6, 2024

(54) 2,3-DIHYDRO-1H-PYRROLIZINE-7-FORMAMIDE DERIVATIVE AND APPLICATION THEREOF

(71) Applicant: CHIA TAI TIANQING PHARMACEUTICAL GROUP CO., LTD., Jiangsu (CN)

(72) Inventors: Haiying He, Shanghai (CN); Jianhua Xia, Shanghai (CN); Zhen Gong, Shanghai (CN); Jian Li, Shanghai (CN); Shuhui Chen, Shanghai (CN)

(73) Assignee: CHIA TAI TIANQING PHARMACEUTICAL GROUP CO., LTD., Jiangsu (CN)

( * ) Notice: Subject to any disclaimer, the term of this patent is extended or adjusted under 35 U.S.C. 154(b) by 706 days.

(21) Appl. No.: 17/058,308

(22) PCT Filed: May 24, 2019

(86) PCT No.: PCT/CN2019/088376
§ 371 (c)(1),
(2) Date: Nov. 24, 2020

(87) PCT Pub. No.: WO2019/223791
PCT Pub. Date: Nov. 28, 2019

(65) Prior Publication Data
US 2022/0204510 A1    Jun. 30, 2022

(30) Foreign Application Priority Data

May 25, 2018  (CN) .......................... 201810528259.1
Jul. 27, 2018   (CN) .......................... 201810843225.1
Oct. 12, 2018  (CN) .......................... 201811189801.1

(51) Int. Cl.
C07D 487/04    (2006.01)
A61P 31/20     (2006.01)

(52) U.S. Cl.
CPC ............ C07D 487/04 (2013.01); A61P 31/20 (2018.01)

(58) Field of Classification Search
CPC .................................................. C07D 487/04
See application file for complete search history.

(56) References Cited

U.S. PATENT DOCUMENTS

| | | | |
|---|---|---|---|
| 8,524,705 B2 | 9/2013 | Payne et al. | |
| 10,836,769 B2 * | 11/2020 | Gutierrez | A61P 31/20 |
| 11,420,974 B2 * | 8/2022 | Gutierrez | A61P 31/20 |
| 11,566,001 B2 * | 1/2023 | Burns | C07D 405/12 |
| 2006/0040945 A1 | 2/2006 | Smolka et al. | |
| 2020/0354366 A1 | 11/2020 | Wang et al. | |
| 2022/0185774 A1 | 6/2022 | Zhang et al. | |

FOREIGN PATENT DOCUMENTS

| | | |
|---|---|---|
| CN | 101743246 | 6/2010 |
| JP | 2010527979 | 8/2010 |
| JP | 2020518671 | 6/2020 |
| JP | 2021519325 | 8/2021 |
| RU | 2336872 C2 | 10/2008 |
| WO | WO 2008/154817 | 12/2008 |
| WO | WO 2017156255 | 9/2017 |
| WO | 2018/039531 | 3/2018 |
| WO | WO 2019165374 | 8/2019 |

OTHER PUBLICATIONS

China National Intellectual Property Administration (ISA/CN), International Search Report for PCT/CN2019/088376 dated Aug. 28, 2019 with English translation.
Extended European Search Report in European Appln. No. 19806616.9, dated Nov. 19, 2021, 9 pages.
Office Action in Chinese Appln. No. 201980005380.9, dated Nov. 10, 2020, 10 pages (with English Translation).
PCT International Preliminary Report on Patentability in International Appln. No. PCT/CN2019/088376, dated Dec. 1, 2020, 9 pages (with English Translation).
PCT International Search Report and Written Opinion in International Appln. No. PCT/CN2019/088376, dated Aug. 19, 2019, 11 pages (with English Translation).
Office Action in Japanese Appln. No. 2020-565885, dated Mar. 27, 2023, 6 pages (with English translation).

* cited by examiner

*Primary Examiner* — Golam M Shameem
(74) *Attorney, Agent, or Firm* — Fish & Richardson P.C.

(57) ABSTRACT

The present application relates to a 2,3-dihydro-1H-pyrrolizine-7-formamide derivative as a nucleoprotein inhibitor and a use in preparation of a drug for treating HBV related diseases. The present application specifically relates to a compound represented by formula (II), and isomers or pharmaceutically acceptable salts thereof.

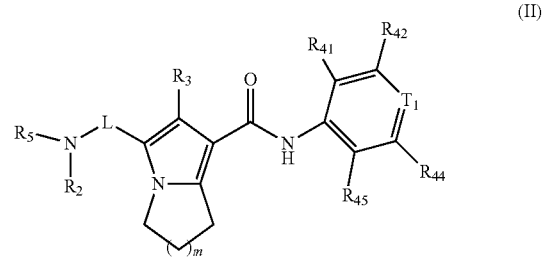

(II)

20 Claims, 1 Drawing Sheet
Specification includes a Sequence Listing.

SEQUENCE LISTING

<160> NUMBER OF SEQ ID NOS: 3

<210> SEQ ID NO 1
<211> LENGTH: 20
<212> TYPE: DNA
<213> ORGANISM: Artificial
<220> FEATURE:
<223> OTHER INFORMATION: Synthetic oligonucleotide

<400> SEQUENCE: 1
gtgtctgcgg cgttttatca        20

<210> SEQ ID NO 2
<211> LENGTH: 21
<212> TYPE: DNA
<213> ORGANISM: Artificial
<220> FEATURE:
<223> OTHER INFORMATION: Synthetic oligonucleotide

<400> SEQUENCE: 2
gacaaacggg caacatacct t        21

<210> SEQ ID NO 3
<211> LENGTH: 28
<212> TYPE: DNA
<213> ORGANISM: Artificial
<220> FEATURE:
<223> OTHER INFORMATION: Synthetic oligonucleotide

<400> SEQUENCE: 3
cctctkcatc ctgctgctat gcctcatc        28

2,3-DIHYDRO-1H-PYRROLIZINE-7-FORMAMIDE DERIVATIVE AND APPLICATION THEREOF

CROSS-REFERENCE TO RELATED APPLICATIONS

The present application is a U.S. national phase filing under 35 U.S.C. § 371 of International Application No. PCT/CN2019/088376, filed May 24, 2019, which claims the benefit and priority to the Chinese Patent Application No. 201810528259.1 filed with the National Intellectual Property Administration, PRC on May 25, 2018, the Chinese Patent Application No. 201810843225.1 filed with the National Intellectual Property Administration, PRC on Jul. 27, 2018, and the Chinese Patent Application No. 201811189801.1 filed with the National Intellectual Property Administration, PRC on Oct. 12, 2018, the content of each of which is incorporated herein by reference in its entirety.

SEQUENCE LISTING

This application contains a Sequence Listing that has been submitted electronically as ASCII text file named (SEQLIST.TXT). The ASCII text file, created on Apr. 21, 2021 is 1.04 kilobytes in size. The material in the ASCII text file is hereby incorporated by reference in its entirety.

TECHNICAL FIELD

The present application relates to a 2,3-dihydro-1H-pyrrolizine-7-formamide derivative as a nucleoprotein inhibitor and a use in preparation of a drug for treating diseases related to hepatitis B virus (HBV). Specifically, the present application relates to a compound of formula (II), a compound of formula (II-A), a compound of formula (II-B), a compound of formula (I), or stereoisomers or pharmaceutically acceptable salts thereof, and a use thereof in preparation of a drug for treating diseases related to HBV.

BACKGROUND

Hepatitis B is an inflammation triggered by hepatitis B virus invasion. It is prone to develop into liver fibrosis and liver cirrhosis, and is a direct cause of 80% of primary liver cancers worldwide.

Hepatitis B is a global health problem. Currently, there is no specific medicine for treating hepatitis B. Nucleosides and interferons occupy the dominant position in the global anti-hepatitis B drug market, and they are major first-line drugs for treating hepatitis B. However, the nucleoside or interferon treatment has disadvantages of high cost, easy relapse and the like. Thus, there is a need to develop a novel anti-hepatitis B drug.

SUMMARY

The present application provides a compound of formula (II), or a stereoisomer or a pharmaceutically acceptable salt thereof,

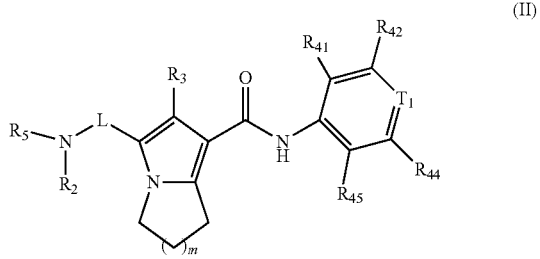

(II)

wherein,
m is 1 or 2;
L is selected from

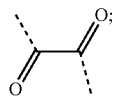

$T_1$ is selected from the group consisting of N and $C(R_{43})$;
$R_2$ is selected from the group consisting of H and $C_{1-6}$ alkyl, wherein the $C_{1-6}$ alkyl is optionally substituted by 1, 2, or 3 $R_b$;
$R_3$ is selected from the group consisting of H, Cl, F, Br, I, OH, $NH_2$, $C_{1-6}$ alkyl, and $C_{1-3}$ alkoxy, wherein the $C_{1-6}$ alkyl and the $C_{1-3}$ alkoxy are optionally substituted by 1, 2, or 3 $R_c$;
$R_{41}$, $R_{42}$, $R_{43}$, $R_{44}$, and $R_{45}$ are each independently selected from the group consisting of H, Cl, F, Br, I, OH, $NH_2$, CN, COOH, and $C_{1-3}$ alkyl, wherein the $C_{1-3}$ alkyl is optionally substituted by 1, 2, or 3 $R_d$;
$R_5$ is selected from the group consisting of $R_{51}$, $C_{3-10}$ cycloalkyl, and 3-6 membered heterocycloalkyl, wherein the $C_{3-10}$ cycloalkyl and the 3-6 membered heterocycloalkyl are optionally substituted by 1, 2, or 3 $R_1$;
$R_{51}$ is selected from the group consisting of $C_{1-10}$ alkyl and $C_{1-6}$ heteroalkyl, wherein the $C_{1-10}$ alkyl and the $C_{1-6}$ heteroalkyl are optionally substituted by 1, 2, or 3 $R_e$;
$R_1$ is each independently selected from the group consisting of H, Cl, F, Br, I, OH, $NH_2$, CN, COOH, $C_{1-6}$ alkyl, —COO—$C_{1-6}$ alkyl, and —$C_{1-3}$ alkyl-COO—$C_{1-6}$ alkyl, wherein the $C_{1-6}$ alkyl, the —COO—$C_{1-6}$ alkyl, and the —$C_{1-3}$ alkyl-COO—$C_{1-6}$ alkyl are optionally substituted by 1, 2, or 3 $R_a$;
$R_a$ is each independently selected from the group consisting of Cl, F, Br, I, OH, $NH_2$, CN, COOH, $C_{1-3}$ alkyl, and $C_{1-3}$ alkoxy, wherein the $C_{1-3}$ is optionally substituted by 1, 2, or 3 R;
$R_b$ is each independently selected from the group consisting of Cl, F, Br, I, OH, $NH_2$, CN, and COOH;
$R_c$ is each independently selected from the group consisting of Cl, F, Br, I, OH, $NH_2$, CN, COOH, and $C_{1-3}$ alkyl, wherein the $C_{1-3}$ is optionally substituted by 1, 2, or 3 R;
$R_d$ is each independently selected from the group consisting of Cl, F, Br, I, OH, $NH_2$, CN, and COOH;
$R_e$ is each independently selected from the group consisting of Cl, F, Br, I, OH, $NH_2$, CN, and COOH;
R is each independently selected from the group consisting of Cl, F, Br, I, OH, $NH_2$, CN, and COOH;

The $C_{1-6}$ heteroalkyl and the 3-6 membered heterocycloalkyl each contain 1, 2, 3, or 4 heteroatoms or heteroatom groups independently selected from the group consisting of —NH—, —O—, —S—, and N.

In some embodiments of the compound of formula (II) or the stereoisomer or the pharmaceutically acceptable salt thereof disclosed herein, the above-mentioned $R_a$ is selected from the group consisting of Cl, F, Br, I, OH, $NH_2$, CN, COOH, and —$OCH_3$, and other variables are as defined herein.

In some embodiments of the compound of formula (II) or the stereoisomer or the pharmaceutically acceptable salt thereof disclosed herein, the above-mentioned $R_c$ is selected from the group consisting of Cl, F, Br, I, OH, $NH_2$, CN, and COOH, and other variables are as defined herein.

In some embodiments of the compound of formula (II) or the stereoisomer or the pharmaceutically acceptable salt thereof disclosed herein, the above-mentioned $R_1$ is each independently selected from the group consisting of H, Cl, F, Br, I, OH, $NH_2$, CN, COOH, $C_{1-3}$ alkyl, —COO—$C_{1-3}$ alkyl, and —$C_{1-3}$ alkyl-COO—$C_{1-3}$ alkyl, wherein the $C_{1-3}$ alkyl, the —COO—$C_{1-3}$ alkyl, and the —$C_{1-3}$ alkyl-COO—$C_{1-3}$ alkyl are optionally substituted by 1, 2, or 3 $R_a$, and other variables are as defined herein.

In some embodiments of the compound of formula (II) or the stereoisomer or the pharmaceutically acceptable salt thereof disclosed herein, the above-mentioned $R_1$ is each independently selected from the group consisting of H, Cl, F, Br, I, OH, $NH_2$, CN, COOH, $CH_3$, Et,

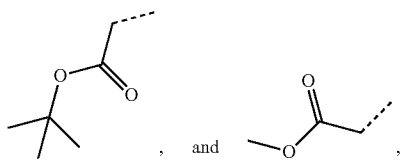

wherein the $CH_3$, the Et, the

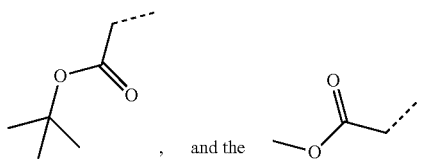

are optionally substituted by 1, 2, or 3 $R_a$, and other variables are as defined herein.

In some embodiments of the compound of formula (II) or the stereoisomer or the pharmaceutically acceptable salt thereof disclosed herein, the above-mentioned $R_1$ is each independently selected from the group consisting of H, Cl, F, Br, I, OH, $NH_2$, CN, COOH, $CH_3$, $CF_3$, Et, —$CH_2$—COOH, —$CH_2$—$OCH_3$, —$(CH_2)_2$—COOH,

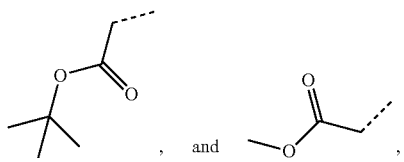

and other variables are as defined herein.

In some embodiments of the compound of formula (II) or the stereoisomer or the pharmaceutically acceptable salt thereof disclosed herein, the above-mentioned $R_2$ is selected from the group consisting of H and $C_{1-3}$ alkyl, wherein the $C_{1-3}$ alkyl is optionally substituted by 1, 2, or 3 $R_b$, and other variables are as defined herein.

In some embodiments of the compound of formula (II) or the stereoisomer or the pharmaceutically acceptable salt thereof disclosed herein, the above-mentioned $R_2$ is selected from the group consisting of H, $CH_3$, and Et, and other variables are as defined herein.

In some embodiments of the compound of formula (II) or the stereoisomer or the pharmaceutically acceptable salt thereof disclosed herein, the above-mentioned $R_3$ is selected from the group consisting of H, Cl, F, Br, I, OH, $NH_2$, and $C_{1-3}$ alkyl, wherein the $C_{1-3}$ alkyl is optionally substituted by 1, 2, or 3 $R_c$, and other variables are as defined herein.

In some embodiments of the compound of formula (II) or the stereoisomer or the pharmaceutically acceptable salt thereof disclosed herein, the above-mentioned $R_3$ is selected from the group consisting of H, Cl, F, Br, I, OH, $NH_2$, $CH_3$, $CF_3$, and Et, and other variables are as defined herein.

In some embodiments of the compound of formula (II) or the stereoisomer or the pharmaceutically acceptable salt thereof disclosed herein, the above-mentioned $R_{41}$, $R_{42}$, $R_{43}$, $R_{44}$, and $R_{45}$ are each independently selected from the group consisting of H, Cl, F, Br, I, OH, $NH_2$, CN, and —COOH, and other variables are as defined herein.

In some embodiments of the compound of formula (II) or the stereoisomer or the pharmaceutically acceptable salt thereof disclosed herein, the above-mentioned $R_{51}$ is selected from the group consisting of $C_{1-7}$ alkyl and $C_{1-6}$ heteroalkyl, wherein the $C_{1-7}$ alkyl and the $C_{1-6}$ heteroalkyl are optionally substituted by 1, 2, or 3 $R_e$, and other variables are as defined herein.

In some embodiments of the compound of formula (II) or the stereoisomer or the pharmaceutically acceptable salt thereof disclosed herein, the above-mentioned $R_{51}$ is selected from the group consisting of $C_{1-7}$ alkyl and $C_{1-3}$ heteroalkyl, wherein the $C_{1-7}$ alkyl and the $C_{1-3}$ heteroalkyl are optionally substituted by 1, 2, or 3 $R_e$, and other variables are as defined herein.

In some embodiments of the compound of formula (II) or the stereoisomer or the pharmaceutically acceptable salt thereof disclosed herein, the above-mentioned $R_{51}$ is selected from the group consisting of methyl, ethyl, propyl, isopropyl,

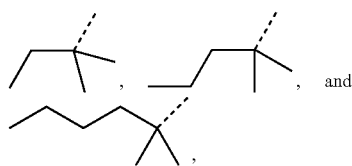

wherein the methyl, the ethyl, the propyl, the isopropyl, the

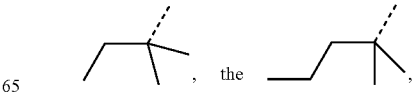

and the

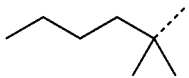

are optionally substituted by 1, 2, or 3 $R_e$, and other variables are as defined herein.

In some embodiments of the compound of formula (II) or the stereoisomer or the pharmaceutically acceptable salt thereof disclosed herein, the above-mentioned $R_{51}$ is selected from the group consisting of

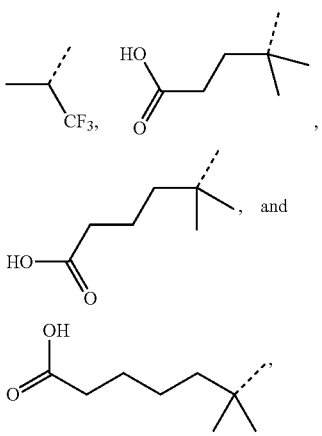

and other variables are as defined herein.

In some embodiments of the compound of formula (II) or the stereoisomer or the pharmaceutically acceptable salt thereof disclosed herein, the above-mentioned the $R_5$ is selected from the group consisting of $R_{51}$, $C_{3-8}$ cycloalkyl, and 5-6 membered heterocycloalkyl, wherein the $C_{3-8}$ cycloalkyl and the 5-6 membered heterocycloalkyl are optionally substituted by 1, 2, or 3 $R_1$, and the other variables are as defined herein.

In some embodiments of the compound of formula (II) or the stereoisomer or the pharmaceutically acceptable salt thereof disclosed herein, the above-mentioned $R_5$ is selected from the group consisting of $R_{51}$, cyclohexyl, tetrahydropyranyl, piperidinyl, and bicyclo[2.2.2]octyl, wherein the cyclohexyl, the tetrahydropyranyl, the piperidinyl, and the bicyclo[2.2.2]octyl are optionally substituted by 1, 2, or 3 $R_1$, and the other variables are as defined herein.

In some embodiments of the compound of formula (II) or the stereoisomer or the pharmaceutically acceptable salt thereof disclosed herein, the above-mentioned $R_5$ is selected from the group consisting of $R_{51}$,

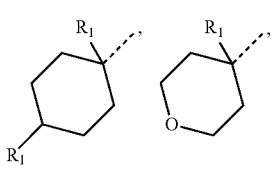

-continued

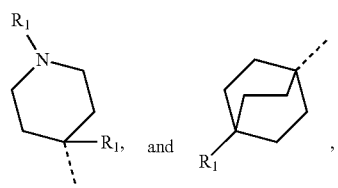

and other variables are as defined herein.

In some embodiments of the compound of formula (II) or the stereoisomer or the pharmaceutically acceptable salt thereof disclosed herein, the above-mentioned $R_5$ is selected from the group consisting of

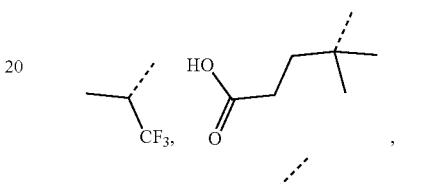

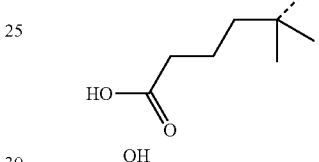

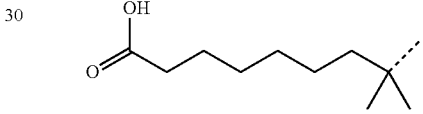

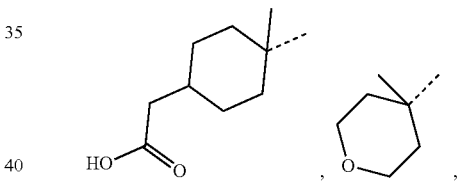

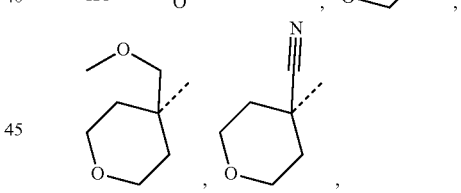

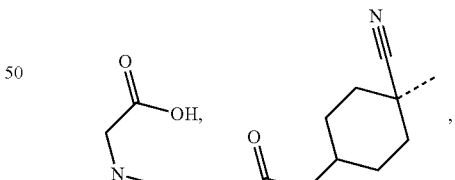

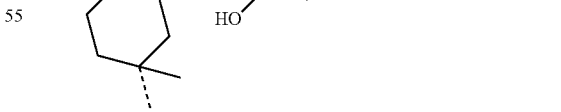

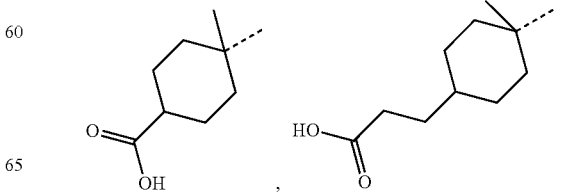

-continued

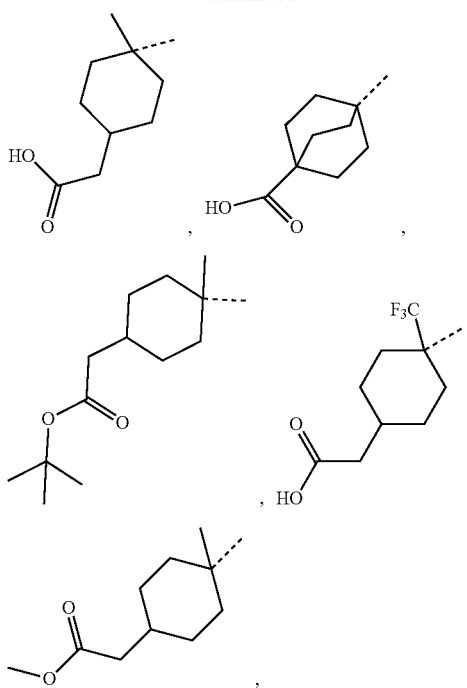

and other variables are as defined herein.

In some embodiments of the compound of formula (II) or the stereoisomer or the pharmaceutically acceptable salt thereof disclosed herein, the above-mentioned structural unit

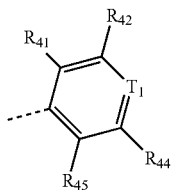

is selected from the group consisting of

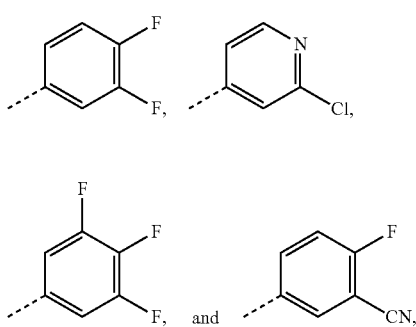

and other variables are as defined herein.

The compound of formula (II), or the stereoisomer or the pharmaceutically acceptable salt thereof described above is selected from a compound of formula (II-A) or a stereoisomer or a pharmaceutically acceptable salt thereof,

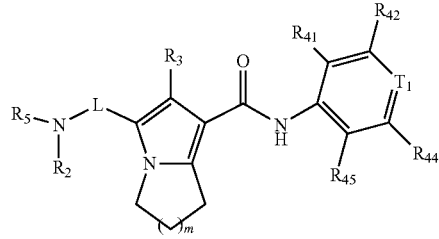

wherein,
m is 1 or 2;
L is selected from

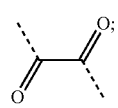

$T_1$ is selected from the group consisting of N and $C(R_{43})$;
$R_2$ is selected from the group consisting of H and $C_{1-6}$ alkyl, wherein the $C_{1-6}$ alkyl is optionally substituted by 1, 2, or 3 $R_b$;
$R_3$ is selected from the group consisting of H, Cl, F, Br, I, OH, $NH_2$, $C_{1-6}$ alkyl, and $C_{1-3}$ alkoxy, wherein the $C_{1-6}$ alkyl and the $C_{1-3}$ alkoxy are optionally substituted by 1, 2, or 3 $R_c$;
$R_{41}$, $R_{42}$, $R_{43}$, $R_{44}$, and $R_{45}$ are each independently selected from the group consisting of H, Cl, F, Br, I, OH, $NH_2$, CN, COOH, and $C_{1-3}$ alkyl, wherein the $C_{1-3}$ alkyl is optionally substituted by 1, 2, or 3 $R_d$;
$R_5$ is selected from the group consisting of $R_{51}$, $C_{3-10}$ cycloalkyl, and 3-6 membered heterocycloalkyl, wherein the $C_{3-10}$ cycloalkyl and the 3-6 membered heterocycloalkyl are optionally substituted by 1, 2, or 3 $R_1$;
$R_{51}$ is selected from the group consisting of $C_{1-7}$ alkyl and $C_{1-6}$ heteroalkyl, wherein the $C_{1-7}$ alkyl and the $C_{1-6}$ heteroalkyl are optionally substituted by 1, 2, or 3 $R_e$;
$R_1$ is selected from the group consisting of H, Cl, F, Br, I, OH, $NH_2$, CN, COOH, $C_{1-6}$ alkyl, —COO—$C_{1-6}$ alkyl, and —$C_{1-3}$ alkyl-COO—$C_{1-6}$ alkyl, wherein the $C_{1-6}$ alkyl, the —COO—$C_{1-6}$ alkyl, and the —$C_{1-3}$ alkyl-COO—$C_{1-6}$ alkyl are optionally substituted by 1, 2, or 3 $R_a$;
$R_a$ is each independently selected from the group consisting of Cl, F, Br, I, OH, $NH_2$, CN, COOH, $C_{1-3}$ alkyl, and $C_{1-3}$ alkoxy, wherein the $C_{1-3}$ is optionally substituted by 1, 2, or 3 R;
$R_b$ is each independently selected from the group consisting of Cl, F, Br, I, OH, $NH_2$, CN, and COOH;
$R_c$ is each independently selected from the group consisting of Cl, F, Br, I, OH, $NH_2$, CN, COOH, and $C_{1-3}$ alkyl, wherein the $C_{1-3}$ is optionally substituted by 1, 2, or 3 R;
$R_d$ is each independently selected from the group consisting of Cl, F, Br, I, OH, $NH_2$, CN, and COOH;
$R_e$ is each independently selected from the group consisting of Cl, F, Br, I, OH, $NH_2$, CN, and COOH;
R is each independently selected from the group consisting of Cl, F, Br, I, OH, $NH_2$, CN, and COOH;
The $C_{1-6}$ heteroalkyl and the 3-6 membered heterocycloalkyl each contain 1, 2, 3, or 4 heteroatoms or heteroatom groups independently selected from the group consisting of —NH—, —O—, —S—, and N.

In some embodiments of the compound of formula (II-A) or the stereoisomer or the pharmaceutically acceptable salt thereof disclosed herein, the above-mentioned $R_a$ is selected from the group consisting of Cl, F, Br, I, OH, $NH_2$, CN, COOH, and —$OCH_3$, and other variables are as defined herein.

In some embodiments of the compound of formula (II-A) or the stereoisomer or the pharmaceutically acceptable salt thereof disclosed herein, the above-mentioned $R_c$ is selected from the group consisting of Cl, F, Br, I, OH, $NH_2$, CN, and COOH, and other variables are as defined herein.

In some embodiments of the compound of formula (II-A) or the stereoisomer or the pharmaceutically acceptable salt thereof disclosed herein, the above-mentioned $R_1$ is selected from the group consisting of H, Cl, F, Br, I, OH, $NH_2$, CN, COOH, $C_{1-3}$ alkyl, —COO—$C_{1-3}$ alkyl, and —$C_{1-3}$ alkyl-COO—$C_{1-3}$ alkyl, wherein the $C_{1-3}$ alkyl, the —COO—$C_{1-3}$ alkyl, and the —$C_{1-3}$ alkyl-COG-$C_{1-3}$ alkyl are optionally substituted by 1, 2, or 3 $R_a$, and other variables are as defined herein.

In some embodiments of the compound of formula (II-A) or the stereoisomer or the pharmaceutically acceptable salt thereof disclosed herein, the above-mentioned $R_1$ is selected from the group consisting of H, Cl, F, Br, I, OH, $NH_2$, CN, COOH, $CH_3$, and Et, wherein the $CH_3$ and the Et are optionally substituted by 1, 2, or 3 $R_a$, and other variables are as defined herein.

In some embodiments of the compound of formula (II-A) or the stereoisomer or the pharmaceutically acceptable salt thereof disclosed herein, the above-mentioned $R_1$ is selected from the group consisting of H, Cl, F, Br, I, OH, $NH_2$, CN, COOH, $CH_3$, Et, —$CH_2$—COOH, —$CH_2$—$OCH_3$, and —$(CH_2)_2$—COOH, and other variables are as defined herein.

In some embodiments of the compound of formula (II-A) or the stereoisomer or the pharmaceutically acceptable salt thereof disclosed herein, the above-mentioned $R_2$ is selected from the group consisting of H and $C_{1-3}$ alkyl, wherein the $C_{1-3}$ alkyl is optionally substituted by 1, 2, or 3 $R_b$, and other variables are as defined herein.

In some embodiments of the compound of formula (II-A) or the stereoisomer or the pharmaceutically acceptable salt thereof disclosed herein, the above-mentioned $R_2$ is selected from the group consisting of H, $CH_3$, and Et, and other variables are as defined herein.

In some embodiments of the compound of formula (II-A) or the stereoisomer or the pharmaceutically acceptable salt thereof disclosed herein, the above-mentioned $R_3$ is selected from the group consisting of H, Cl, F, Br, I, OH, $NH_2$, and $C_{1-3}$ alkyl, wherein the $C_{1-3}$ alkyl is optionally substituted by 1, 2, or 3 $R_c$, and other variables are as defined herein.

In some embodiments of the compound of formula (II-A) or the stereoisomer or the pharmaceutically acceptable salt thereof disclosed herein, the above-mentioned $R_3$ is selected from the group consisting of H, Cl, F, Br, I, OH, $NH_2$, $CH_3$, $CF_3$, and Et, and other variables are as defined herein.

In some embodiments of the compound of formula (II-A) or the stereoisomer or the pharmaceutically acceptable salt thereof disclosed herein, the above-mentioned $R_{41}$, $R_{42}$, $R_{43}$, $R_{44}$ and $R_{45}$ are each independently selected from the group consisting of H, Cl, F, Br, I, OH, $NH_2$, CN, and —COOH, and other variables are as defined herein.

In some embodiments of the compound of formula (II-A) or the stereoisomer or the pharmaceutically acceptable salt thereof disclosed herein, the above-mentioned $R_{51}$ is selected from the group consisting of $C_{1-6}$ alkyl and $C_{1-3}$ heteroalkyl, wherein the $C_{1-6}$ alkyl and the $C_{1-3}$ heteroalkyl are optionally substituted by 1, 2, or 3 $R_e$, and other variables are as defined herein.

In some embodiments of the compound of formula (II-A) or the stereoisomer or the pharmaceutically acceptable salt thereof disclosed herein, the above-mentioned $R_{51}$ is selected from the group consisting of methyl, ethyl, propyl, isopropyl,

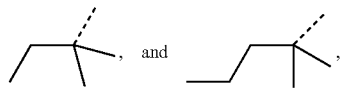

wherein the methyl, the ethyl, the propyl, the isopropyl, the

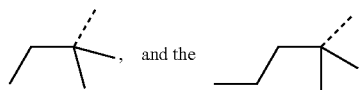

are optionally substituted by 1, 2, or 3 $R_e$, and other variables are as defined herein.

In some embodiments of the compound of formula (II-A) or the stereoisomer or the pharmaceutically acceptable salt thereof disclosed herein, the above-mentioned $R_{51}$ is selected from the group consisting of

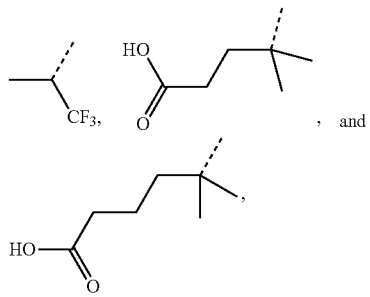

and other variables are as defined herein.

In some embodiments of the compound of formula (II-A) or the stereoisomer or pharmaceutically acceptable salt thereof disclosed herein, the above-mentioned $R_5$ is selected from the group consisting of $R_{51}$, $C_{3-8}$ cycloalkyl, and 5-6 membered heterocycloalkyl, wherein the $C_{3-8}$ cycloalkyl and the 5-6 membered heterocycloalkyl are optionally substituted by 1, 2, or 3 $R_1$, and the other variables are as defined herein.

In some embodiments of the compound of formula (II-A) or the stereoisomer or the pharmaceutically acceptable salt thereof disclosed herein, the above-mentioned $R_5$ is selected from the group consisting of $R_{51}$, cyclohexyl, tetrahydropyranyl, piperidinyl, and bicyclo[2.2.2]octyl, wherein the cyclohexyl, the tetrahydropyranyl, the piperidinyl, and the bicyclo[2.2.2]octyl are optionally substituted by 1, 2, or 3 $R_1$, and the other variables are as defined herein.

In some embodiments of the compound of formula (II-A) or the stereoisomer or the pharmaceutically acceptable salt thereof disclosed herein, the above-mentioned $R_5$ is selected from the group consisting of $R_{51}$,

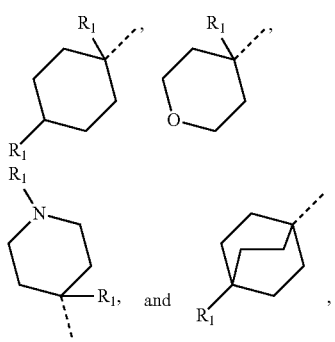

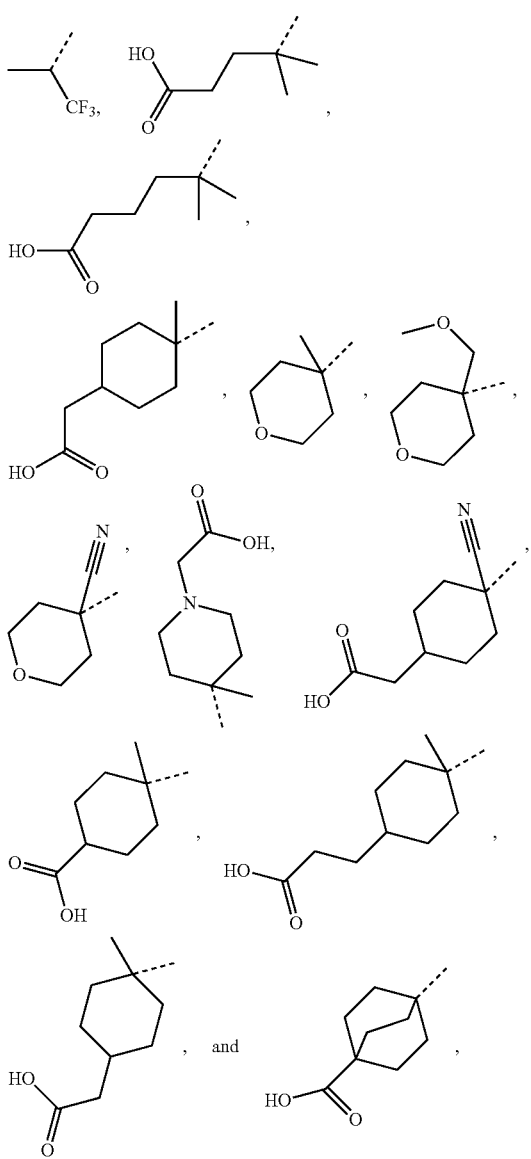

and other variables are as defined herein.

In some embodiments of the compound of formula (II-A) or the stereoisomer or the pharmaceutically acceptable salt thereof disclosed herein, the above-mentioned $R_5$ is selected from the group consisting of In some embodiments of the compound of formula (II-A) or the stereoisomer or the pharmaceutically acceptable salt thereof disclosed herein, the above-mentioned structural unit

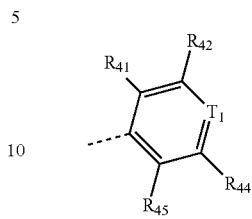

is selected from the group consisting of

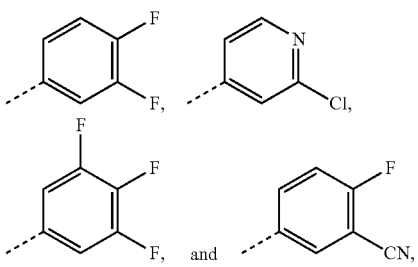

and other variables are as defined herein.

The compound of formula (II) or the stereoisomer or the pharmaceutically acceptable salt thereof described above is selected from a compound of formula (II-B) or a stereoisomer or a pharmaceutically acceptable salt thereof,

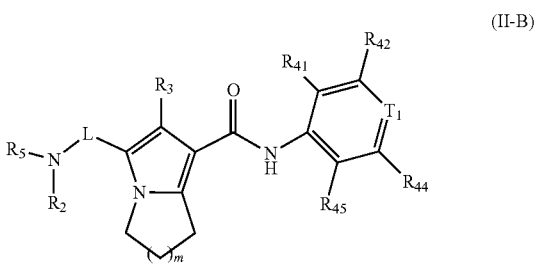

(II-B)

wherein,
m is 1 or 2;
L is selected from

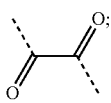

$T_1$ is selected from the group consisting of N and $C(R_{43})$;
$R_2$ is selected from the group consisting of H and $C_{1-6}$ alkyl, wherein the $C_{1-6}$ alkyl is optionally substituted by 1, 2, or 3 $R_b$;
$R_3$ is selected from the group consisting of H, Cl, F, Br, I, OH, $NH_2$, $C_{1-6}$ alkyl, and $C_{1-3}$ alkoxy, wherein the $C_{1-6}$ alkyl and the $C_{1-3}$ alkoxy are optionally substituted by 1, 2, or 3 $R_c$;
$R_{41}$, $R_{42}$, $R_{43}$, $R_{44}$, and $R_{45}$ are each independently selected from the group consisting of H, Cl, F, Br, I, OH, $NH_2$, CN, COOH, and $C_{1-3}$ alkyl, wherein the $C_{1-3}$ alkyl is optionally substituted by 1, 2, or 3 $R_d$;

$R_5$ is selected from the group consisting of $R_{51}$, $C_{3-6}$ cycloalkyl, and 3-6 membered heterocycloalkyl, wherein the 5-6 membered cycloalkyl and the 3-6 membered heterocycloalkyl are optionally substituted by 1, 2, or 3 $R_1$;

$R_{51}$ is selected from the group consisting of $C_{1-6}$ alkyl and $C_{1-6}$ heteroalkyl, wherein the $C_{1-6}$ alkyl and the $C_{1-6}$ heteroalkyl are optionally substituted by 1, 2, or 3 $R_e$;

$R_1$ is selected from the group consisting of H, Cl, F, Br, I, OH, $NH_2$, CN, COOH, $C_{1-6}$ alkyl, —COO—$C_{1-6}$ alkyl, and —$C_{1-3}$ alkyl-COO—$C_{1-6}$ alkyl, wherein the $C_{1-6}$ alkyl, the —COO—$C_{1-6}$ alkyl, and the —$C_{1-3}$ alkyl-COO—$C_{1-6}$ alkyl are optionally substituted by 1, 2, or 3 $R_a$;

$R_a$ is each independently selected from the group consisting of Cl, F, Br, I, OH, $NH_2$, CN, COOH, $C_{1-3}$ alkyl, and $C_{1-3}$ alkoxy, wherein the $C_{1-3}$ is optionally substituted by 1, 2, or 3 R;

$R_b$ is each independently selected from the group consisting of Cl, F, Br, I, OH, $NH_2$, CN, and COOH;

$R_c$ is each independently selected from the group consisting of Cl, F, Br, I, OH, $NH_2$, CN, COOH, and $C_{1-3}$ alkyl, wherein the $C_{1-3}$ is optionally substituted by 1, 2, or 3 R;

$R_d$ is each independently selected from the group consisting of Cl, F, Br, I, OH, $NH_2$, CN, and COOH;

$R_e$ is each independently selected from the group consisting of Cl, F, Br, I, OH, $NH_2$, CN, and COOH;

R is each independently selected from the group consisting of Cl, F, Br, I, OH, $NH_2$, CN, and COOH;

The $C_{1-6}$ heteroalkyl and the 3-6 membered heterocycloalkyl each contain 1, 2, 3, or 4 heteroatoms or heteroatom groups independently selected from the group consisting of —NH—, —O—, —S—, and N.

In some embodiments of the compound of formula (II-B) or the stereoisomer or the pharmaceutically acceptable salt thereof disclosed herein, the above-mentioned $R_a$ is selected from the group consisting of Cl, F, Br, I, OH, $NH_2$, CN, COOH, and —$OCH_3$, and other variables are as defined herein.

In some embodiments of the compound of formula (II-B) or the stereoisomer or the pharmaceutically acceptable salt thereof disclosed herein, the above-mentioned $R_c$ is selected from the group consisting of Cl, F, Br, I, OH, $NH_2$, CN, and COOH, and other variables are as defined herein.

In some embodiments of the compound of formula (II-B) or the stereoisomer or pharmaceutically acceptable salt thereof disclosed herein, the above-mentioned $R_1$ is selected from the group consisting of H, Cl, F, Br, I, OH, $NH_2$, CN, COOH, $C_{1-3}$ alkyl, —COO—$C_{1-3}$ alkyl, and —$C_{1-3}$ alkyl-COO—$C_{1-3}$ alkyl, wherein the $C_{1-3}$ alkyl, the —COO—$C_{1-3}$ alkyl, and the —$C_{1-3}$ alkyl-COO—$C_{1-3}$ alkyl are optionally substituted by 1, 2, or 3 $R_a$, and other variables are as defined herein.

In some embodiments of the compound of formula (II-B) or the stereoisomer or the pharmaceutically acceptable salt thereof disclosed herein, the above-mentioned $R_1$ is selected from the group consisting of H, Cl, F, Br, I, OH, $NH_2$, CN, COOH, $CH_3$, and Et, wherein the $CH_3$ and the Et are optionally substituted by 1, 2, or 3 $R_a$, and other variables are as defined herein.

In some embodiments of the compound of formula (II-B) or the stereoisomer or pharmaceutically acceptable salt thereof disclosed herein, the above-mentioned $R_1$ is selected from the group consisting of H, Cl, F, Br, I, OH, $NH_2$, CN, COOH, $CH_3$, Et, —$CH_2$—COOH, and —$CH_2$—$OCH_3$, and other variables are as defined herein.

In some embodiments of the compound of formula (II-B) or the stereoisomer or the pharmaceutically acceptable salt thereof disclosed herein, the above-mentioned $R_2$ is selected from the group consisting of H and $C_{1-3}$ alkyl, wherein the $C_{1-3}$ alkyl is optionally substituted by 1, 2, or 3 $R_b$, and other variables are as defined herein.

In some embodiments of the compound of formula (II-B) or the stereoisomer or the pharmaceutically acceptable salt thereof disclosed herein, the above-mentioned $R_2$ is selected from the group consisting of H, $CH_3$ and Et, and other variables are as defined herein.

In some embodiments of the compound of formula (II-B) or the stereoisomer or the pharmaceutically acceptable salt thereof disclosed herein, the above-mentioned $R_3$ is selected from the group consisting of H, Cl, F, Br, I, OH, $NH_2$, and $C_{1-3}$ alkyl, wherein the $C_{1-3}$ alkyl is optionally substituted by 1, 2, or 3 $R_c$, and other variables are as defined herein.

In some embodiments of the compound of formula (II-B) or the stereoisomer or the pharmaceutically acceptable salt thereof disclosed herein, the above-mentioned $R_3$ is selected from the group consisting of H, Cl, F, Br, I, OH, $NH_2$, $CH_3$, $CF_3$, and Et, and other variables are as defined herein.

In some embodiments of the compound of formula (II-B) or the stereoisomer or the pharmaceutically acceptable salt thereof disclosed herein, the above-mentioned $R_{41}$, $R_{42}$, $R_{43}$, $R_{44}$, and $R_{45}$ are each independently selected from the group consisting of H, Cl, F, Br, I, OH, $NH_2$, CN, and —COOH, and other variables are as defined herein.

In some embodiments of the compound of formula (II-B) or the stereoisomer or the pharmaceutically acceptable salt thereof disclosed herein, the above-mentioned $R_{51}$ is selected from the group consisting of $C_{1-3}$ alkyl and $C_{1-3}$ heteroalkyl, wherein the $C_{1-3}$ alkyl and the $C_{1-3}$ heteroalkyl are optionally substituted by 1, 2, or 3 $R_e$, and other variables are as defined herein.

In some embodiments of the compound of formula (II-B) or the stereoisomer or the pharmaceutically acceptable salt thereof disclosed herein, the above-mentioned $R_{51}$ is selected from the group consisting of methyl, ethyl, propyl, and isopropyl, wherein the methyl, the ethyl, the propyl, and the isopropyl are optionally substituted by 1, 2, or 3 $R_e$, and other variables are as defined herein.

In some embodiments of the compound of formula (II-B) or the stereoisomer or the pharmaceutically acceptable salt thereof disclosed herein, the above-mentioned $R_{51}$ is

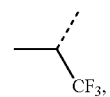

and other variables are as defined herein.

In some embodiments of the compound of formula (II-B) or the stereoisomer or the pharmaceutically acceptable salt thereof disclosed herein, the above-mentioned $R_5$ is selected from the group consisting of $R_{51}$, $C_{5-6}$ cycloalkyl, and 5-6 membered heterocycloalkyl, wherein the 5-6 membered cycloalkyl and the 5-6 membered heterocycloalkyl are optionally substituted by 1, 2, or 3 $R_1$, and the other variables are as defined herein.

In some embodiments of the compound of formula (II-B) or the stereoisomer or the pharmaceutically acceptable salt thereof disclosed herein, the above-mentioned $R_5$ is selected from the group consisting of $R_{51}$, cyclohexyl, tetrahydropyranyl, and piperidinyl, wherein the cyclohexyl, the tetrahydropyranyl, and the piperidinyl are optionally substituted by 1, 2, or 3 $R_1$, and other variables are as defined herein.

In some embodiments of the compound of formula (II-B) or the stereoisomer or the pharmaceutically acceptable salt thereof disclosed herein, the above-mentioned $R_5$ is selected from the group consisting of $R_{51}$,

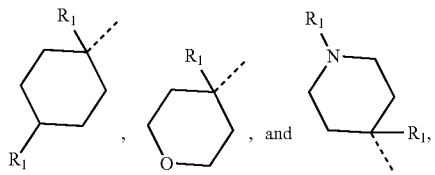

and other variables are as defined herein.

In some embodiments of the compound of formula (II-B) or the stereoisomer or the pharmaceutically acceptable salt thereof disclosed herein, the above-mentioned $R_5$ is selected from the group consisting of

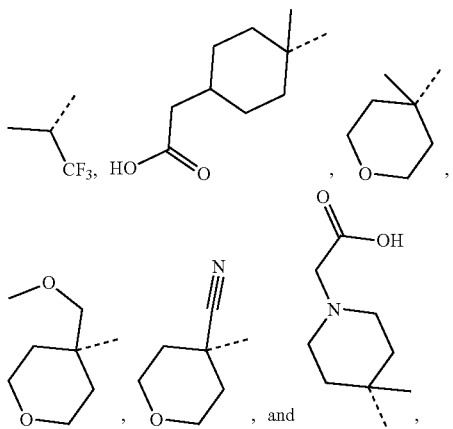

and other variables are as defined herein.

In some embodiments of the compound of formula (II-B) or the stereoisomer or the pharmaceutically acceptable salt thereof disclosed herein, the above-mentioned structural unit

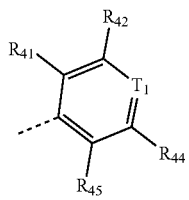

is selected from the group consisting of

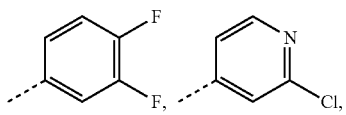

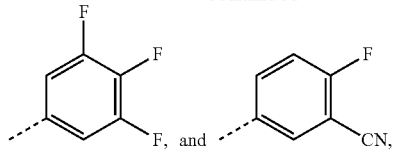

and other variables are as defined herein.

The compound of formula (II) or the stereoisomer or the pharmaceutically acceptable salt thereof is selected from a compound of formula (I) or a pharmaceutically acceptable salt thereof,

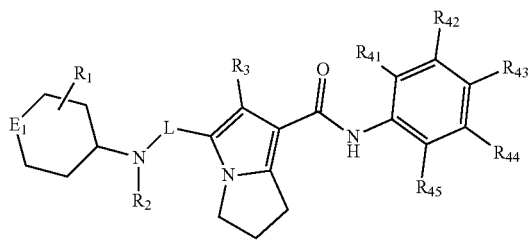

(I)

wherein,
L is selected from

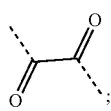

$E_1$ is selected from the group consisting of —O—, —S—, and —NH—;

$R_1$ is selected from the group consisting of H, Cl, F, Br, I, OH, $NH_2$, CN, COOH, $C_{1-6}$ alkyl, —COO—$C_{1-6}$ alkyl, and —$C_{1-3}$ alkyl-COO—$C_{1-6}$ alkyl, wherein the $C_{1-6}$ alkyl, the —COO—$C_{1-6}$ alkyl, and the —$C_{1-3}$ alkyl-COO—$C_{1-6}$ alkyl are optionally substituted by 1, 2, or 3 $R_a$;

$R_2$ is selected from the group consisting of H and $C_{1-6}$ alkyl, wherein the $C_{1-6}$ alkyl is optionally substituted by 1, 2, or 3 $R_b$;

$R_3$ is selected from the group consisting of H, Cl, F, Br, I, OH, $NH_2$, $C_{1-6}$ alkyl, and $C_{1-3}$ alkoxy, wherein the $C_{1-6}$ alkyl and the $C_{1-3}$ alkoxy are optionally substituted by 1, 2, or 3 $R_c$;

$R_{41}$, $R_{42}$, $R_{43}$, $R_{44}$, and $R_{45}$ are each independently selected from the group consisting of H, Cl, F, Br, I, OH, $NH_2$, CN, COOH, and $C_{1-3}$ alkyl, wherein the $C_{1-3}$ alkyl is optionally substituted by 1, 2, or 3 $R_d$;

$R_a$ is selected from the group consisting of Cl, F, Br, I, OH, $NH_2$, CN, COOH, and $C_{1-3}$ alkyl, wherein the $C_{1-3}$ is optionally substituted by 1, 2, or 3 R;

$R_b$ is selected from the group consisting of Cl, F, Br, I, OH, $NH_2$, CN, and COOH;

$R_c$ is selected from the group consisting of Cl, F, Br, I, OH, $NH_2$, CN, COOH, and $C_{1-3}$ alkyl, wherein the $C_{1-3}$ is optionally substituted by 1, 2, or 3 R;

$R_d$ is each independently selected from the group consisting of Cl, F, Br, I, OH, $NH_2$, CN, and COOH;

and R is each independently selected from the group consisting of Cl, F, Br, I, OH, NH$_2$, CN, and COOH.

In some embodiments of the compound of formula (I) or the stereoisomer or the pharmaceutically acceptable salt thereof disclosed herein, the above-mentioned R$_a$ is selected from the group consisting of Cl, F, Br, I, OH, NH$_2$, CN, and COOH, and other variables are as defined herein.

In some embodiments of the compound of formula (I) or the stereoisomer or the pharmaceutically acceptable salt thereof disclosed herein, the above-mentioned R$_c$ is selected from the group consisting of Cl, F, Br, I, OH, NH$_2$, CN, and COOH, and other variables are as defined herein.

In some embodiments of the compound of formula (I) or the stereoisomer or the pharmaceutically acceptable salt thereof disclosed herein, the above-mentioned R$_1$ is selected from the group consisting of H, Cl, F, Br, I, OH, NH$_2$, CN, COOH, C$_{1-3}$ alkyl, —COO—C$_{1-3}$ alkyl, and —C$_{1-3}$ alkyl-COO—C$_{1-3}$ alkyl, wherein the C$_{1-3}$ alkyl, the —COO—C$_{1-3}$ alkyl, and the —C$_{1-3}$ alkyl-COO—C$_{1-3}$ alkyl are optionally substituted by 1, 2, or 3 R$_a$, and other variables are as defined herein.

In some embodiments of the compound of formula (I) or the stereoisomer or the pharmaceutically acceptable salt thereof disclosed herein, the above-mentioned R$_1$ is selected from the group consisting of H, Cl, F, Br, I, OH, NH$_2$, CN, COOH, CH$_3$, and Et, wherein the CH$_3$ and the Et are optionally substituted by 1, 2, or 3 R$_a$, and other variables are as defined herein.

In some embodiments of the compound of formula (I) or the stereoisomer or the pharmaceutically acceptable salt thereof disclosed herein, the above-mentioned R$_1$ is selected from the group consisting of H, Cl, F, Br, I, OH, NH$_2$, CN, COOH, CH$_3$, and Et, and other variables are as defined herein.

In some embodiments of the compound of formula (I) or the stereoisomer or the pharmaceutically acceptable salt thereof disclosed herein, the above-mentioned R$_2$ is selected from the group consisting of H and C$_{1-3}$ alkyl, wherein the C$_{1-3}$ alkyl is optionally substituted by 1, 2, or 3 R$_b$, and other variables are as defined herein.

In some embodiments of the compound of formula (I) or the stereoisomer or the pharmaceutically acceptable salt thereof disclosed herein, the above-mentioned R$_2$ is selected from the group consisting of H, CH$_3$, and Et, and other variables are as defined herein.

In some embodiments of the compound of formula (I) or the stereoisomer or the pharmaceutically acceptable salt thereof disclosed herein, the above-mentioned R$_3$ is selected from the group consisting of H, Cl, F, Br, I, OH, NH$_2$, and C$_{1-3}$ alkyl, wherein the C$_{1-3}$ alkyl is optionally substituted by 1, 2, or 3 R$_c$, and other variables are as defined herein.

In some embodiments of the compound of formula (I) or the stereoisomer or the pharmaceutically acceptable salt thereof disclosed herein, the above-mentioned R$_3$ is selected from the group consisting of H, Cl, F, Br, I, OH, NH$_2$, CH$_3$, and Et, and other variables are as defined herein.

In some embodiments of the compound of formula (I) or the stereoisomer or the pharmaceutically acceptable salt thereof disclosed herein, the above-mentioned R$_{41}$, R$_{42}$, R$_{43}$, R$_{44}$, and R$_{45}$ are each independently selected from the group consisting of H, Cl, F, Br, I, OH, NH$_2$, CN, and —COOH, and other variables are as defined herein.

Some other embodiments of the present application are derived from any combination of the variables as described above.

In some embodiments of the present application, the compounds or the stereoisomers or the pharmaceutically acceptable salts thereof described above are selected from the group consisting of

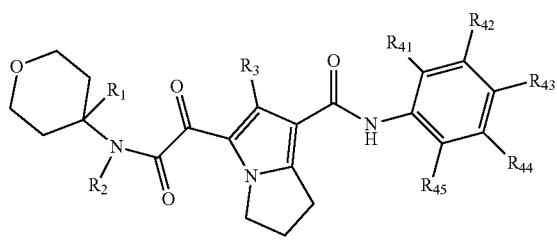

(I-1)

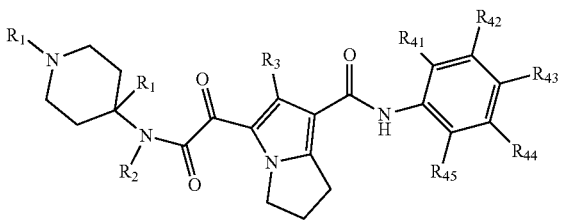

(II-1)

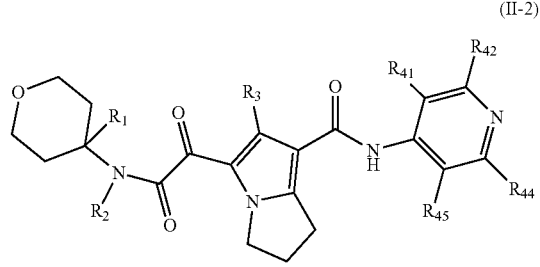

(II-2)

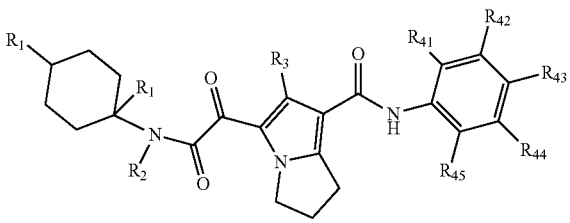

(II-3)

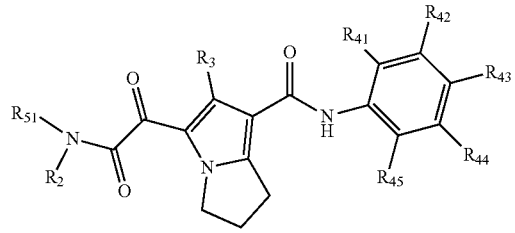

(II-4)

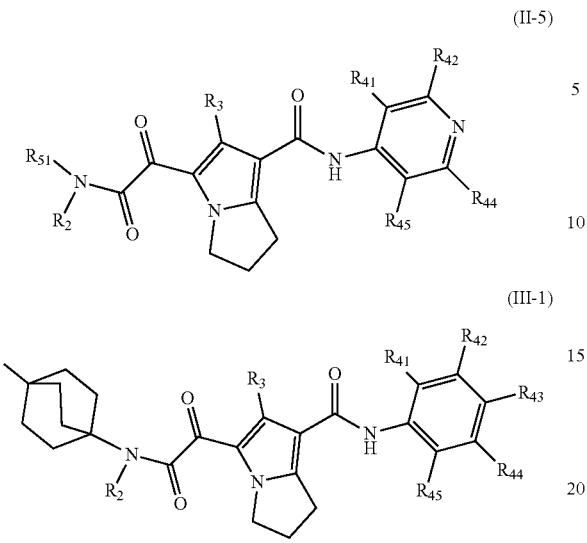
wherein,
R₁, R₂, R₃, R₄₁, R₄₂, R₄₃, R₄₄, R₄₅, and R₅₁ are as defined herein.
The present application further provides compounds of the following formulas or stereoisomers or pharmaceutically acceptable salts thereof:
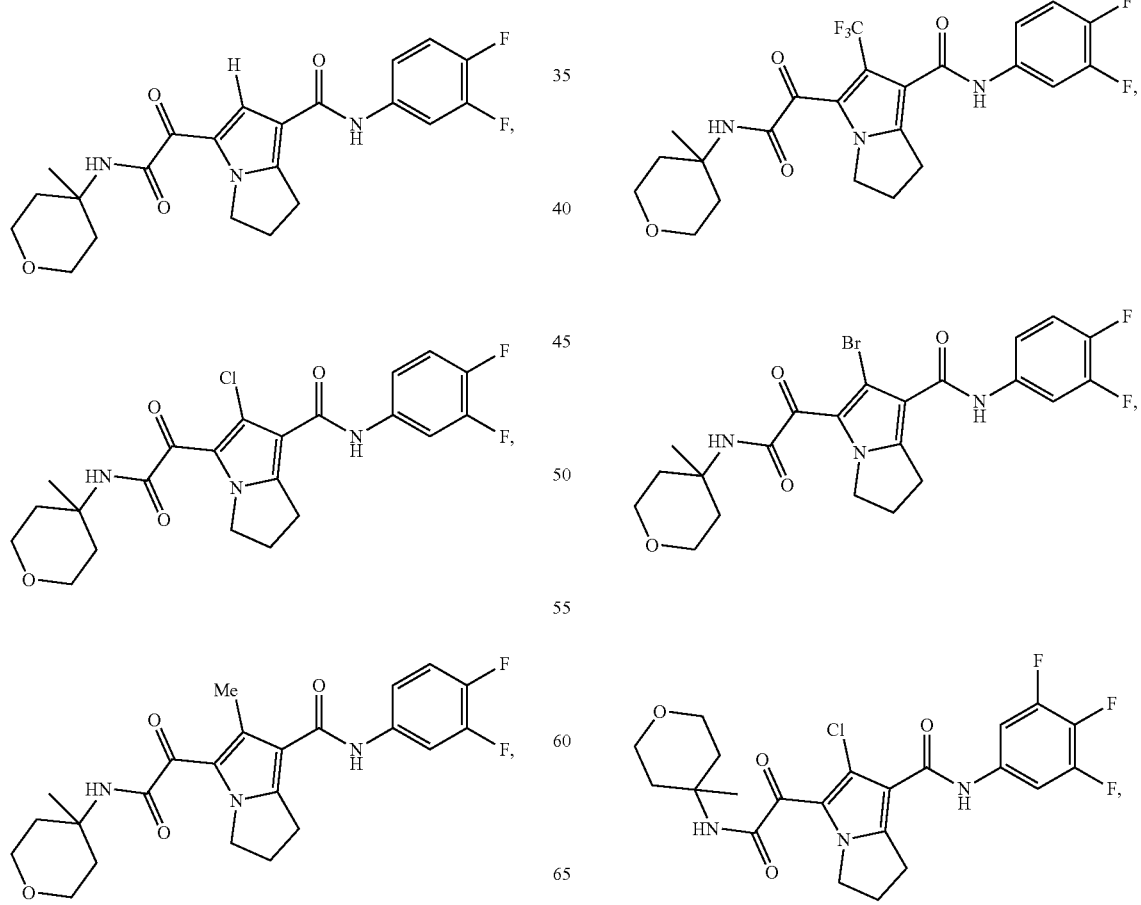
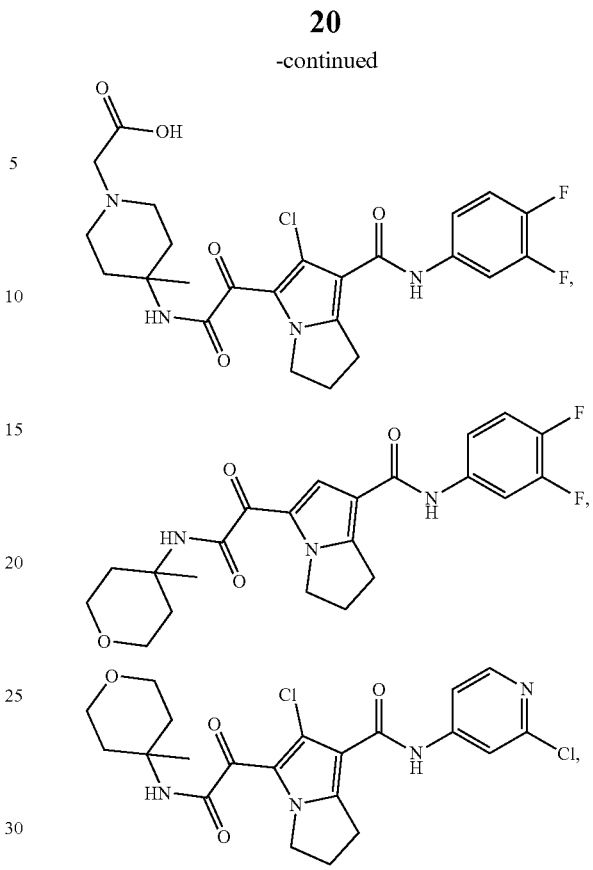

-continued
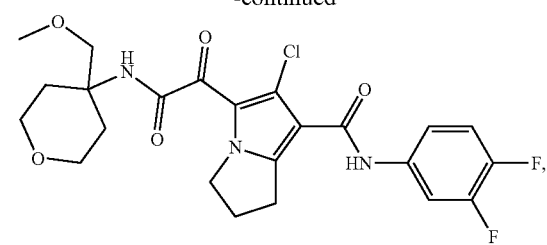
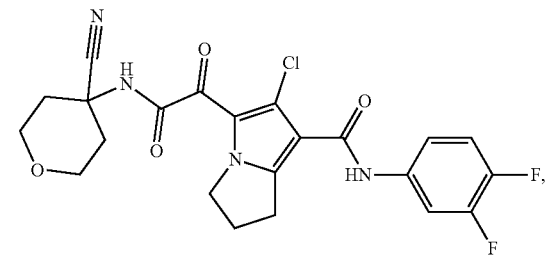
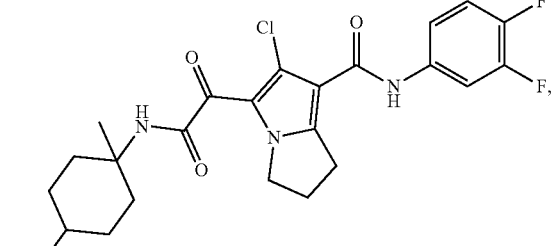
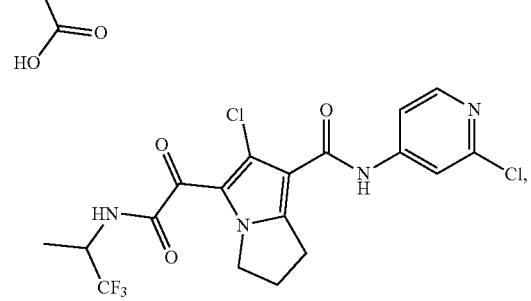
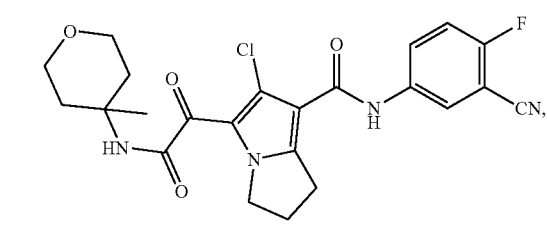
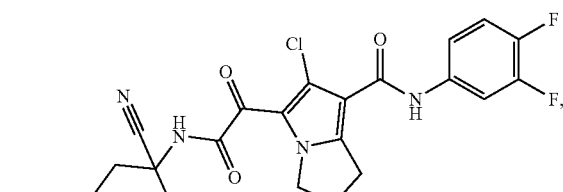
-continued
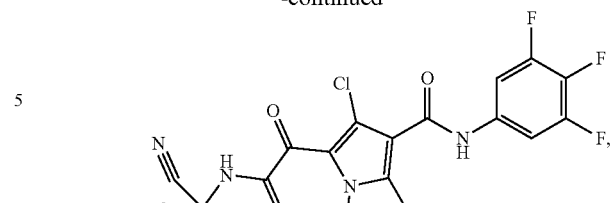
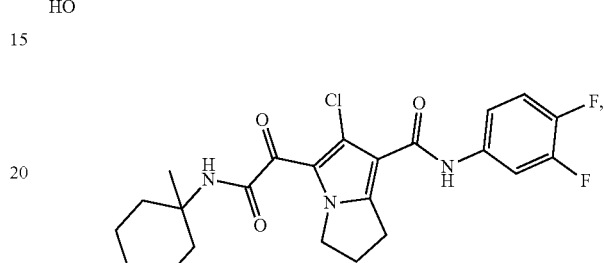
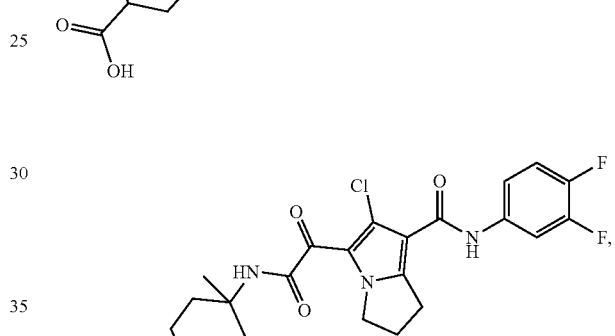
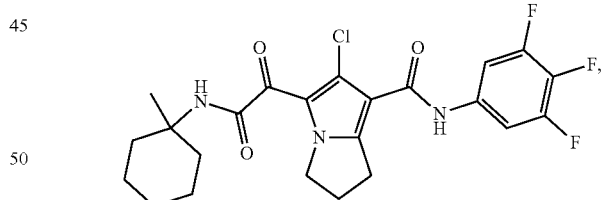
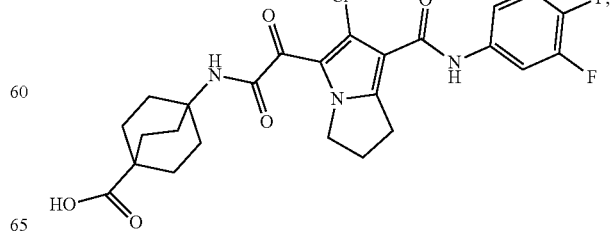

-continued
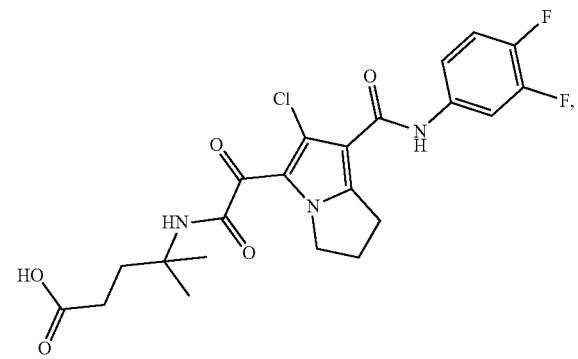
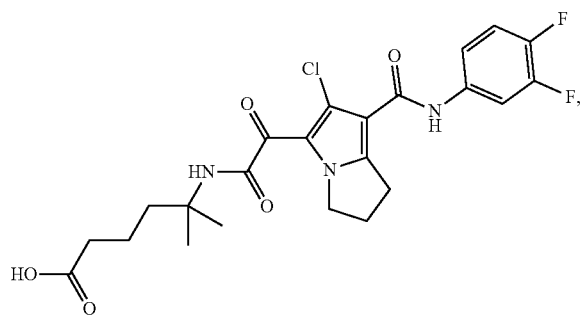
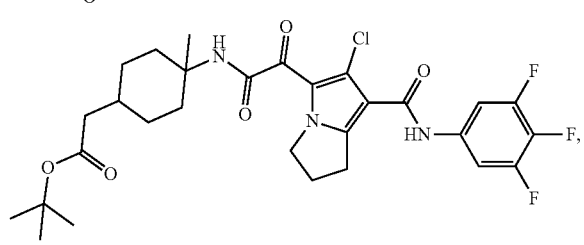
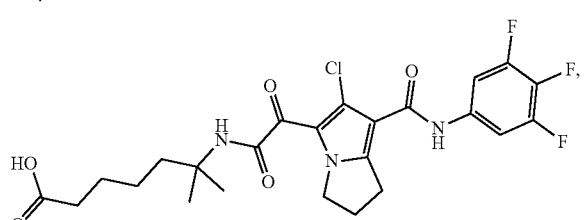
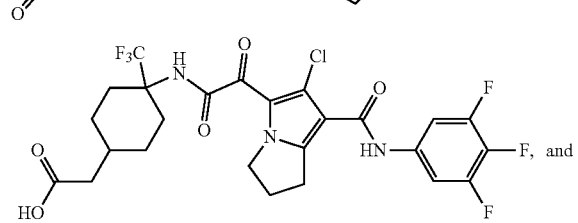
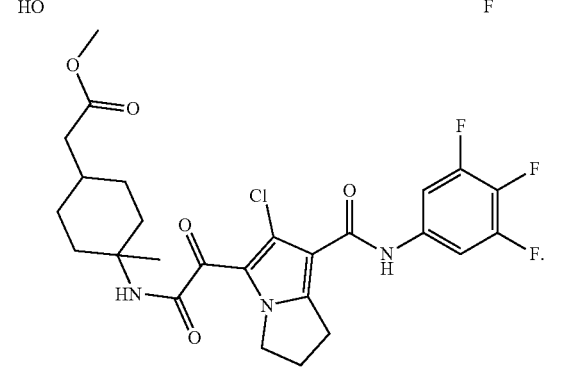
In some embodiments of the present application, the compounds or the stereoisomers or the pharmaceutically acceptable salts thereof described above are selected from the group consisting of
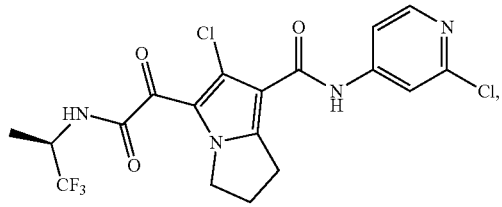
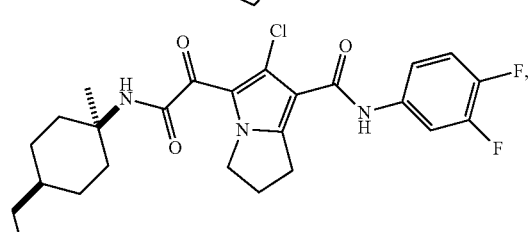
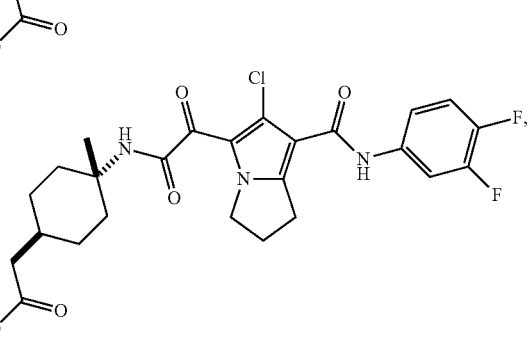
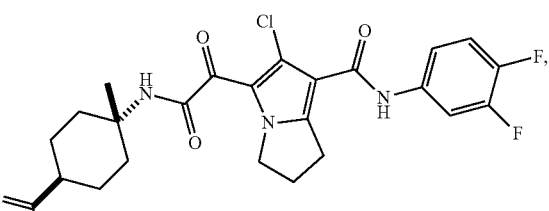
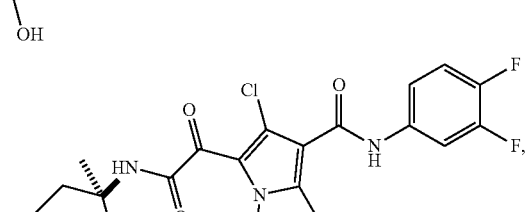
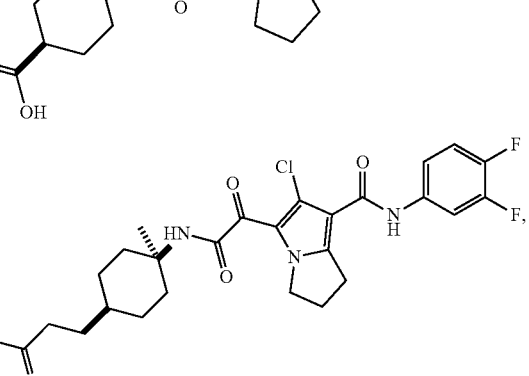

-continued

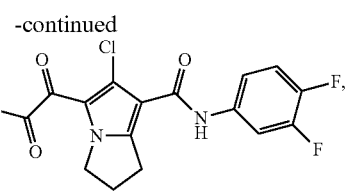
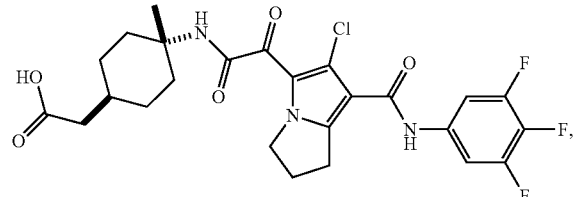
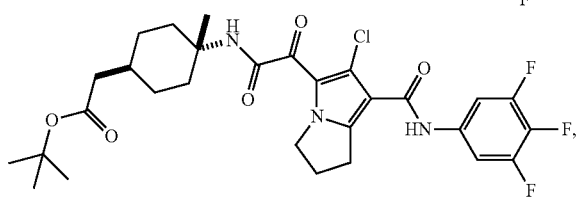
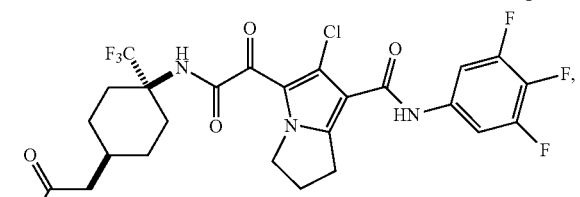

and

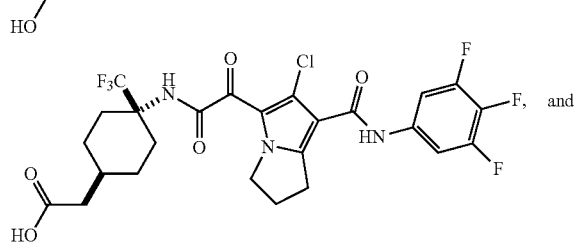
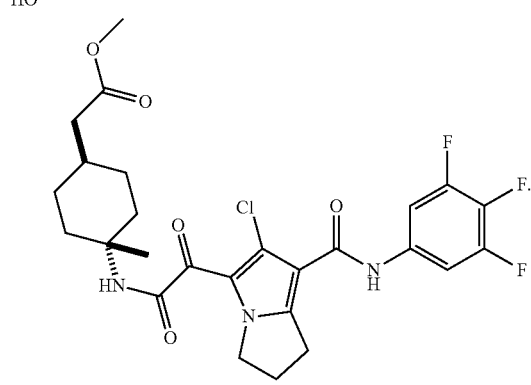

The present application further provides a pharmaceutical composition, comprising a therapeutically effective amount of the compounds or the stereoisomers or the pharmaceutically acceptable salts thereof described above as an active ingredient, and a pharmaceutically acceptable carrier.

The present application further provides a use of the compounds or the stereoisomers or the pharmaceutically acceptable salts thereof described above in preparation of a drug for inhibiting nucleoprotein.

The present application further provides a use of the compounds or the stereoisomers or the pharmaceutically acceptable salts thereof described above as a nucleoprotein inhibitor.

The present application further provides a method for inhibiting nucleoprotein, comprising administering to a mammal, preferably a human, in need of such treatment or prevention a therapeutically effective amount of the compounds or the stereoisomers or the pharmaceutically acceptable salts thereof, or the pharmaceutical composition thereof described above.

The present application further provides the compounds, the stereoisomers or the pharmaceutically acceptable salts thereof, or the pharmaceutical composition thereof described above for use as a nucleoprotein inhibitor.

In some embodiments of the present application, the above-mentioned use is characterized in that the pharmaceutical nucleoprotein inhibitor is a drug for use in treating or preventing diseases related to HBV infection.

The present application further provides a use of the compounds or the stereoisomers or pharmaceutically acceptable salts thereof described above in preparation of a drug for treating or preventing diseases related to HBV infection.

The present application further provides a use of the compounds or the stereoisomer or the pharmaceutically acceptable salts thereof described above in treating or preventing diseases related to HBV infection.

The present application further provides a method for treating diseases related to HBV infection, comprising administering to a mammal, preferably a human, in need of such treatment or prevention a therapeutically effective amount of the compounds or the stereoisomers or the pharmaceutically acceptable salts thereof, or the pharmaceutical composition thereof described above.

The present application further provides the compounds or the stereoisomers or the pharmaceutically acceptable salts thereof, or the pharmaceutical composition thereof described above for use in treating or preventing diseases related to HBV infection.

Technical Effects

As a novel anti-hepatitis B drug, the compounds described herein have a remarkable inhibitory effect on HBV. The compounds disclosed herein show good pharmacokinetic properties in terms of absorption, in vivo distribution, metabolism, etc., e.g. a good liver-targeting effect in vivo. The compounds disclosed herein have low toxic side effect.

Definitions and Description

Unless otherwise stated, the following terms and phrases used herein are intended to have the following meanings. A particular term or phrase, unless otherwise specifically defined, should not be considered as indefinite or unclear, but construed according to its common meaning. When referring to a trade name, it is intended to refer to its corresponding commercial product or its active ingredient.

The term "pharmaceutically acceptable" is used herein for those compounds, materials, compositions, and/or dosage forms which are, within the scope of sound medical judgment, suitable for use in contact with the tissues of human beings and animals without excessive toxicity, irritation, allergic response, or other problems or complications, and commensurate with a reasonable benefit/risk ratio.

The term "pharmaceutically acceptable salt" refers to a salt of the compound of the present application disclosed herein, which is prepared from the compound having particular substituents disclosed herein and a relatively nontoxic acid or base. When the compound disclosed herein contains a relatively acidic functional group, a base addition salt can be obtained by contacting the neutral form of such a compound with a sufficient amount of a base in a pure solution or a suitable inert solvent. Pharmaceutically acceptable base addition salts include sodium, potassium, calcium, ammonium, organic amine, or magnesium salts, or similar salts. When the compound disclosed herein contains a relatively basic functional group, an acid addition salt can be obtained by contacting the neutral form of such a compound with a sufficient amount of an acid in a pure solution or a suitable inert solvent. Examples of pharmaceutically acceptable acid addition salts include salts derived from inorganic acids, such as hydrochloric acid, hydrobromic acid, nitric acid, carbonic acid, bicarbonate radical, phosphoric acid, monohydrogen phosphate, dihydrogen phosphate, sulfuric acid, hydrogen sulfate, hydroiodic acid, phosphorous acid, and the like; and salts derived from organic acids, such as acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, methanesulfonic acid, and the like. Also included are salts of amino acids (e.g., arginine, etc.) and salts of organic acids such as glucuronic acid. Certain specific compounds disclosed herein contain both basic and acidic functional groups that allow the compounds to be converted into either base or acid addition salts.

The compounds described herein can be in the form of a geometric isomer or stereoisomer. All such compounds are contemplated herein, including cis and trans isomers, (−)- and (+)-enantiomers, (R)- and (S)-enantiomers, diastereomers, (D)-isomers, (L)-isomers, and racemic mixtures and other mixtures thereof, such as an enantiomer or diastereomer enriched mixture, all of which are encompassed within the scope of the present application. The substituents such as alkyl may have an additional asymmetric carbon atom. All these isomers and mixtures thereof are encompassed within the scope of the present application.

Unless otherwise stated, the term "enantiomer" or "optical isomer" refers to stereoisomers that are mirror images of each other.

Unless otherwise stated, the term "cis-trans isomer" or "geometric isomer" results from the inability of a double bond or a single bond of a cyclic carbon atom to freely rotate.

Unless otherwise stated, the term "diastereomer" refers to stereoisomers whose molecules have two or more chiral centers and are not mirror images of each other.

Unless otherwise stated, "(D)" or "(+)" stands for dextrorotation, "(L)" or "(−)" stands for levorotation, and "(DL)" or "(±)" stands for racemization.

Unless otherwise stated, the absolute configuration of a stereogenic center is represented by a wedged solid bond (╱) and a wedged dashed bond (╲), and the relative configuration of a stereogenic center is represented by a straight solid bond (╱) and a straight dashed bond (╲). A wavy line (∿) represents a wedged solid bond (╱) or a wedged dashed bond (╲), or a wavy line (∿) represents a straight solid bond (╱) and a straight dashed bond (╲).

Unless otherwise stated, when a double bond structure such as a carbon-carbon double bond, a carbon-nitrogen double bond, and a nitrogen-nitrogen double bond is present in the compound, and each atom on the double bond is linked to two different substituents (in the double bond including an nitrogen atom, a lone pair of electrons on the nitrogen atom is regarded as a substituent to which the nitrogen atom is linked), if the atom on the double bond of the compound and its substituents are linked using a wavy line (∿), it means that the compound exists in the form of a (Z)-type isomer, a (E)-type isomer, or a mixture of the two isomers. For example, the following formula (A) represents that the compound exists in the form of a single isomer of formula (A-1) or formula (A-2) or in the form of a mixture of both isomers of formula (A-1) and formula (A-2); the following formula (B) represents that the compound exists in the form of a single isomer of formula (B-1) or formula (B-2) or in the form of a mixture of both isomers of formula (B-1) and formula (B-2); and the following formula (C) represents that the compound exists in the form of a single isomer of formula (C-1) or formula (C-2) or in the form of a mixture of both isomers of formula (C-1) and formula (C-2).

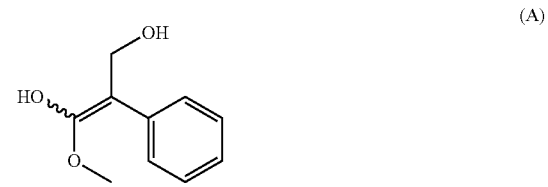
(A)

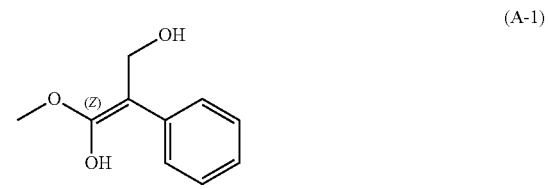
(A-1)

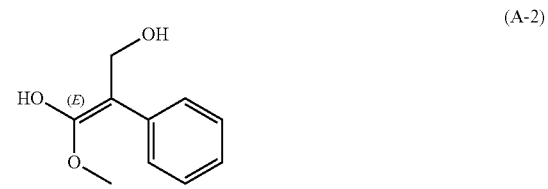
(A-2)

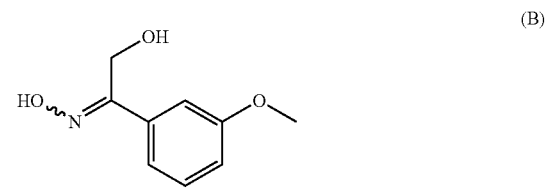
(B)

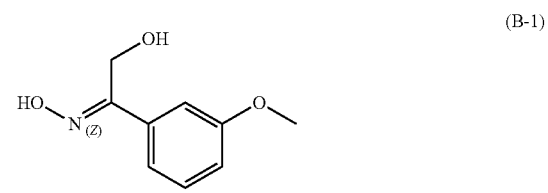
(B-1)

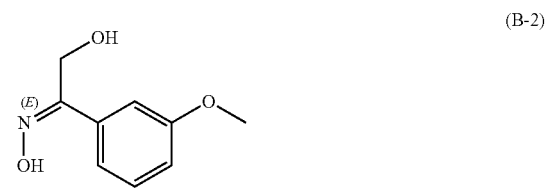
(B-2)

-continued

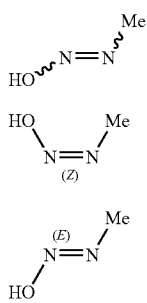

The compounds disclosed herein may be present in particular form. Unless otherwise stated, the term "tautomer" or "tautomeric form" means that different functional isomers are in dynamic equilibrium at room temperature and can be rapidly converted into each other. If tautomers are possible (e.g., in solution), the chemical equilibrium of the tautomers can be achieved. For example, a proton tautomer, also known as a prototropic tautomer, includes the interconversion by proton transfer, such as keto-enol isomerization and imine-enamine isomerization. A valence isomer includes the interconversion by recombination of some bonding electrons. A specific example of the keto-enol tautomerization is the interconversion between two tautomers pentane-2,4-dione and 4-hydroxypent-3-en-2-one.

Unless otherwise stated, the term "be rich in one isomer", "isomer enriched", "be rich in one enantiomer", or "enantiomer enriched" means that the content of one of the isomers or enantiomers is less than 100% and more than or equal to 60%, 70%, 80%, 90%, 95%, 96%, 97%, 98%, 99%, 99.5%, 99.6%, 99.7%, 99.8%, or 99.9%.

Unless otherwise stated, the term "isomeric excess" or "enantiomeric excess" refers to the difference between the relative percentages of two isomers or enantiomers. For example, if the content of one isomer or enantiomer is 90% and the content of the other isomer or enantiomer is 10%, the isomeric or enantiomeric excess (ee) is 80%.

Optically active (R)- and (S)-isomers and D and L isomers can be prepared by chiral synthesis or chiral reagents or other conventional techniques. An enantiomer of certain compound of the present application described herein can be prepared by asymmetric synthesis or derivatization using a chiral auxiliary, wherein the resulting diastereomeric mixture is separated and the auxiliary group is cleaved so as to give the desired pure enantiomer. Alternatively, when the molecule contains a basic functional group (such as amino) or an acidic functional group (such as carboxyl), the compound reacts with an appropriate optically active acid or base to form a salt of the diastereoisomer, which is then subjected to diastereomeric resolution through conventional methods in the art to give the pure enantiomer. Furthermore, the enantiomer and the diastereoisomer are generally isolated through chromatography using a chiral stationary phase, optionally in combination with chemical derivatization (e.g., carbamate formation from amines).

The compound disclosed herein may contain an unnatural proportion of atomic isotope at one or more of the atoms that constitute the compound. For example, the compound may be labeled with a radioisotope, such as tritium ($^3H$), iodine-125 ($^{125}I$), or C-14 ($^{14}C$). For another example, hydrogen can be substituted by deuterium to form a deuterated drug, and the bond formed by deuterium and carbon is firmer than that formed by common hydrogen and carbon. Compared with an un-deuterated drug, the deuterated drug has the advantages of reduced toxic side effect, increased stability, enhanced efficacy, prolonged biological half-life and the like. All isotopic variations of the compound described herein, whether radioactive or not, are encompassed within the scope of the present application.

"Optional" or "optionally" means that the subsequently described event or circumstance may, but not necessarily, occur, and the description includes instances where the event or circumstance occurs and instances where it does not.

The term "substituted" means that one or more hydrogen atoms on a specific atom are substituted by substituents which may include deuterium and hydrogen variants, as long as the valence of the specific atom is normal and the compound after substitution is stable. When the substituent is oxygen (i.e., =O), it means that two hydrogen atoms are substituted. Substitution by oxygen does not occur on aromatic groups. The term "optionally substituted" means that an atom can be or cannot be substituted by a substituent. Unless otherwise specified, the type and number of the substituent may be arbitrary as long as being chemically achievable.

When any variable (e.g., R) occurs more than once in the constitution or structure of a compound, the definition of the variable in each case is independent. Thus, for example, if a group is substituted by 0-2 R, the group can be optionally substituted by two R at most, and the definition of R in each case is independent. Furthermore, a combination of the substituent and/or the variant thereof is permissible only if the combination can result in a stable compound.

When a substituent is absent, it means that the substituent does not exist. For example, when X is absent in A-X, the structure of A-X is actually A. When it is not specified by which atom the listed substituent is linked to the group to be substituted, the substituent can be linked via any atom of the group. For example, pyridinyl as a substituent can be linked to the group to be substituted through any carbon atom on the pyridine ring.

When the listed linking group does not indicate the direction for linking, the direction for linking is arbitrary. For example, when the linking group L contained in

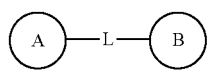

is -M-W-, -M-W- can either link ring A and ring B to form

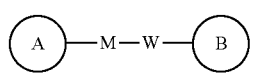

in a direction same as left-to-right reading order, or link ring A and ring B to form

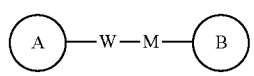

in a direction contrary to the left-to-right reading order. A combination of the linking group, the substituent and/or the variant thereof is permissible only if the combination can result in a stable compound.

Unless otherwise specified, the number of atoms on a ring is generally defined as the number of ring members. For example, "5-7 membered ring" refers to a "ring" on which 5 to 7 atoms are arranged in a circle.

Unless otherwise specified, "3-10 membered ring" refers to cycloalkyl, heterocycloalkyl, cycloalkenyl, or heterocycloalkenyl consisting of 3 to 10 ring atoms. The ring may be monocyclic, bicyclic, or polycyclic, wherein the bicyclic or polycyclic system includes a spiro ring, a fused ring, a bridged ring, etc. Unless otherwise specified, the ring optionally contains 1, 2, or 3 heteroatoms independently selected from the group consisting of O, S, and N. The 3-10 membered ring may be a 3-10 membered, 3-9 membered, 3-8 membered, 3-7 membered, 3-6 membered, 3-5 membered, 4-10 membered, 4-9 membered, 4-8 membered, 4-7 membered, 4-6 membered, 4-5 membered, 5-10 membered, 5-9 membered, 5-8 membered, 5-7 membered, 5-6 membered, 6-10 membered, 6-9 membered, 6-8 membered, or 6-7 membered ring, or the like. The term "5-7 membered heterocycloalkyl" includes piperidinyl and the like, but does not include phenyl. The term "ring" also includes a ring system containing at least one ring, in which each "ring" independently meets the above definition.

Unless otherwise specified, the "5-6 membered ring" refers to cycloalkyl, heterocycloalkyl, cycloalkenyl, heterocycloalkenyl, cycloalkynyl, heterocycloalkynyl, aryl, or heteroaryl consisting of 5 to 6 ring atoms. The ring may be monocyclic or bicyclic, wherein the bicyclic ring system includes a spiro ring, a fused ring, a bridged ring, etc. Unless otherwise specified, the ring optionally contains 1, 2, or 3 heteroatoms independently selected from the group consisting of O, S, and N. The 5-6 membered ring includes a 5-membered ring, a 6-membered ring and the like. The "5-6 membered ring" includes, for example, phenyl, pyridinyl, piperidinyl and the like. On the other hand, the term "5-6 membered heterocycloalkyl" includes piperidinyl and the like, but does not include phenyl. The term "ring" also includes a ring system containing at least one ring, in which each "ring" independently meets the above definition.

Unless otherwise specified, the terms "5-6 membered heteroaromatic ring" and "5-6 membered heteroaryl" can be used interchangeably herein. The term "5-6 membered heteroaryl" refers to a monocyclic group which consists of 5 to 6 ring atoms and has a conjugated pi-electron system, of which 1, 2, 3, or 4 ring atoms are heteroatoms independently selected from the group consisting of O, S, and N, the others being carbon atoms. The nitrogen atom is optionally quaternized and the nitrogen and sulfur heteroatom is optionally oxidized (i.e., NO and $S(O)_p$, where p is 1 or 2). The 5-6 membered heteroaryl can be linked to the rest of the molecule through a heteroatom or a carbon atom. The 5-6 membered heteroaryl includes 5-membered heteroaryl and 6-membered heteroaryl. Examples of the 5-6 membered heteroaryl include, but are not limited to, pyrrolyl (including N-pyrrolyl, 2-pyrrolyl, 3-pyrrolyl, etc.), pyrazolyl (including 2-pyrazolyl, 3-pyrazolyl, etc.), imidazolyl (including N-imidazolyl, 2-imidazolyl, 4-imidazolyl, 5-imidazolyl, etc.), oxazolyl (including 2-oxazolyl, 4-oxazolyl, 5-oxazolyl, etc.), triazolyl (including 1H-1,2,3-triazolyl, 2H-1,2,3-triazolyl, 1H-1,2,4-triazolyl, 4H-1,2,4-triazolyl, etc.), tetrazolyl, isoxazolyl (3-isoxazolyl, 4-isoxazolyl, 5-isoxazolyl, etc.), thiazolyl (including 2-thiazolyl, 4-thiazolyl, 5-thiazolyl, etc.), furanyl (including 2-furanyl, 3-furanyl, etc.), thienyl (including 2-thienyl, 3-thienyl, etc.), pyridinyl (including 2-pyridinyl, 3-pyridinyl, 4-pyridinyl, etc.), pyrazinyl, or pyrimidinyl (including 2-pyrimidinyl, 4-pyrimidinyl, etc.).

Unless otherwise specified, the term "alkyl" refers to a linear or branched saturated hydrocarbon group. In some embodiments, the alkyl is $C_{1-12}$ alkyl. In other embodiments, the alkyl is $C_{1-6}$ alkyl. In still other embodiments, the alkyl is $C_{1-3}$ alkyl. The alkyl can be monovalent (e.g., methyl), divalent (e.g., methylene), or polyvalent (e.g., methenyl). Examples of alkyl include methyl (Me), ethyl (Et), propyl (including n-propyl, and isopropyl), butyl (including n-butyl, isobutyl, s-butyl, and t-butyl), pentyl (including n-pentyl, isopentyl, and neopentyl), hexyl, and the like. For example, the term "$C_{1-10}$ alkyl" refers to a linear or branched saturated hydrocarbon group consisting of 1 to 10 carbon atoms. The $C_{1-10}$ alkyl includes, but is not limited to, $C_{1-10}$, $C_{1-9}$, $C_{1-8}$, $C_{1-6}$, $C_{1-5}$, $C_{1-4}$, $C_{1-3}$, $C_{1-2}$, $C_{2-6}$, $C_{2-4}$, $C_{10}$, $C_8$, $C_7$, $C_6$, and $C_5$ alkyl, and the like, and it may be monovalent (e.g., methyl), divalent (e.g., methylene), or polyvalent (e.g., methenyl). Examples of $C_{1-12}$ alkyl include, but are not limited to, methyl (Me), ethyl (Et), propyl (including n-propyl and isopropyl), butyl (including n-butyl, isobutyl, s-butyl, and t-butyl), pentyl (including n-pentyl, isopentyl, and neopentyl), hexyl, heptyl, octyl, and the like. For example, the term "$C_{1-6}$ alkyl" refers to a linear or branched saturated hydrocarbon group consisting of 1 to 6 carbon atoms. The $C_{1-6}$ alkyl includes, but is not limited to, $C_{1-5}$, $C_{1-4}$, $C_{1-3}$, $C_{1-2}$, $C_{2-6}$, $C_{2-4}$, $C_6$, and $C_5$ alkyl, and the like, and it may be monovalent (e.g., methyl), divalent (e.g., methylene), or polyvalent (e.g., methenyl). Examples of $C_{1-6}$ alkyl include, but are not limited to, methyl (Me), ethyl (Et), propyl (including n-propyl and isopropyl), butyl (including n-butyl, isobutyl, s-butyl, and t-butyl), pentyl (including n-pentyl, isopentyl, and neopentyl), hexyl, and the like. For example, the term "$C_{1-3}$ alkyl" refers to a linear or branched saturated hydrocarbon group consisting of 1 to 3 carbon atoms. The $C_{1-3}$ alkyl includes, but is not limited to, $C_{1-2}$ and $C_{2-3}$ alkyl, and the like, and it may be monovalent (e.g., methyl), divalent (e.g., methylene), or polyvalent (e.g., methenyl). Examples of $C_{1-3}$ alkyl include, but are not limited to, methyl (Me), ethyl (Et), propyl (including n-propyl and isopropyl), and the like.

The term "heteroalkyl", by itself or in combination with another term, refers to a stable linear or branched alkyl radical or a combination thereof consisting of a specified number of carbon atoms and at least one heteroatom or heteroatom group. In some embodiments, the heteroatom is selected from the group consisting of B, O, N, and S, wherein nitrogen and sulfur atoms are optionally oxidized and the nitrogen heteroatom is optionally quaternized. In other embodiments, the heteroatom group is selected from the group consisting of —C(=O)O—, —C(=O)—, —C(=S)—, —S(=O), —S(=O)$_2$—, —C(=O)N(H)—, —N(H)—, —C(=NH)—, —S(=O)$_2$N(H)—, and —S(=O)N(H)—. In some embodiments, the heteroalkyl is $C_{1-6}$ heteroalkyl. In other embodiments, the heteroalkyl is $C_{1-3}$ heteroalkyl. The heteroatom or heteroatom group can be located at any interior position of heteroalkyl, including the position where the alkyl is linked to the rest part of the molecule. However, the terms "alkoxy", "alkylamino" and "alkylthio" (or thioalkxoy) are commonly used expressions and refer to those alkyl groups linked to the rest part of the molecule via an oxygen atom, an amino, or a sulfur atom, respectively. Examples of heteroalkyl include, but are not limited to, —OCH$_3$, —OCH$_2$CH$_3$, —OCH$_2$CH$_2$CH$_3$, —OCH$_2$(CH$_3$)$_2$, —CH$_2$—CH$_2$—O—CH$_3$, —NHCH$_3$, —N(CH$_3$)$_2$, —NHCH$_2$CH$_3$, —N(CH$_3$)(CH$_2$CH$_3$), —CH$_2$—CH$_2$—NH—CH$_3$, —CH$_2$—CH$_2$—N(CH$_3$)—CH$_3$, —SCH$_3$, —SCH$_2$CH$_3$, —SCH$_2$CH$_2$CH$_3$, —SCH$_2$(CH$_3$)$_2$, —CH$_2$—S—CH$_2$—CH$_3$, —CH$_2$—CH$_2$, —S(=O)—CH$_3$, and —CH$_2$—CH$_2$—S(=O)$_2$—CH$_3$. At most two heteroatoms can be consecutive, such as, —CH$_2$—NH—OCH$_3$.

Unless otherwise specified, the term "alkoxy" refers to those alkyl groups each linked to the rest part of the molecule via an oxygen atom. Unless otherwise specified, C$_{1-6}$ alkoxy includes C$_1$, C$_2$, C$_3$, C$_4$, C$_5$, and C$_6$ alkoxy. In some embodiments, the alkoxy is C$_{1-3}$ alkoxy. Examples of alkoxy include, but are not limited to, methoxy, ethoxy, n-propoxy, isopropoxy, n-butoxy, sec-butoxy, tert-butoxy, n-pentyloxy, and S-pentyloxy. For example, the term "C$_{1-3}$ alkoxy" refers to those alkyl groups that each contains 1-3 carbon atoms and is linked to the rest part of the molecule via an oxygen atom. The C$_{1-3}$ alkoxy includes, but is not limited to, C$_{1-2}$, C$_{2-3}$, C$_3$ and C$_2$ alkoxy, and the like. Examples of C$_{1-3}$ alkoxy include, but are not limited to, methoxy, ethoxy, propoxy (including n-propoxy and isopropoxy), and the like.

Unless otherwise specified, C$_{n-n+m}$ or C$_n$-C$_{n+m}$ includes any specific case involving n to n+m carbons (for example, C$_{1-12}$ includes C$_1$, C$_2$, C$_3$, C$_4$, C$_5$, C$_6$, C$_7$, C$_8$, C$_9$, C$_{10}$, C$_{11}$, and C$_{12}$) or any case involving a range between n and n+m, (for example, C$_{1-12}$ includes C$_{1-3}$, C$_{1-6}$, C$_{1-9}$, C$_{3-6}$, C$_{3-9}$, C$_{3-12}$, C$_{6-9}$, C$_{6-12}$, C$_{9-12}$, and the like). Similarly, n membered to n+m membered suggests that the number of atoms on the ring is n to n+m. For example, a 3-12 membered ring includes a 3-membered ring, a 4-membered ring, a 5-membered ring, a 6-membered ring, a 7-membered ring, an 8-membered ring, a 9-membered ring, a 10-membered ring, a 11-membered ring, and a 12-membered ring. The n membered to n+m membered also includes any case involving any range between n and n+m. For example, a 3-12 membered ring includes a 3-6 membered ring, a 3-9 membered ring, a 5-6 membered ring, a 5-7 membered ring, a 6-7 membered ring, a 6-8 membered ring, a 6-10 membered ring, and the like.

Unless otherwise specified, "cycloalkyl" includes any stable cyclic alkyl which may be a monocyclic, a bicyclic, or a tricyclic system, wherein the bicyclic and tricyclic systems include spiro ring, fused ring, and bridged ring. In some embodiments, the cycloalkyl is C$_{3-8}$ cycloalkyl. In other embodiments, the cycloalkyl is C$_{3-6}$ cycloalkyl. In still other embodiments, the cycloalkyl is C$_{5-6}$ cycloalkyl. The cycloalkyl may be monovalent, divalent, or polyvalent. Examples of the cycloalkyl include, but are not limited to, cyclopropyl, cyclobutyl, cyclopentyl, cyclohexyl, cycloheptyl, norbornyl, [2.2.2]bicyclooctane, [4.4.0]bicyclodecane, and the like. For example, "C$_{3-10}$ cycloalkyl" refers to a saturated cyclic hydrocarbon group consisting of 3-10 carbon atoms, and it may be a monocyclic, a bicyclic, or a tricyclic system, wherein the bicyclic and tricyclic systems include spiro ring, fused ring, and bridged ring. The C$_{3-10}$ cycloalkyl includes, but is not limited to, C$_{3-8}$, C$_{3-6}$, C$_{3-5}$, C$_{4-10}$, C$_{4-8}$, C$_{4-6}$, C$_{4-5}$, C$_{5-8}$ and C$_{5-6}$ cycloalkyl, and the like, and it may be monovalent, divalent, or polyvalent. Examples of C$_{3-10}$ cycloalkyl include, but are not limited to, cyclopropyl, cyclobutyl, cyclopentyl, cyclohexyl, cycloheptyl, norbornyl, [2.2.2]bicyclooctane, [4.4.0]bicyclodecane, and the like. For example, "C$_{3-8}$ cycloalkyl" refers to a saturated cyclic hydrocarbon group consisting of 3 to 8 carbon atoms, and it may be a monocyclic or a bicyclic system, wherein the bicyclic system includes spiro ring, fused ring and bridged ring. The C$_{3-8}$ cycloalkyl includes, but is not limited to, C$_{3-6}$, C$_{3-5}$, C$_{4-8}$, C$_{4-6}$, C$_{4-5}$, C$_{5-8}$, or C$_{5-6}$ cycloalkyl, or the like, and it may be monovalent, divalent, or polyvalent. Examples of C$_{3-8}$ cycloalkyl include, but are not limited to, cyclopropyl, cyclobutyl, cyclopentyl, cyclohexyl, cycloheptyl, norbornyl, [2.2.2]bicyclooctane, and the like.

Unless otherwise specified, the term "heterocycloalkyl", by itself or in combination with other terms, refers to a cyclized "heteroalkyl", and it may be a monocyclic, a bicyclic, or a tricyclic system, wherein the bicyclic and tricyclic systems include spiro ring, fused ring, and bridged ring. In addition, with respect to the "heterocycloalkyl", a heteroatom may occupy the position where the heterocycloalkyl is linked to the rest part of the molecule. In some embodiments, the heterocycloalkyl is 4-6 membered heterocycloalkyl. In other embodiments, the heterocycloalkyl is 5-6 membered heterocycloalkyl. Examples of heterocycloalkyl include, but are not limited to, azetidinyl, oxetanyl, thietanyl, pyrrolidinyl, pyrazolidinyl, imidazolidinyl, tetrahydrothienyl (including tetrahydrothien-2-yl, tetrahydrothien-3-yl, etc.), tetrahydrofuranyl (including tetrahydrofuran-2-yl, etc.), tetrahydropyranyl, piperidinyl (including 1-piperidinyl, 2-piperidinyl, 3-piperidinyl, etc.), piperazinyl (including 1-piperazinyl, 2-piperazinyl, etc.), morpholinyl (including 3-morpholinyl, 4-morpholinyl, etc.), dioxanyl, dithianyl, isoxazolidinyl, isothiazolidinyl, 1,2-oxazinyl, 1,2-thiazinyl, hexahydropyridazinyl, homopiperazinyl, homopiperidinyl, or oxacycloheptanyl. For example, the term "3-6 membered heterocycloalkyl", by itself or in combination with other terms, refers to a saturated cyclic group consisting of 3 to 6 ring atoms, of which 1, 2, 3, or 4 ring atoms are heteroatoms independently selected from the group consisting of O, S, and N, with the remaining being carbon atoms. The nitrogen atom is optionally quaternized, and the nitrogen and sulfur heteroatoms can be optionally oxidized (i.e., NO and S(O)$_p$, where p is 1 or 2). The "3-6 membered heterocycloalkyl" may be a monocyclic or a bicyclic system, wherein the bicyclic system includes spiro ring, fused ring, and bridged ring. Furthermore, with respect to the "3-6 membered heterocycloalkyl", a heteroatom may occupy the position where the heterocycloalkyl is linked to the rest part of the molecule. The 3-6 membered heterocycloalkyl includes, but is not limited to, 4-6 membered, 5-6 membered, 4-membered, 5-membered, and 6-membered heterocycloalkyl, and the like. Examples of 3-6 membered heterocycloalkyl include, but are not limited to, azetidinyl, oxetanyl, thietanyl, pyrrolidinyl, pyrazolidinyl, imidazolidinyl, tetrahydrothienyl (including tetrahydrothien-2-yl, tetrahydrothien-3-yl, etc.), tetrahydrofuranyl (including tetrahydrofuran-2-yl, etc.), tetrahydropyranyl, piperidinyl (including 1-piperidinyl, 2-piperidinyl, 3-piperidinyl, etc.), piperazinyl (including 1-piperazinyl, 2-piperazinyl, etc.), morpholinyl (including 3-morpholinyl, 4-morpholinyl, etc.), dioxanyl, dithianyl, isoxazolidinyl, isothiazolidinyl, 1,2-oxazinyl, 1,2-thiazinyl, hexahydropyridazinyl, homopiperazinyl, homopiperidinyl, etc. For example, the term "4-6 membered heterocycloalkyl", by itself or in combination with other terms, refers to a saturated cyclic group consisting of 4 to 6 ring atoms, of which 1, 2, 3, or 4 ring atoms are heteroatoms independently selected from the group consisting of O, S, and N, with the remaining being carbon atoms. The nitrogen atom is optionally quaternized, and the nitrogen and sulfur heteroatoms can be optionally oxidized (i.e., NO and S(O)$_p$, where p is 1 or 2). The "4-6 membered heterocycloalkyl" may be a monocyclic or a bicyclic system, wherein the bicyclic system includes spiro ring, fused ring, and bridged ring. Furthermore, with respect to the "4-6 membered heterocycloalkyl", a heteroatom may occupy the position where the heterocycloalkyl is linked to the rest part of the molecule. The 4-6 membered heterocycloalkyl includes, but is not limited to, 5-6 membered, 4-membered, 5-membered, and 6-membered heterocycloalkyl, and the like. Examples of 4-6 membered heterocycloalkyl include, but are not limited to, azetidinyl, oxetanyl, thietanyl, pyrrolidinyl, pyrazolidinyl, imidazolidinyl, tetrahydrothienyl (including tetrahydrothien-2-yl, tetrahydrothien-3-yl, etc.), tetrahydrofuranyl (including tetrahydrofuran-2-yl, etc.), tetrahydropyranyl, piperidinyl (including 1-piperidinyl, 2-piperidinyl, 3-piperidinyl, etc.), piperazinyl (including 1-piperazinyl, 2-piperazinyl, etc.), morpholinyl (including 3-morpholinyl, 4-morpholinyl, etc.), dioxanyl, dithianyl, isoxazolidinyl, isothiazolidinyl, 1,2-oxazinyl, 1,2-thiazinyl, hexahydropyridazinyl, homopiperazinyl, homopiperidinyl, etc. For example, the term "5-6 membered heterocycloalkyl", by itself or in combination with other terms, refers to a saturated cyclic group consisting of 5 to 6 ring atoms, of which 1, 2, 3, or 4 ring atoms are heteroatoms independently selected from the group consisting of O, S, and N, with the remaining being carbon atoms. The nitrogen atom is optionally quaternized, and the nitrogen and sulfur heteroatoms can be optionally oxidized (i.e., NO and $S(O)_p$, where p is 1 or 2). The "5-6 membered heterocycloalkyl" may be a monocyclic or a bicyclic system, wherein the bicyclic system includes spiro ring, fused ring, and bridged ring. Furthermore, with respect to the "5-6 membered heterocycloalkyl", a heteroatom may occupy the position where the heterocycloalkyl is linked to the rest part of the molecule. The 5-6 membered heterocycloalkyl includes 5-membered heterocycloalkyl and 6-membered heterocycloalkyl. Examples of 5-6 membered heterocycloalkyl include, but are not limited to, pyrrolidinyl, pyrazolidinyl, imidazolidinyl, tetrahydrothienyl (including tetrahydrothien-2-yl, tetrahydrothien-3-yl, etc.), tetrahydrofuranyl (including tetrahydrofuran-2-yl, etc.), tetrahydropyranyl, piperidinyl (including 1-piperidinyl, 2-piperidinyl, 3-piperidinyl, etc.), piperazinyl (including 1-piperazinyl, 2-piperazinyl, etc.), morpholinyl (including 3-morpholinyl, 4-morpholinyl, etc.), dioxanyl, dithianyl, isoxazolidinyl, isothiazolidinyl, 1,2-oxazinyl, 1,2-thiazinyl, hexahydropyridazinyl, homopiperazinyl, homopiperidinyl, etc.

The term "pharmaceutically acceptable carrier" refers to any agent or carrier medium which is capable of delivering an effective amount of the active substance disclosed herein, does not interfere with the biological activity of the active substance and has no toxic side effect on the host or patient. Representative carriers include water, oil, vegetable and mineral, cream base, lotion base, ointment base and the like. These bases include a suspending agent, a thickener, a penetration enhancer, and the like. Their formulations are well known to those skilled in the cosmetic field or the topical pharmaceutical field.

The term "excipient" generally refers to a carrier, diluent, and/or medium necessary to formulate an effective pharmaceutical composition.

The word "comprise" and variations thereof such as "comprises" or "comprising" will be understood in an open, non-exclusive sense, i.e., "including but not limited to".

The term "treating" means administering the compound or formulation described herein to ameliorate or eliminate a disease or one or more symptoms associated with the disease, and includes:
  (i) inhibiting a disease or disease state, i.e., arresting its development;
  (ii) alleviating a disease or disease state, i.e., causing its regression.

The term "preventing" means administering the compound or formulation described herein to prevent a disease or one or more symptoms associated with the disease, and includes: preventing the occurrence of the disease or disease state in a mammal, particularly when such a mammal is predisposed to the disease state but has not yet been diagnosed as having it.

For drugs and pharmacological active agents, the term "effective amount" or "therapeutically effective amount" refers to an amount of a drug or a medicament that is sufficient to provide the desired effect but is non-toxic. With respect to the oral dosage form disclosed herein, the "effective amount" of one active substance in the composition is an amount that is required to achieve the desired effect when the active agent is used in combination with another active agent in the composition. The determination of the effective amount varies from person to person, depending on the age and general condition of a subject and also depending on the particular active substance. The appropriate effective amount in a case may be determined by those skilled in the art in the light of routine tests.

The term "active ingredient", "therapeutic agent", "active substance" or "active agent" refers to a chemical entity that is effective in treating a target disorder, disease, or condition.

The compounds disclosed herein can be prepared by a variety of synthetic methods well known to those skilled in the art, including the specific embodiments listed below, embodiments formed by combinations thereof with other chemical synthetic methods, and equivalents thereof known to those skilled in the art. The preferred embodiments include, but are not limited to, the examples disclosed herein.

The solvent used herein can be commercially available. The present application employs the following abbreviations: aq represents aqueous; HATU represents O-(7-azabenzotriazol-1-yl)-N,N,N',N'-tetramethyluronium hexafluorophosphate; EDC represents N-(3-dimethylaminopropyl)-N'-ethyl carbodiimide hydrochloride; m-CPBA represents 3-chloroperoxybenzoic acid; eq represents equivalent or equivalence; CDI represents carbonyldiimidazole; DCM represents dichloromethane; PE represents petroleum ether; DIAD represents diisopropyl azodiformate; DMF represents N,N-dimethylformamide; DMSO represents dimethyl sulfoxide; EtOAc represents ethyl acetate; EtOH represents ethanol; MeOH represents methanol; CBz represents benzyloxycarbonyl, an amine protecting group; BOC represents tert-butoxycarbonyl, which is an amine protecting group; HOAc represents acetic acid; $NaCNBH_3$ represents sodium cyanoborohydride; r.t. represents room temperature; O/N represents overnight; THF represents tetrahydrofuran; $Boc_2O$ represents di-tert-butyl dicarbonate; TFA represents trifluoroacetic acid; DIPEA represents diisopropylethylamine; $SOCl_2$ represents thionyl chloride; $CS_2$ represents carbon disulfide; TsOH represents p-toluenesulfonic acid; NFSI represents N-fluoro-N-(phenylsulfonyl)benzenesulfonamide; NCS represents N-chlorosuccinimide; $n-Bu_4NF$ represents tetrabutylammonium fluoride; iPrOH represents 2-propanol; mp represents melting point; LDA represents lithium diisopropylamide; $POCl_3$ represents phosphorus oxychloride; LiHMDS represents lithium hexamethyldisilazide; DCE represents dichloroethane; DIEA represents N,N-diisopropylethylamine; MTBE represents methyl tert-butyl ether; TEA represents triethylamine; DIPEA represents N,N-diisopropylethylamine; and LLOQ represents the lower limit of quantitation.

DETAILED DESCRIPTION

Figure 1:
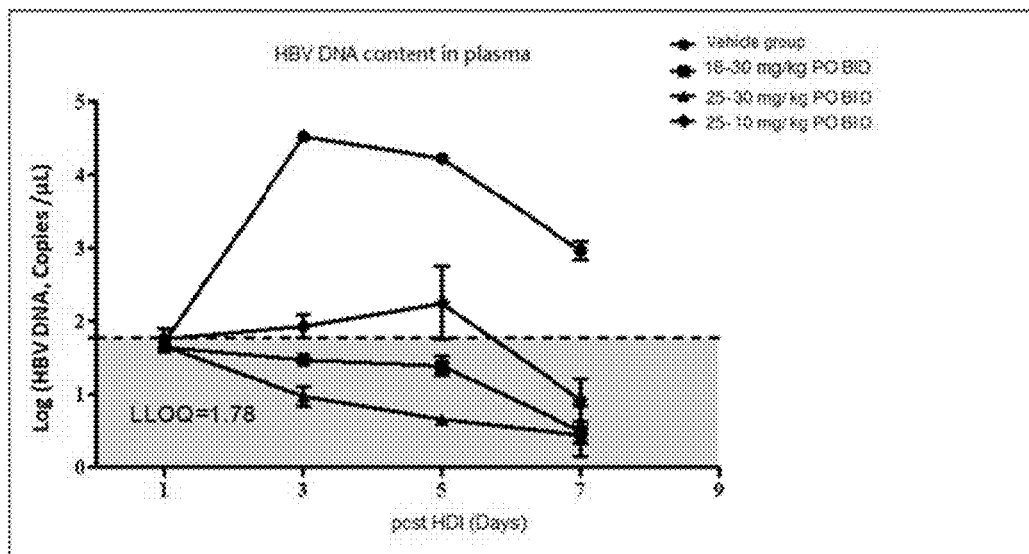
FIG. 1: HBV DNA levels in plasma.

The present application is described in detail below by way of examples. However, this is by no means disadvantageously limiting the scope of the application. Although the present application has been described in detail herein and specific examples have also been disclosed, it will be apparent to those skilled in the art that various changes and modifications can be made to the specific examples without departing from the spirit and scope of the application.

Example 1

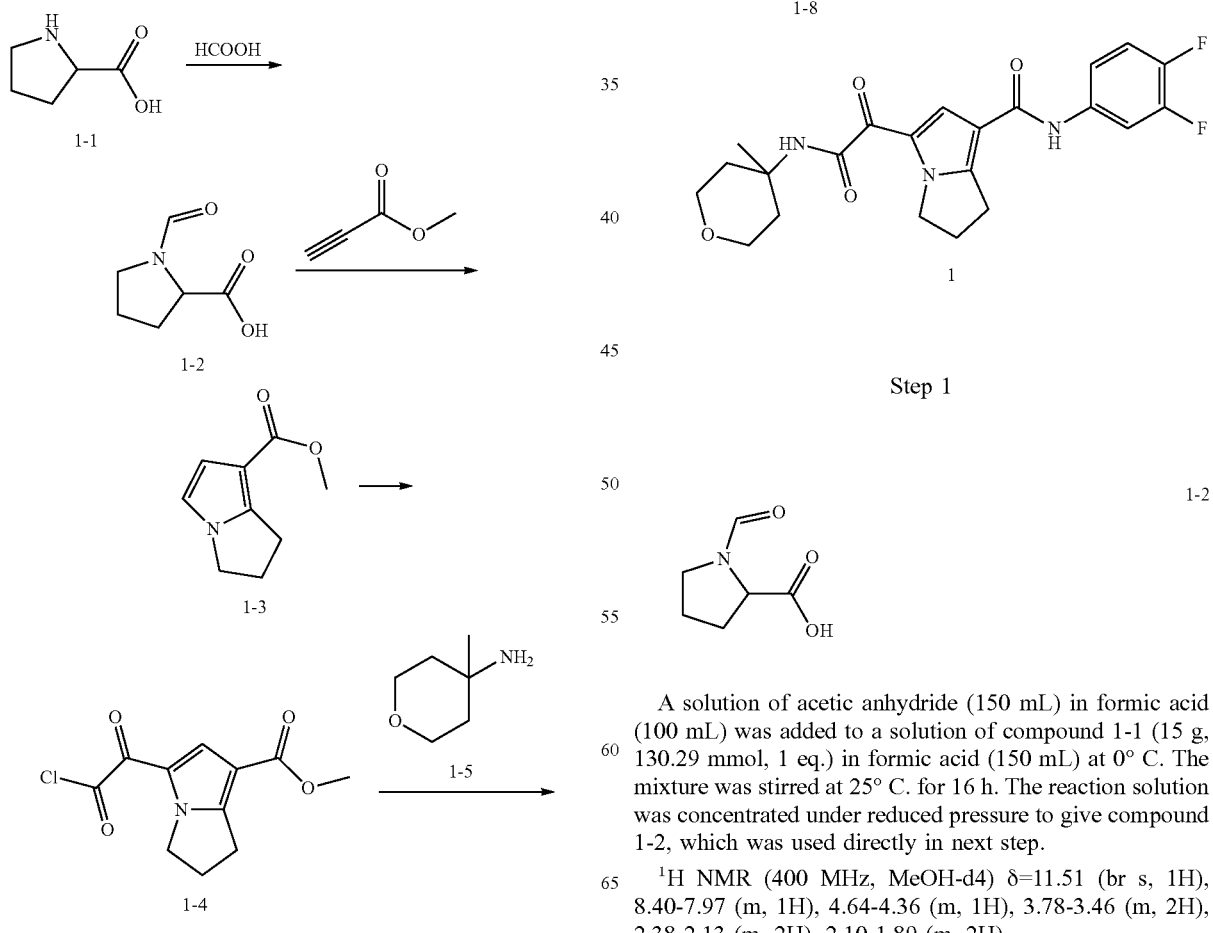

Synthetic Route:

Step 1

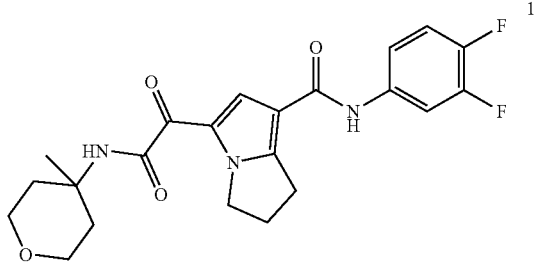 [SMILES: CC1(NC(=O)C(=O)c2cc(C(=O)Nc3ccc(F)c(F)c3)c3n2CCC3)CCOCC1]

A solution of acetic anhydride (150 mL) in formic acid (100 mL) was added to a solution of compound 1-1 (15 g, 130.29 mmol, 1 eq.) in formic acid (150 mL) at 0° C. The mixture was stirred at 25° C. for 16 h. The reaction solution was concentrated under reduced pressure to give compound 1-2, which was used directly in next step.

$^1$H NMR (400 MHz, MeOH-d4) δ=11.51 (br s, 1H), 8.40-7.97 (m, 1H), 4.64-4.36 (m, 1H), 3.78-3.46 (m, 2H), 2.38-2.13 (m, 2H), 2.10-1.89 (m, 2H).

Step 2

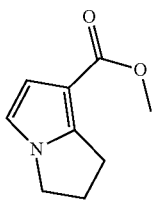

1-3

Methyl propiolate (35.24 g, 419.17 mmol, 34.89 mL, 6 eq.) was added to a solution of compound 1-2 (10 g, 69.86 mmol, 1 eq.) in acetic anhydride (100 mL) in a 250 mL flask. The mixture was stirred at 130° C. for 6 h. The reaction solution was concentrated under reduced pressure to give compound 1-3. MS (ESI) m/z: 165.8 [M+H]$^+$.

$^1$H NMR (400 MHz, MeOH-d4) δ=6.61 (d, J=2.8 Hz, 1H), 6.55 (d, J=2.8 Hz, 1H), 3.97 (t, J=7.2 Hz, 2H), 3.79 (s, 3H), 3.06 (t, J=7.4 Hz, 2H), 2.54 (quin, J=7.3 Hz, 2H).

Step 3

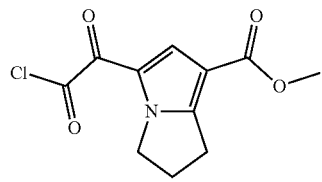

1-4

Oxalyl chloride (535.10 mg, 4.22 mmol, 369.03 µL, 2 eq.) was added to a solution of compound 1-3 (500 mg, 2.11 mmol, 1 eq.) in dichloromethane (5 mL) at 0° C. under nitrogen atmosphere, and then N,N-dimethylformamide (0.05 mL) was added. The mixture was stirred at 25° C. for 1 h. The reaction solution was concentrated under reduced pressure to give compound 1-4, which was directly used in next step.

Step 4

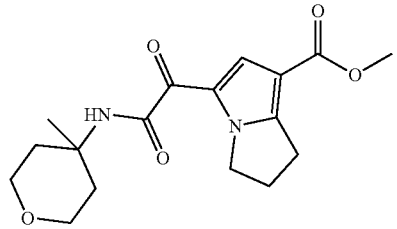

1-6

Triethylamine (870.23 mg, 8.60 mmol, 1.20 mL, 4 eq.) was added to a solution of compound 1-4 (550 mg, 2.15 mmol, 1 eq.) in dichloromethane (10 mL), and then compound 1-5 (247.62 mg, 2.15 mmol, 1 eq.) was added. The mixture was stirred at 20° C. for 1 h. The reaction solution was concentrated under reduced pressure. The residue was separated by an automated chromatographic system COMBI-FLASH (petroleum ether:ethyl acetate=100:0 to 80:20, V/V) to give compound 1-6. MS (ESI) m/z: 357.2 [M+Na]$^+$.

$^1$H NMR (400 MHz, CDCl$_3$) δ=8.23 (s, 1H), 7.10 (br s, 1H), 4.28 (t, J=7.3 Hz, 2H), 3.73 (s, 3H), 3.69-3.66 (m, 2H), 3.60-3.52 (m, 2H), 3.05 (t, J=7.7 Hz, 2H), 2.52 (q, J=7.5 Hz, 2H), 2.06 (br d, J=13.8 Hz, 2H), 1.68 (m, 2H), 1.42 (s, 3H).

Step 5

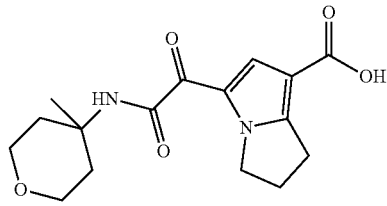

1-7

A solution of lithium hydroxide monohydrate (131.78 mg, 3.14 mmol, 3 eq.) in H$_2$O (1 mL) was added to a solution of compound 1-6 (350 mg, 1.05 mmol, 1 eq.) in tetrahydrofuran (5 mL). The mixture was stirred at 30° C. for 12 h. The reaction solution was adjusted to pH=1-2 with 2 mol/L diluted hydrochloric acid, and extracted with ethyl acetate (10 mL×2). The combined organic phases were washed with saturated brine (10 mL), dried over anhydrous sodium sulfate, and concentrated under reduced pressure to give compound 1-7. MS (ESI) m/z: 343.2 [M+Na]$^+$.

$^1$H NMR (400 MHz, MeOH-d$_4$) δ=7.89 (s, 1H), 4.37 (br d, J=7.0 Hz, 2H), 3.70-3.63 (m, 2H), 3.14-3.10 (m, 2H), 2.66-2.52 (m, 4H), 2.25-2.19 (m, 2H), 1.73-1.67 (m, 2H), 1.49 (s, 3H).

Step 6

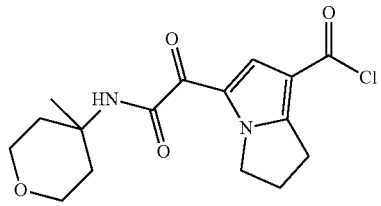

1-8

Oxalyl chloride (237.74 mg, 1.87 mmol, 163.96 µL, 2 eq.) was added to a solution of compound 1-7 (300 mg, 936.51 µmol, 1 eq.) in dichloromethane (3 mL) at 0° C. under nitrogen atmosphere, and then N,N-dimethylformamide (0.01 mL) was added. The mixture was stirred at 20° C. for 1 h to give compound 1-8.

Step 7

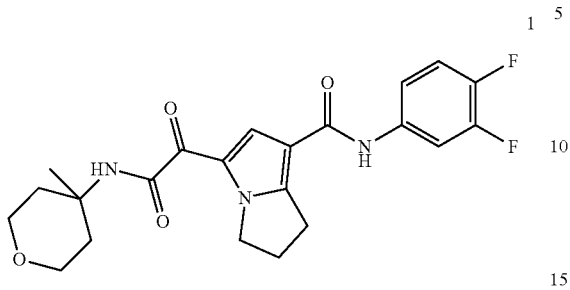

Triethylamine (358.42 mg, 3.54 mmol, 493.01 μL, 4 eq.) was added to a solution of compound 1-8 (300 mg, 885.52 μmol, 1 eq.) in dichloromethane (5 mL) under nitrogen atmosphere, and then compound 1-9 (114.33 mg, 885.52 μmol, 1 eq.) was added. The mixture was stirred at 20° C. for 12 h. The reaction solution was concentrated under reduced pressure, and the residue was separated by an automated chromatographic system COMBI-FLASH (petroleum ether: ethyl acetate=100:0 to 50:50, V/V) to give compound 1. MS (ESI) m/z: 432.2 [M+H]⁺.

¹H NMR (400 MHz, CDCl₃) δ=8.18 (s, 1H), 7.73-7.64 (m, 1H), 7.59 (s, 1H), 7.23 (s, 1H), 7.09-7.02 (m, 2H), 4.31 (t, J=7.3 Hz, 2H), 3.71 (td, J=4.3, 12.0 Hz, 2H), 3.62-3.52 (m, 2H), 3.21-3.12 (m, 2H), 2.63-2.50 (m, 2H), 2.07 (br d, J=14.1 Hz, 2H), 1.70 (ddd, J=4.3, 9.9, 14.0 Hz, 2H), 1.43 (s, 3H).

Example 2

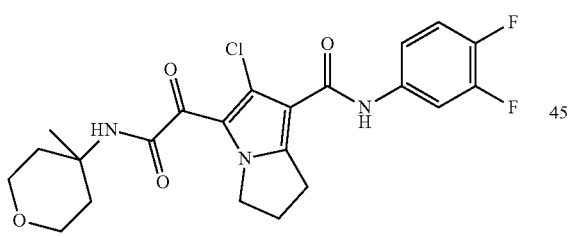

Synthetic Route:

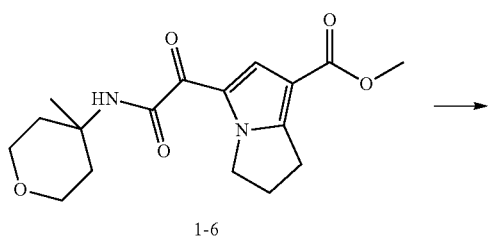

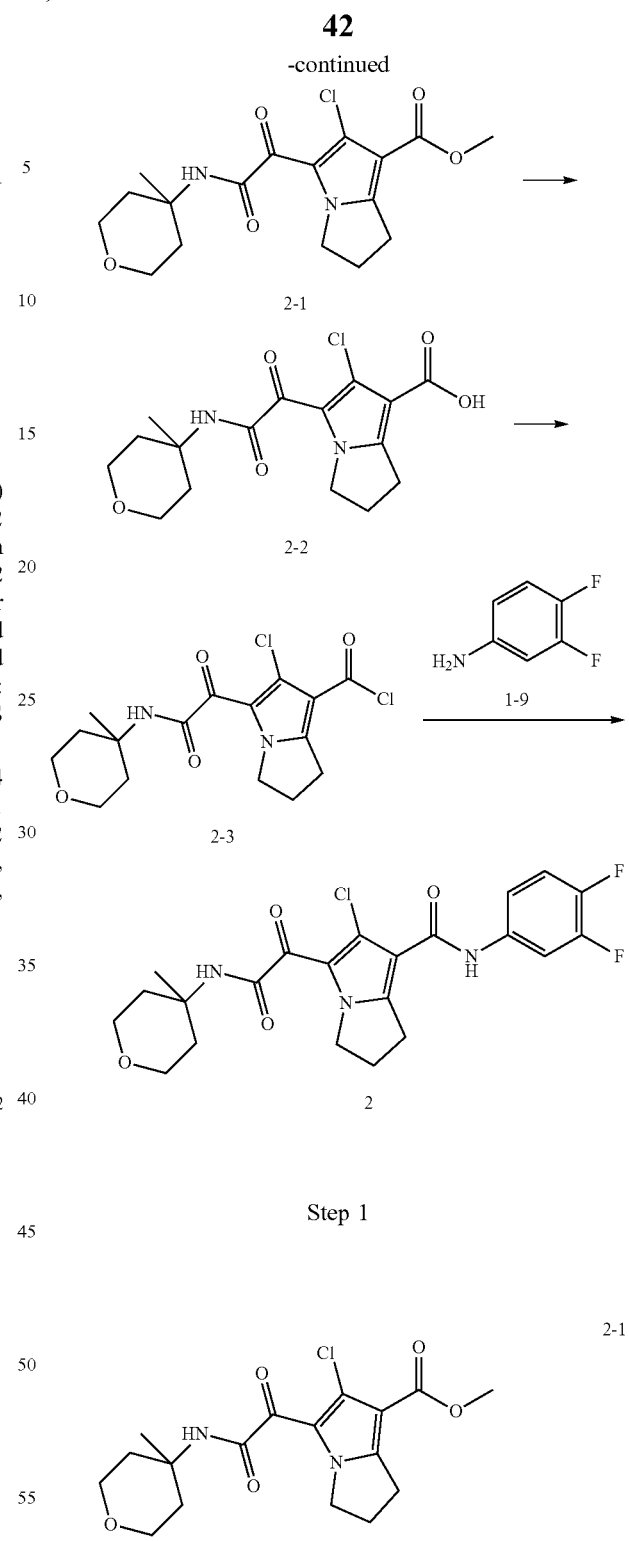

Step 1

N-chlorosuccinimide (77.87 mg, 583.19 μmol, 1.3 eq.) was added to a solution of compound 1-6 (150 mg, 448.61 μmol, 1 eq.) in acetonitrile (10 mL). The mixture was stirred at 40° C. for 6 h. The reaction solution was concentrated under reduced pressure. The residue was separated by an automated chromatographic system COMBI-FLASH (petroleum ether:ethyl acetate=100:0 to 80:20, V/V) to give compound 2-1. MS (ESI) m/z: 369.1 [M+H]⁺.

Step 2

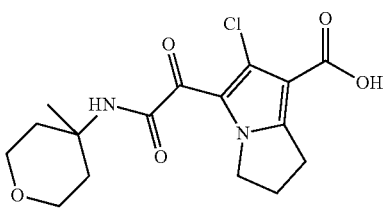
2-2

A solution of lithium hydroxide monohydrate (34.13 mg, 813.42 μmol, 5 eq.) in H$_2$O (0.5 mL) was added to a solution of compound 2-1 (60 mg, 162.68 μmol, 1 eq.) in ethanol (2 mL). The mixture was stirred at 40° C. for 3 h. The reaction solution was adjusted to pH=1-2 with 2 mol/L diluted hydrochloric acid, and extracted with ethyl acetate (10 mL×2). The combined organic phases were washed with saturated brine (10 mL), dried over anhydrous sodium sulfate, and concentrated under reduced pressure to give crude compound 2-2. MS (ESI) m/z: 377.1 [M+Na]$^+$.

Step 3

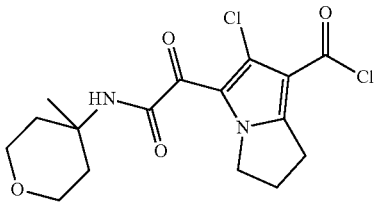
2-3

Oxalyl chloride (28.62 mg, 225.49 μmol, 19.74 μL, 2 eq.) was added to a solution of compound 2-2 (40 mg, 112.74 μmol, 1 eq.) in dichloromethane (2 mL) at 0° C. under nitrogen atmosphere, and then N,N-dimethylformamide (0.01 mL) was added. The mixture was stirred at 25° C. for 45 min. The reaction solution was concentrated under reduced pressure to give compound 2-3.

Step 4

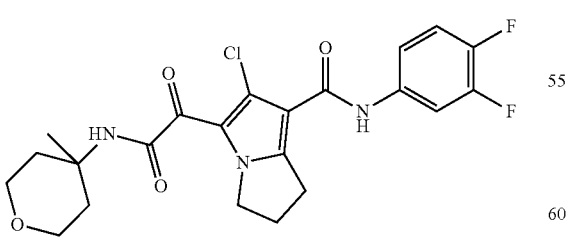
2

Triethylamine (43.38 mg, 428.69 μmol, 59.67 μL, 4 eq) was added to a solution of compound 2-3 (40 mg, 107.17 μmol, 1 eq.) in dichloromethane (3 mL) under nitrogen atmosphere. Then, compound 1-9 (13.84 mg, 107.17 μmol, 1 eq.) was added. The mixture was stirred at 25° C. for 12 h. The reaction solution was concentrated under reduced pressure, and the residue was separated by prep-HPLC (column: Waters Xbridge 150 mm×25 mm×5 μm; mobile phase: water (containing 0.225% formic acid)-acetonitrile; acetonitrile %: 73%-83%, 7 min) to give compound 2. MS (ESI) m/z: 466.0 [M+H]$^+$.

$^1$H NMR (400 MHz, CDCl$_3$) δ=8.40 (s, 1H), 7.72-7.61 (m, 1H), 7.11-6.99 (m, 2H), 6.23 (s, 1H), 4.25 (t, J=7.4 Hz, 2H), 3.80-3.57 (m, 4H), 3.19 (t, J=7.7 Hz, 2H), 2.46 (quin, J=7.5 Hz, 2H), 2.08 (br d, J=14.1 Hz, 2H), 1.73 (ddd, J=4.4, 9.6, 13.9 Hz, 2H), 1.48 (s, 3H).

Example 3

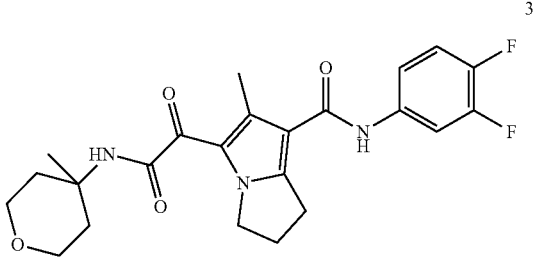 [SMILES: Cc1c(C(=O)Nc2ccc(F)c(F)c2)c2n(c1C(=O)C(=O)NC1(C)CCOCC1)CCC2]
3

Synthetic Route:

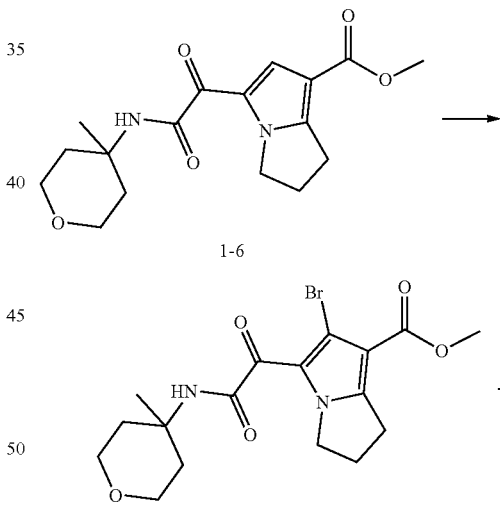

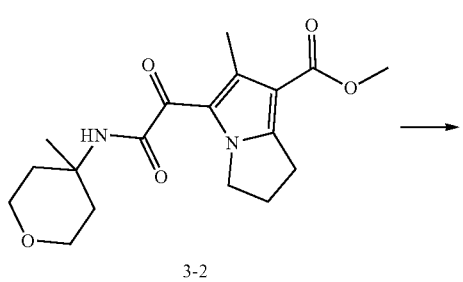
3-2

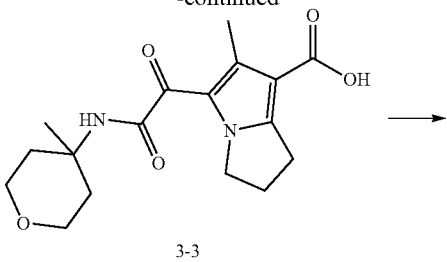

3-3

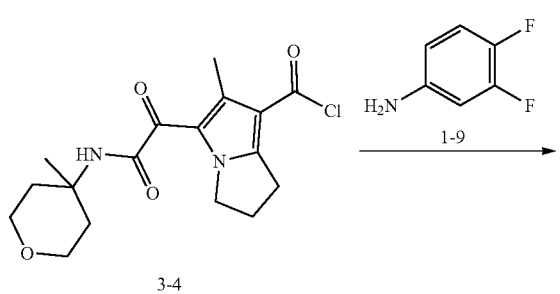

3-4

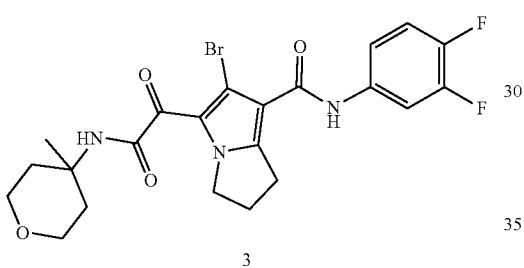

3

Step 1

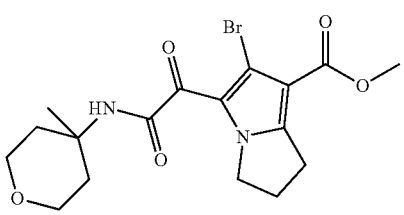

3-1

Compound 1-6 (300 mg, 897.22 μmol, 1 eq.) and acetonitrile (3 mL) were added into a thumb bottle, and then N-bromosuccinimide (191.62 mg, 1.08 mmol, 1.2 eq.) was added. The mixture was stirred at 25° C. for 12 h. The reaction solution was concentrated under reduced pressure. The residue was separated by an automated chromatographic system COMBI-FLASH (petroleum ether:ethyl acetate=100:0 to 80:20, V/V) to give compound 3-1. MS (ESI) m/z: 435.0 [M+Na]$^+$.

$^1$H NMR (400 MHz, CDCl$_3$) δ=4.30 (t, J=7.4 Hz, 2H), 3.83 (s, 3H), 3.80-3.67 (m, 4H), 3.13 (t, J=7.7 Hz, 2H), 2.50 (q, J=7.5 Hz, 2H), 2.15 (d, J=14.1 Hz, 2H), 1.78 (m, 2H), 1.55 (s, 3H).

Step 2

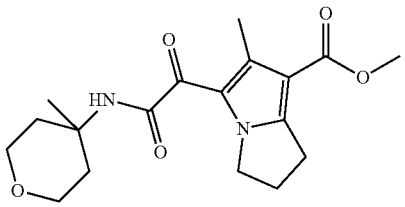

3-2

Compound 3-1 (100 mg, 241.98 μmol, 1 eq.), methylboronic acid (28.97 mg, 483.95 μmol, 2 eq.), potassium carbonate (100.33 mg, 725.93 μmol, 3 eq.), 1,4-dioxane (2.5 mL) and water (0.5 mL) were added into a thumb bottle under nitrogen atmosphere, and then Pd(dppf)Cl$_2$ (17.71 mg, 24.20 μmol, 0.1 eq.) was added. The mixture was stirred at 80° C. for 2 h. The reaction solution was added with water (5 mL) and extracted with ethyl acetate (10 mL×3). The combined organic phases were washed with diluted hydrochloric acid (10 mL) and saturated brine (10 mL), dried over anhydrous sodium sulfate, and concentrated under reduced pressure to give compound 3-2. MS (ESI) m/z: 348.9 [M+H]$^+$.

Step 3

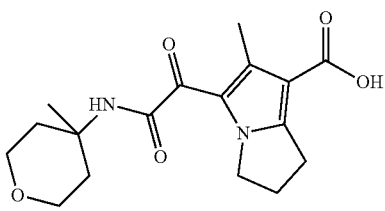

3-3

Compound 3-2 (80 mg, 229.63 μmol, 1 eq.) and ethanol (2 mL) were added into a thumb bottle, and then a solution of sodium hydroxide (27.56 mg, 688.88 μmol, 3 eq.) in water (0.5 mL) was added. The mixture was stirred at 25° C. for 12 h. The reaction solution was added with water (5 mL) and washed with ethyl acetate (5 mL). The aqueous phase was adjusted to pH=1-2 with 2 mol/L diluted hydrochloric acid and extracted with ethyl acetate (10 mL×2). The combined organic phases were washed with saturated brine (10 mL), dried over anhydrous sodium sulfate, and concentrated under reduced pressure to give compound 3-3.

Step 4

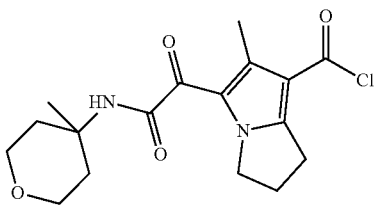

3-4

Oxalyl chloride (26.57 mg, 209.35 μmol, 18.33 μL, 1 eq.) was added to a solution of compound 3-3 (70 mg, 209.35 μmol, 1 eq.) in dichloromethane (3 mL) at 0° C., and then N,N-dimethylformamide (15.30 mg, 209.35 μmol, 16.11 μL, 1 eq.) was added. The mixture was stirred at 25° C. for 1 h. The reaction solution was concentrated under reduced pressure to give compound 3-4.

Step 5

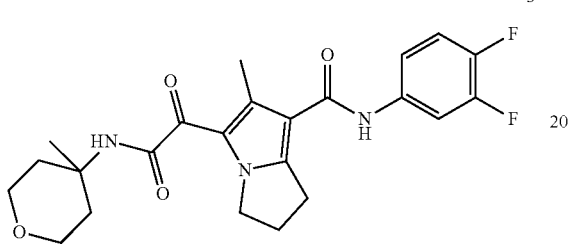

Triethylamine (86.04 mg, 850.31 μmol, 118.35 μL, 4 eq.) was added to a solution of compound 3-4 (75 mg, 212.58 μmol, 1 eq.) in dichloromethane (3 mL), and then compound 1-9 (27.45 mg, 212.58 μmol, 1 eq.) was added. The mixture was stirred at 25° C. for 1 h. The reaction solution was concentrated under reduced pressure. The residue was separated by prep-HPLC chromatography (column: Boston Green ODS 150 mm×30 mm×5 μm; mobile phase: water (containing 0.075% trifluoroacetic acid)-acetonitrile; acetonitrile %: 47%-67%, 7 min) to give compound 3. MS (ESI) m/z: 446.1 [M+H]⁺.

¹H NMR (400 MHz, CDCl₃) δ=7.76-7.66 (m, 1H), 7.37 (s, 1H), 7.19-7.05 (m, 1H), 6.64-6.46 (m, 1H), 6.56 (s, 1H), 4.30 (t, J=7.3 Hz, 2H), 3.87-3.76 (m, 2H), 3.75-3.66 (m, 2H), 3.15 (t, J=7.5 Hz, 2H), 2.62-2.52 (m, 5H), 2.15 (d, J=13.8 Hz, 2H), 1.81 (m, 2H), 1.56 (s, 3H).

Example 4

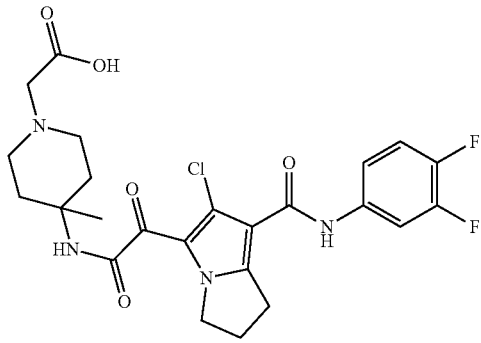

Synthetic Route:

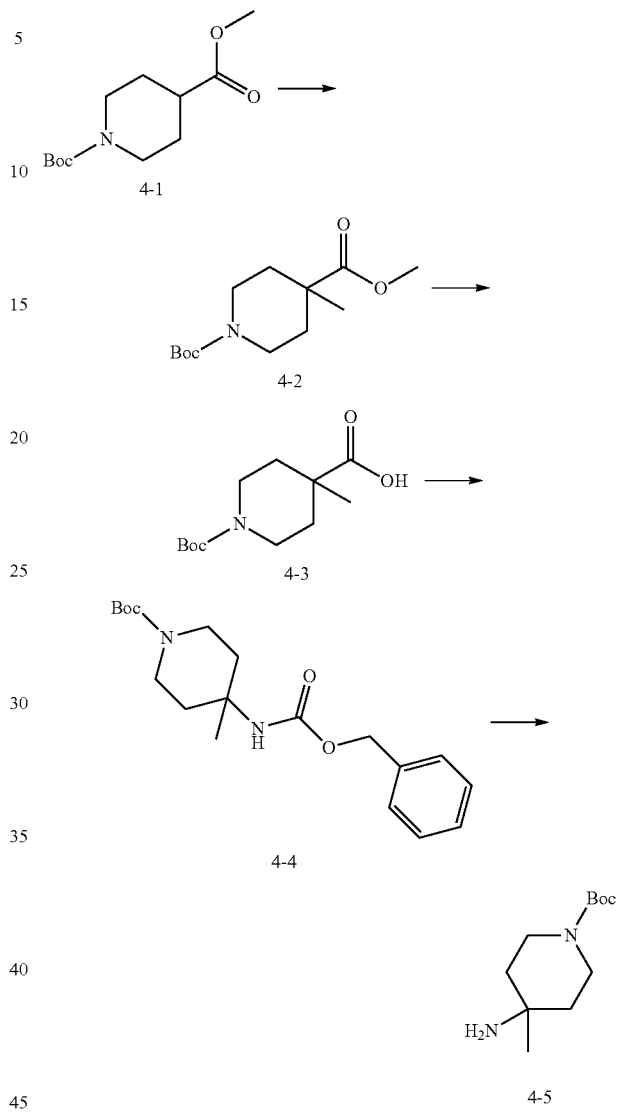

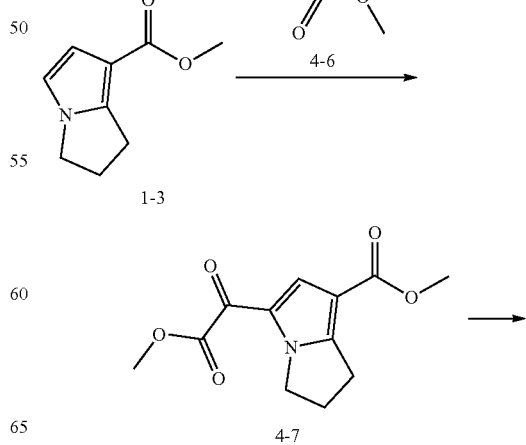

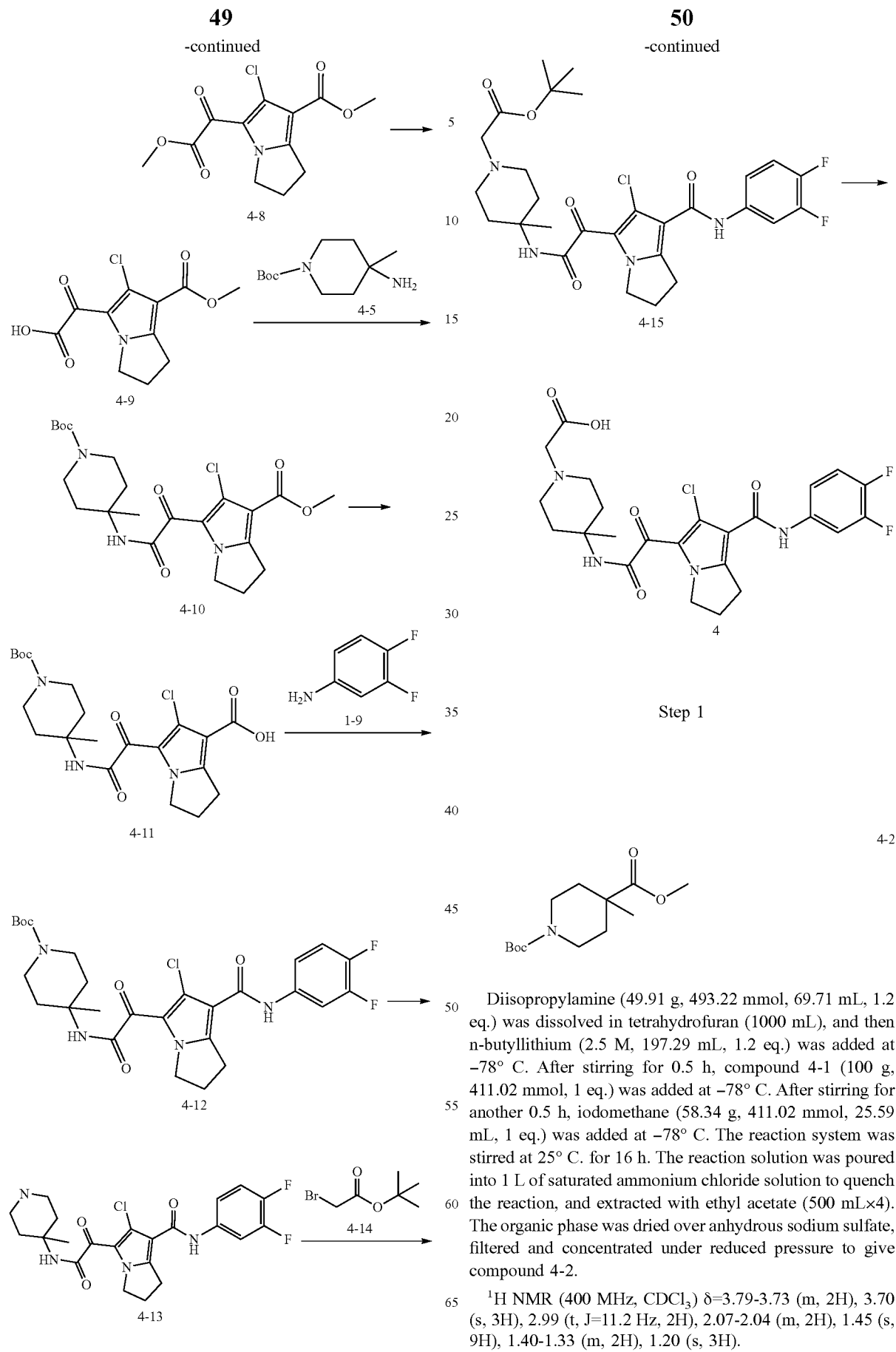

Step 1

Diisopropylamine (49.91 g, 493.22 mmol, 69.71 mL, 1.2 eq.) was dissolved in tetrahydrofuran (1000 mL), and then n-butyllithium (2.5 M, 197.29 mL, 1.2 eq.) was added at −78° C. After stirring for 0.5 h, compound 4-1 (100 g, 411.02 mmol, 1 eq.) was added at −78° C. After stirring for another 0.5 h, iodomethane (58.34 g, 411.02 mmol, 25.59 mL, 1 eq.) was added at −78° C. The reaction system was stirred at 25° C. for 16 h. The reaction solution was poured into 1 L of saturated ammonium chloride solution to quench the reaction, and extracted with ethyl acetate (500 mL×4). The organic phase was dried over anhydrous sodium sulfate, filtered and concentrated under reduced pressure to give compound 4-2.

$^1$H NMR (400 MHz, CDCl$_3$) δ=3.79-3.73 (m, 2H), 3.70 (s, 3H), 2.99 (t, J=11.2 Hz, 2H), 2.07-2.04 (m, 2H), 1.45 (s, 9H), 1.40-1.33 (m, 2H), 1.20 (s, 3H).

Step 2

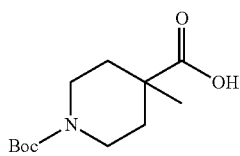
4-3

Compound 4-2 (107 g, 415.81 mmol, 1 eq.) was dissolved in water (500 mL) and ethanol (1000 mL), and then potassium hydroxide (116.65 g, 2.08 mol, 5 eq.) was added. The reaction system was stirred at 25° C. for 16 h. TLC (dichloromethane:methanol=20:1) showed that compound 4-2 was completely consumed and new spots were produced. The reaction solution was concentrated under reduced pressure at 40° C. to remove the solvent, and the residue was extracted with 500 mL of ethyl acetate. The aqueous phase was adjusted to pH=3-5 with 1 M hydrochloric acid, and extracted with ethyl acetate (1 L×3). The organic phase was dried over anhydrous sodium sulfate, filtered, and concentrated under reduced pressure to give compound 4-3.

$^1$H NMR (400 MHz, MeOH-d$_4$) δ=3.77 (td, J=4.0, 13.8 Hz, 2H), 3.02 (s, 2H), 2.05-2.00 (m, 2H), 1.45 (s, 9H), 1.38-1.31 (m, 2H), 1.22 (s, 3H).

Step 3

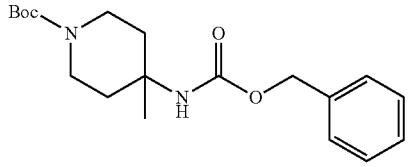
4-4

Compound 4-3 (10 g, 41.10 mmol, 1 eq.) was dissolved in toluene (100 mL), and then triethylamine (4.99 g, 49.32 mmol, 6.87 mL, 1.2 eq.) and benzyl alcohol (6.67 g, 61.65 mmol, 6.41 mL, 1.5 eq.) were added. Diphenylphosphoryl azide (16.97 g, 61.65 mmol, 13.36 mL, 1.5 eq.) was then added at 25° C. under nitrogen atmosphere. The reaction system was stirred at 110° C. for 3 h. TLC (petroleum ether:ethyl acetate=5:1) showed that compound 4-3 was completely consumed and new spots were produced. The reaction solution was poured into 100 mL of saturated ammonium chloride solution to quench the reaction, and then extracted with ethyl acetate (50 mL×3). The organic phase was dried over anhydrous sodium sulfate, filtered, and concentrated under reduced pressure to give residue. The residue was purified by column chromatography (100-200 mesh silica gel, petroleum ether:ethyl acetate=20:1 to 5:1, V/V). The purified product was concentrated under reduced pressure to give compound 4-4.

$^1$H NMR (400 MHz, CDCl$_3$) δ=7.34-7.30 (m, 3H), 7.20-7.17 (m, 2H), 4.70-4.64 (m, 2H), 3.64 (s, 2H), 3.37-3.21 (m, 2H), 1.95 (s, 2H), 1.62-1.51 (m, 2H), 1.46 (s, 9H), 1.38 (s, 3H).

Step 4

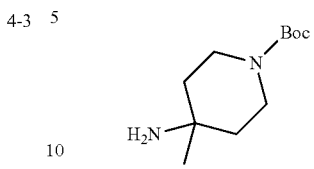
4-5

Compound 4-4 (14 g, 40.18 mmol, 1 eq.) was dissolved in methanol (150 mL), and then wet palladium on carbon (5 g, content 10%) was added. The reaction system was stirred at 25° C. for 6 h under hydrogen atmosphere (50 psi). TLC (dichloromethane:methanol=10:1) showed that compound 4-4 was completely consumed and new spots were produced. The reaction solution was concentrated under reduced pressure to give residue. The residue was purified by column chromatography (100-200 mesh silica gel, dichloromethane:methanol=10:1 to 5:1, V/V) and concentrated under reduced pressure to give compound 4-5.

$^1$H NMR (400 MHz, CDCl$_3$) δ=7.02 (br s, 2H), 3.59-3.49 (m, 4H), 1.98-1.51 (m, 4H), 1.46-1.44 (m, 12H).

Step 5

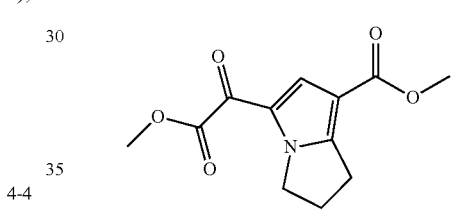
4-7

Compound 1-3 (20 g, 121.07 mmol, 1 eq.) was dissolved in DCM (400 mL) in a dry single-neck flask. Compound 4-6 (29.66 g, 242.15 mmol, 22.30 mL, 2 eq.) was added dropwise at 0° C. under nitrogen atmosphere. The reaction system was stirred at 20° C. for 16 h. LCMS showed that the reaction was completed. The reaction solution was poured into 100 mL of water. Then, the aqueous phase was extracted with DCM (20 mL×3), and the organic phase was dried over anhydrous sodium sulfate, filtered and concentrated. The crude product was purified by column chromatography (100-200 mesh silica gel, petroleum ether:ethyl acetate=20:1 to 1:1, V/V) to give compound 4-7. MS(ESI) m/s: 252.2 [M+H]$^+$.

$^1$H NMR (400 MHz, CDCl$_3$) δ=7.76 (s, 1H), 4.38 (t, J=7.6 Hz, 2H), 3.93 (s, 3H), 3.82 (s, 3H), 3.14-3.10 (m, 2H), 2.62-2.55 (m, 2H).

Step 6

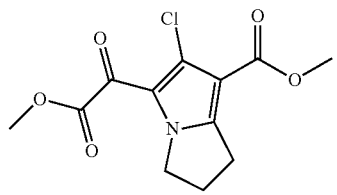
4-8

Compound 4-7 (5 g, 19.90 mmol, 1 eq.) was dissolved in acetonitrile (100 mL) in a dry 50 mL single-neck flask, and then N-chlorosuccinimide (3.59 g, 26.87 mmol, 1.35 eq.) was added. The reaction system was stirred at 40° C. for 16 h. LCMS and TLC (petroleum ether:ethyl acetate=3:1) showed that the reaction was completed. The reaction solution was poured into a saturated sodium bicarbonate solution (200 mL) and then concentrated under reduced pressure to remove acetonitrile. The aqueous phase was extracted with dichloromethane (50 mL×3), and the organic phase was dried over anhydrous sodium sulfate, filtered and concentrated. The crude product was purified by column chromatography (100-200 mesh silica gel, petroleum ether:ethyl acetate=20:1 to 3:1, V/V) to give compound 4-8. MS(ESI) m/s: 286.0 [M+H]$^+$.

$^1$H NMR (400 MHz, CDCl$_3$) δ=4.40 (t, J=7.6 Hz, 2H), 3.95 (s, 3H), 3.85 (s, 3H), 3.15 (t, J=7.6 Hz, 2H), 2.59-2.49 (m, 2H).

Step 7

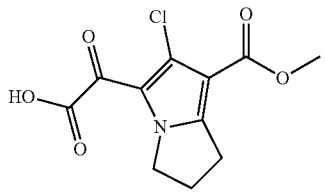

4-9

Compound 4-8 (2.5 g, 8.75 mmol, 1 eq.) was added to a mixture of tetrahydrofuran (40 mL), ethanol (10 mL), and water (10 mL) at 20° C., and then potassium carbonate (3.63 g, 26.25 mmol, 3 eq.) was added to the reaction system. The reaction system was stirred at 45° C. for 12 h. TLC (petroleum ether:ethyl acetate=2:1) showed that the reaction was completed. The reaction solution was added with 100 mL of water, adjusted to pH=3 with 1 mol/L hydrochloric acid, and extracted with ethyl acetate (50 mL×2). The organic phase was dried over anhydrous sodium sulfate, filtered and concentrated under reduced pressure to give compound 4-9.

$^1$H NMR (400 MHz, DMSO-d$_6$) δ=4.29 (t, J=7.2 Hz, 2H), 3.75 (s, 3H), 3.05 (t, J=7.6 Hz, 2H), 2.48-2.40 (m, 2H).

Step 8

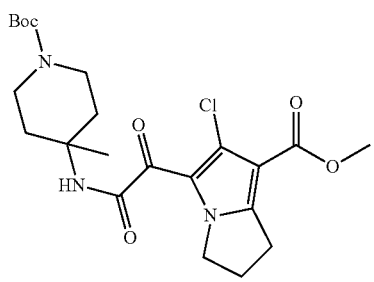

4-10

Compound 4-9 (0.4 g, 1.47 mmol, 1 eq.), N,N-diisopropylethylamine (380.61 mg, 2.94 mmol, 512.95 μL, 2 eq.), and O-(7-azabenzotriazol-1-yl)-N,N,N',N'-tetramethyluronium hexafluorophosphate (1.68 g, 4.42 mmol, 3 eq.) were dissolved in tetrahydrofuran (10 mL). After stirring for 0.5 h, compound 4-5 (473.34 mg, 2.21 mmol, 1.5 eq.) was added. The reaction system was stirred at 25° C. for 1 h. TLC (petroleum ether:ethyl acetate=1:1) showed that compound 4-9 was completely consumed and new spots were produced. LCMS confirmed that compound 4-10 was produced. The reaction solution was poured into saturated ammonium chloride solution (20 mL) to quench the reaction, and then extracted with ethyl acetate (20 mL×3). The organic phase was dried over anhydrous sodium sulfate, filtered and concentrated under reduced pressure. The residue was purified by column chromatography (100-200 mesh silica gel, petroleum ether:ethyl acetate=20:1 to 1:1, V/V) and concentrated under reduced pressure to give compound 4-10. MS(ESI) m/s: 412.1 [M+H-(t-Bu)]$^+$.

$^1$H NMR (400 MHz, CDCl$_3$) δ=6.03 (s, 1H), 4.32 (t, J=7.2 Hz, 2H), 3.85 (s, 3H), 3.70 (s, 2H), 3.25-3.12 (m, 4H), 2.54-2.47 (m, 2H), 1.69-1.62 (m, 4H), 1.52 (s, 3H), 1.47 (s, 9H).

Step 9

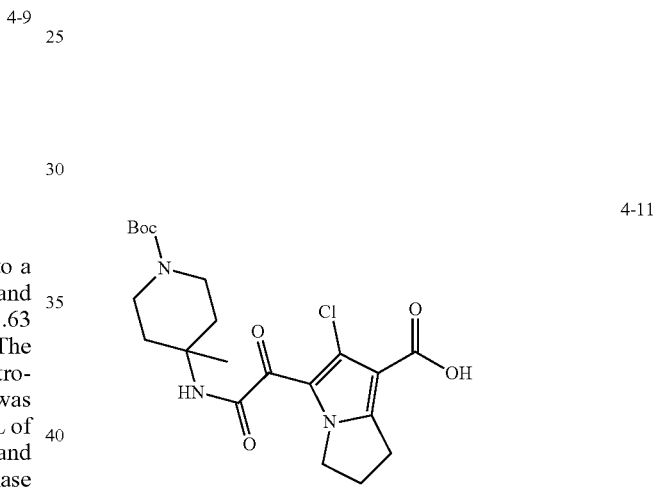

4-11

Compound 4-10 (0.5 g, 1.07 mmol, 1 eq.) was dissolved in a mixture of methanol (5 mL), tetrahydrofuran (5 mL) and water (5 mL), and then lithium hydroxide monohydrate (134.52 mg, 3.21 mmol, 3 eq.) was added. The reaction system was stirred at 25° C. for 3 h. TLC (dichloromethane:methanol=10:1) showed that compound 4-10 was completely consumed and new spots were produced. The reaction solution was adjusted to pH=1-3 with 1 mol/L hydrochloric acid and extracted with ethyl acetate (15 mL×3). The organic phase was dried over anhydrous sodium sulfate, filtered and concentrated under reduced pressure to give compound 4-11.

$^1$H NMR (400 MHz, MeOH-d$_4$) δ=4.36 (t, J=7.2 Hz, 2H), 3.72-3.67 (m, 2H), 3.24 (s, 2H), 3.13 (t, J=4.4 Hz, 2H), 2.56-2.48 (m, 2H), 2.20 (d, J=13.6 Hz, 2H), 1.60-1.53 (m, 2H), 1.49 (s, 3H), 1.46 (s, 9H).

Step 10

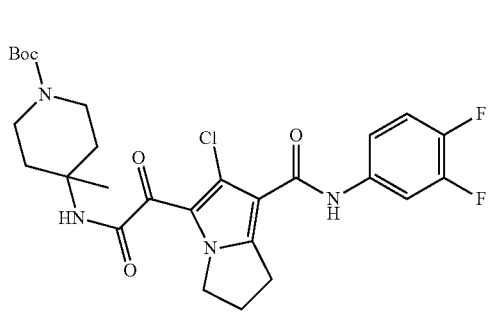

4-12

Compound 4-11 (0.38 g, 837.16 µmol, 1 eq.), 0-(7-azabenzotriazol-1-yl)-N,N,N',N'-tetramethyluronium hexafluorophosphate (954.94 mg, 2.51 mmol, 3 eq.), and triethylamine (254.14 mg, 2.51 mmol, 349.57 µL, 3 eq.) were dissolved in N,N-dimethylformamide (10 mL). After stirring at 25° C. for 0.5 h, compound 1-9 (216.17 mg, 1.67 mmol, 2 eq.) was added. The reaction system was stirred at 55° C. for 5 h, then heated to 70° C., and stirred for 1 h. TLC (petroleum ether:ethyl acetate=1:1) showed that compound 4-11 was completely consumed and new spots were produced. LCMS confirmed that compound 4-11 was completely consumed and compound 4-12 was produced. The reaction was quenched with 20 mL of water, and then the reaction solution was extracted with ethyl acetate (20 mL×3). The organic phase was dried over anhydrous sodium sulfate, filtered and concentrated under reduced pressure. The residue was purified by column chromatography (100-200 mesh silica gel, petroleum ether:ethyl acetate=20:1 to 1:1, V/V) and concentrated under reduced pressure to give compound 4-12. MS(ESI) m/s: 465.1 [M-Boc+H]$^+$.

Step 11

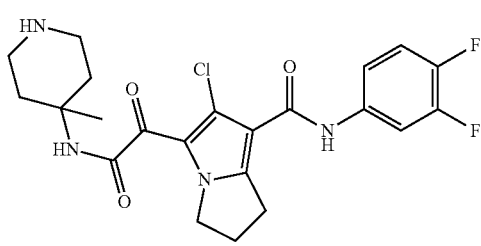

4-13

Compound 4-12 (0.3 g, 530.97 µmol, 1 eq.) was dissolved in ethyl acetate (15 mL), and then hydrochloric acid/ethyl acetate (4 mol/L, 5 mL, 37.67 eq.) was added. The reaction system was stirred at 25° C. for 0.5 h. TLC (petroleum ether:ethyl acetate=1:1) showed that compound 4-12 was completely consumed and new spots were produced. The reaction solution was concentrated under reduced pressure to give compound 4-13.

Step 12

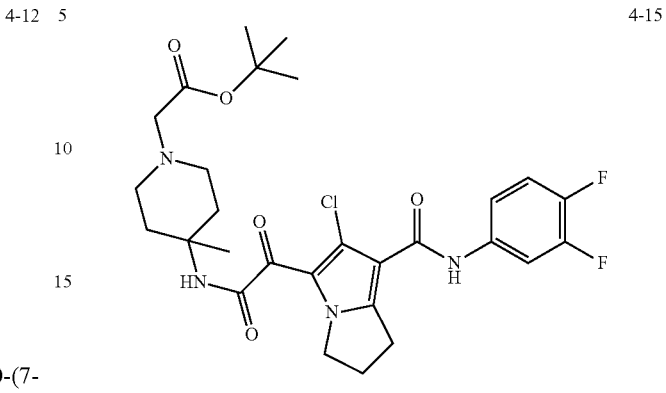

4-15

Compound 4-13 (0.2 g, 430.21 µmol, 1 eq.) was dissolved in tetrahydrofuran (10 mL), and then triethylamine (174.13 mg, 1.72 mmol, 239.52 µL, 4 eq.) and compound 4-14 (83.91 mg, 430.21 µmol, 63.57 µL, 1 eq.) were added. The reaction system was stirred at 25° C. for 1 h. LCMS showed that compound 4-13 was completely consumed and compound 4-15 was produced. The reaction solution was added with 20 mL of water to quench the reaction, and extracted with ethyl acetate (20 mL×3). The organic phase was dried over anhydrous sodium sulfate, filtered and concentrated under reduced pressure to give compound 4-15. MS(ESI) m/s: 579.2 [M+H]$^+$.

$^1$H NMR (400 MHz, CDCl$_3$) δ=8.49 (s, 1H), 7.77-7.72 (m, 1H), 7.15-7.09 (m, 2H), 6.20 (s, 1H), 4.33 (t, J=7.6 Hz, 2H), 3.27 (t, J=7.2 Hz, 2H), 3.14 (s, 2H), 2.78-2.75 (m, 2H), 2.57-2.44 (m, 4H), 2.20-2.16 (m, 2H), 1.89-1.84 (m, 2H), 1.52 (s, 3H), 1.47 (s, 9H).

Step 13

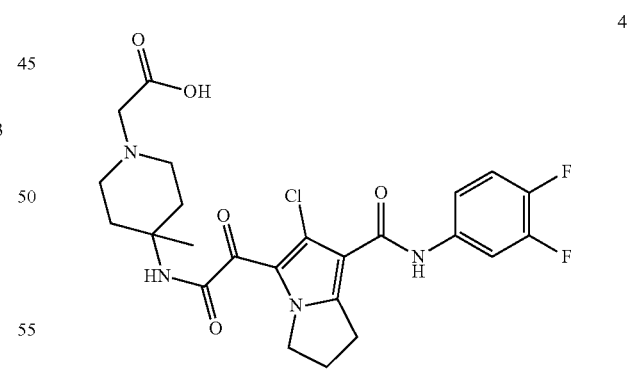

4

Compound 4-15 (0.2 g, 345.40 µmol, 1 eq.) was dissolved in dichloromethane (10 mL), and then trifluoroacetic acid (7.70 g, 67.53 mmol, 5 mL, 195.51 eq.) was added. The reaction system was stirred at 25° C. for 0.5 h. LCMS and HPLC confirmed that the reaction was completed. The reaction solution was concentrated under reduced pressure to give residue. The residue was purified by prep-HPLC (column: Xtimate C18 150 mm×25 mm×5 µm; mobile phase: water (containing 0.04% ammonium hydroxide+10 mM ammonium bicarbonate)-acetonitrile; acetonitrile %: 22%-42%, 10.5 min) to give compound 4. MS(ESI) m/s: 523.1 [M+H]⁺.

$^1$H NMR (400 MHz, DMSO-d$_6$) δ=9.95 (s, 1H), 8.40 (s, 1H), 7.87-7.82 (m, 1H), 7.43-7.39 (m, 2H), 4.29 (t, J=7.2 Hz, 2H), 3.18 (s, 2H), 3.09 (t, J=7.6 Hz, 2H), 2.88-2.71 (m, 4H), 2.46-2.43 (m, 2H), 2.18 (d, J=14.0 Hz, 2H), 1.73 (t, J=10.0 Hz, 2H), 1.39 (s, 3H).

Example 5

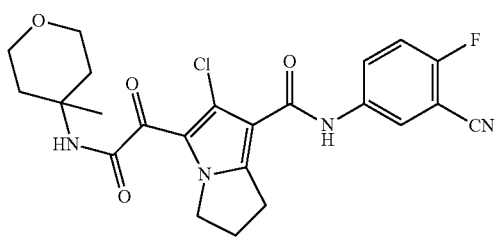

Synthetic Route:

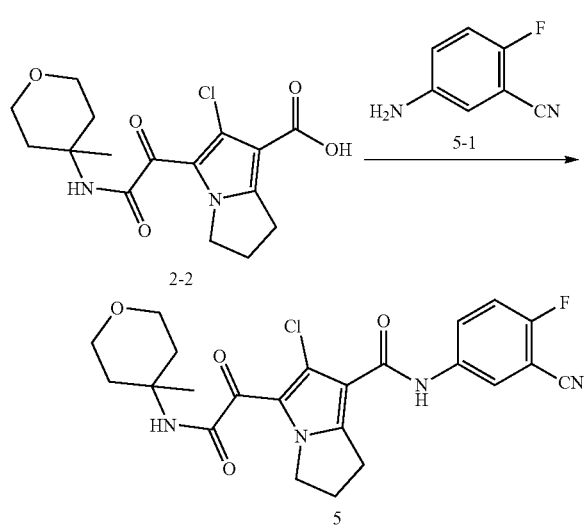

Step 1

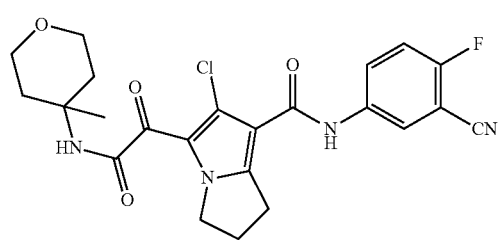

Compound 2-2 (0.13 g, 366.42 μmol, 1 eq.), triethylamine (55.62 mg, 549.63 μmol, 76.50 μL, 1.5 eq.), and 0-(7-azabenzotriazol-1-yl)-N,N,N',N'-tetramethyluronium hexafluorophosphate (167.19 mg, 439.70 μmol, 1.2 eq.) were dissolved in N,N-dimethylformamide (3 mL). After stirring at 25° C. for 0.5 h, compound 5-1 (99.76 mg, 732.84 μmol, 2 eq.) was added. The reaction system was heated to 70° C. and stirred for 3 h. LCMS and HPLC confirmed that compound 2-2 was completely consumed and compound 5 was produced. The reaction solution was added with 2 drops of water to quench the reaction and then filtered. The filtrate was purified by prep-HPLC (neutral system; column: Waters Xbridge 150 mm×25 mm×5 μm; mobile phase: water (containing 10 mM ammonium bicarbonate)-acetonitrile; acetonitrile %: 30%-50%, 12 min) to give compound 5. MS(ESI) m/s: 473.1 [M+H]⁺.

$^1$H NMR (400 MHz, DMSO-d$_6$) δ=10.05 (s, 1H), 8.42 (s, 1H), 8.18 (dd, J=2.8, 5.8 Hz, 1H), 7.97 (ddd, J=2.8, 5.0, 9.2 Hz, 1H), 7.52 (t, J=9.2 Hz, 1H), 4.30 (t, J=7.2 Hz, 2H), 3.65-3.53 (m, 4H), 3.10 (t, J=7.6 Hz, 2H), 2.48-2.41 (m, 2H), 2.07 (d, J=13.6 Hz, 2H), 1.56 (ddd, J=4.8, 8.8, 13.6 Hz, 2H), 1.40 (s, 3H).

Example 6

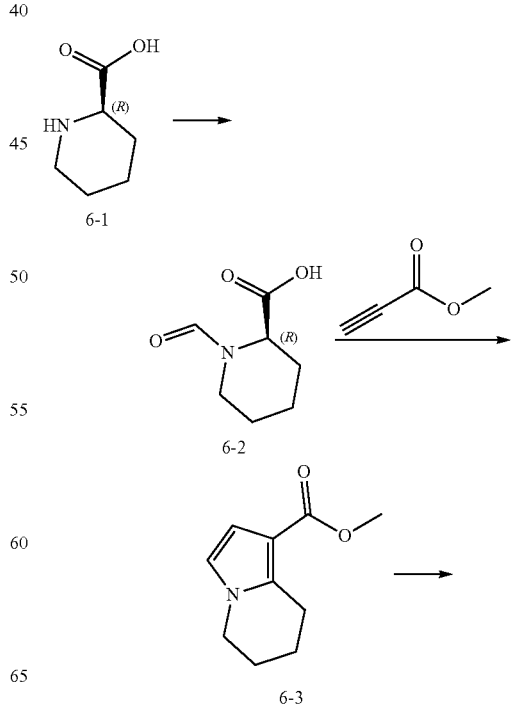

Synthetic Route:

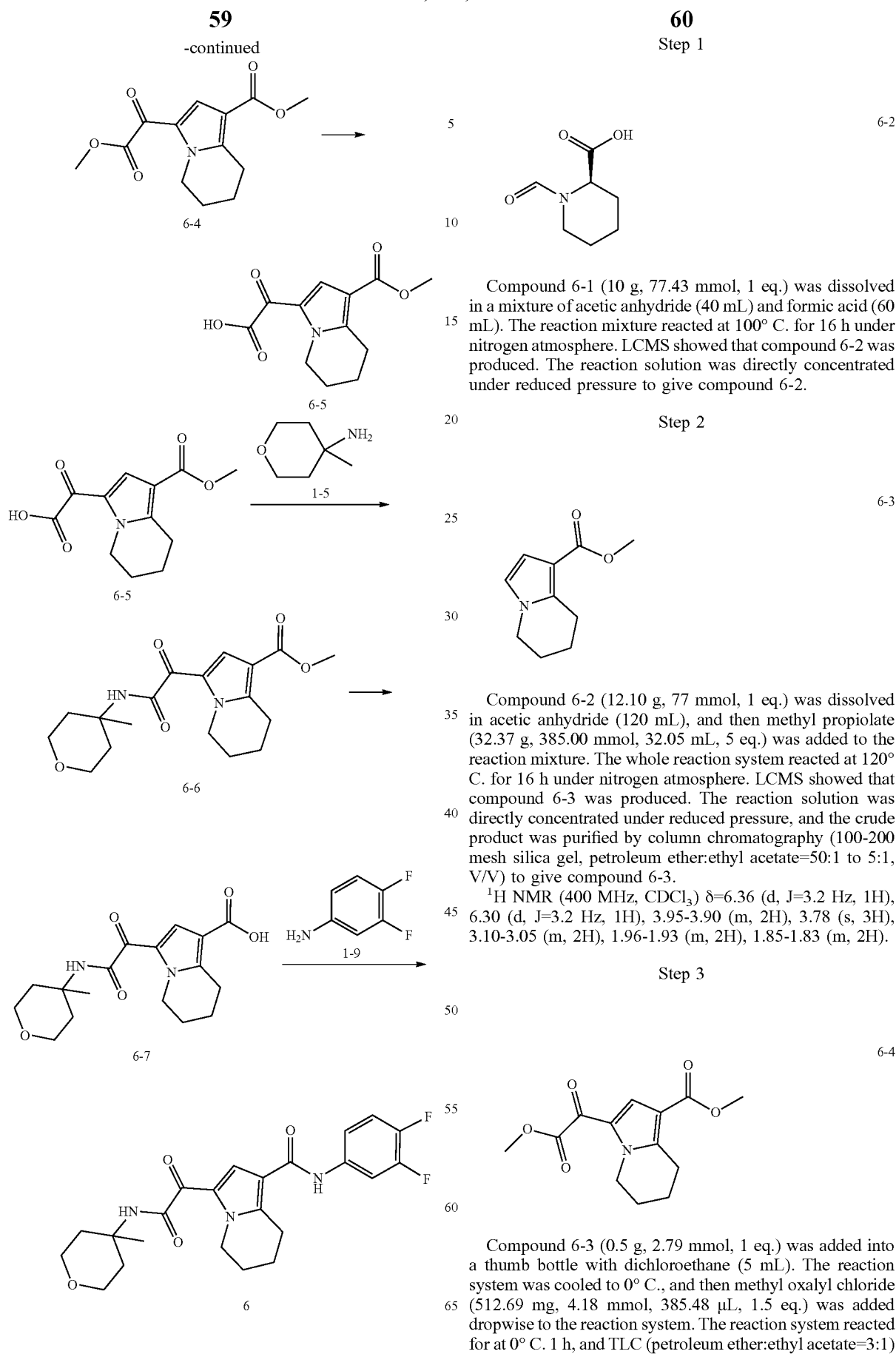

Step 1

Compound 6-1 (10 g, 77.43 mmol, 1 eq.) was dissolved in a mixture of acetic anhydride (40 mL) and formic acid (60 mL). The reaction mixture reacted at 100° C. for 16 h under nitrogen atmosphere. LCMS showed that compound 6-2 was produced. The reaction solution was directly concentrated under reduced pressure to give compound 6-2.

Step 2

Compound 6-2 (12.10 g, 77 mmol, 1 eq.) was dissolved in acetic anhydride (120 mL), and then methyl propiolate (32.37 g, 385.00 mmol, 32.05 mL, 5 eq.) was added to the reaction mixture. The whole reaction system reacted at 120° C. for 16 h under nitrogen atmosphere. LCMS showed that compound 6-3 was produced. The reaction solution was directly concentrated under reduced pressure, and the crude product was purified by column chromatography (100-200 mesh silica gel, petroleum ether:ethyl acetate=50:1 to 5:1, V/V) to give compound 6-3.

$^1$H NMR (400 MHz, CDCl$_3$) δ=6.36 (d, J=3.2 Hz, 1H), 6.30 (d, J=3.2 Hz, 1H), 3.95-3.90 (m, 2H), 3.78 (s, 3H), 3.10-3.05 (m, 2H), 1.96-1.93 (m, 2H), 1.85-1.83 (m, 2H).

Step 3

Compound 6-3 (0.5 g, 2.79 mmol, 1 eq.) was added into a thumb bottle with dichloroethane (5 mL). The reaction system was cooled to 0° C., and then methyl oxalyl chloride (512.69 mg, 4.18 mmol, 385.48 μL, 1.5 eq.) was added dropwise to the reaction system. The reaction system reacted for at 0° C. 1 h, and TLC (petroleum ether:ethyl acetate=3:1)

showed that compound 6-3 was almost completely consumed. The reaction solution was poured into icy saturated sodium bicarbonate solution (20 mL), and extracted with ethyl acetate (20 mL×2). The organic phase was dried over anhydrous sodium sulfate, filtered and concentrated under reduced pressure. The crude product was purified by column chromatography (100-200 mesh silica gel, petroleum ether:ethyl acetate=100:0 to 10:1, V/V) to give compound 6-4. MS(ESI) m/s: 266.1 [M+H]⁺.

¹H NMR (400 MHz, CDCl₃) δ=7.68 (s, 1H), 4.40 (t, J=6.0 Hz, 2H), 3.96 (s, 3H), 3.84 (s, 3H), 3.17 (t, J=6.0 Hz, 2H), 2.05-1.94 (m, 2H), 1.91-1.81 (m, 2H).

Step 4

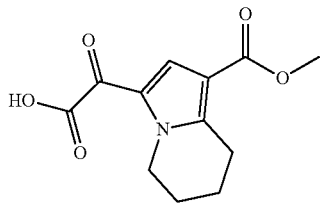

6-5

Compound 6-4 (0.3 g, 1.13 mmol, 1 eq.) was added into a thumb bottle with ethanol (5 mL) and water (2 mL) at 25° C., and then potassium carbonate (468.93 mg, 3.39 mmol, 3 eq.) was added to the reaction system. The reaction system was stirred at 25° C. for 1 h. TLC (petroleum ether:ethyl acetate=2:1) showed that compound 6-4 was completely consumed. The reaction solution was extracted with methyl tert-butyl ether (20 mL×2), adjusted to pH=3 with 1 M hydrochloric acid, and then extracted with ethyl acetate (10 mL×3). The organic phase was dried over anhydrous sodium sulfate, filtered, and concentrated under reduced pressure to give compound 6-5.

Step 5

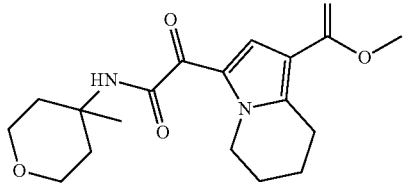

6-6

Compound 1-5 (55.01 mg, 477.64 μmol, 1.2 eq.) was added into a flask with dichloroethane (3 mL) at 20° C., and then O-(7-azabenzotriazol-1-yl)-N,N,N',N'-tetramethyluronium hexafluorophosphate (227.02 mg, 597.05 μmol, 1.5 eq.) and N,N-diisopropylethylamine (154.33 mg, 1.19 mmol, 207.99 μL, 3 eq.) were added to the reaction system. After the reaction system reacted at 0° C. for 10 min, compound 6-5 (0.1 g, 398.03 μmol, 1 eq.) was dissolved in dichloroethane (3 mL) and added dropwise to the reaction system. The resulting reaction system reacted at 20° C. for 20 min, and LCMS showed that compound 6-6 was produced. The reaction solution was washed with saturated ammonium chloride solution (10 mL×2), and the organic phase was dried over anhydrous sodium sulfate, filtered and concentrated under reduced pressure. The crude product was purified by prep-TLC (petroleum ether:ethyl acetate=2:1, V/V) to give compound 6-6.

MS(ESI) m/s: 349.1 [M+H]⁺.

Step 6

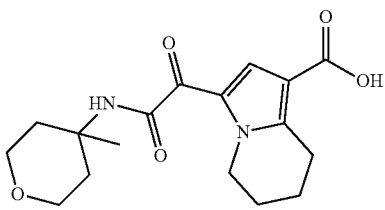

6-7

Compound 6-6 (0.1 g, 287.03 μmol, 1 eq.) was added into a thumb bottle with tetrahydrofuran (2 mL), ethanol (2 mL), and water (2 mL), and then lithium hydroxide monohydrate (48.18 mg, 1.15 mmol, 4 eq.) was added to the reaction system. The reaction system was stirred at 20° C. for 1 h. TLC (petroleum ether:ethyl acetate=2:1) showed that compound 6-6 was completely consumed. The reaction solution was diluted with 10 mL of water, adjusted to pH=3 with 1 M hydrochloric acid, and extracted with ethyl acetate (10 mL×3). The organic phase was dried over anhydrous sodium sulfate, filtered and concentrated under reduced pressure to give compound 6-7.

Step 7

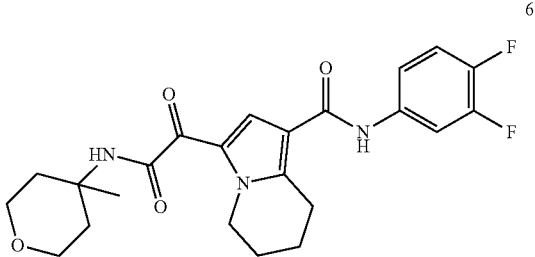 [SMILES: CC1(NC(=O)C(=O)c2cc(C(=O)Nc3ccc(F)c(F)c3)c3n2CCCC3)CCOCC1]

6

Compound 1-9 (42.28 mg, 327.49 μmol, 1.5 eq.) was added into a thumb bottle with dichloromethane (2 mL) at 20° C., and then the reaction system was cooled to 0° C. Then O-(7-azabenzotriazol-1-yl)-N,N,N',N'-tetramethyluronium hexafluorophosphate (107.92 mg, 283.82 μmol, 1.3 eq.) and N,N-diisopropylethylamine (84.65 mg, 654.97 μmol, 114.08 μL, 3 eq.) were added to the reaction system. After the reaction system was stirred at 0° C. for 10 min, compound 6-7 (73 mg, 218.32 μmol, 1 eq.) was dissolved in dichloromethane (2 mL) and added dropwise to the reaction system. The resulting reaction system reacted at 0° C. for 20 min, then heated to 70° C. and stirred for 12 h. TLC (petroleum ether:ethyl acetate=1:1) showed that main spots were produced, and LCMS showed that compound 6 was produced. The reaction solution was washed with saturated ammonium chloride (10 mL), and the organic phase was dried over anhydrous sodium sulfate, filtered and concentrated under reduced pressure. The crude product was purified by prep-HPLC (column: Xtimate C18 150 mm×25 mm×5 μm; mobile phase: water (containing 0.04% ammonium hydroxide+10 mM ammonium bicarbonate)-acetonitrile; acetonitrile %: 45%-65%, 10.5 min) to give compound 6.

MS(ESI) m/s: 446.2 [M+H]$^+$.

$^1$H NMR (400 MHz, MeOH-d$_4$) δ=8.04 (s, 1H), 7.79-7.69 (m, 1H), 7.38-7.30 (m, 1H), 7.26-7.16 (m, 1H), 4.42 (t, J=6.8 Hz, 2H), 3.79-3.62 (m, 4H), 3.20 (t, J=6.8 Hz, 2H), 2.23 (m, 2H), 2.00 (m, 2H), 1.88 (m, 2H), 1.71 (m, 2H), 1.50 (s, 3H).

Example 7

7

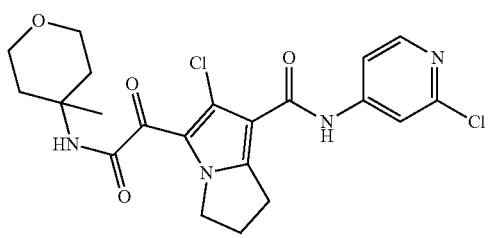

Synthetic Route:

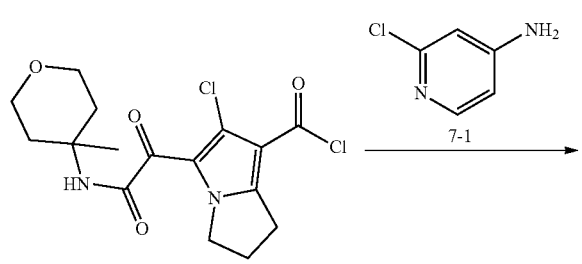

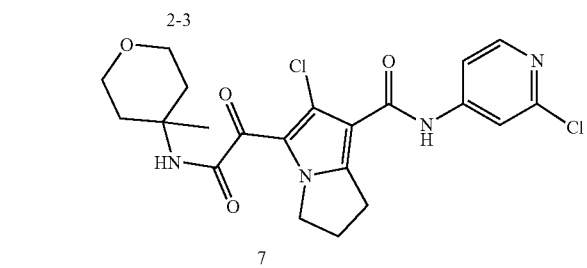

Step 1

7

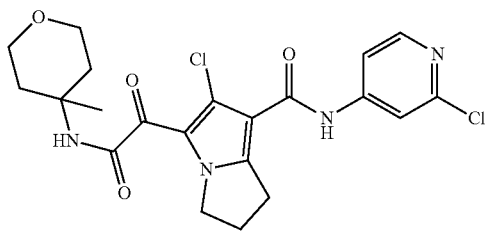

Compound 7-1 (36.17 mg, 281.33 μmol, 1.5 eq.) and triethylamine (56.94 mg, 562.65 μmol, 78.32 μL, 3 eq.) were dissolved in dichloromethane (5 mL), and then compound 2-3 (70 mg, 187.55 μmol, 1 eq.) dissolved in dichloromethane (5 mL) was added at 0° C. The reaction system was stirred at 25° C. for 2 h. LCMS and HPLC showed that the reaction was completed. The reaction was quenched with 15 mL of water, and then the reaction solution was extracted with dichloromethane (15 mL×3). The organic phase was dried over anhydrous sodium sulfate, filtered and concentrated under reduced pressure to give residue. The residue was purified by prep-HPLC (column: Xtimate C18 150 mm×25 mm×5 μm; mobile phase: water (containing 0.04% ammonium hydroxide+10 mM ammonium bicarbonate)-acetonitrile; acetonitrile %: 28%-58%, 10.5 min) to give compound 7. MS(ESI) m/s: 465.1 [M+H]$^+$.

$^1$H NMR (400 MHz, DMSO-d$_6$) δ=10.28 (s, 1H), 8.42 (s, 1H), 8.29 (d, J=5.6 Hz, 1H), 7.81 (d, J=1.6 Hz, 1H), 7.62-7.60 (m, 1H), 4.30 (t, J=7.2 Hz, 2H), 3.63-3.57 (m, 4H), 3.10 (t, J=7.2 Hz, 2H), 2.47-2.45 (m, 2H), 2.07 (d, J=13.2 Hz, 2H), 1.59-1.53 (m, 2H), 1.41 (s, 3H).

Example 8

8

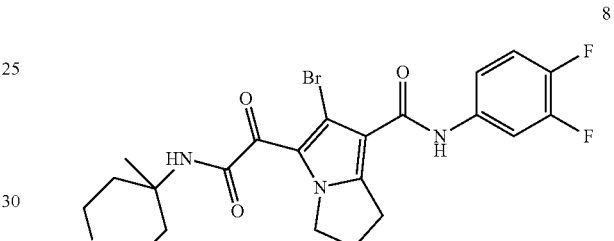

Synthetic Route:

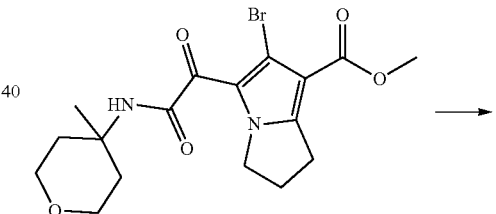

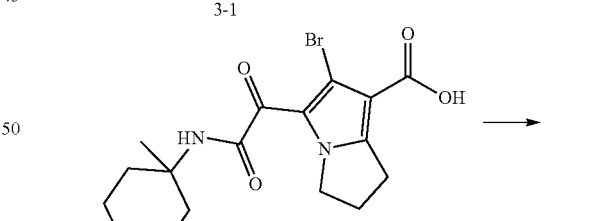

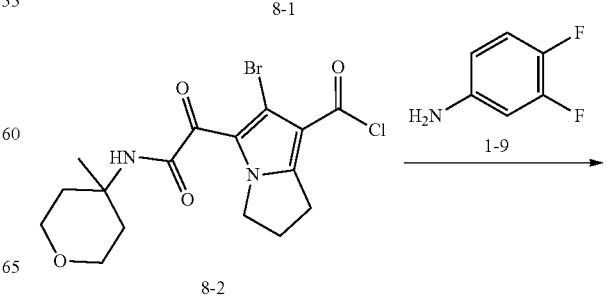

-continued

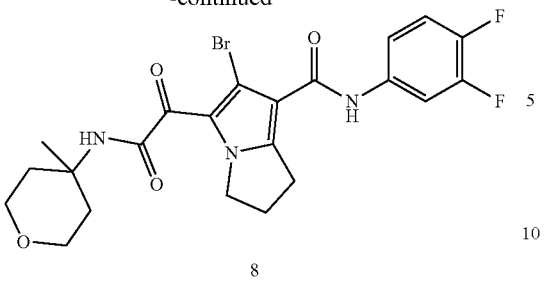

8

Step 1

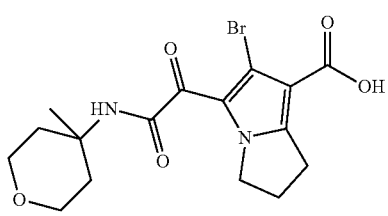

8-1

A solution of sodium hydroxide (87.11 mg, 2.18 mmol, 3 eq.) in water (2 mL) was added to a solution of compound 3-1 (300 mg, 725.93 μmol, 1 eq.) in tetrahydrofuran (5 mL), and the mixture was stirred at 40° C. for 12 h. The reaction solution was adjusted to pH=1-2 with 2 mol/L diluted hydrochloric acid, and extracted with ethyl acetate (10 mL×3). The combined organic phases were washed with saturated brine (10 mL), dried over anhydrous sodium sulfate, and concentrated under reduced pressure to give compound 8-1. MS m/s (ESI): 398.9 [M+H]$^+$.

$^1$H NMR (400 MHz, MeOH-d$_4$) δ=4.34 (t, J=7.2 Hz, 2H), 3.82-3.70 (m, 4H), 3.15 (t, J=7.8 Hz, 2H), 2.50-2.48 (m, 2H), 2.22 (d, J=13.8 Hz, 2H), 1.77-1.65 (m, 2H), 1.55 (s, 3H).

Step 2

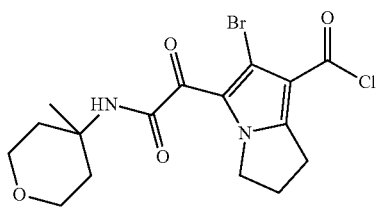

8-2

Thionyl chloride (166.88 mg, 1.40 mmol, 101.75 μL, 2 eq.) was added dropwise to a solution of compound 8-1 (280 mg, 701.34 μmol, 1 eq.) in dichloromethane (5 mL) at 0° C. under nitrogen atmosphere, and then N,N-dimethylformamide (25.63 mg, 350.67 μmol, 26.98 μL, 0.5 eq.) was added. The mixture was stirred at 25° C. for 1 h. The reaction solution was concentrated under reduced pressure to give compound 8-2, which was used directly in next step.

Step 3

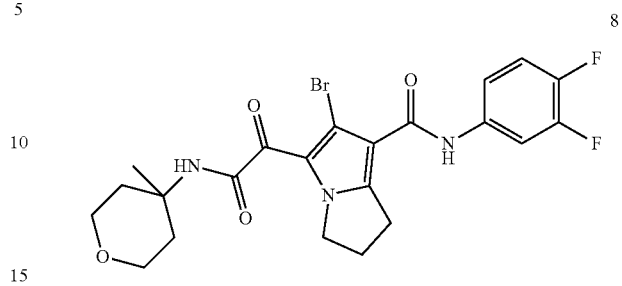

8

Triethylamine (290.72 mg, 2.87 mmol, 399.89 μL, 4 eq.) was added to a solution of compound 8-2 (300 mg, 718.25 μmol, 1 eq.) in dichloromethane (5 mL), and then compound 1-9 (92.73 mg, 718.25 μmol, 1 eq.) was added. The mixture was stirred at 25° C. for 1 h. The reaction solution was concentrated under reduced pressure. The residue was separated by column chromatography (100-200 mesh silica gel, petroleum ether:ethyl acetate=100:0 to 40:60, V/V) and then by prep-HPLC (column: Xtimate C18 150 mm×25 mm×5 μm; mobile phase: water (containing 0.225% formic acid)-acetonitrile; acetonitrile %: 48%-68%, 7 min) to give compound 8. MS m/s (ESI): 510.0 [M+H]$^+$.

$^1$H NMR (400 MHz, CDCl$_3$) δ=8.54 (s, 1H), 7.73-7.62 (m, 1H), 7.11-7.01 (m, 2H), 6.30 (s, 1H), 4.25 (t, J=7.4 Hz, 2H), 3.76-3.57 (m, 4H), 3.21 (t, J=7.8 Hz, 2H), 2.46-2.43 (m, 2H), 2.08 (d, J=13.8 Hz, 2H), 1.74 (m, 2H), 1.49 (s, 3H).

Example 9

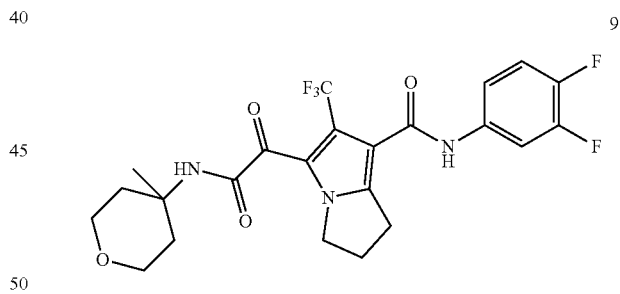

9

Synthetic Route:

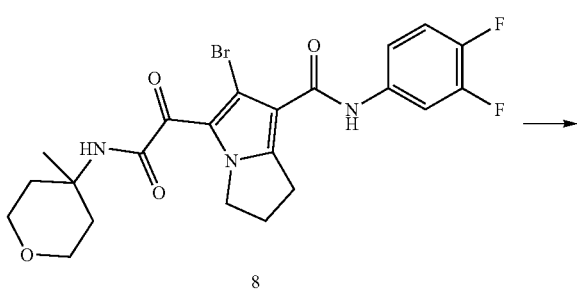

8

-continued

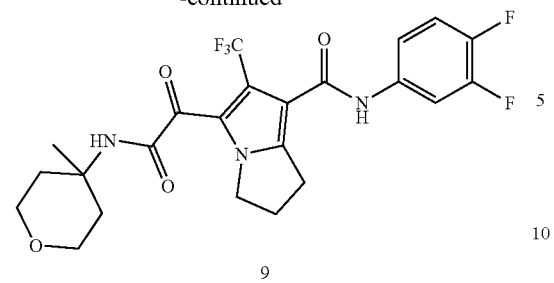

9

Step 1

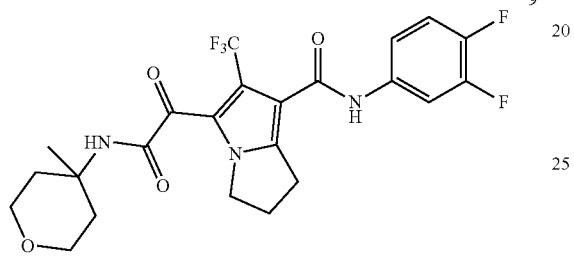

9

Methyl fluorosulphonyldifluoroacetate (180.70 mg, 940.57 μmol, 119.67 μL, 6 eq.) and hexamethylphosphoric triamide (28.09 mg, 156.76 μmol, 27.54 μL, 1 eq.) were added to a solution of compound 8 (80 mg, 156.76 mol, 1 eq.) in DMF (3 mL). After three nitrogen purges, copper(I) iodide (29.86 mg, 156.76 μmol, 1 eq.) was added. The mixture was stirred at 80° C. for 12 h. The reaction solution was diluted with water (10 mL) and then extracted with ethyl acetate (10 mL×3). The combined organic phases were washed with saturated brine (10 mL), dried over anhydrous sodium sulfate, and concentrated under reduced pressure. The residue was separated by prep-HPLC (column: Xtimate C18 150 mm×25 mm×5 μm; mobile phase: water (containing 0.225% formic acid)-acetonitrile; acetonitrile %: 50%-70%, 7 min) to give compound 9. MS m/s (ESI): 500.2 [M+H1]+.

$^1$H NMR (400 MHz, CDCl$_3$) δ=7.68-7.59 (m, 1H), 7.55 (s, 1H), 7.12-6.95 (m, 2H), 6.51 (s, 1H), 4.16 (t, J=7.2 Hz, 2H), 3.77-3.66 (m, 2H), 3.64-3.51 (m, 2H), 3.09 (t, J=7.4 Hz, 2H), 2.50-2.48 (m, 2H), 2.06 (d, J=13.6 Hz, 2H), 1.71 (t, J=9.6 Hz, 2H), 1.44 (s, 3H).

Example 10

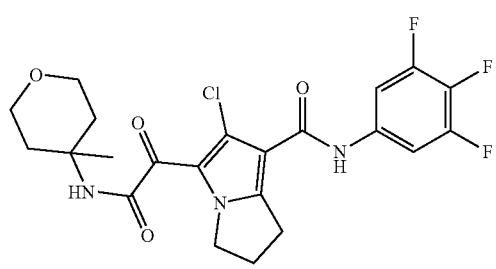

10

Synthetic Route:

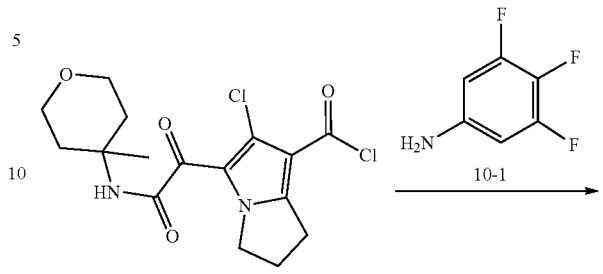

Step 1

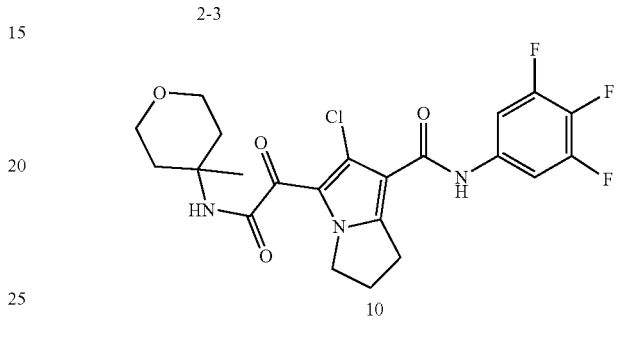

10

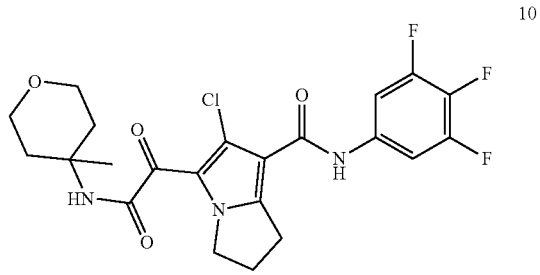 [SMILES: CC1(NC(=O)C(=O)c2c(Cl)c(C(=O)Nc3cc(F)c(F)c(F)c3)c3n2CCC3)CCOCC1]

10

Compound 10-1 (59.12 mg, 401.90 μmol, 1.5 eq.) and triethylamine (81.34 mg, 803.79 μmol, 111.88 μL, 3 eq.) were dissolved in dichloromethane (5 mL), and then compound 2-3 (0.1 g, 267.93 μmol, 1 eq.) dissolved in dichloromethane (5 mL) was added at 0° C. The reaction system was stirred at 25° C. for 1 h. LCMS and HPLC showed that compound 2-3 was completely consumed and compound 10 was produced. The reaction was quenched with water (10 mL), and then the reaction solution was extracted with dichloromethane (10 mL×3). The organic phase was dried over anhydrous sodium sulfate, filtered and concentrated under reduced pressure to give residue. The residue was purified by prep-HPLC (column: Xtimate C18 150 mm×25 mm×5 μm; mobile phase: water (containing 0.04% ammonium hydroxide+10 mM ammonium bicarbonate)-acetonitrile; acetonitrile %: 42%-62%, 10.5 min) to give compound 10. MS(ESI) m/s: 484.1 [M+H]+.

$^1$H NMR (400 MHz, DMSO-d$_6$) δ=10.03 (s, 1H), 8.42 (s, 1H), 7.64-7.60 (m, 2H), 4.30 (t, J=7.2 Hz, 2H), 3.63-3.55 (m, 4H), 3.08 (t, J=7.6 Hz, 2H), 2.47-2.43 (m, 2H), 2.07 (d, J=13.2 Hz, 2H), 1.59-1.52 (m, 2H), 1.40 (s, 3H).

Example 11

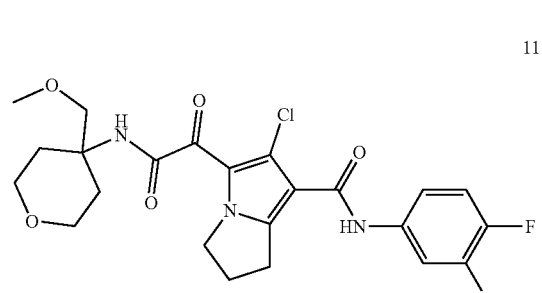

11

Synthetic Route:

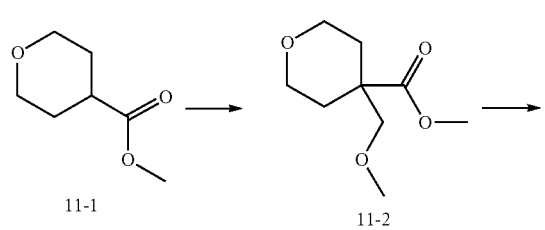

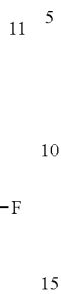

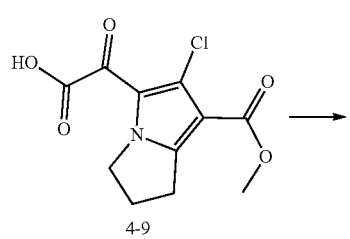

4-9

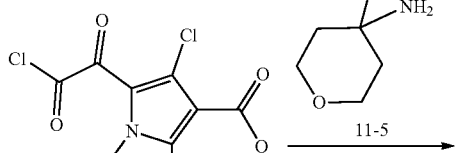

11-7

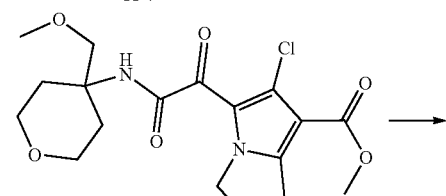

11-8

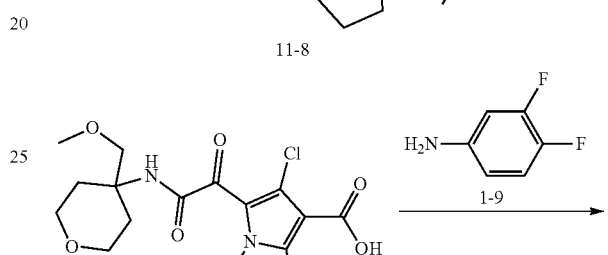

11-9

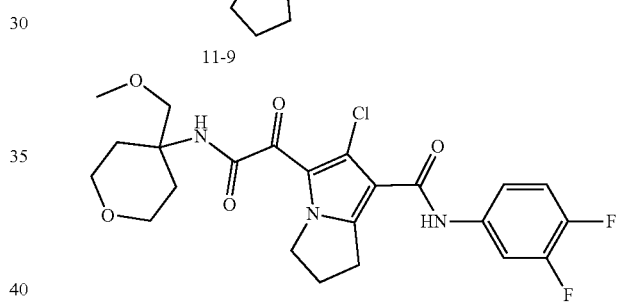

11

Step 1

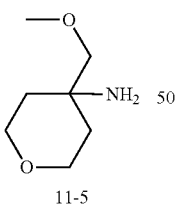

11-5

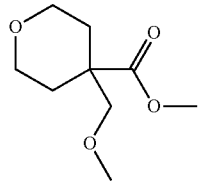

11-2

Compound 11-1 (10 g, 69.36 mmol, 9.26 mL, 1 eq.) was dissolved in tetrahydrofuran (100 mL), and then lithium diisopropylamide (2 M, 52.02 mL, 1.5 eq.) was added at −78° C. After stirring for 0.5 h, chloromethyl ether (8.38 g, 104.05 mmol, 7.90 mL, 1.5 eq.) was added at −78° C. The reaction system was stirred at 25° C. for 2 h. TLC (petroleum ether:ethyl acetate=5:1) showed that compound 11-1 was completely consumed and new spots were produced. The reaction solution was poured into 50 mL of saturated ammonium chloride solution, and extracted with ethyl acetate (50 mL×3). The organic phase was dried over anhydrous sodium sulfate, filtered and concentrated under reduced pressure to give compound 11-2.

$^1$H NMR (400 MHz, CDCl$_3$) δ=3.82 (td, J=4.0, 11.8 Hz, 2H), 3.76 (s, 3H), 3.52-3.46 (m, 2H), 3.40 (s, 2H), 3.30 (s, 3H), 2.09-2.05 (m, 2H), 1.62-1.54 (m, 2H).

Step 2

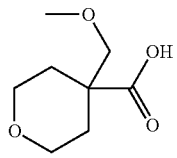

11-3

Compound 11-2 (12 g, 63.76 mmol, 1 eq.) was dissolved in a mixture of methanol (100 mL) and water (50 mL), and then sodium hydroxide (5.10 g, 127.51 mmol, 2 eq.) was added. The reaction system was stirred at 40° C. for 16 h. The reaction solution was extracted with ethyl acetate (50 mL×2). The aqueous phase was adjusted to pH=1-3 with 1 mol/L hydrochloric acid and extracted with ethyl acetate (50 mL×3). The organic phase was dried over anhydrous sodium sulfate, filtered and concentrated under reduced pressure to give compound 11-3.

$^1$H NMR (400 MHz, MeOH-d$_4$) δ=3.80 (td, J=4.0, 11.6 Hz, 2H), 3.58-3.51 (m, 2H), 3.43 (s, 2H), 3.31 (s, 3H), 2.04-1.99 (m, 2H), 1.62-1.54 (m, 2H).

Step 3

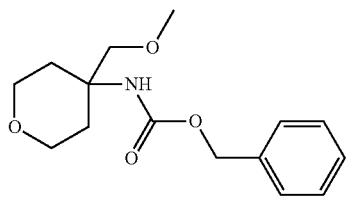

11-4

Compound 11-3 (8.5 g, 48.80 mmol, 1 eq.), triethylamine (7.41 g, 73.19 mmol, 10.19 mL, 1.5 eq.), and benzyl alcohol (10.55 g, 97.59 mmol, 10.15 mL, 2 eq.) were dissolved in toluene (100 mL), and then diphenylphosphoryl azide (16.11 g, 58.56 mmol, 12.69 mL, 1.2 eq.) was added at 25° C. under nitrogen atmosphere. The reaction system was stirred at 110° C. for 5 h. TLC (petroleum ether:ethyl acetate=5:1) showed that new spots were produced. The reaction solution was poured into 100 mL of saturated ammonium chloride solution, and then extracted with ethyl acetate (80 mL×3). The organic phase was dried over anhydrous sodium sulfate, filtered and concentrated under reduced pressure. The residue was purified by column chromatography (100-200 mesh silica gel, petroleum ether:ethyl acetate=100:0 to 10:1, V/V). The purified product was concentrated under reduced pressure to give compound 11-4.

$^1$H NMR (400 MHz, CDCl$_3$) δ=7.34-7.29 (m, 5H), 3.74-3.49 (m, 4H), 3.36 (s, 2H), 3.33 (s, 3H), 2.18 (s, 2H), 2.04-1.96 (m, 2H), 1.74-1.66 (m, 2H).

Step 4

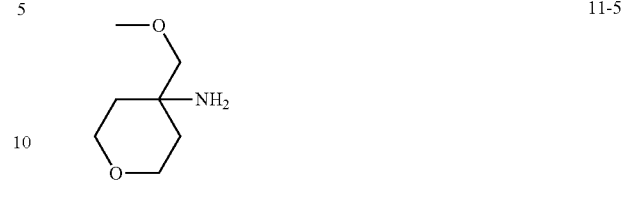

11-5

Compound 11-4 (14 g, 50.12 mmol, 1 eq.) was dissolved in methanol (200 mL) in a dry 250 mL hydrogenation flask, and then wet palladium on carbon (3 g, purity: 10%) was added. The reaction system was stirred at 25° C. for 16 h under hydrogen atmosphere (50 psi). TLC (petroleum ether:ethyl acetate=5:1) showed that the reaction was completed. The reaction solution was filtered and concentrated. The crude product was homogenized with methyl tert-butyl ether (30 mL) and filtered. The filter cake was concentrated under reduced pressure to give compound 11-5.

$^1$H NMR (400 MHz, MeOH-d$_4$) δ=3.84-3.81 (m, 2H), 3.68-3.62 (m, 4H), 3.45 (s, 3H), 1.93-1.88 (m, 2H), 1.84-1.80 (m, 2H).

Step 5

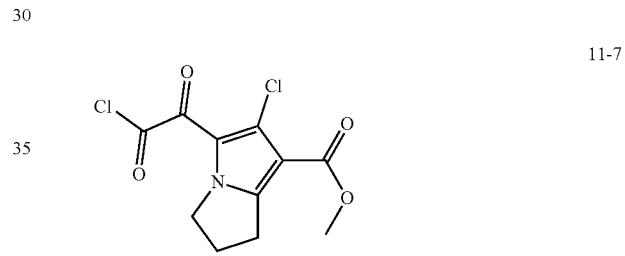

11-7

Compound 4-9 (0.2 g, 736.23 μmol, 1 eq.) was dissolved in dichloromethane (10 mL), and then oxalyl chloride (186.89 mg, 1.47 mmol, 128.89 μL, 2 eq.) and N,N-dimethylformamide (5.38 mg, 73.62 μmol, 5.66 μL, 0.1 eq.) were added at 0° C. The reaction system was stirred for 0.5 h at 25° C. under nitrogen atmosphere. TLC (petroleum ether:ethyl acetate=1:1) showed that compound 4-9 was completely consumed and new spots were produced. The reaction solution was concentrated under reduced pressure to give compound 11-7.

Step 6

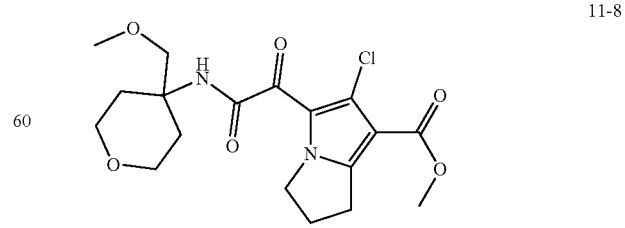

11-8

Compound 11-5 (150.16 mg, 826.58 μmol, 1.20 eq., HCl) and triethylamine (209.29 mg, 2.07 mmol, 287.88 μL, 3 eq.)

were dissolved in dichloromethane (5 mL), and then a solution of compound 11-7 (0.2 g, 689.42 mol, 1 eq.) in dichloromethane (5 mL) was added at 0° C. under nitrogen atmosphere. The reaction system was stirred at 25° C. for 1 h. LCMS confirmed that compound 11-7 was completely consumed and compound 11-8 was produced. The reaction was quenched with 15 mL of water, and then the reaction solution was extracted with dichloromethane (15 mL×3). The organic phase was dried over anhydrous sodium sulfate, filtered and concentrated under reduced pressure to give compound 11-8.

MS(ESI) m/s: 399.1 [M+H]⁺.

Step 7

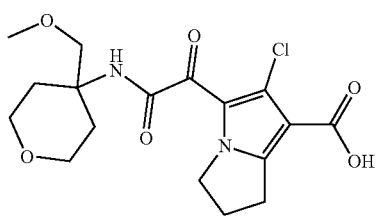

11-9

Compound 11-8 (0.4 g, 1.00 mmol, 1 eq.) was dissolved in a mixture of tetrahydrofuran (8 mL) and water (4 mL), and then lithium hydroxide monohydrate (126.26 mg, 3.01 mmol, 3 eq.) was added. The reaction system was stirred at 25° C. for 12 h. LCMS confirmed that compound 11-8 was completely consumed and compound 11-9 was produced. The reaction solution was adjusted to pH=1-3 with 1 M diluted hydrochloric acid, and extracted with ethyl acetate (20 mL×3). The organic phase was dried over anhydrous sodium sulfate, filtered and concentrated under reduced pressure to give compound 11-9. MS(ESI) m/s: 385.0 [M+H]⁺.

¹H NMR (400 MHz, MeOH-d₄) δ=4.36 (t, J=7.2 Hz, 2H), 3.77-3.72 (m, 4H), 3.64 (s, 2H), 3.37 (s, 3H), 3.15 (t, J=7.6 Hz, 2H), 2.54-2.50 (m, 2H), 2.19 (d, J=12.8 Hz, 2H), 1.84-1.77 (m, 2H).

Step 8

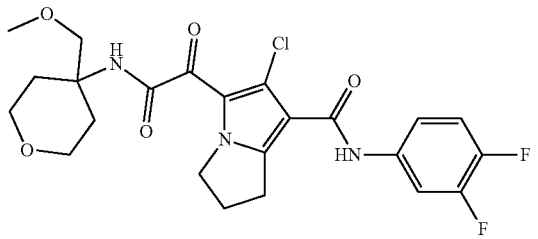

11

Compound 11-9 (0.2 g, 519.74 μmol, 1 eq.), triethylamine (210.37 mg, 2.08 mmol, 289.37 μL, 4 eq.), and O-(7-azabenzotriazol-1-yl)-N,N,N',N'-tetramethyluronium hexafluorophosphate (592.86 mg, 1.56 mmol, 3 eq.) were dissolved in N,N-dimethylformamide (3 mL). After stirring at 25° C. for 0.5 h, compound 1-9 (134.20 mg, 1.04 mmol, 2 eq.) was added. The reaction system was stirred at 55° C.

for 3 h. LCMS and HPLC confirmed that the reaction was completed. The reaction solution was added with 2 drops of water to quench the reaction and then filtered to give filtrate. The filtrate was purified by prep-HPLC (neutral system; column: Xtimate C18 150 mm×25 mm×5 μm; mobile phase: water (containing 10 mM ammonium bicarbonate)-acetonitrile; acetonitrile %: 30%-60%, 12 min) to give compound 11. MS(ESI) m/s: 496.1 [M+H]⁺.

¹H NMR (400 MHz, DMSO-d₆) δ=9.95 (s, 1H), 8.42 (s, 1H), 7.87-7.81 (m, 1H), 7.43-7.39 (m, 2H), 4.29 (t, J=7.2 Hz, 2H), 3.67-3.55 (m, 6H), 3.28 (s, 3H), 3.08 (t, J=7.6 Hz, 2H), 2.43 (s, 2H), 2.07 (d, J=13.4 Hz, 2H), 1.68-1.60 (m, 2H).

Example 12

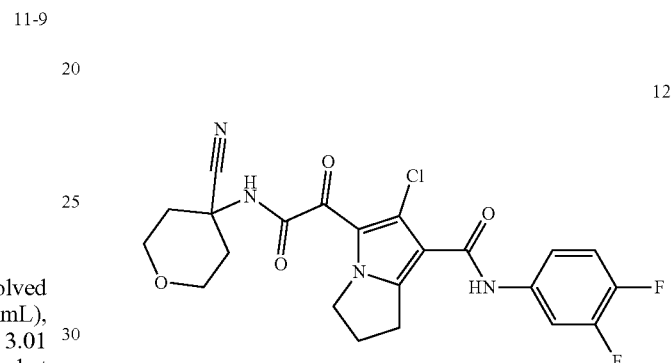

12

Synthetic Route:

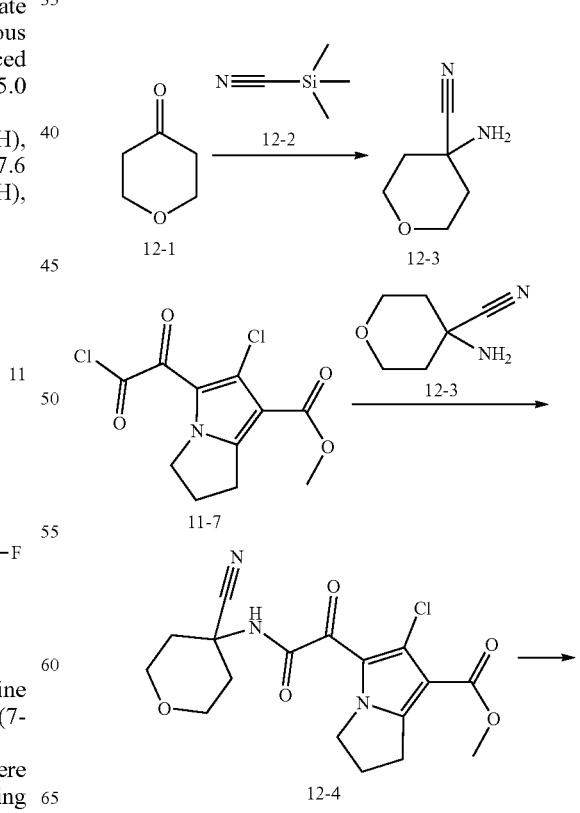

-continued

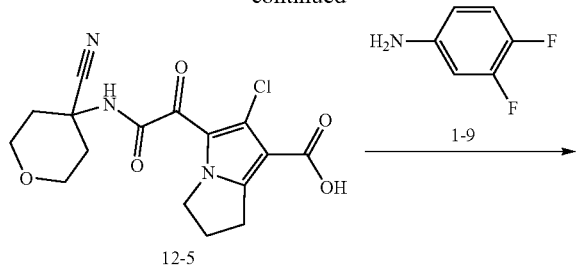

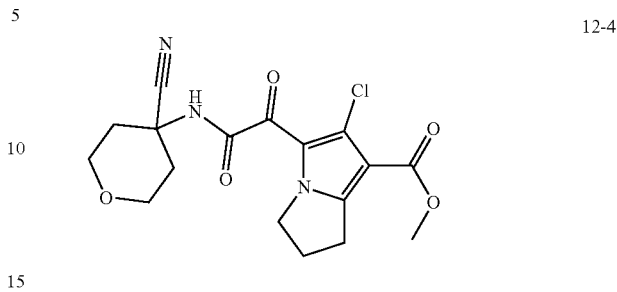

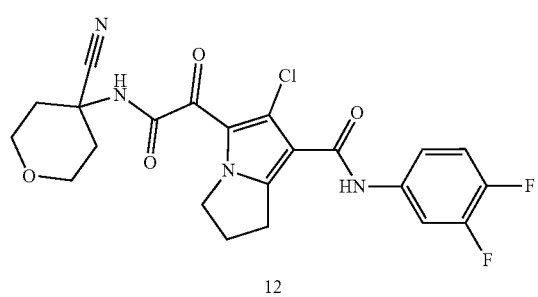

Step 1

Titanium tetraisopropanolate (3.41 g, 11.99 mmol, 3.54 mL, 1.2 eq.) was dissolved in ammonia/methanol (7 M, 5.71 mL, 4 eq.) in a dry 40 mL flask, and then compound 12-1 (1 g, 9.99 mmol, 917.43 μL, 1 eq.) was added dropwise under nitrogen atmosphere at 30° C. After stirring for 2 h, the mixture was cooled to −5° C., and then compound 12-2 (1.04 g, 10.49 mmol, 1.31 mL, 1.05 eq.) was added dropwise at this temperature. After stirring for 2 h, the resulting mixture was heated to 30° C. and stirred for 12 h. TLC (petroleum ether:ethyl acetate=1:1) showed that the reaction was completed. The reaction was quenched with water (1 mL), and then the reaction solution was added with ethanol (20 mL), stirred for 30 min and filtered. The mother liquor was concentrated under reduced pressure. The crude product was purified by column chromatography (100-200 mesh silica gel, petroleum ether:ethyl acetate=10:1 to 1:1, V/V) to give compound 12-3.

$^1$H NMR (400 MHz, CDCl$_3$) δ=4.02-3.95 (m, 2H), 3.68-3.62 (m, 2H), 2.01-1.96 (m, 2H), 1.87 (s, 2H), 1.78-1.74 (m, 2H).

Step 2

Compound 12-3 (97.85 mg, 775.60 μmol, 1.5 eq.) was dissolved in dichloromethane (10 mL) in a dry 40 mL flask, and a solution of triethylamine (156.97 mg, 1.55 mmol, 215.91 μL, 3 eq.) and compound 11-7 (150 mg, 517.06 μmol, 1 eq.) in dichloromethane (5 mL) was added dropwise under nitrogen atmosphere at 0° C. The reaction system was stirred at 30° C. for 1 h. LCMS showed that the reaction was completed. The reaction solution was diluted with dichloromethane (50 mL) and washed with diluted hydrochloric acid (0.5 mol/L) (10 mL×3). The organic phase was dried over anhydrous sodium sulfate, filtered and concentrated under reduced pressure to give compound 12-4. MS(ESI) m/s: 380.1 [M+H]$^+$.

Step 3

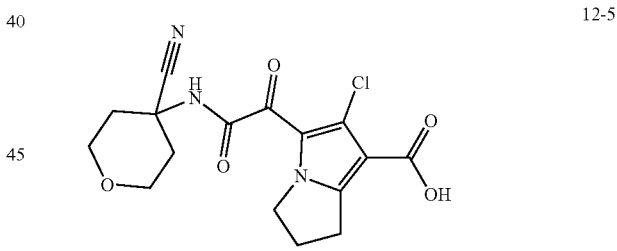

Compound 12-4 (200 mg, 526.60 μmol, 1 eq.) was dissolved in a mixture of tetrahydrofuran (3 mL), methanol (3 mL), and water (3 mL) in a dry 50 mL single-neck flask, and then lithium hydroxide monohydrate (44.19 mg, 1.05 mmol, 2 eq.) was added. The reaction solution was stirred at 30° C. for 16 h. LCMS showed that the reaction was completed. Tetrahydrofuran and methanol were concentrated under reduced pressure and diluted with 20 mL of water. The aqueous phase was washed with ethyl acetate (5 mL×2), adjusted to pH=1 with 0.5 M diluted hydrochloric acid, and extracted with ethyl acetate (10 mL×3). The organic phase was dried over anhydrous sodium sulfate, filtered, and concentrated under reduced pressure to give compound 12-5. MS(ESI) m/s: 366.1 [M+H]$^+$.

Step 4

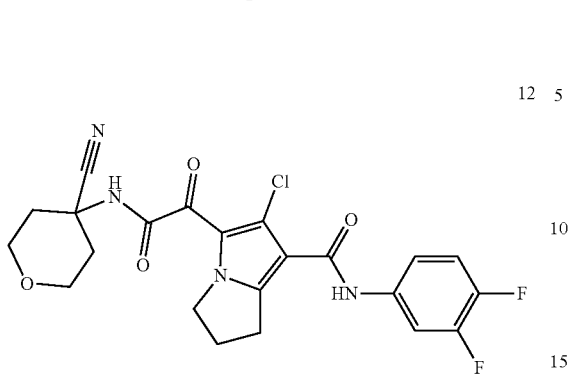

12-5

Compound 12-5 (130 mg, 355.42 µmol, 1 eq.) was dissolved in N,N-dimethylformamide (5 mL) in a dry 50 mL single-neck flask. O-(7-azabenzotriazol-1-yl)-N,N,N',N'-tetramethyluronium hexafluorophosphate (270.28 mg, 710.83 µmol, 2 eq.) and triethylamine (107.89 mg, 1.07 mmol, 148.41 µL, 3 eq.) were added under nitrogen atmosphere at 30° C. After stirring for 0.5 h, compound 1-9 (68.83 mg, 533.13 µmol, 1.5 eq.) was added. After reaction, the mixture was heated to 60° C. and stirred for 15.5 h. LCMS and HPLC showed that the reaction was completed. The reaction solution was added with water (1 mL) and then concentrated. The crude product was purified by prep-HPLC (neutral system, column: Waters Xbridge 150×25 mm×5 µm; mobile phase: water (containing 10 mM ammonium bicarbonate)-acetonitrile; acetonitrile %: 30%-50%, 12 min) to give compound 12. MS(ESI) m/s: 477.1 [M+H]$^+$.

$^1$H NMR (400 MHz, DMSO-d$_6$) δ=9.96 (s, 1H), 9.58 (s, 1H), 7.85-7.80 (m, 1H), 7.42-7.38 (m, 2H), 4.29 (t, J=7.2 Hz, 2H), 3.86-3.82 (m, 2H), 3.57 (t, J=10.0 Hz, 2H), 3.09 (t, J=7.6 Hz, 2H), 2.46-2.44 (m, 2H), 2.30-2.27 (m, 2H), 1.95-1.90 (m, 2H).

Example 13

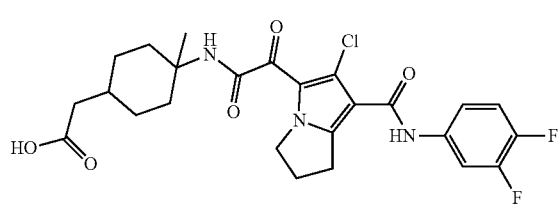

13

Synthetic Route:

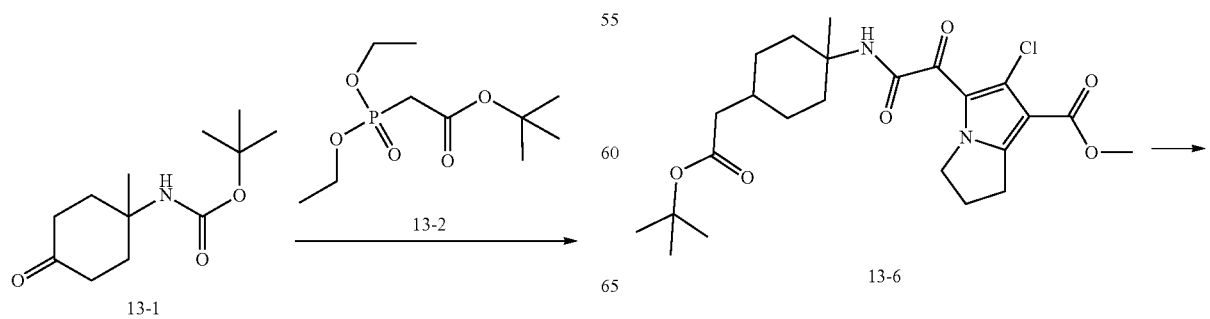

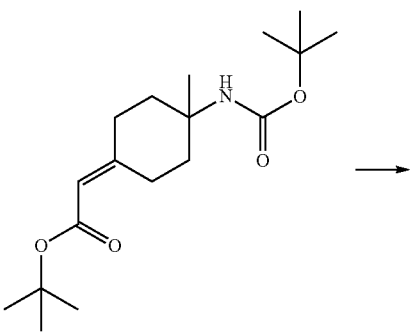

13-3

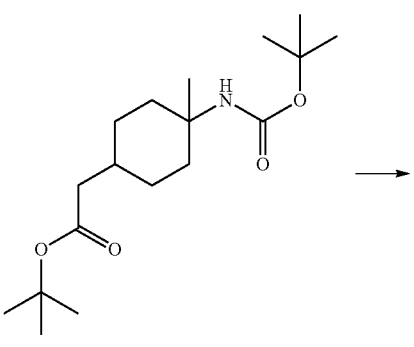

13-4

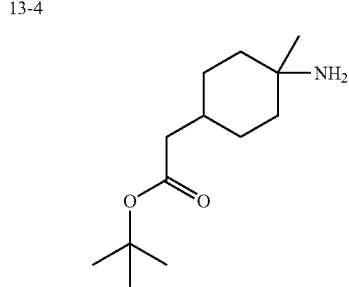

13-5

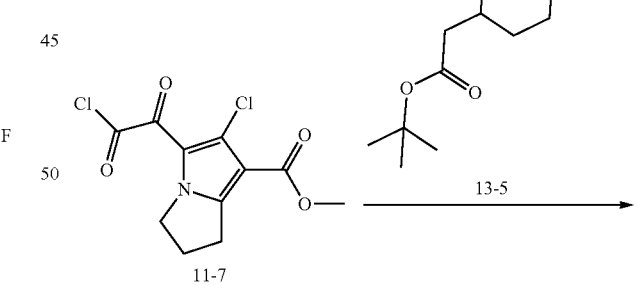

-continued

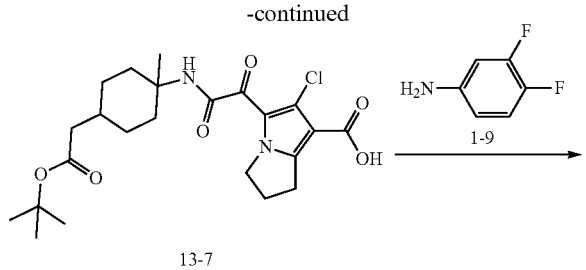

13-7

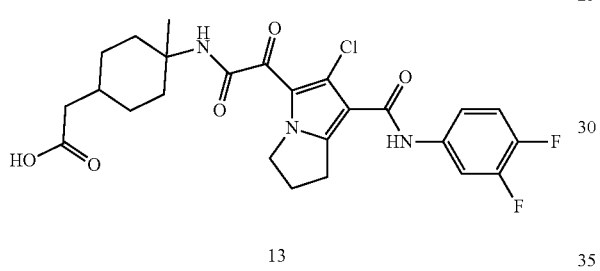

13-8

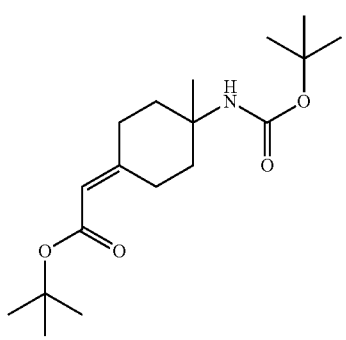

13

Step 1

13-3

Compound 13-1 (1 g, 4.40 mmol, 1 eq.) was dissolved in tetrahydrofuran (20 mL) in a single-neck flask, and sodium hydride (615.93 mg, purity: 60%, 3.5 eq.) was added at 0° C. under nitrogen atmosphere. After stirring for 0.5 h, compound 13-2 (2.33 g, 9.24 mmol, 2.1 eq.) was added, and the reaction system was stirred for 30 min at 30° C. TLC (petroleum ether:ethyl acetate=10:1) showed that the reaction was completed. The reaction system was poured into 0.5 mol/L diluted hydrochloric acid (100 mL). The crude product was purified by column chromatography (100-200 mesh silica gel, petroleum ether:ethyl acetate=50:1 to 20:1) to give compound 13-3.

$^1$H NMR (400 MHz, CDCl$_3$) δ=5.55 (s, 1H), 4.43 (s, 1H), 3.32-3.26 (m, 1H), 2.41-2.38 (m, 1H), 2.30-2.28 (m, 1H), 2.15-2.14 (m, 1H), 2.13-2.04 (m, 1H), 2.03-2.01 (m, 1H), 1.54-1.49 (m, 2H), 1.46 (s, 9H), 1.43 (s, 9H), 1.33 (s, 3H).

Step 2

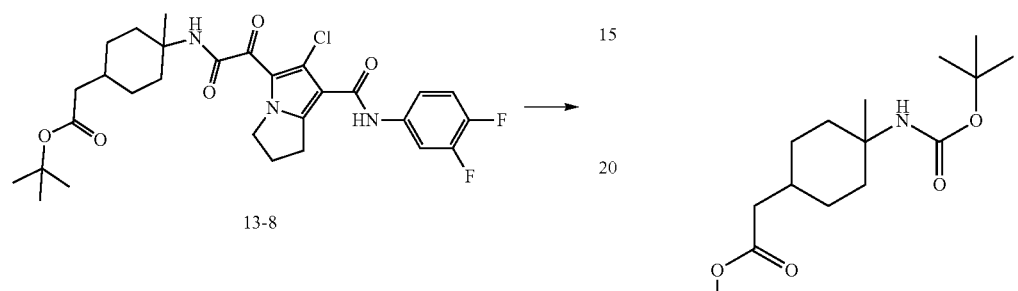

13-4

Wet palladium on carbon (200 mg, content: 10%) was dissolved in tetrahydrofuran (40 mL) in a hydrogenation flask, and compound 13-3 (1.35 g, 4.15 mmol, 1 eq.) was added. The reaction system was stirred at 25° C. for 2 h under hydrogen atmosphere (15 psi). TLC (petroleum ether: ethyl acetate=10:1) showed that the reaction was completed. The reaction solution was filtered and concentrated to give compound 13-4.

Step 3

13-5

Compound 13-4 (1.3 g, 3.97 mmol, 1 eq.) was dissolved in ethyl acetate (30 mL) in a dry single-neck flask, and hydrochloric acid/ethyl acetate (4 mol/L, 10 mL, 10.08 eq.) was added. The reaction system was stirred at 30° C. for 16 h. The reaction solution was directly concentrated to give compound 13-5.

$^1$H NMR (400 MHz, MeOH-d$_4$) δ=1.85-1.83 (m, 4H), 1.77-1.76 (m, 2H), 1.63-1.60 (m, 3H), 1.45 (s, 9H), 1.35-1.31 (m, 5H).

Step 4

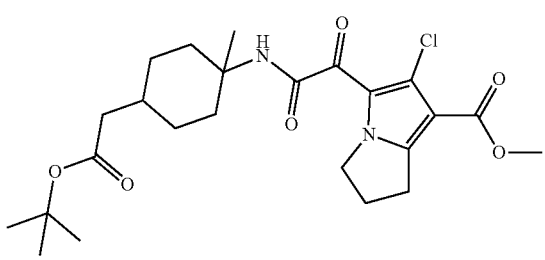
13-6

Compound 13-5 (250 mg, 861.77 μmol, 1 eq.) was dissolved in dichloromethane (10 mL) in a dry single-neck flask, and triethylamine (261.61 mg, 2.59 mmol, 359.85 μL, 3 eq.) was added. The resulting mixture was added with a solution of compound 11-7 (293.88 mg, 1.29 mmol, 1.5 eq.) in dichloromethane (10 mL) dropwise under nitrogen atmosphere at 0° C. The reaction system was stirred at 30° C. for 1 h. LCMS showed that the reaction was completed. The reaction solution was poured into water (50 mL). Then the aqueous phase was extracted with dichloromethane (20 mL×3), and the organic phase was washed with 0.5 mol/L diluted hydrochloric acid (20 mL×3), dried over anhydrous sodium sulfate, filtered and concentrated under reduced pressure to give compound 13-6. MS(ESI) m/s: 425.2 [M+H-(t-Bu)]$^+$.

$^1$H NMR (400 MHz, CDCl$_3$) δ=5.99 (s, 1H), 4.32 (t, J=7.6 Hz, 2H), 3.84 (s, 3H), 3.14 (t, J=7.6 Hz, 2H), 2.52-2.48 (m, 2H), 2.31-2.28 (m, 2H), 2.14-2.12 (m, 2H), 1.68-1.65 (m, 2H), 1.45-1.42 (m, 2H), 1.39-1.36 (m, 12H), 1.24-1.22 (m, 2H), 1.18-1.14 (m, 2H).

Step 5

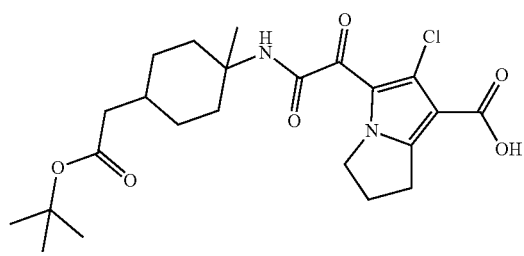
13-7

Compound 13-6 (90 mg, 187.12 μmol, 1 eq.) was dissolved in a mixture of tetrahydrofuran (3 mL), methanol (3 mL) and water (3 mL) in a flask, and lithium hydroxide monohydrate (23.55 mg, 561.35 μmol, 3 eq.) was added. The reaction system was stirred at 30° C. for 16 h. LCMS showed that the reaction was completed. The reaction solution was concentrated under reduced pressure to remove tetrahydrofuran and methanol, and diluted with 20 mL of water. Then the aqueous phase was washed with ethyl acetate (5 mL×2), adjusted to pH=1 with 0.5 mol/L diluted hydrochloric acid, and extracted with ethyl acetate (5 mL×3), and the organic phase was dried over anhydrous sodium sulfate, filtered, and concentrated under reduced pressure. The crude product was purified by prep-TLC (dichloromethane:methanol=10:1, V/V) to give compound 13-7. MS(ESI) m/s: 411.1 [M+H-(t-Bu)]$^+$.

$^1$H NMR (400 MHz, MeOH-d$_4$) δ=4.38-4.31 (m, 2H), 3.16-3.12 (m, 2H), 2.55-2.48 (m, 2H), 2.32-2.30 (m, 2H), 2.14-2.11 (m, 2H), 1.75-1.70 (m, 1H), 1.65-1.55 (m, 2H), 1.44 (s, 9H), 1.35-1.31 (m, 4H), 1.22 (s, 3H).

Step 6

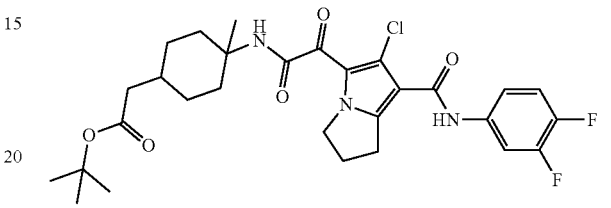
13-8

Compound 13-7 (70 mg, 149.91 μmol, 1 eq.) was dissolved in N,N-dimethylformamide (4 mL) in a dry flask, and O-(7-azabenzotriazol-1-yl)-N,N,N',N'-tetramethyluronium hexafluorophosphate (114.00 mg, 299.82 μmol, 2 eq.) and triethylamine (45.51 mg, 449.72 μmol, 62.60 μL, 3 eq.) were added under nitrogen atmosphere at 30° C. After stirring for 30 min, compound 1-9 (29.03 mg, 224.86 μmol, 1.5 eq.) was added, and the reaction system was heated to 60° C. and stirred for 15.5 h. LCMS showed that the reaction was completed. The reaction solution was poured into 0.2 mol/L diluted hydrochloric acid (50 mL), and then extracted with ethyl acetate (10 mL×3). The organic phase was dried over anhydrous sodium sulfate, filtered and concentrated under reduced pressure to give compound 13-8. MS(ESI) m/s: 522.1 [M+H-(t-Bu)]$^+$.

Step 7

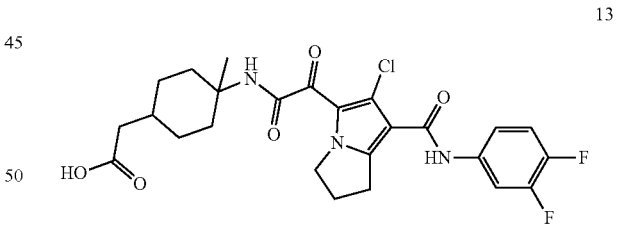
13

Compound 13-8 (50 mg, 86.50 μmol, 1 eq.) was dissolved in a mixture of trifluoroacetic acid (1 mL) and dichloromethane (2 mL) in a dry single-neck flask, and the reaction system was stirred at 25° C. for 1 h. LCMS and HPLC showed that the reaction was completed. The reaction solution was directly concentrated. The crude product was purified by prep-HPLC (neutral system, column: Waters Xbridge 150×25 mm×5 μm; mobile phase: water (containing 10 mM ammonium bicarbonate)-acetonitrile; acetonitrile %: 20%-40%, 12 min) to give compound 13. MS(ESI) m/s: 522.1 [M+H]$^+$.

$^1$H NMR (400 MHz, DMSO-d$_6$) δ=9.93 (s, 1H), 8.10 (s, 1H), 7.88-7.83 (m, 1H), 7.44-7.42 (m, 2H), 4.29 (t, J=6.8 Hz, 2H), 3.09 (t, J=8.0 Hz, 2H), 2.47-2.45 (m, 2H), 2.24-

2.22 (m, 2H), 2.09-2.07 (m, 2H), 1.65-1.60 (m, 1H), 1.54-1.51 (m, 2H), 1.35 (s, 3H), 1.24-1.23 (m, 4H).

Example 14

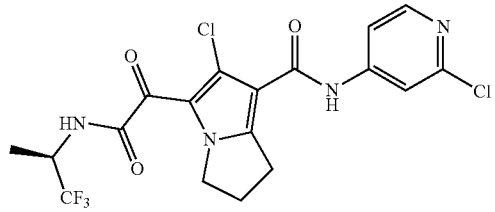

Synthetic Route:

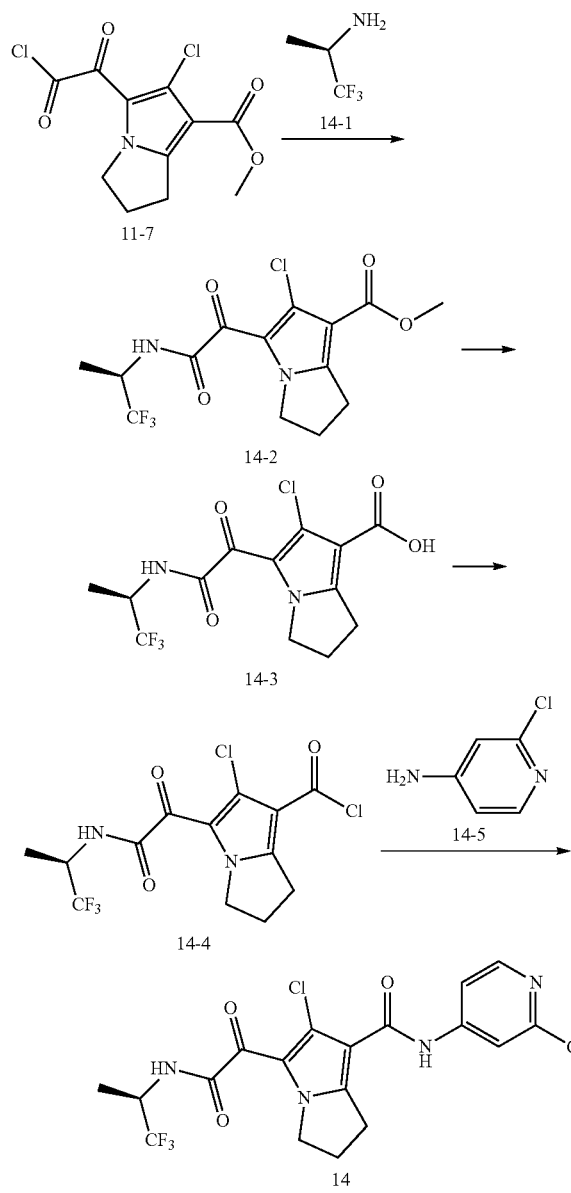

Step 1

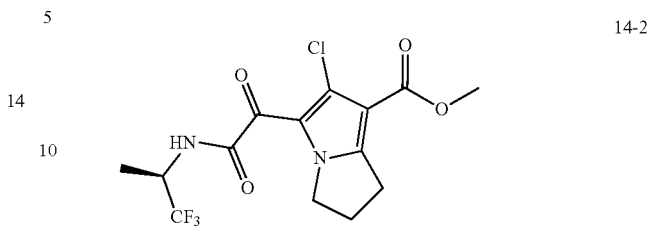

Compound 14-1 (124.74 mg, 1.10 mmol, 2 eq.) and triethylamine (167.43 mg, 1.65 mmol, 230.30 μL, 3 eq.) were dissolved in dichloromethane (5 mL), and then a solution of compound 11-7 (0.16 g, 551.54 μmol, 1 eq.) in dichloromethane (5 mL) was added at 0° C. under nitrogen atmosphere. The reaction system was stirred at 25° C. for 16 h. LCMS showed that compound 11-7 was completely consumed and compound 14-2 was produced. The reaction was quenched with 20 mL of water, and then the reaction solution was extracted with dichloromethane (15 mL×3). The organic phase was dried over anhydrous sodium sulfate, filtered and concentrated under reduced pressure to give compound 14-2. MS(ESI) m/s: 367.0 [M+H]$^+$.

$^1$H NMR (400 MHz, CDCl$_3$) δ=6.53 (d, J=9.6 Hz, 1H), 4.38-4.25 (m, 2H), 3.85 (s, 3H), 3.15-3.10 (m, 2H), 2.55-2.48 (m, 2H), 1.45-1.42 (m, 4H).

Step 2

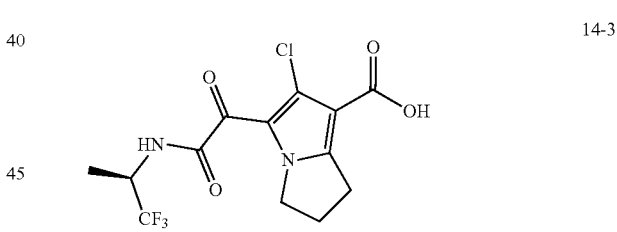

Compound 14-2 (0.19 g, 518.11 μmol, 1 eq.) was dissolved in a mixture of methanol (5 mL), tetrahydrofuran (5 mL) and water (5 mL), and then lithium hydroxide monohydrate (65.22 mg, 1.55 mmol, 3 eq.) was added. The reaction system was stirred at 25° C. for 2 h. TLC (dichloromethane:methanol=20:1) showed that compound 14-2 was completely consumed and new spots were produced. The reaction solution was adjusted to pH=1-3 with 1 M hydrochloric acid, and extracted with ethyl acetate (20 mL×3). The organic phase was dried over anhydrous sodium sulfate, filtered and concentrated under reduced pressure to give compound 14-3.

$^1$H NMR (400 MHz, MeOH-d$_4$) δ=4.76-4.69 (m, 1H), 4.36 (t, J=7.2 Hz, 2H), 3.15 (t, J=7.6 Hz, 2H), 2.56-2.49 (m, 2H), 1.40 (d, J=7.0 Hz, 3H).

Step 3

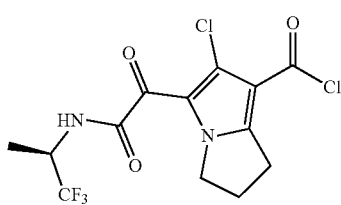
14-4

Compound 14-3 (0.1 g, 283.53 μmol, 1 eq.) was dissolved in dichloromethane (5 mL), and then oxalyl chloride (71.98 mg, 567.07 μmol, 49.64 μL, 2 eq.) and N,N-dimethylformamide (2.07 mg, 28.35 μmol, 2.18 μL, 0.1 eq.) were added at 0° C. under nitrogen atmosphere. The reaction system was stirred at 25° C. for 0.5 h. TLC (petroleum ether:ethyl acetate=3:1) showed that compound 14-3 was completely consumed and new spots were produced. The reaction solution was directly concentrated under reduced pressure to give compound 14-4.

Step 4

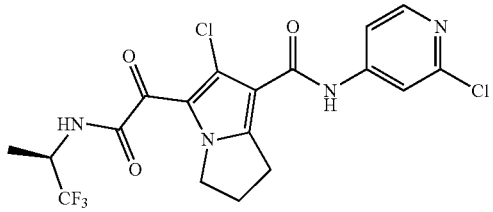
14

Compound 14-5 (69.28 mg, 538.88 μmol, 2 eq.) and triethylamine (81.79 mg, 808.32 μmol, 112.51 μL, 3 eq.) were dissolved in dichloromethane (5 mL), and then a solution of compound 14-4 (0.1 g, 269.44 μmol, 1 eq.) in dichloromethane (5 mL) was added at 0° C. under nitrogen atmosphere. The reaction system was heated to 25° C. and stirred for 1 h. LCMS and HPLC confirmed that compound 14-4 was completely consumed and compound 14 was produced. The reaction solution was poured into 20 mL of water to quench the reaction, and extracted with dichloromethane (15 mL×3). The organic phase was dried over anhydrous sodium sulfate, filtered and concentrated under reduced pressure. The residue was purified by prep-HPLC (neutral; column: Waters Xtimate C18 150 mm×25 mm×5 μm; mobile phase: water (containing 0.04% ammonium hydroxide+10 mM ammonium bicarbonate)-acetonitrile; acetonitrile %: 37%-57%, 10.5 min) to give compound 14. MS(ESI) m/s: 463.0 [M+H]$^+$.

$^1$H NMR (400 MHz, DMSO-d$_6$) δ=10.37 (s, 1H), 9.45 (s, 1H), 8.25 (d, J=6.0 Hz, 1H), 7.79 (d, J=1.6 Hz, 1H), 7.57 (dd, J=2.0, 6.0 Hz, 1H), 4.72-4.67 (m, 1H), 4.30 (t, J=7.2 Hz, 2H), 3.13-3.10 (m, 2H), 2.47-2.43 (m, 2H), 1.31 (d, J=6.8 Hz, 3H).

Example 15

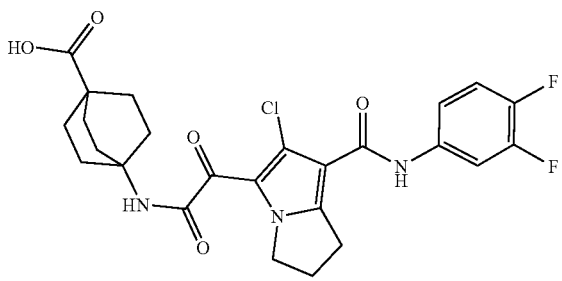
15

Synthetic Route:

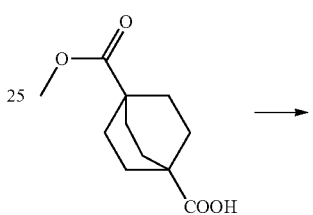
15-1

15-2

15-3

1-9

1-3

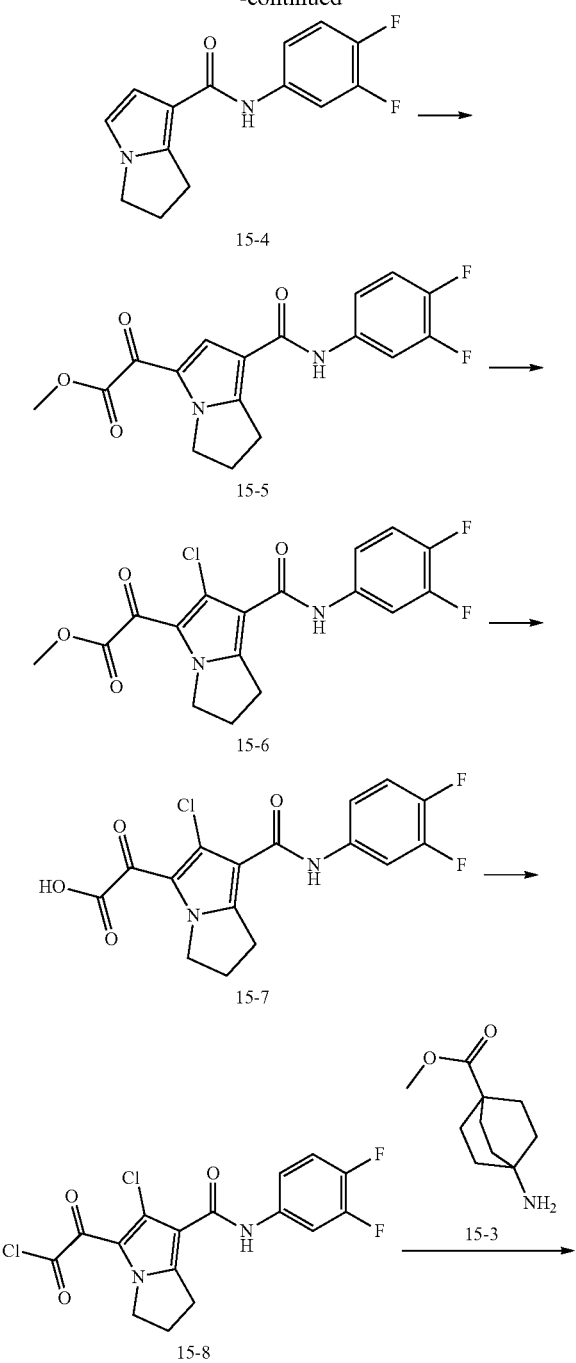

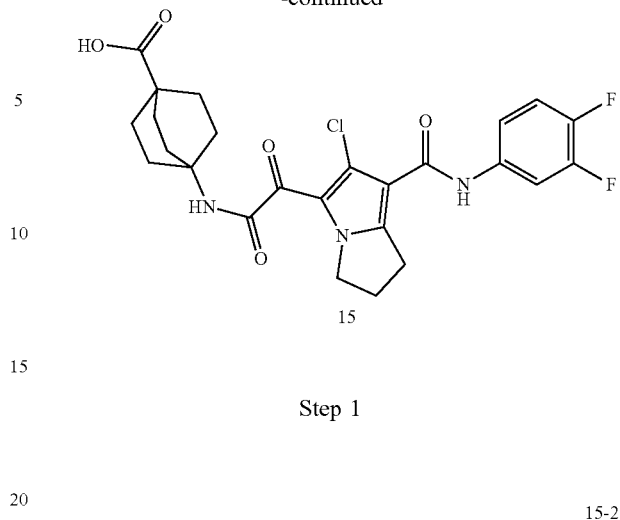

Step 1

Compound 15-1 (1.5 g, 7.07 mmol, 1 eq.), triethylamine (1.07 g, 10.60 mmol, 1.48 mL, 1.5 eq.) and benzyl alcohol (1.53 g, 14.13 mmol, 1.47 mL, 2 eq.) were added to toluene (15 mL), and then diphenylphosphoryl azide (2.33 g, 8.48 mmol, 1.84 mL, 1.2 eq.) was added. The reaction system was stirred at 110° C. for 16 h. LCMS confirmed that compound 15-1 was completely consumed and compound 15-2 was produced; TLC (petroleum ether:ethyl acetate=5:1) showed that new spots were produced. The reaction solution was poured into saturated ammonium chloride solution (30 mL) to quench the reaction, and extracted with ethyl acetate (20 mL×3). The organic phase was dried over anhydrous sodium sulfate, filtered and concentrated under reduced pressure. The crude product was purified by column chromatography (100-200 mesh silica gel, petroleum ether: ethyl acetate=100:1 to 10:1, V/V) to give compound 15-2. MS(ESI) m/s: 318.1 [M+H]$^+$.

Step 2

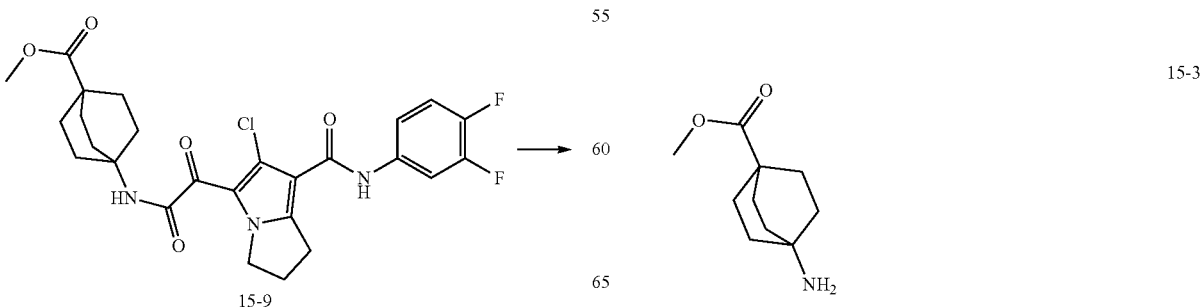

Wet palladium on carbon (1 g, purity: 10%) was dissolved in methanol (20 mL), and then compound 15-2 (2 g, 6.30 mmol, 1 eq.) was added. The reaction system was stirred at 25° C. for 16 h under hydrogen atmosphere (50 psi). TLC (petroleum ether:ethyl acetate=5:1) showed that compound 15-2 was completely consumed and new spots were produced. After the reaction solution was filtered, hydrochloric acid in methanol (4 mol/L, 50 mL) was added. The resulting mixture was stirred for 0.5 h, and concentrated under reduced pressure to give compound 15-3.

$^1$H NMR (400 MHz, MeOH-$d_4$) δ=3.65 (s, 3H), 1.99-1.81 (m, 12H).

Step 3

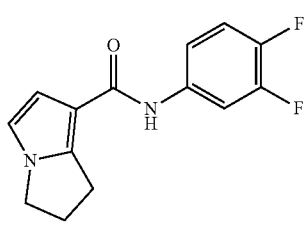

15-4

Compound 1-3 (15 g, 90.81 mmol, 1 eq.) and compound 1-9 (17.59 g, 136.21 mmol, 1.5 eq.) were dissolved in toluene (450 mL) in a dry flask, and lithium hexamethyldisilazide (1 mol/L, 181.61 mL, 2 eq.) was slowly added at 0° C. The reaction system was stirred at 25° C. for 16 h. TLC (petroleum ether:ethyl acetate=3:1) showed that compound 1-3 was completely consumed. The reaction solution was poured into saturated ammonium chloride (200 mL), and extracted with ethyl acetate (200 mL×3). The organic phase was dried over anhydrous sodium sulfate, filtered and concentrated under reduced pressure to give a crude product. The crude product was purified by column chromatography (100-200 mesh silica gel, petroleum ether:ethyl acetate=5:1 to 1:1, V/V) to give compound 15-4.

$^1$H NMR (400 MHz, CDCl$_3$) δ=7.70-7.66 (m, 2H), 7.13-7.11 (m, 1H), 7.02-7.00 (m, 1H), 6.54 (d, J=2.8 Hz, 1H), 6.48 (d, J=2.8 Hz, 1H), 3.93 (t, J=7.6 Hz, 2H), 3.09 (t, J=7.2 Hz, 2H), 2.56-2.48 (m, 2H).

Step 4

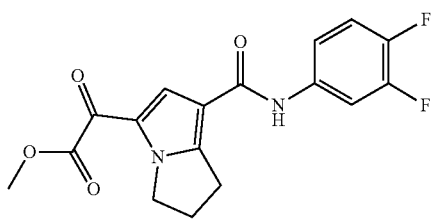

15-5

Compound 15-4 (12 g, 45.76 mmol, 1 eq.) was dissolved in dichloromethane (20 mL), and then methyl oxalyl chloride (11.21 g, 91.51 mmol, 8.43 mL, 2 eq.) was added. The reaction system reacted at 25° C. for 16 h. LCMS showed that compound 15-4 was completely consumed and compound 15-5 was produced. The reaction solution was poured into saturated sodium bicarbonate solution (200 mL), and extracted with ethyl acetate (200 mL×3). The organic phase was dried over anhydrous sodium sulfate, filtered and concentrated under reduced pressure. The crude product was purified by column chromatography (100-200 mesh silica gel, petroleum ether:ethyl acetate=5:1 to 1:1, V/V) to give compound 15-5. MS(ESI) m/s: 349.0 [M+H]$^+$.

$^1$H NMR (400 MHz, CDCl$_3$) δ=7.74-7.69 (m, 3H), 7.16-7.09 (m, 2H), 4.39 (t, J=7.6 Hz, 2H), 3.93 (s, 3H), 3.21 (t, J=7.6 Hz, 2H), 2.65-2.55 (m, 2H).

Step 5

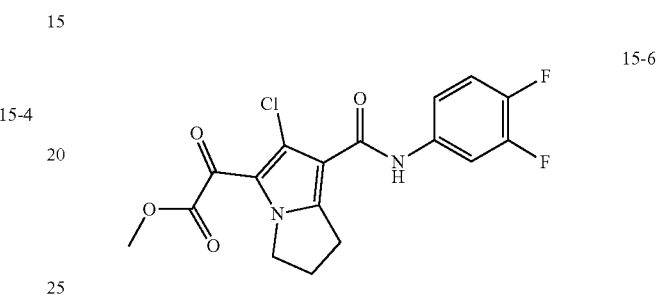

15-6

Compound 15-5 (5.37 g, 15.42 mmol, 1 eq.) was dissolved in acetic acid (110 mL), and then N-chlorosuccinimide (3.29 g, 24.67 mmol, 1.6 eq.) was added. The reaction system reacted at 40° C. for 16 h. LCMS showed that compound 15-6 was produced. The reaction solution was poured into water (200 mL), and extracted with ethyl acetate (200 mL×3). The organic phase was washed with saturated sodium bicarbonate (1000 mL), dried over anhydrous sodium sulfate, filtered and concentrated under reduced pressure to give a crude product. The crude product was purified by column chromatography (100-200 mesh silica gel, petroleum ether:ethyl acetate=3:1 to 1:5, V/V) to give compound 15-6. MS(ESI) m/s: 383.0 [M+H]$^+$.

Step 6

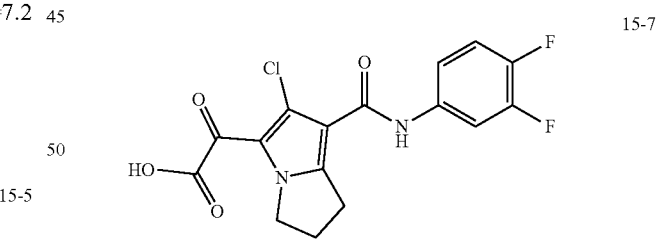

15-7

Compound 15-6 (6.6 g, 17.24 mmol, 1 eq.) was dissolved in a mixture of tetrahydrofuran (40 mL), ethanol (40 mL) and water (40 mL), and lithium hydroxide monohydrate (2.17 g, 51.73 mmol, 3 eq.) was added. The reaction system was stirred at 40° C. for 1 h. LCMS showed that the reaction was completed. The reaction solution was concentrated under reduced pressure to remove the solvent, then diluted with water (100 mL) and washed with ethyl acetate (30 mL×2). The aqueous phase was adjusted to pH=1 with 0.5 M diluted hydrochloric acid and then filtered directly. The filter cake was slurried and washed with dichloromethane (50 mL) and filtered. The resulting filter cake was concentrated under reduced pressure to give compound 15-7. MS(ESI) m/s: 369.1 [M+H]⁺.

¹H NMR (400 MHz, MeOH-d4) δ=7.78-7.73 (m, 1H), 7.31-7.25 (m, 1H), 7.24-7.19 (m, 1H), 4.40-4.39 (m, 2H), 3.19-3.13 (m, 2H), 2.63-2.54 (m, 2H).

Step 7

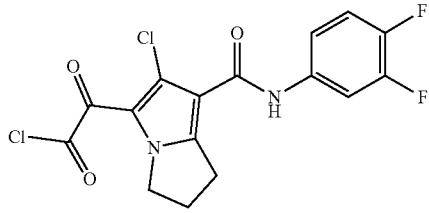

15-8

Compound 15-7 (1.1 g, 2.98 mmol, 1 eq.) was dissolved in dichloromethane (20 mL), and oxalyl chloride (757.34 mg, 5.97 mmol, 522.30 µL, 2 eq.) and N,N-dimethylformamide (21.80 mg, 298.33 µmol, 22.95 µL, 0.1 eq.) were added dropwise under nitrogen atmosphere at 0° C. The reaction system was stirred at 25° C. for 0.5 h. LCMS showed that the reaction was completed. The reaction solution was directly concentrated under reduced pressure to give compound 15-8.

Step 8

15-9

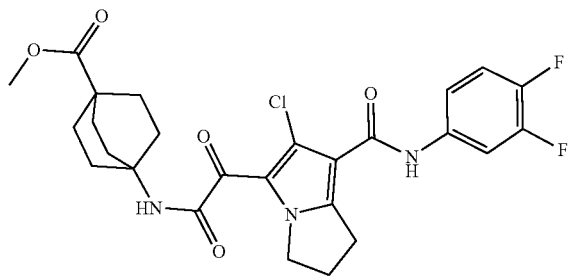

Compound 15-3 (170.24 mg, 774.86 µmol, 1.5 eq., HCl) and triethylamine (156.82 mg, 1.55 mmol, 215.70 µL, 3 eq.) were dissolved in dichloromethane (10 mL), and then a solution of compound 15-8 (0.2 g, 516.58 µmol, 1 eq.) in dichloromethane (10 mL) was added at 0° C. under nitrogen atmosphere. The reaction system was stirred at 30° C. for 16 h. LCMS confirmed that compound 15-8 was completely consumed and compound 15-9 was produced. The reaction solution was diluted with 1 M diluted hydrochloric acid (20 mL), and extracted with dichloromethane (20 mL×2). The organic phase was dried over anhydrous sodium sulfate, filtered and concentrated under reduced pressure to give compound 15-9. MS(ESI) m/s: 534.2 [M+H]⁺.

¹H NMR (400 MHz, CDCl₃) δ=8.48 (s, 1H), 7.76-7.71 (m, 1H), 7.47-7.40 (m, 1H), 7.15-7.11 (m, 2H), 4.32 (t, J=7.6 Hz, 2H), 3.67 (s, 3H), 3.26 (t, J=8.0 Hz, 2H), 2.56-2.48 (m, 2H), 2.07-1.97 (m, 12H).

Step 9

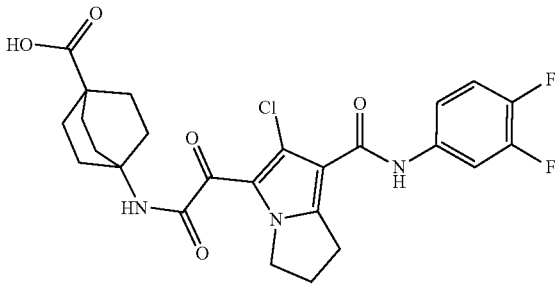

15

Compound 15-9 (0.3 g, 561.85 µmol, 1 eq.) was dissolved in a mixture of water (3 mL) and dimethyl sulfoxide (6 mL), and then lithium hydroxide monohydrate (70.73 mg, 1.69 mmol, 3 eq.) was added. The reaction system was stirred at 30° C. for 2 h. LCMS and HPLC confirmed that the reaction was completed. The reaction solution was filtered, and the filtrate was collected. The filtrate was purified by prep-HPLC (neutral, column: Xtimate C18 150 mm×25 mm×5 µm; mobile phase: water (containing 10 mM ammonium bicarbonate)-acetonitrile; acetonitrile %: 5%-50%, 20 min) to give compound 15. MS(ESI) m/s: 518.2 [M-H]⁺.

¹H NMR (400 MHz, DMSO-d₆) δ=9.92 (s, 1H), 8.35 (s, 1H), 7.87-7.82 (m, 1H), 7.43-7.39 (m, 2H), 4.26 (t, J=7.0 Hz, 2H), 3.07 (t, J=7.4 Hz, 2H), 2.45-2.42 (m, 2H), 1.92-1.75 (m, 12H).

Example 16

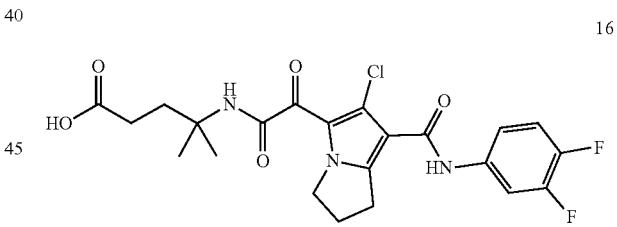

16

Synthetic Route:

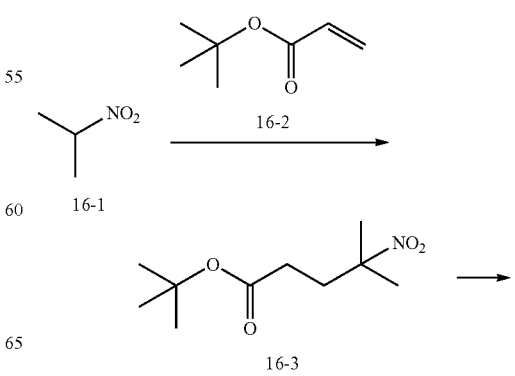

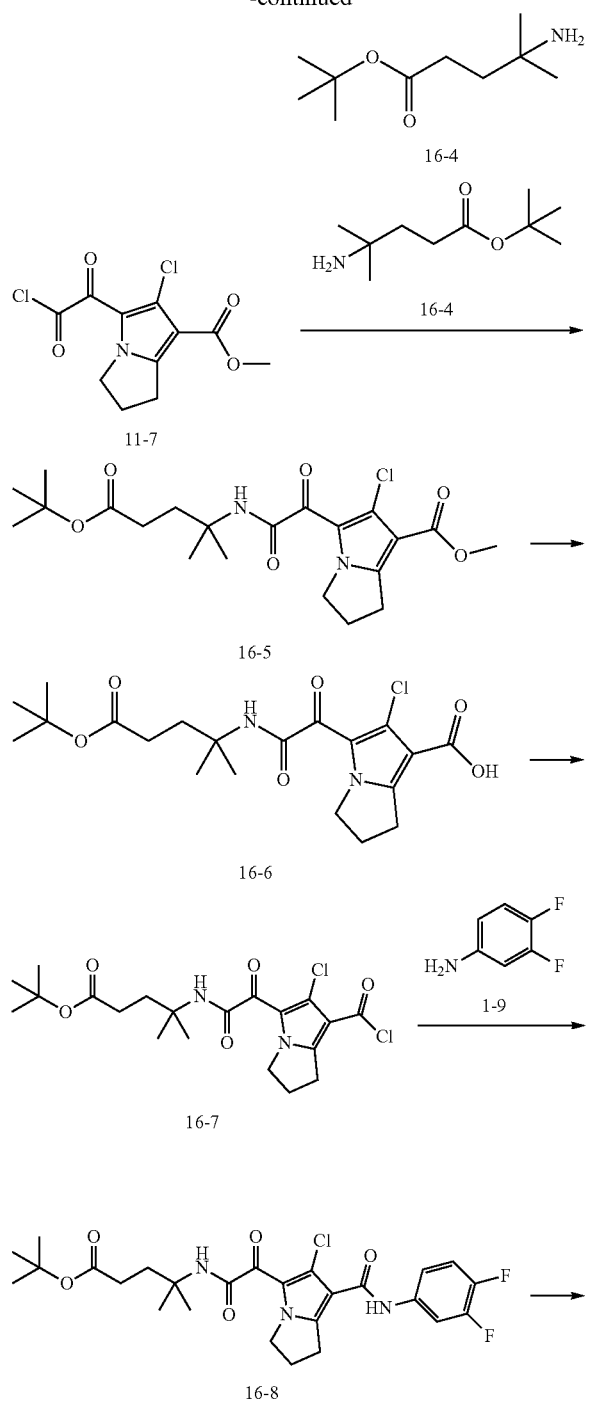

Step 1

Compound 16-1 (1 g, 11.22 mmol, 1.01 mL, 1 eq.) and 1,8-diazabicyclo[5.4.0]undec-7-ene (3.42 g, 22.45 mmol, 3.38 mL, 2 eq.) were added to anhydrous dichloromethane (10 mL), and then the reaction system was added with compound 16-2 (1.73 g, 13.47 mmol, 1.2 eq.) and stirred at 45° C. for 12 h. TLC (petroleum ether:ethyl acetate=5:1) showed that compound 16-1 was completely consumed. The reaction solution was poured into saturated ammonium chloride solution (20 mL), and extract with dichloromethane (10 mL×3). The organic phase was dried over anhydrous sodium sulfate, filtered and concentrated under reduced pressure. The crude product was purified by column chromatography (100-200 mesh silica gel, petroleum ether:ethyl acetate=100:1 to 5:1, V/V) to give compound 16-3.

Step 2

Raney nickel (266.67 mg, 3.11 mmol, 1.69 eq.) was added into a hydrogenation flask, and rinsed with ethanol (10 mL×2). Ethanol (5 mL) and compound 16-3 (0.4 g, 1.84 mmol, 1 eq.) were added. The reaction system was stirred at 25° C. for 4 h under hydrogen atmosphere (50 psi). TLC (petroleum ether:ethyl acetate=5:1) showed that compound 16-3 was completely consumed and new spots were produced. The reaction solution was directly filtered, and the filtrate was concentrated under reduced pressure to give compound 16-4.

$^1$H NMR (400 MHz, DMSO-$d_6$) δ=2.21 (t, J=8.0 Hz, 2H), 1.49 (t, J=8.0 Hz, 2H), 1.39 (s, 9H), 0.96 (s, 6H).

Step 3

Compound 16-4 (0.32 g, 1.71 mmol, 1.24 eq.) was added to dichloromethane (10 mL), and then triethylamine (697.62 mg, 6.89 mmol, 959.59 µL, 5 eq.) was added to the reaction system. Then the reaction system was cooled to 0° C. Compound 11-7 (0.4 g, 1.38 mmol, 1 eq.) was dissolved in anhydrous dichloromethane (10 mL) and the resulting solution was added dropwise to the reaction system. The reaction system was stirred at 20° C. for 1 h. LCMS showed that the reaction was completed. The reaction solution was washed with saturated ammonium chloride (10 mL×3). The organic phase was dried over anhydrous sodium sulfate, filtered and concentrated under reduced pressure to give compound 16-5. MS(ESI) m/s: 385.1 [M+H-(t-Bu)]⁺.

¹H NMR (400 MHz, DMSO-$d_6$) δ=8.29 (s, 1H), 4.26 (t, J=7.6 Hz, 2H), 3.74 (s, 3H), 3.05 (t, J=7.6 Hz, 2H), 2.46-2.40 (m, 2H), 2.25-2.21 (m, 2H), 1.93-1.88 (m, 2H), 1.39 (s, 9H), 1.28 (s, 6H).

Step 4

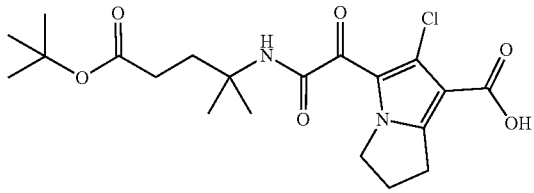

16-6

Compound 16-5 (0.1 g, 226.80 μmol, 1 eq.) was added into a flask with tetrahydrofuran (3 mL), methanol (3 mL) and water (3 mL), and then the reaction system was added with lithium hydroxide monohydrate (47.58 mg, 1.13 mmol, 5 eq.) and stirred at 25° C. for 12 h. LCMS showed that compound 16-5 was completely consumed. The reaction solution was added with water (20 mL), adjusted to pH=3 with 1 M hydrochloric acid, and extracted with ethyl acetate (10 mL×2). The organic phase was dried over anhydrous sodium sulfate, filtered and concentrated under reduced pressure. The crude product was purified by prep-HPLC (neutral, column: Xtimate C18 150 mm×25 mm×5 μm; mobile phase: water (containing 0.04% ammonium hydroxide+10 mM ammonium bicarbonate)-acetonitrile; acetonitrile %: 15%-45%, 10.5 min) to give compound 16-6. MS(ESI) m/s: 371.1 [M+H-(t-Bu)]⁺.

¹H NMR (400 MHz, DMSO-$d_6$) δ=12.50 (s, 1H), 8.26 (s, 1H), 4.25 (t, J=6.8 Hz, 2H), 3.09 (t, J=6.8 Hz, 2H), 2.43-2.41 (m, 2H), 2.26-2.22 (m, 2H), 1.93-1.89 (m, 2H), 1.40 (s, 9H), 1.29 (s, 6H).

Step 5

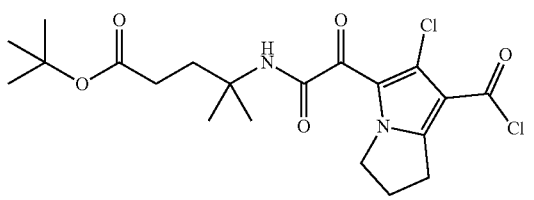

16-7

Compound 16-6 (20 mg, 46.85 μmol, 1 eq.) was added to anhydrous dichloromethane (2 mL). The reaction system was cooled to 0° C., successively added with oxalyl chloride (11.89 mg, 93.70 μmol, 8.20 μL, 2 eq.) and N,N-dimethylmethanamide (3.42 mg, 46.85 μmol, 3.60 μL, 1 eq.), and stirred at 0° C. for 10 min. A drop of the reaction solution was taken and added with 1 mL of methanol to quench the reaction. LCMS showed that compound 16-6 was completely consumed and new spots were produced. The reaction solution was directly concentrated under reduced pressure to give compound 16-7.

Step 6

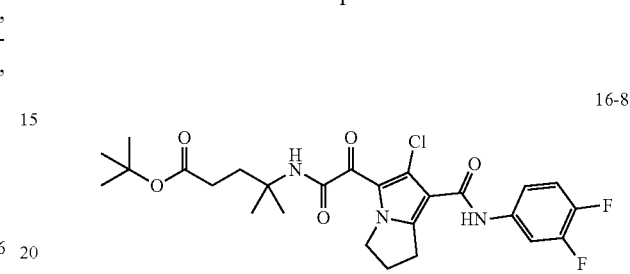

16-8

Compound 1-9 (18.14 mg, 140.52 μmol, 3 eq.) and triethylamine (23.70 mg, 234.21 μmol, 32.60 μL, 5 eq.) were added to anhydrous dichloromethane (5 mL), and the reaction system was cooled to 0° C. Compound 16-7 (20.86 mg, 46.84 μmol, 1 eq.) was dissolved in anhydrous dichloromethane (5 mL), and the resulting solution was added dropwise to the reaction system. The reaction system reacted at 0° C. for 1 h. LCMS showed that compound 16-7 was completely consumed. The reaction solution was poured into saturated ammonium chloride (10 mL) and extracted with dichloromethane (10 mL×3). The organic phase was dried over anhydrous sodium sulfate, filtered and concentrated under reduced pressure to give compound 16-8, which was directly used in the next step.

MS(ESI) m/s: 482.1 [M+H-(t-Bu)]⁺.

Step 7

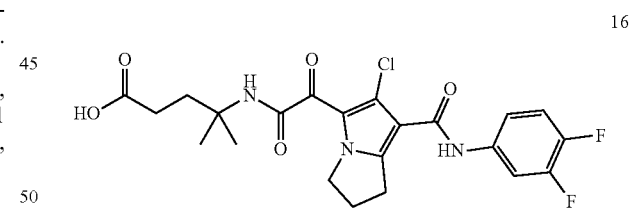

16

Compound 16-8 (25.2 mg, 46.84 μmol, 1 eq.) was added to anhydrous dichloromethane (2 mL). The reaction system was then added with triethylamine (267.04 mg, 2.34 mmol, 173.41 μL, 50 eq.) and stirred at 25° C. for 0.5 h. LCMS showed that compound 16-8 was completely consumed and compound 16 was produced. The reaction solution was washed with water (20 mL×2), and the obtained organic phase was dried over anhydrous sodium sulfate, filtered and concentrated under reduced pressure. The crude product was purified by prep-HPLC (neutral, column: Xtimate C18 150 mm×25 mm×5 μm; mobile phase: water (containing 0.04% ammonium hydroxide+10 mM ammonium bicarbonate)-acetonitrile; acetonitrile %: 15%-35%, 20 min) to give compound 16.

MS(ESI) m/s: 482.0 [M+H]⁺.

¹H NMR (400 MHz, DMSO-d₆) δ=9.97 (s, 1H), 8.49 (s, 1H), 7.57 (d, J=11.6 Hz, 1H), 7.43 (s, 2H), 4.28-4.26 (m, 2H), 3.07 (m, 2H), 2.25 (m, 4H), 1.94-1.92 (m, 2H), 1.38 (s, 6H).

Example 17

Synthetic Route:

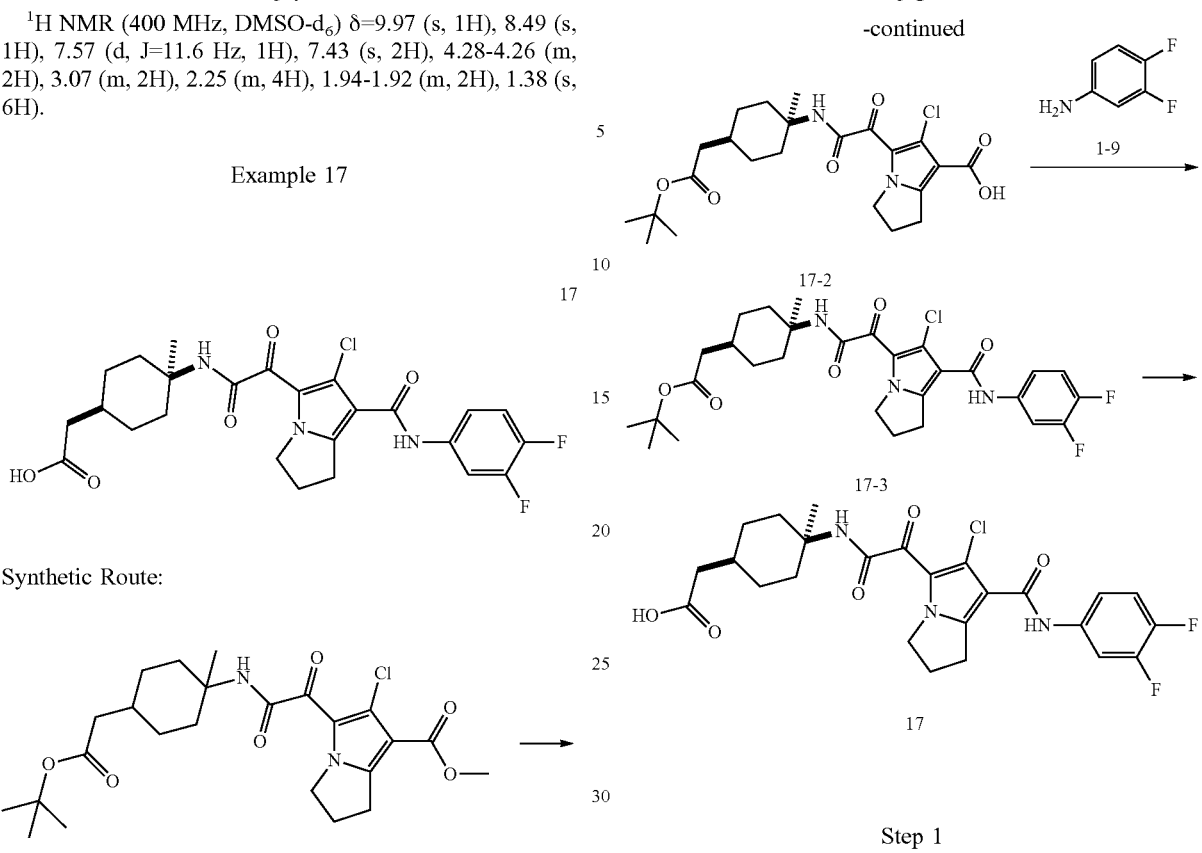

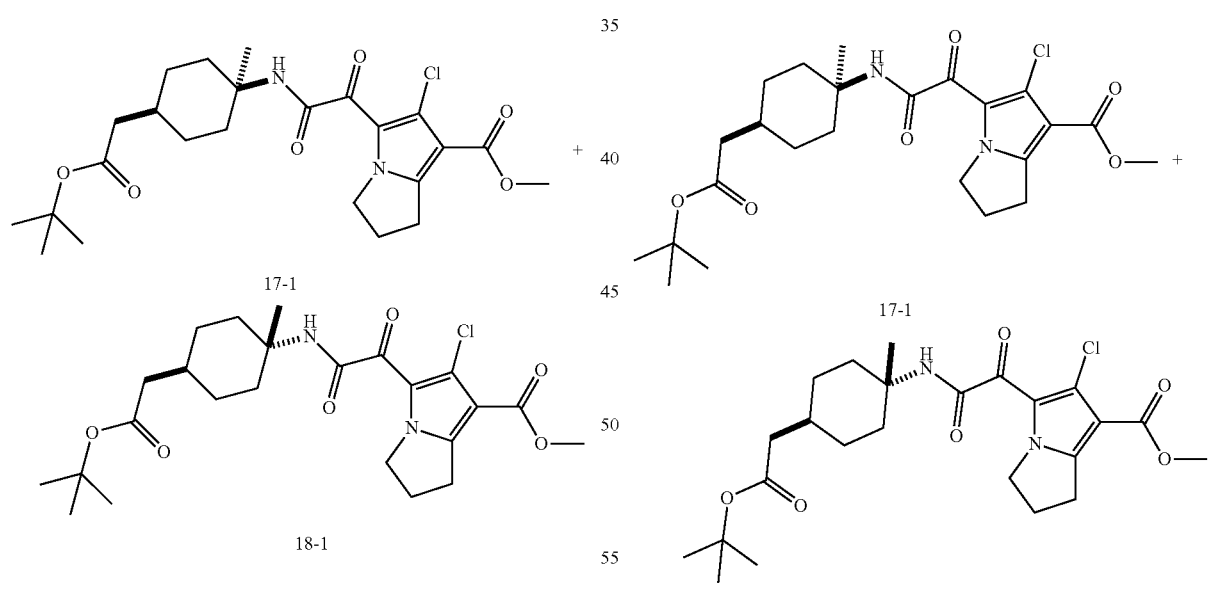

Step 1

Compound 13-6 was separated by SFC (column: DAICELCHIRALCELOJ (250 mm×30 mm, 10 μm); mobile phase: Neu-ETOH; B %: 30%-30%, 9 min). Compound 17-1 (retention time in SFC: 1.16 min) and compound 18-1 (retention time in SFC: 1.7 min) were obtained. SFC analysis conditions: column: Daicel OJ-3 chiral column, with a specification of 0.46 cm id×5 cm; mobile phase: A: carbon dioxide, B: ethanol for chromatography (containing 0.05% isopropylamine); B %: 5%-40%; flow rate: 4 mL/min; 4 min; system back pressure: 100 bar.

Compound 17-1: $^1$H NMR (400 MHz, CDCl$_3$) δ=6.00 (s, 1H), 4.32 (t, J=7.2 Hz, 2H), 3.84 (s, 3H), 3.14 (t, J=7.8 Hz, 2H), 2.52-2.48 (m, 2H), 2.31-2.28 (d, J=12.8 Hz, 2H), 2.14-2.12 (d, J=7.2 Hz, 2H), 1.76-1.74 (m, 1H), 1.74-1.67 (m, 2H), 1.48 (s, 3H), 1.44 (s, 9H), 1.42-1.38 (m, 2H), 1.35-1.18 (m, 2H).

Compound 18-1: $^1$H NMR (400 MHz, CDCl$_3$) δ=6.08 (s, 1H), 4.31 (t, J=7.4 Hz, 2H), 3.83 (s, 3H), 3.12 (t, J=7.6 Hz, 2H), 2.51-2.47 (m, 2H), 2.17-2.15 (m, 2H), 2.14-2.00 (m, 2H), 1.83-1.70 (m, 3H), 1.48 (s, 3H), 1.47-1.45 (m, 10H), 1.45-1.26 (m, 3H).

Step 2

17-2

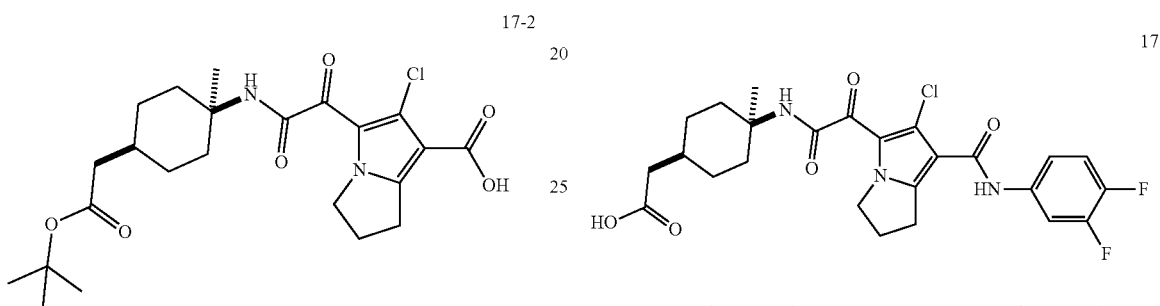

Compound 17-1 (360.00 mg, 748.47 μmol, 1 eq.) was dissolved in a mixture of tetrahydrofuran (10 mL), methanol (10 mL) and water (10 mL) in a single-neck flask, and lithium hydroxide monohydrate (157.03 mg, 3.74 mmol, 5 eq.) was added. The reaction system was stirred at 30° C. for 16 h. LCMS showed that the reaction was completed. The reaction solution was adjusted to pH=1 with 0.5 M diluted hydrochloric acid. The aqueous phase was extracted with ethyl acetate (20 mL×3). The organic phase was dried over anhydrous sodium sulfate, filtered and concentrated under reduced pressure to give compound 17-2.

MS(ESI) m/s: 411.1 [M+H-(t-Bu)]$^+$.

Step 3

17-3

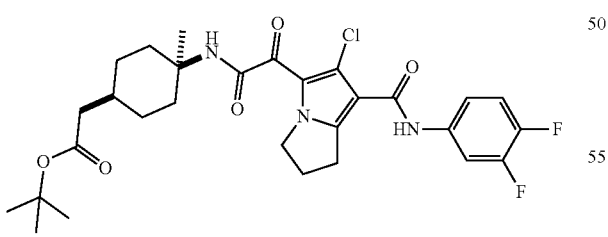

Compound 17-2 (330.00 mg, 706.71 μmol, 1 eq.) was dissolved in N,N-dimethylformamide (15 mL) in a dry flask, and triethylamine (214.54 mg, 2.12 mmol, 295.10 μL, 3 eq.), O-(7-azabenzotriazol-1-yl)-N,N,N',N'-tetramethyluronium hexafluorophosphate (537.42 mg, 1.41 mmol, 2 eq.) and compound 1-9 (182.48 mg, 1.41 mmol, 2 eq.) were added. The reaction system was stirred at 60° C. for 16 h under nitrogen atmosphere. LCMS showed that the reaction was completed. The reaction solution was diluted with ethyl acetate (50 mL), and then washed with 0.5 M diluted hydrochloric acid (10 mL×2). The organic phase was dried over anhydrous sodium sulfate, filtered and concentrated under reduced pressure. The crude product was purified by column chromatography (100-200 mesh silica gel, petroleum ether:ethyl acetate=10:1 to 1:1, V/V) to give compound 17-3. MS(ESI) m/s: 578.2 [M+H]$^+$.

$^1$H NMR (400 MHz, CDCl$_3$) δ=8.48 (d, 7.6 Hz, 1H), 7.77-7.72 (m, 1H), 7.16-7.09 (m, 2H), 6.20 (s, 1H), 4.33 (t, J=7.6 Hz, 2H), 3.26 (t, J=7.6 Hz, 2H), 2.56-2.49 (m, 2H), 2.32-2.30 (m, 2H), 1.78-1.67 (m, 5H), 1.48 (s, 3H), 1.45 (s, 9H), 1.41-1.38 (m, 2H), 1.37-1.17 (m, 2H).

Step 4

17

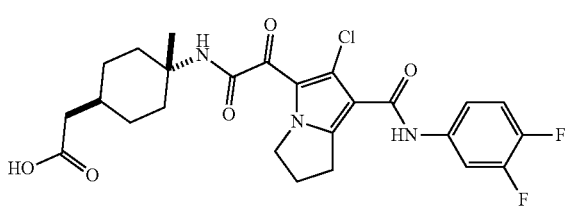

Compound 17-3 (280 mg, 484.39 μmol, 1 eq.) was dissolved in dichloromethane (6 mL) in a dry single-neck flask, and trifluoroacetic acid (4.62 g, 40.52 mmol, 3 mL, 83.65 eq.) was added. The reaction system was stirred at 25° C. for 1 h. LCMS and HPLC showed that the reaction was completed. The reaction solution was concentrated under reduced pressure. The crude product was purified by prep-HPLC (neutral system, column: Waters Xbridge 150 mm×25 mm×5 μm; mobile phase: water (containing 0.04% ammonium hydroxide+10 mM ammonium bicarbonate)-acetonitrile; acetonitrile %: 16%-46%, 10.5 min) to give compound 17 (column: Daicel AS-3 chiral column, with a specification of 0.46 cm id×10 cm; mobile phase: A: carbon dioxide, B: ethanol for chromatography (containing 0.05% isopropylamine); B %: 5%-40%; flow rate: 4 mL/min; 5 min; system back pressure: 100 bar), and the retention time in SFC was 2.18 min. MS(ESI) m/s: 522.1 [M+H]$^+$.

$^1$H NMR (400 MHz, DMSO-d$_6$) δ=9.91 (s, 1H), 8.08 (s, 1H), 7.87-7.82 (m, 1H), 7.43-7.39 (m, 2H), 4.29 (t, J=7.2 Hz, 2H), 3.08 (t, J=7.4 Hz, 2H), 2.46-2.45 (m, 2H), 2.23 (d, J=10.4 Hz, 2H), 2.07 (d, J=6.8 Hz, 2H), 1.63 (s, 1H), 1.50 (d, J=7.6 Hz, 2H), 1.34 (s, 3H), 1.29-1.20 (m, 4H).

Example 18

18

Synthetic Route:

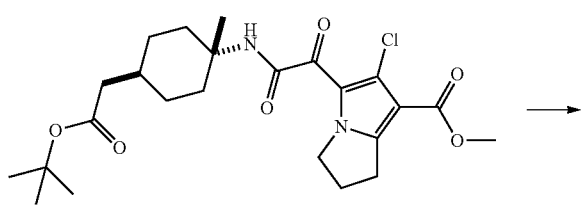

18-1

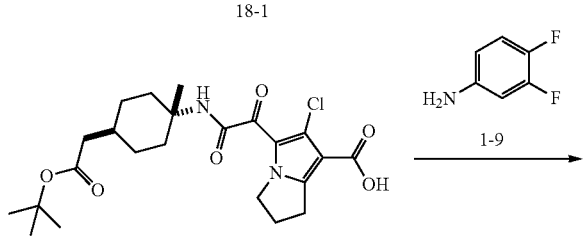

18-2

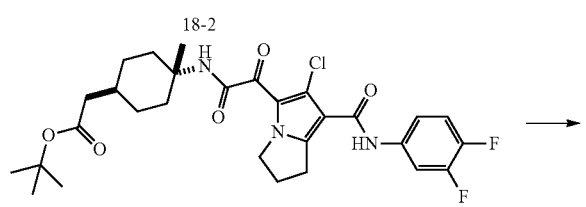

18-3

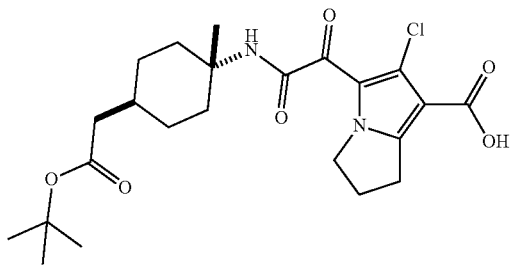

18

Step 1

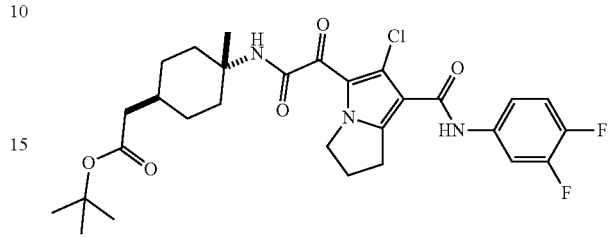

18-2

Compound 18-1 (550.00 mg, 1.14 mmol, 1 eq.) was dissolved in a mixture of tetrahydrofuran (10 mL), water (10 mL) and methanol (10 mL) in a single-neck flask, and lithium hydroxide monohydrate (239.91 mg, 5.72 mmol, 5 eq.) was added. The reaction system was stirred at 30° C. for 16 h. LCMS showed that the reaction was completed. The reaction solution was adjusted to pH=1 with 0.5 mol/L diluted hydrochloric acid. The aqueous phase was extracted with ethyl acetate (20 mL×3), and the organic phase was dried over anhydrous sodium sulfate, filtered and concentrated under reduced pressure to give compound 18-2. MS(ESI) m/s: 467.1 [M+H]$^+$.

Step 2

18-3

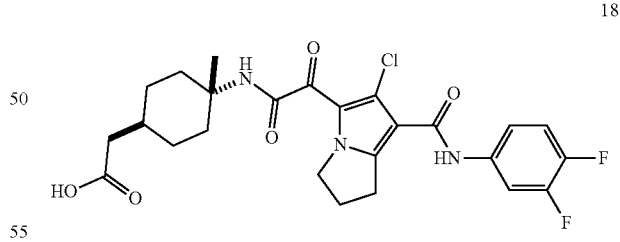

Compound 18-2 was dissolved in N,N-dimethylformamide (15 mL), and O-(7-azabenzotriazol-1-yl)-N,N,N',N'-tetramethyluronium hexafluorophosphate (879.42 mg, 2.31 mmol, 2 eq.) and triethylamine (351.06 mg, 3.47 mmol, 482.89 µL, 3 eq.) were added at 30° C. under nitrogen atmosphere. After stirring for 30 min, compound 1-9 (298.61 mg, 2.31 mmol, 2 eq.) was added, and the reaction system was heated to 60° C. and stirred for 15.5 h. LCMS showed that the reaction was completed. The reaction solution was poured into 0.2 mol/L diluted hydrochloric acid (50 mL), and then extracted with ethyl acetate (10 mL×3). The organic phase was dried over anhydrous sodium sulfate, filtered and concentrated under reduced pressure. The crude product was purified by column chromatography (100-200 mesh silica gel, petroleum ether:ethyl acetate=10:1 to 1:1, V/V) to give compound 18-3. MS(ESI) m/s: 578.2 [M+H]$^+$.
$^1$H NMR (400 MHz, CDCl$_3$) δ=8.48 (s, 1H), 7.76-7.71 (m, 1H), 7.27-7.11 (m, 2H), 6.25 (s, 1H), 4.32-4.30 (m, 2H), 3.25 (t, J=7.6 Hz, 2H), 2.55-2.50 (m, 2H), 2.18-2.15 (m, 3H), 2.01-1.92 (m, 2H), 1.84-1.81 (m, 2H), 1.72-1.71 (m, 2H), 1.50 (s, 3H), 1.46 (s, 9H), 1.28-1.25 (m, 2H).

Step 3

18

Compound 18-3 was dissolved in dichloromethane (6 mL), and trifluoroacetic acid (4.62 g, 40.52 mmol, 3.00 mL, 78.07 eq.) was added. The reaction system was stirred at 25° C. for 1 h. LCMS and HPLC showed that the reaction was completed. The reaction solution was concentrated under reduced pressure. The crude product was purified by prep-HPLC (neutral system, column: Waters Xbridge 150 mm×25 mm×5 µm; mobile phase: water (containing 0.04% ammonium hydroxide+10 mM ammonium bicarbonate)-acetonitrile; acetonitrile %: 16%-46%, 10.5 min) to give compound 18 (column: Daicel AS-3 chiral column, with a specification of 0.46 cm id×10 cm; mobile phase: A: carbon dioxide, B: ethanol for chromatography (containing 0.05% isopropylamine); B %: 5%-40%; flow rate: 4 mL/min; 5 min; system back pressure: 100 bar), and the retention time in SFC was 2.40 min. MS(ESI) m/s: 522.1 [M+H]$^+$.
$^1$H NMR (400 MHz, DMSO-d$_6$) δ=9.90 (s, 1H), 8.29 (s, 1H), 7.87-7.81 (m, 1H), 7.45-7.38 (m, 2H), 4.28 (t, J=7.2 Hz, 2H), 3.08 (t, J=7.6 Hz, 2H), 2.48-2.44 (m, 2H), 2.15 (d, J=6.8 Hz, 2H), 1.85 (d, J=12.8 Hz, 2H), 1.76-1.61 (m, 5H), 1.37 (s, 3H), 1.18-1.15 (m, 2H).
Example 19
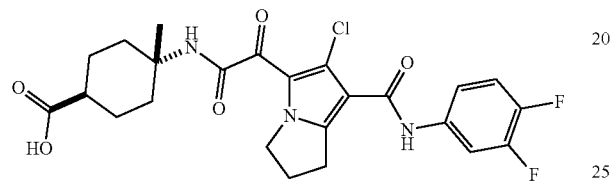
19
Synthetic Route:
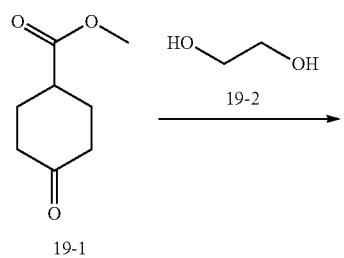
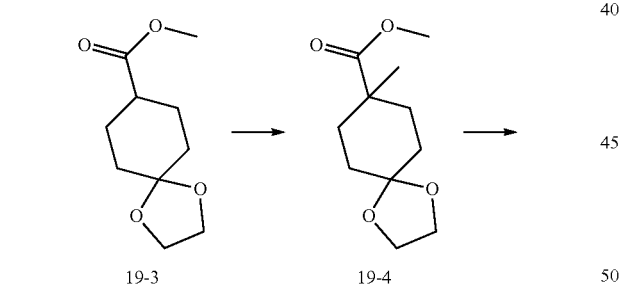
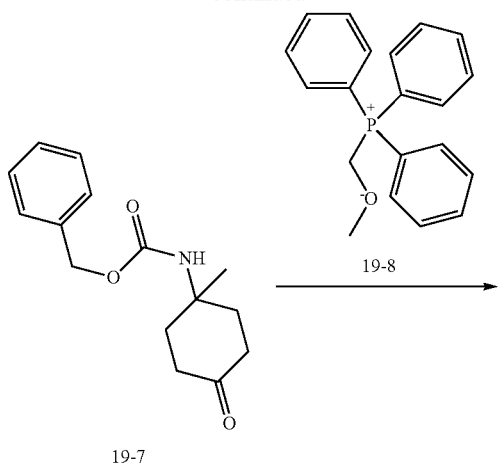
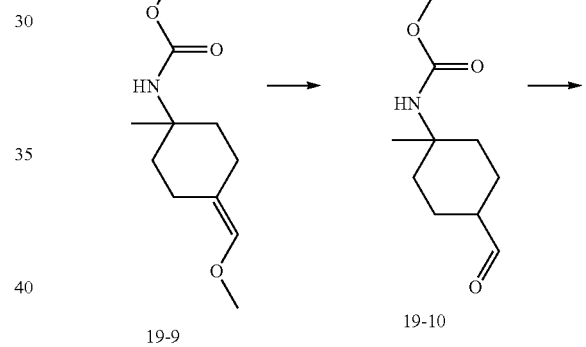
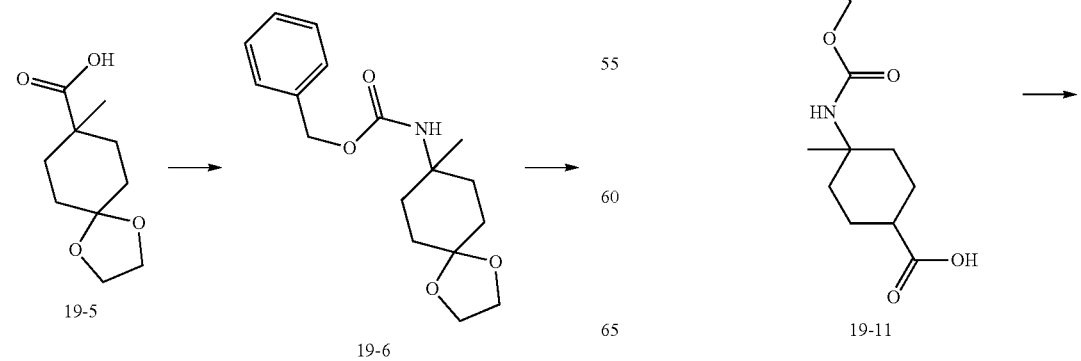

-continued

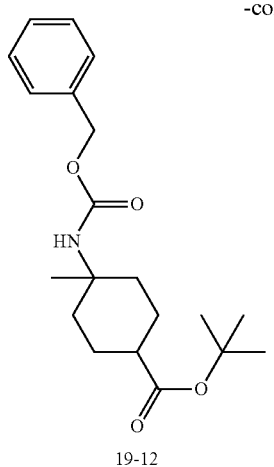

19-12

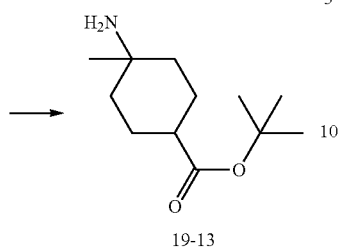

19-13

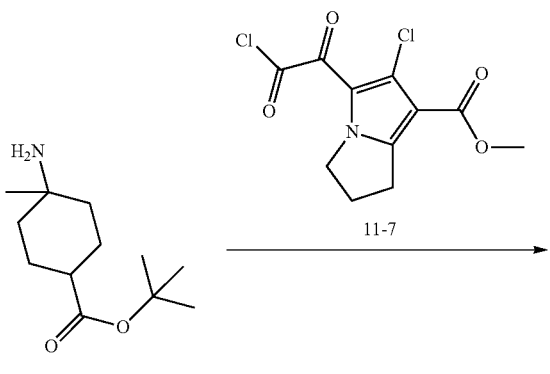

11-7

19-14

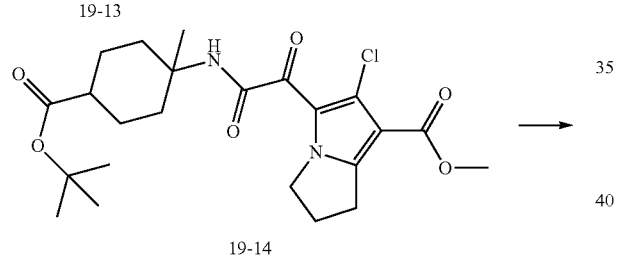

19-15

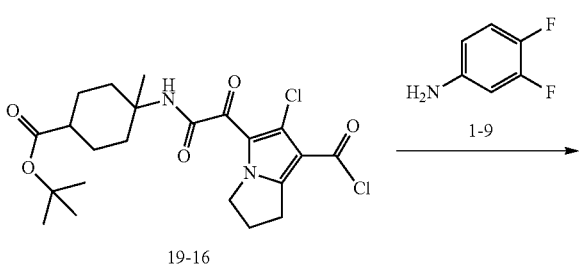

19-16

-continued

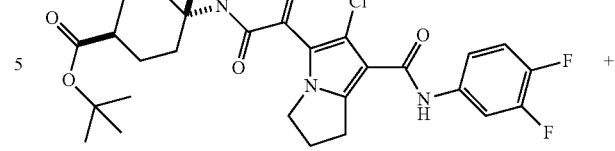

19-17

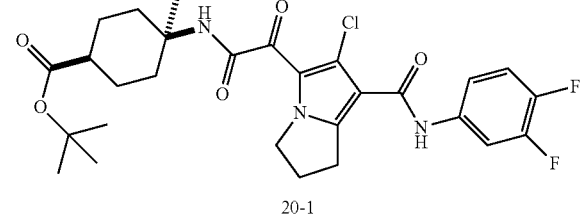

20-1

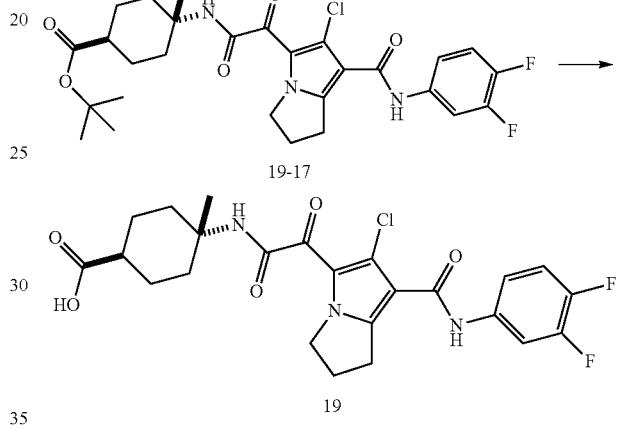

19-17

19

Step 1

19-3

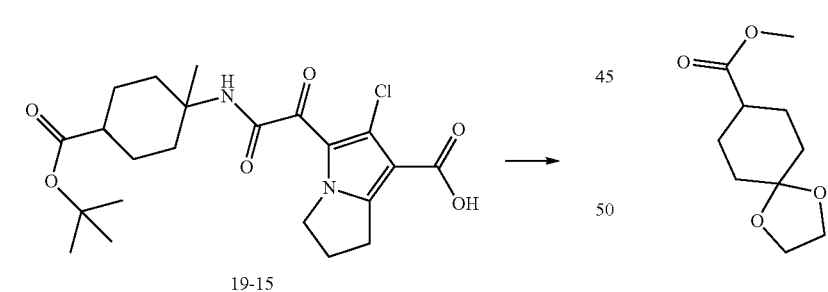

Compound 19-1 (65 g, 416.19 mmol, 1 eq.) and compound 19-2 (32.29 g, 520.24 mmol, 29.09 mL, 1.25 eq.) were dissolved in toluene (1 L), and compound (7.17 g, 41.62 mmol, 0.1 eq.) was added. The reaction system was heated to 130° C. and stirred for 48 h. TLC (petroleum ether:ethyl acetate=5:1) showed that the reaction was completed. The reaction solution was directly concentrated, and the crude product was purified by column chromatography (100-200 mesh silica gel, petroleum ether:ethyl acetate=20:1 to 5:1, V/V) to give compound 19-3.

$^1$H NMR (400 MHz, CDCl$_3$) δ=3.95 (s, 4H), 3.68 (s, 3H), 2.37-2.35 (m, 1H), 1.93-1.91 (m, 2H), 1.82-1.76 (m, 4H), 1.58-1.54 (m, 2H).

Step 2

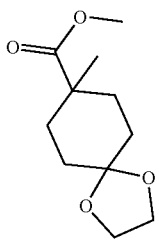

19-4

Diisopropylethylamine (47.00 g, 464.46 mmol, 65.64 mL, 1.5 eq.) was dissolved in tetrahydrofuran (800 mL), and n-butyllithium (2.5 M, 185.79 mL, 1.5 eq.) was added dropwise at −78° C. under nitrogen atmosphere. After stirring for 30 min, a solution of compound 19-3 (62 g, 309.64 mmol, 1 eq.) in tetrahydrofuran (200 mL) was added dropwise. After stirring for another 30 min, iodomethane (65.93 g, 464.46 mmol, 28.91 mL, 1.5 eq.) was added dropwise. Finally the reaction system was heated to 25° C. and stirred for 16 h. TLC (petroleum ether:ethyl acetate=3:1) showed that the reaction was completed. The reaction solution was poured into 0.5 M diluted hydrochloric acid (500 mL). The aqueous phase was extracted with ethyl acetate (100 mL×3), and the organic phase was dried over anhydrous sodium sulfate, filtered and concentrated under reduced pressure. The crude product was purified by column chromatography (100-200 mesh silica gel, petroleum ether:ethyl acetate=20:1 to 10:1, V/V) to give compound 19-4.

$^1$H NMR (400 MHz, CDCl$_3$) δ=3.93 (s, 4H), 3.66 (s, 3H), 2.14-2.10 (m, 2H), 1.64-1.60 (m, 4H), 1.59-1.50 (m, 2H), 1.18 (s, 3H).

Step 3

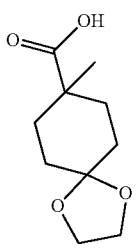

19-5

Compound 19-4 (70 g, 326.71 mmol, 1 eq.) was dissolved in a mixture of tetrahydrofuran (150 mL), methanol (150 mL) and water (150 mL), and potassium hydroxide (91.66 g, 1.63 μmol, 5 eq.) was added. The reaction system was stirred at 25° C. for 16 h. LCMS showed that the reaction was completed. The reaction solution was concentrated under reduced pressure to remove the solvent and diluted with water (100 mL). The aqueous phase was washed with ethyl acetate (20 mL×2), adjusted to pH=4 with 0.5 M diluted hydrochloric acid, and extracted with ethyl acetate (50 mL×3), and the organic phase was dried over anhydrous sodium sulfate, filtered, and concentrated under reduced pressure to give compound 19-5.

$^1$H NMR (400 MHz, CDCl$_3$) δ=3.92 (s, 4H), 2.13-2.08 (m, 2H), 1.67-1.64 (m, 4H), 1.55-1.50 (m, 2H), 1.23 (s, 3H).

Step 4

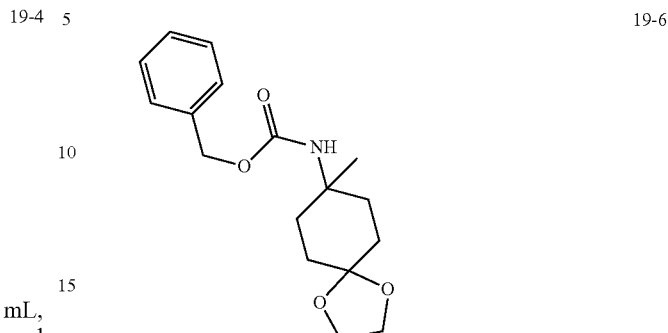

19-6

Compound 19-5 (54 g, 269.69 mmol, 1 eq.) was dissolved in toluene (500 mL), and triethylamine (81.87 g, 809.07 mmol, 112.61 mL, 3 eq.), diphenylphosphoryl azide (89.06 g, 323.63 mmol, 70.13 mL, 1.2 eq.) and benzyl alcohol (35.00 g, 323.63 mmol, 33.65 mL, 1.2 eq.) were added. The reaction system was stirred at 100° C. for 16 h under nitrogen atmosphere. TLC (petroleum ether:ethyl acetate=5:1) showed that the reaction was completed. The reaction solution was poured into water (500 mL). The aqueous phase was extracted with ethyl acetate (100 mL×2), and the organic phase was dried over anhydrous sodium sulfate, filtered and concentrated under reduced pressure. The crude product was purified by column chromatography (100-200 mesh silica gel, petroleum ether:ethyl acetate=20:1 to 5:1, V/V) to give compound 19-6.

$^1$H NMR (400 MHz, CDCl$_3$) δ=7.37-7.27 (m, 5H), 5.05 (s, 1H), 4.69 (s, 2H), 3.95 (s, 4H), 2.04 (s, 2H), 1.68-1.59 (m, 6H), 1.40-1.37 (m, 3H).

Step 5

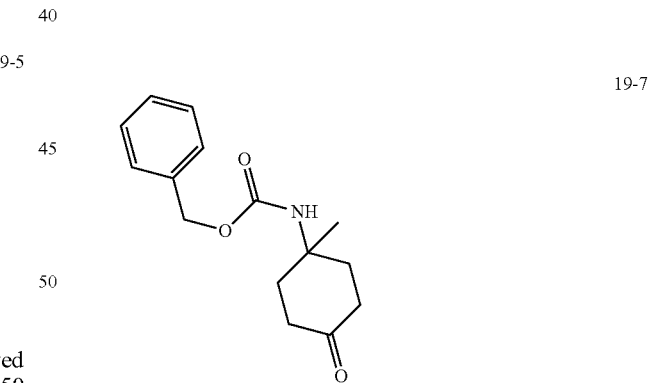

19-7

Compound 19-6 (80 g, 261.98 mmol, 1 eq.) was dissolved in tetrahydrofuran (1 L), and hydrochloric acid (2 M, 1 L, 7.63 eq.) was added. The reaction system was stirred at 50° C. for 16 h. TLC (petroleum ether:ethyl acetate=3:1) showed that the reaction was completed. The reaction solution was concentrated under reduced pressure. The crude product was purified by column chromatography (100-200 mesh silica gel, petroleum ether:ethyl acetate=25:1 to 5:1, V/V) to give compound 19-7.

$^1$H NMR (400 MHz, CDCl$_3$) δ=7.40-7.29 (m, 5H), 5.09 (s, 2H), 4.87 (s, 1H), 2.45-2.38 (m, 4H), 2.31-2.27 (m, 2H), 1.85-1.82 (m, 2H), 146 (s, 3H).

Step 6

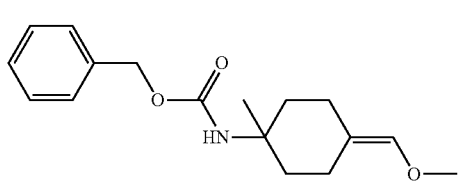
19-9

Compound 19-8 (13.16 g, 38.27 mmol, 2 eq., HCl) was dissolved in tetrahydrofuran (100 mL), and potassium tert-butoxide (4.29 g, 38.27 mmol, 2 eq.) was added at −10° C. under nitrogen atmosphere. After the reaction system was stirred at −10° C. for 1 h, a solution of compound 19-7 (5 g, 19.13 mmol, 1 eq.) in tetrahydrofuran (100 mL) was added dropwise to the above reaction solution, and the reaction solution was stirred at 25° C. for 2 h. TLC (petroleum ether:ethyl acetate=3:1) showed that the reaction was completed. The reaction solution was diluted with ethyl acetate (500 mL), and then filtered. The mother liquor was concentrated under reduced pressure. The crude product was purified by column chromatography (100-200 mesh silica gel, petroleum ether:ethyl acetate=30:1 to 10:1, V/V) to give compound 19-9.

$^1$H NMR (400 MHz, CDCl$_3$) δ=7.37-7.27 (m, 5H), 5.78 (s, 1H), 5.07 (s, 2H), 4.67 (s, 1H), 4.55 (s, 3H), 2.45-2.40 (m, 1H), 2.04-1.93 (m, 5H), 1.47-1.44 (m, 2H), 1.36 (s, 3H).

Step 7

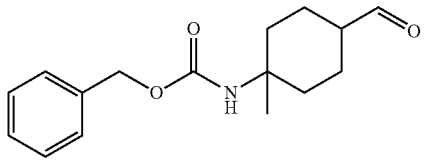
19-10

Compound 19-9 (4 g, 13.82 mmol, 1 eq.) was dissolved in tetrahydrofuran (6.5 mL), and hydrochloric acid (6 M, 3.23 mL, 1.4 eq.) was added dropwise at 0° C. The reaction system was stirred at 0° C. for 1 h. TLC (petroleum ether:ethyl acetate=3:1) showed that the reaction was completed. The reaction solution was diluted with water (10 mL). The aqueous phase was extracted with ethyl acetate (5 mL×3), and the organic phase was dried over anhydrous sodium sulfate, filtered and concentrated under reduced pressure to give compound 19-10.

$^1$H NMR (400 MHz, CDCl$_3$) δ=9.65 (d, J=17.2 Hz, 2H), 7.37-7.27 (m, 5H), 5.06 (s, 2H), 4.61 (d, J=56.4 Hz, 1H), 2.33-2.21 (m, 2H), 1.87-1.81 (m, 3H), 1.80-1.68 (m, 2H), 1.37 (s, 3H).

Step 8

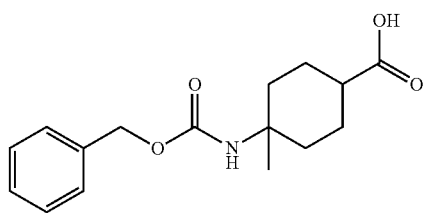
19-11

Compound 19-10 (1.8 g, 6.54 mmol, 1 eq.) was dissolved in a mixture of tert-butanol (27 mL) and isoamylene (2.58 g, 36.74 mmol, 3.89 mL, 5.62 eq.), and a solution of sodium dihydrogen phosphate (831.41 mg, 6.93 mmol, 1.06 eq.) and a solution of sodium chlorite (709.48 mg, 7.84 mmol, 1.2 eq.) in water (36 mL) was slowly added at 0° C. The reaction system was stirred at 0° C. for 10 min. TLC (petroleum ether:ethyl acetate=3:1) showed that the reaction was completed. The reaction solution was diluted with water (20 mL). The aqueous phase was extracted with ethyl acetate (5 mL×3), and the organic phase was dried over anhydrous sodium sulfate, filtered and concentrated under reduced pressure. The crude product was purified by column chromatography (100-200 mesh silica gel, petroleum ether:ethyl acetate=10:1 to 3:1, V/V) to give compound 19-11.

$^1$H NMR (400 MHz, CDCl$_3$) δ=7.37-7.27 (m, 5H), 5.06 (s, 2H), 4.65 (d, J=4.0 Hz, 1H), 2.44-2.30 (m, 1H), 2.20-2.17 (m, 1H), 1.88-1.66 (m, 6H), 1.36-1.31 (m, 3H).

Step 9

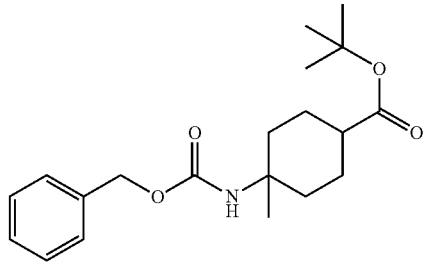
19-12

Compound 19-11 (1.7 g, 5.84 mmol, 1 eq.) was dissolved in dichloromethane (15 mL), and oxalyl chloride (1.48 g, 11.67 mmol, 1.02 mL, 2 eq.) and N,N-dimethylformamide (42.65 mg, 583.51 μmol, 44.89 μL, 0.1 eq.) were added dropwise at 0° C. under nitrogen atmosphere. The reaction system was stirred at 25° C. for 1 h and then concentrated under reduced pressure. The crude product was dissolved in dichloromethane (5 mL), and the resulting solution was slowly added dropwise to a solution of tert-butanol (4.32 g, 58.35 mmol, 5.58 mL, 10 eq.) in dichloromethane (10 mL). The reaction system was stirred at 50° C. for 16 h. LCMS showed that the reaction was completed. The reaction solution was directly concentrated under reduced pressure. The crude product was purified by column chromatography (100-200 mesh silica gel, petroleum ether:ethyl acetate=30:1 to 10:1, V/V) to give compound 19-12.

$^1$H NMR (400 MHz, CDCl$_3$) δ=7.37-7.27 (m, 5H), 5.05 (s, 2H), 4.64 (d, J=14.8 Hz, 1H), 2.27-2.14 (m, 2H), 1.82-1.64 (m, 6H), 1.44 (d, J=3.2 Hz, 9H), 1.36-1.31 (m, 3H).

Step 10

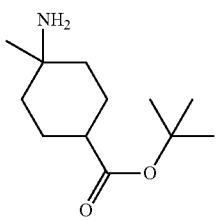

19-13

Wet palladium on carbon (200 mg, content: 10%), methanol (20 mL), and compound 19-12 (1 g, 2.88 mmol, 1 eq.) were added into a hydrogenation flask. After 3 hydrogen purges, the reaction system was stirred for 16 h at 25° C. under hydrogen atmosphere (50 psi). The reaction solution was filtered and concentrated under reduced pressure to give compound 19-13.

$^1$H NMR (400 MHz, MeOH-d$_4$) δ=2.18-2.15 (m, 2H), 1.79-1.55 (m, 4H), 1.45 (d, J=2.4, Hz, 9H), 1.43-1.37 (m, 2H), 1.12 (s, 3H).

Step 11

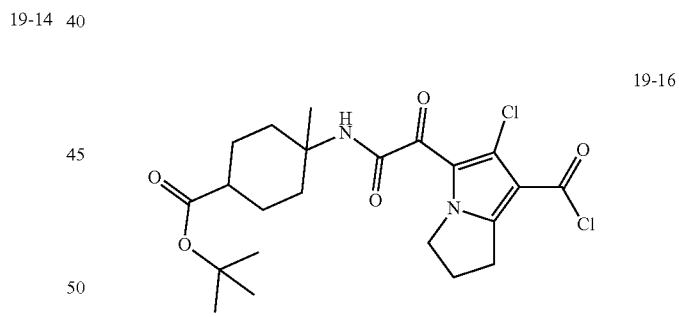

19-14

Compound 19-13 (294.13 mg, 1.38 mmol, 1 eq.) was dissolved in dichloromethane (20 mL), and triethylamine (418.57 mg, 4.14 mmol, 575.76 μL, 3 eq.) was added. A solution of compound 11-7 (400 mg, 1.38 mmol, 1 eq.) in dichloromethane (10 mL) was added dropwise under nitrogen atmosphere at 0° C. The reaction system was stirred at 25° C. for 1 h. LCMS showed that the reaction was completed. The reaction solution was poured into diluted hydrochloric acid (0.5 mol/L, 50 mL), and extracted with dichloromethane (20 mL×2). The organic phase was dried over anhydrous sodium sulfate, filtered and concentrated under reduced pressure to give compound 19-14.

MS (ESI) m/z: 467.2 [M+H]$^+$

Step 12

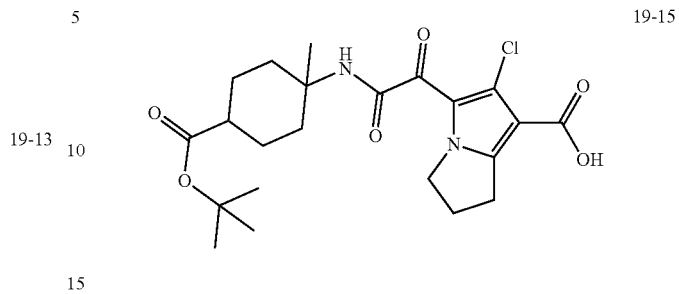

19-15

Compound 19-14 (700 mg, 1.50 mmol, 1 eq.) was dissolved in a mixture of tetrahydrofuran (10 mL), methanol (10 mL) and water (10 mL), and lithium hydroxide monohydrate (188.70 mg, 4.50 mmol, 3 eq.) was added. The reaction system was stirred at 25° C. for 16 h. LCMS showed that the reaction was completed. The reaction solution was concentrated under reduced pressure to remove the solvent. The aqueous phase was adjusted to pH=1 with 0.5 mol/L diluted hydrochloric acid and extracted with ethyl acetate (20 mL×3), and the organic phase was dried over anhydrous sodium sulfate, filtered and concentrated under reduced pressure to give compound 19-15. MS (ESI) m/z: 453.1 [M+H]$^+$.

$^1$H NMR (400 MHz, MeOH-d$_4$) δ=4.39-4.33 (m, 2H), 3.31-3.11 (m, 2H), 2.53-2.49 (m, 2H), 2.38-2.35 (m, 2H), 1.88-1.70 (m, 6H), 1.46-1.29 (m, 13H).

Step 13

19-16

Compound 19-15 (470 mg, 1.04 mmol, 1 eq.) was dissolved in dichloromethane (20 mL), and oxalyl chloride (263.43 mg, 2.08 mmol, 181.68 μL, 2 eq.) and N,N-dimethylformamide (7.58 mg, 103.77 μmol, 7.98 μL, 0.1 eq.) were added dropwise under nitrogen atmosphere at 0° C. The reaction system was stirred at 25° C. for 30 min. 1 mL of the reaction solution was taken and added with methanol to quench the reaction, and LCMS detection showed that the reaction was completed. The reaction solution was directly concentrated under reduced pressure to give compound 19-16.

Step 14

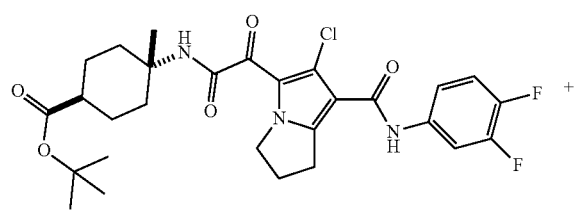

19-17

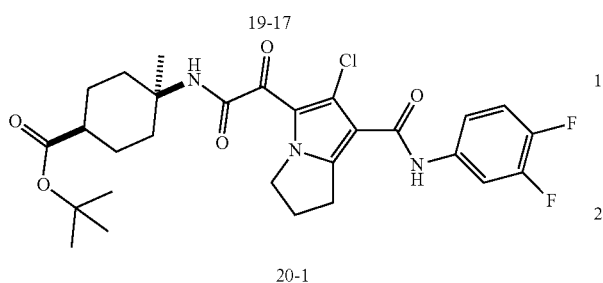

20-1

Compound 1-9 (273.90 mg, 2.12 mmol, 2 eq.) was dissolved in dichloromethane (20 mL), and triethylamine (322.01 mg, 3.18 mmol, 442.92 μL, 3 eq.) was added. A solution of compound 19-16 (500 mg, 1.06 mmol, 1 eq.) in dichloromethane (10 mL) was added dropwise under nitrogen atmosphere at 0° C. The reaction system was stirred at 25° C. for 1 h. LCMS showed that the reaction was completed. The reaction solution was poured into diluted hydrochloric acid (0.5 mol/L, 50 mL). The aqueous phase was extracted with ethyl acetate (20 mL×2), and the organic phase was dried over anhydrous sodium sulfate, filtered and concentrated under reduced pressure. The crude product was purified by prep-TLC (petroleum ether:ethyl acetate=1:1, V/V) to give compound 19-17 (Rf=0.35) and compound 20-1 (Rf=0.32).

Compound 19-17: MS (ESI) m/z: 508.1 [M+H-(t-Bu)]$^+$.
Compound 20-1: MS (ESI) m/z: 508.1 [M+H-(t-Bu)]$^+$.

Step 15

19

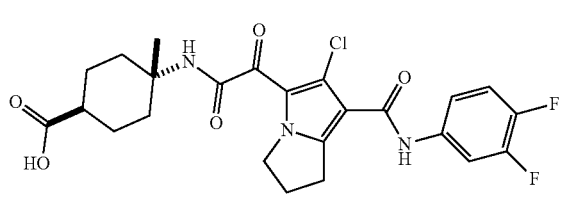

Compound 19-17 (90 mg, 159.57 umol, 1 eq.) was dissolved in dichloromethane (1 mL), and trifluoroacetic acid (363.88 mg, 3.19 mmol, 236.29 μL, 20 eq.) was added. The reaction system was stirred at 25° C. for 1 h.

LCMS and HPLC showed that the reaction was completed. The reaction solution was concentrated under reduced pressure, and the crude product was purified by prep-HPLC (neutral system, column: Waters Xbridge 150 mm×25 mm×5 μm; mobile phase: water (containing 0.04% ammonium hydroxide+10 mM ammonium bicarbonate)-acetonitrile; B (acetonitrile) %: 23%-43%, 10.5 min) to give compound 19 (column: Daicel AS-3 chiral column, with a specification of 0.46 cm id×10 cm; mobile phase: A: carbon dioxide, B: ethanol for chromatography (containing 0.05% isopropylamine); B %: 5%-40%; flow rate: 4 mL/min; 5 min; system back pressure: 100 bar), and the retention time in SFC was 2.44 min. MS (ESI) m/z: 508.1 [M+H]$^+$.

$^1$H NMR (400 MHz, DMSO-d$_6$) δ=9.96 (s, 1H), 8.15 (s, 1H), 7.87-7.82 (m, 1H), 7.43-7.36 (m, 2H), 4.29 (t, J=7.0 Hz, 2H), 3.08 (t, J=7.6 Hz, 2H), 2.50-2.46 (m, 2H), 2.22 (d, J=12.8 Hz, 2H), 2.11 (s, 1H), 1.63-1.58 (m, 4H), 1.34 (s, 3H), 1.29-1.23 (m, 2H).

Example 20

20

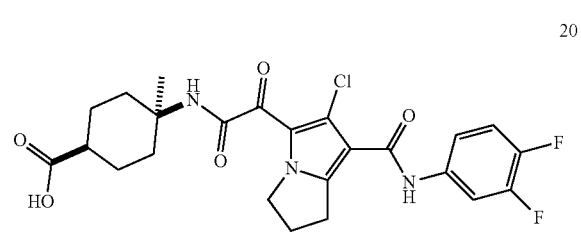

Synthetic Route:

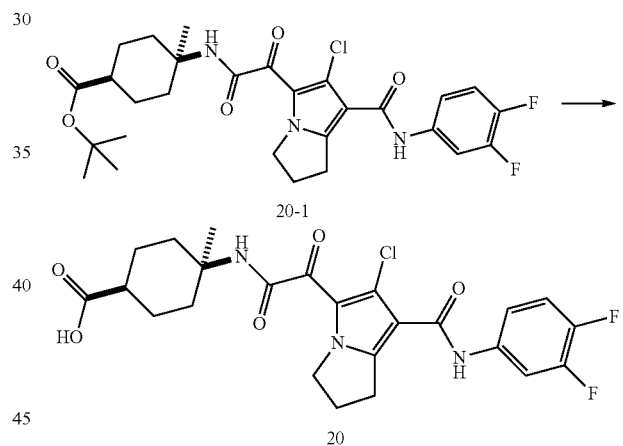

Compound 20-1 (140 mg, 248.22 μmol, 1 eq.) was dissolved in dichloromethane (1 mL), and trifluoroacetic acid (566.04 mg, 4.96 mmol, 367.56 μL, 20 eq.) was added. The reaction system was stirred at 25° C. for 1 h. LCMS and HPLC showed that the reaction was completed. The reaction solution was concentrated under reduced pressure, and the crude product was purified by prep-HPLC (neutral system, column: Waters Xbridge 150 mm×25 mm×5 μm; mobile phase: water (containing 0.04% ammonium hydroxide+10 mM ammonium bicarbonate)-acetonitrile; B (acetonitrile) %: 18%-38%, 10.5 min) to give compound 20 (column: Daicel AS-3 chiral column, with a specification of 0.46 cm id×10 cm; mobile phase: A: carbon dioxide, B: ethanol for chromatography (containing 0.05% isopropylamine); B %: 5%-40%; flow rate: 4 mL/min; 5 min; system back pressure: 100 bar), and the retention time in SFC was 2.20 min. MS (ESI) m/z: 508.2 [M+H]$^+$.

$^1$H NMR (400 MHz, DMSO-d$_6$) δ=9.95 (s, 1H), 8.30 (s, 1H), 7.87-7.82 (m, 1H), 7.45-7.39 (m, 2H), 4.28 (t, J=7.2

Hz, 2H), 3.08 (t, J=7.6 Hz, 2H), 2.50-2.46 (m, 2H), 2.24 (s, 1H), 1.83-1.74 (m, 6H), 1.59-1.55 (m, 2H), 1.36 (s, 3H).
Example 21
Synthetic Route:
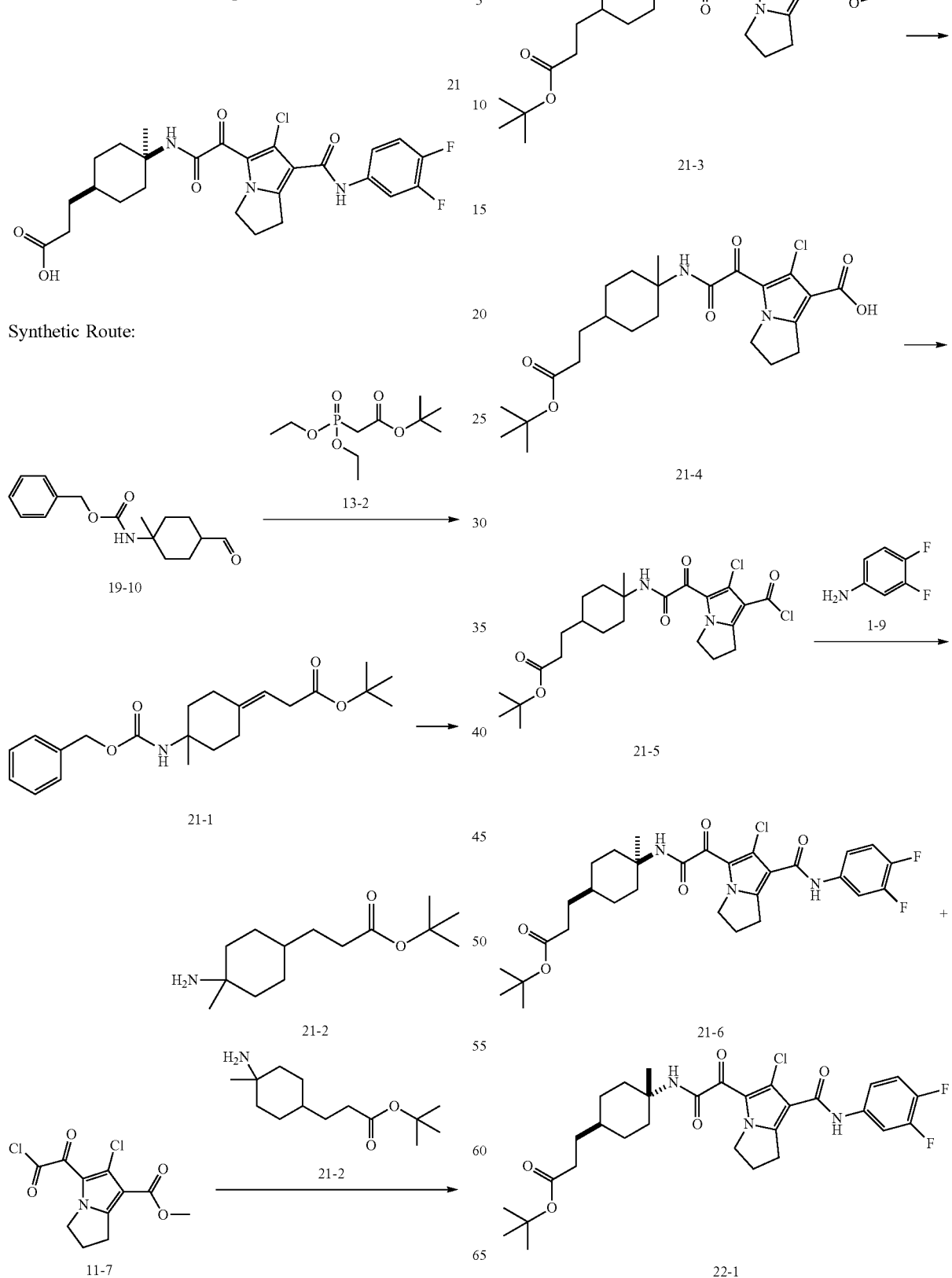

117

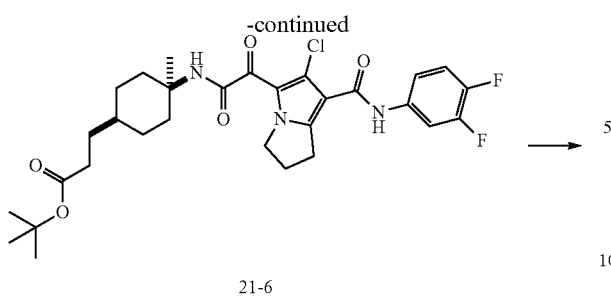

21-6

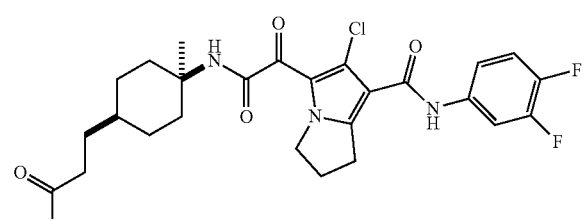

21

Step 1

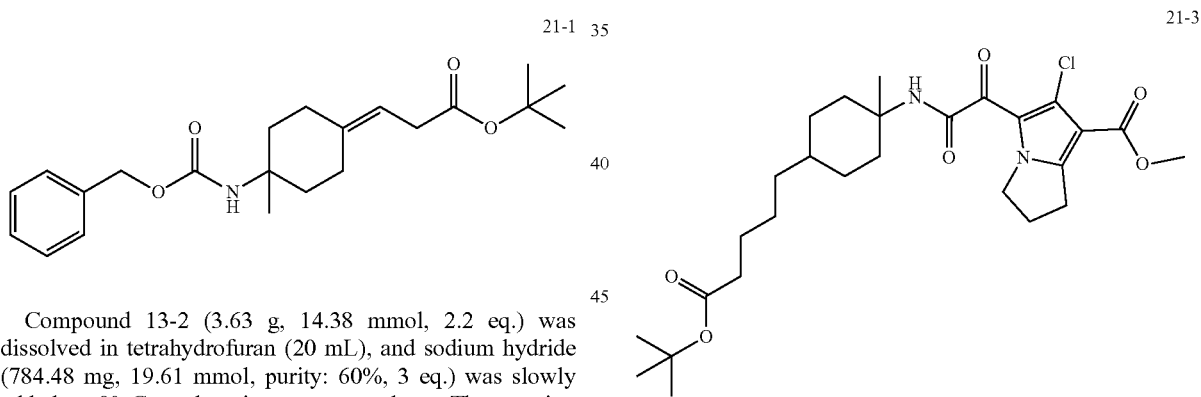

21-1

Compound 13-2 (3.63 g, 14.38 mmol, 2.2 eq.) was dissolved in tetrahydrofuran (20 mL), and sodium hydride (784.48 mg, 19.61 mmol, purity: 60%, 3 eq.) was slowly added at 0° C. under nitrogen atmosphere. The reaction solution was stirred for 30 min, and then slowly added with a solution of compound 19-10 (1.8 g, 6.54 mmol, 1 eq.) in THF (20 mL) dropwise. The reaction system was heated to 25° C. and stirred for 1 h. TLC (petroleum ether:ethyl acetate=3:1) showed that the reaction was completed. The reaction solution was poured into 0.5 mol/L diluted hydrochloric acid (10 mL). The aqueous phase was extracted with ethyl acetate (20 mL×3), and the organic phase was dried over anhydrous sodium sulfate, filtered and concentrated under reduced pressure. The crude product was purified by column chromatography (100-200 mesh silica gel, petroleum ether:ethyl acetate=20:1 to 10:1, V/V) to give compound 21-1.

$^1$H NMR (400 MHz, CDCl$_3$) δ=7.37-7.33 (m, 5H), 6.83-6.77 (m, 1H), 5.75-5.69 (m, 1H), 5.06 (s, 2H), 4.71-4.53 (m, 2H), 2.21-2.16 (m, 2H), 1.87-1.82 (m, 1H), 1.76-1.71 (m, 2H), 1.63 (s, 2H), 1.49 (s, 9H), 1.38-1.32 (m, 4H).

118

Step 2

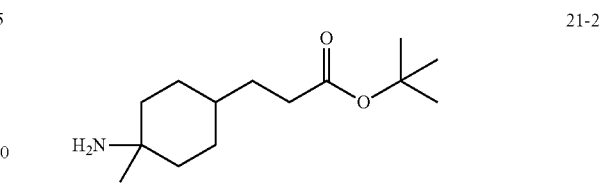

21-2

Palladium on carbon (200 mg, content: 10%) was dissolved in methanol (30 mL) in a hydrogenation flask, and compound 21-1 (2 g, 5.35 mmol, 1 eq.) was added. After 3 hydrogen purges, the reaction system was stirred for 16 h at 25° C. under hydrogen atmosphere (50 psi). TLC (petroleum ether:ethyl acetate=3:1) showed that the reaction was completed. The reaction solution was filtered and concentrated under reduced pressure to give compound 21-2.

$^1$H NMR (400 MHz, MeOH-d$_4$) δ=2.27-2.22 (m, 2H), 1.70-1.50 (m, 6H), 1.44 (s, 9H), 1.39-1.36 (m, 2H), 1.24-1.18 (m, 2H), 1.13-1.11 (m, 4H).

Step 3

21-3

Compound 21-2 (332.81 mg, 1.38 mmol, 1 eq.) was dissolved in dichloromethane (20 mL), and triethylamine (418.57 mg, 4.14 mmol, 575.76 μL, 3 eq.) was added. A solution of compound 11-7 (400 mg, 1.38 mmol, 1 eq.) in dichloromethane (10 mL) was added dropwise under nitrogen atmosphere at 0° C. The reaction system was stirred at 25° C. for 1 h. LCMS showed that the reaction was completed. The reaction solution was poured into 0.5 mol/L diluted hydrochloric acid (50 mL). The aqueous phase was extracted with dichloromethane (20 mL×2), and the organic phase was dried over anhydrous sodium sulfate, filtered and concentrated under reduced pressure to give compound 21-3.

MS(ESI) m/s: 439.2 [M+H-(t-Bu)]$^+$.

Step 4

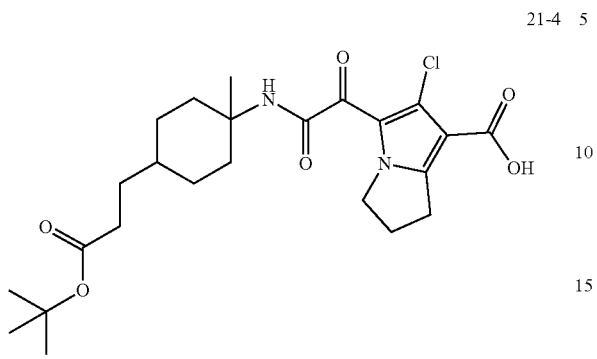

21-4

Compound 21-3 (700 mg, 1.41 mmol, 1 eq.) was dissolved in a mixture of tetrahydrofuran (10 mL), methanol (10 mL) and water (10 mL), and lithium hydroxide monohydrate (178.01 mg, 4.24 mmol, 3 eq.) was added. The reaction system was stirred at 25° C. for 16 h. LCMS showed that the reaction was completed. The reaction solution was concentrated under reduced pressure to remove the solvent. The aqueous phase was adjusted to pH=1 with 0.5 mol/L diluted hydrochloric acid and extracted with ethyl acetate (20 mL×3), and the organic phase was dried over anhydrous sodium sulfate, filtered and concentrated under reduced pressure to give compound 21-4.

MS(ESI) m/s: 425.1 [M+H-(t-Bu)]$^+$.

$^1$H NMR (400 MHz, MeOH-d$_4$) δ 4.39-4.33 (m, 2H), 3.17-3.11 (m, 2H), 2.53-2.51 (m, 2H), 2.32-2.23 (m, 3H), 2.03-2.00 (m, 1H), 1.81-1.55 (m, 2H), 1.58-1.52 (m, 6H), 1.44 (s, 9H), 1.30-1.27 (m, 4H).

Step 5

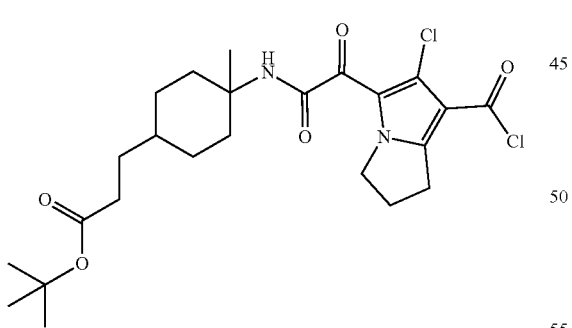

21-5

Compound 21-4 (570 mg, 1.19 mmol, 1 eq.) was dissolved in dichloromethane (30 mL), and oxalyl chloride (300.84 mg, 2.37 mmol, 207.48 µL, 2 eq.) and N,N-dimethylformamide (8.66 mg, 118.51 µmol, 9.12 µL, 0.1 eq.) were added dropwise under nitrogen atmosphere at 0° C. The reaction system was stirred at 25° C. for 30 min. Two drops of the reaction solution were taken and added with methanol to quench the reaction, and LCMS showed that the reaction was completed. The reaction solution was directly concentrated under reduced pressure to give compound 21-5.

Step 6

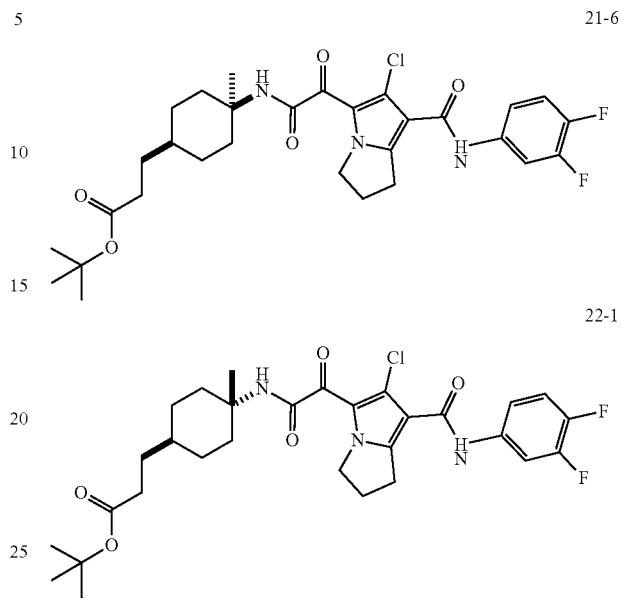

21-6

22-1

Compound 1-9 (310.21 mg, 2.40 mmol, 2 eq.) was dissolved in dichloromethane (20 mL), and triethylamine (364.70 mg, 3.60 mmol, 501.65 µL, 3 eq.) was added. A solution of compound 21-5 (600 mg, 1.20 mmol, 1 eq.) in dichloromethane (10 mL) was added dropwise under nitrogen atmosphere at 0° C. The reaction system was stirred at 25° C. for 1 h. TLC (petroleum ether:ethyl acetate=1:1) and LCMS showed that the reaction was completed. The reaction solution was poured into diluted hydrochloric acid (0.5 mol/L, 50 mL). The aqueous phase was extracted with ethyl acetate (20 mL×2), and the organic phase was dried over anhydrous sodium sulfate, filtered and concentrated under reduced pressure. The crude product was purified by prep-TLC (petroleum ether:ethyl acetate=1:1, V/V) to give compound 21-6 (Rf=0.35) and compound 22-1 (Rf=0.32).

Compound 21-6: MS(ESI) m/s: 536.2 [M+H-(t-Bu)]$^+$.
Compound 21-6: MS(ESI) m/s: 536.2 [M+H-(t-Bu)]$^+$.

Step 7

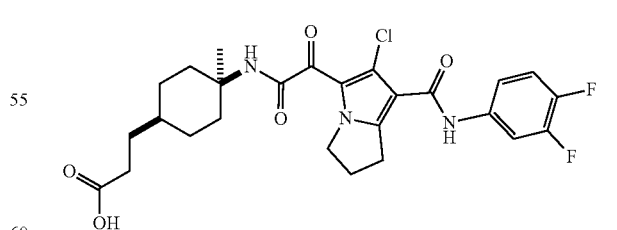

21

Compound 21-6 (70 mg, 118.23 µmol, 1 eq.) was dissolved in dichloromethane (1 mL), and trifluoroacetic acid (269.61 mg, 2.36 mmol, 175.07 µL, 20 eq.) was added. The reaction system was stirred at 25° C. for 1 h. LCMS and HPLC showed that the reaction was completed. The reaction solution was concentrated under reduced pressure. The crude product was purified by prep-HPLC (neutral system, column: Xtimate C18 150 mm×25 mm×5 μm; mobile phase: water (containing 10 mM ammonium bicarbonate)-acetonitrile; acetonitrile %: 10%-50%, 20 min) to give compound 21 (column: Daicel OJ-3 chiral column, with a specification of 0.46 cm id×5 cm; mobile phase: A: carbon dioxide, B: ethanol for chromatography (containing 0.05% isopropylamine); B %: 5%-40%; flow rate: 4 mL/min; 3 min; system back pressure: 100 bar), and the retention time in SFC was 1.27 min. MS(ESI) m/s: 536.2 [M+H]⁺.

$^1$H NMR (400 MHz, DMSO-d$_6$) δ=9.93 (s, 1H), 8.09 (s, 1H), 7.88-7.83 (m, 1H), 7.46-7.40 (m, 2H), 4.31-4.28 (m, 2H), 3.11-3.07 (m, 2H), 2.47-2.43 (m, 2H), 2.23-2.20 (m, 4H), 1.50-1.41 (m, 4H), 1.34 (s, 3H), 1.24-1.19 (m, 5H).

Example 22

22

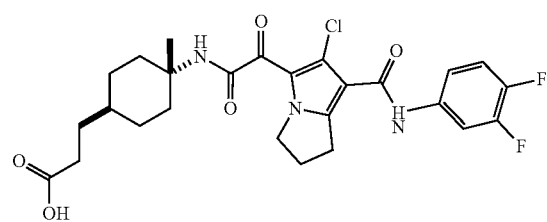

Synthetic Route:

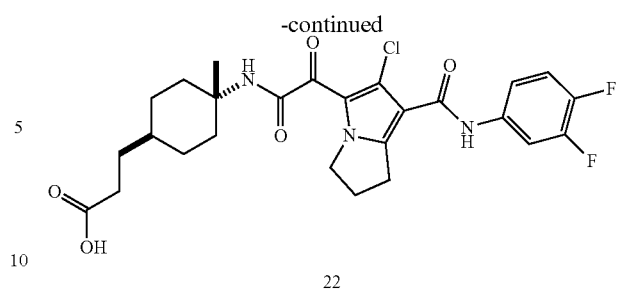

Compound 22-1 (80 mg, 135.12 μmol, 1 eq.) was dissolved in dichloromethane (1 mL), and trifluoroacetic acid (308.12 mg, 2.70 mmol, 200.08 μL, 20 eq.) was added. The reaction system was stirred at 25° C. for 1 h. LCMS and HPLC showed that the reaction was completed. The reaction solution was concentrated under reduced pressure. The crude product was purified by prep-HPLC (neutral system, column: Xtimate C18 150 mm×25 mm×5 μm; mobile phase: water (containing 10 mM ammonium bicarbonate)-acetonitrile; acetonitrile %: 10%-50%, 20 min) to give compound 22 (column: Daicel OJ-3 chiral column, with a specification of 0.46 cm id×5 cm; mobile phase: A: carbon dioxide, B: ethanol for chromatography (containing 0.05% isopropylamine); B %: 5%-40%; flow rate: 4 mL/min; 3 min; system back pressure: 100 bar), and the retention time in SFC was 1.39 min. MS(ESI) m/s: 536.2 [M+H]⁺.

$^1$H NMR (400 MHz, DMSO-d$_6$) δ=9.92 (s, 1H), 8.29 (s, 1H), 7.87-7.82 (m, 1H), 7.43-7.39 (m, 2H), 4.29-4.25 (m, 2H), 3.09-3.04 (m, 2H), 2.47-2.44 (m, 2H), 2.19-2.15 (m, 2H), 1.86-1.83 (m, 2H), 1.69-1.59 (m, 4H), 1.45-1.43 (m, 2H), 1.36 (s, 3H), 1.17 (s, 1H), 1.09-1.06 (m, 2H).

Example 23

23

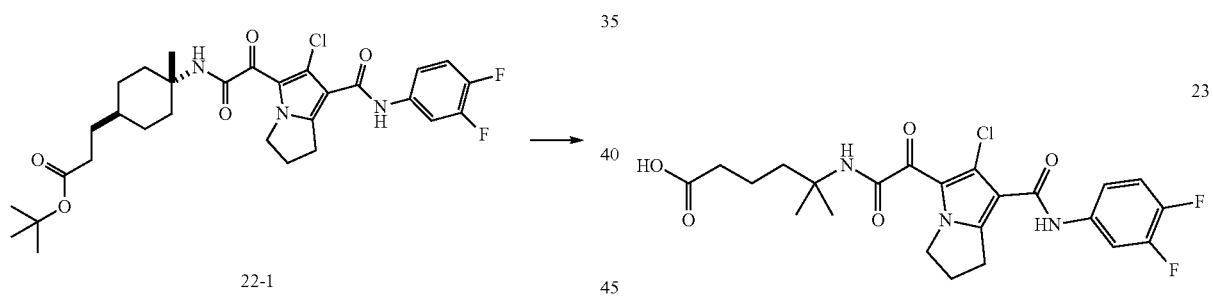

Synthetic Route:

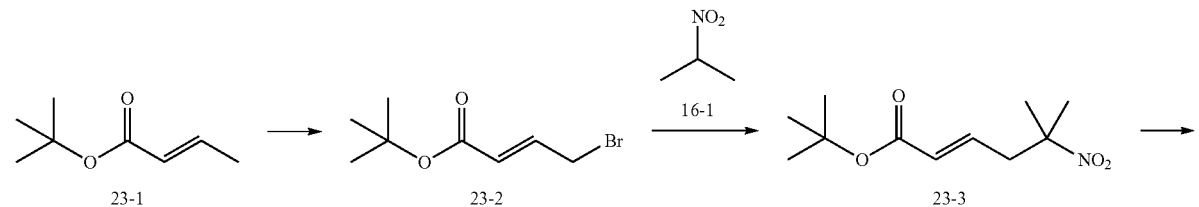

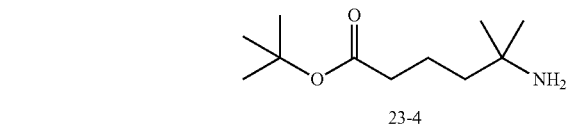

-continued
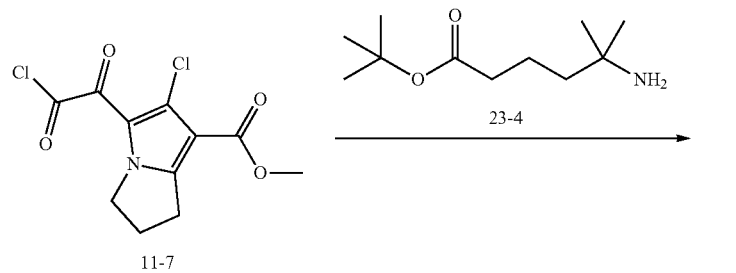
11-7
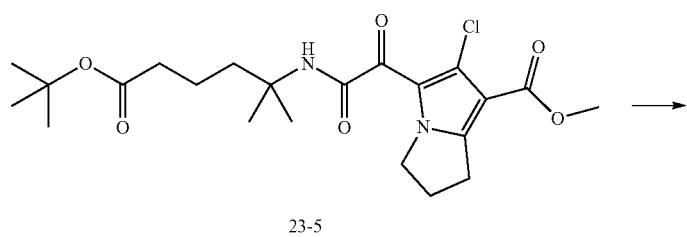
23-5
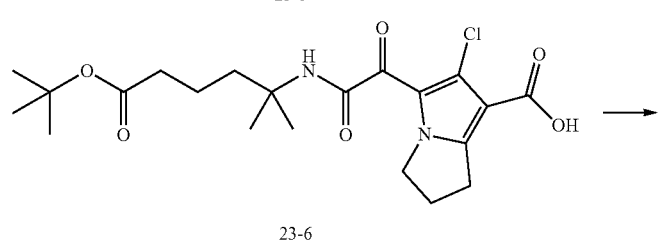
23-6
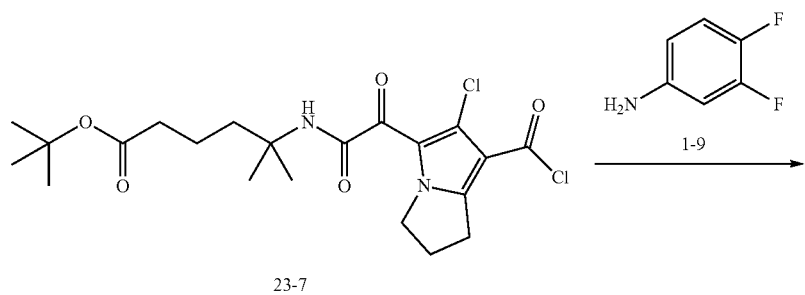
23-7
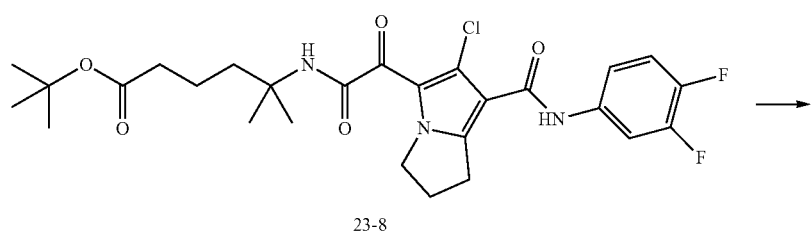
23-8
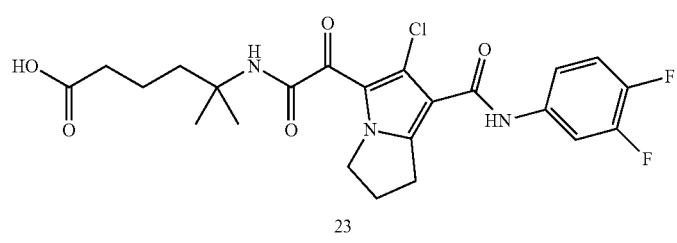
23

Step 1

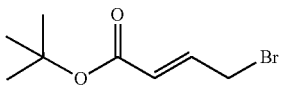

23-2

Compound 23-1 (5 g, 35.16 mmol, 1 eq.) was dissolved in carbon tetrachloride (50 mL), and then N-bromosuccinimide (7.51 g, 42.20 mmol, 1.2 eq.) and azobisisobutyronitrile (1.73 g, 10.55 mmol, 0.3 eq.) were added. The reaction solution was heated to 90° C. and stirred for 12 h. TLC (petroleum ether:ethyl acetate=5:1) showed that a small amount of compound 23-1 remained and new spots were produced. The reaction solution was cooled to room temperature, added with water (50 mL) and stirred, and then let stand to separate organic phase. The separated organic phase was washed with saturated aqueous sodium chloride solution (50 mL×1), dried over anhydrous sodium sulfate, filtered and concentrated under reduced pressure. The residue was purified by a chromatographic system COMBI-FLASH (petroleum ether:ethyl acetate=100:1 to 15:1, V/V) to give compound 23-2.

$^1$H NMR (400 MHz, CDCl$_3$) δ=6.95-6.88 (m, 1H), 5.99 (dd, J=1.2, 1.2 Hz, 1H), 4.02 (t, J=3.8 Hz, 2H), 1.52 (s, 9H).

Step 2

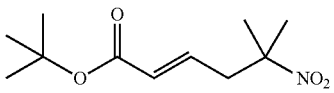

23-3

Compound 23-2 (1.60 g, 17.91 mmol, 1.61 mL, 1.1 eq.) was dissolved in methanol (50 mL), and tetrakis(triphenylphosphine)palladium (940.79 mg, 814.14 μmol, 0.05 eq.), sodium methoxide (967.63 mg, 17.91 mmol, 1.1 eq.) and compound 16-1 (3.6 g, 16.28 mmol, 1 eq.) were added at 26° C. under nitrogen atmosphere. The reaction mixture was heated to 60° C. and stirred for 12 h. TLC (petroleum ether:ethyl acetate=5:1) showed that compound 23-2 was completely consumed and new spots were produced. The reaction solution was poured into water (100 mL), and then extracted with ethyl acetate (50 mL×2). The organic phase was washed with saturated aqueous sodium chloride solution (100 mL×1), dried over anhydrous sodium sulfate, filtered and concentrated under reduced pressure. The residue was purified by a chromatographic system COMBI-FLASH (petroleum ether:ethyl acetate=100:1 to 10:1, V/V) to give compound 23-3.

$^1$H NMR (400 MHz, CDCl$_3$) δ=6.71-6.63 (m, 1H), 5.86-5.82 (m, 1H), 2.78 (dd, J=1.2, 1.2 Hz, 2H), 1.61 (s, 6H), 1.48 (s, 9H).

Step 3

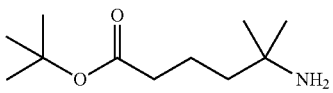

23-4

Compound 23-3 (200 mg, 872.33 μmol, 1 eq.) and ethanol (10 mL) were added into a dry hydrogenation flask, Raney nickel (200 mg, 2.33 mmol, 2.68 eq.) was added under nitrogen atmosphere, and hydrogen was purged. The reaction system was stirred for 12 h at 50° C. under hydrogen atmosphere (50 psi). TLC (petroleum ether:ethyl acetate=5:1) showed that the conversion of the starting materials was completed and new spots were produced. The reaction solution was filtered through celite and then washed with ethanol (20 mL). The filtrate was dried over anhydrous sodium sulfate, filtered and concentrated under reduced pressure to give compound 23-4.

$^1$H NMR (400 MHz, CDCl$_3$) δ=2.22 (t, J=7.4 Hz, 2H), 1.55-1.52 (m, 2H), 1.31 (s, 9H), 1.30-1.28 (m, 2H), 1.03 (s, 6H).

Step 4

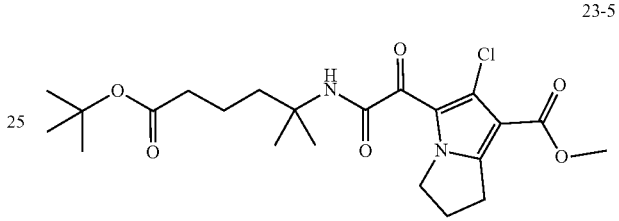

23-5

Compound 23-4 (150 mg, 745.61 μmol, 7.21e-1 eq.) was dissolved in dichloromethane (5 mL) at 26° C., and sodium bicarbonate (434.37 mg, 5.17 mmol, 201.10 μL, 5 eq.) was added. A mixture of compound 11-7 (300 mg, 1.03 mmol, 1 eq.) and dichloromethane (5 mL) was added dropwise slowly while stirring, and then the reaction system was stirred at 26° C. for 0.5 h. LCMS showed that compound 23-5 was produced. The reaction solution was added with water (10 mL) while being stirred, and let stand for liquid separation to give organic phases. The separated aqueous phase was extracted with dichloromethane (10 mL×1), and the organic phases were combined, washed with saturated aqueous sodium chloride solution, dried over anhydrous sodium sulfate, filtered and concentrated under reduced pressure. The crude product was purified by a chromatographic system COMBI-FLASH (petroleum ether:ethyl acetate=50:1 to 2:1, V/V) to give compound 23-5. MS (ESI) m/z: 477.1 [M+Na]$^+$.

$^1$H NMR (400 MHz, CDCl$_3$) δ=6.11 (s, 1H), 4.24 (t, J=7.4 Hz, 2H), 3.76 (s, 3H), 3.05 (t, J=7.6 Hz, 2H), 2.43-2.40 (m, 2H), 2.17 (t, J=7.0 Hz, 2H), 1.70-1.69 (m, 2H), 1.57-1.55 (m, 2H), 1.37 (s, 9H), 1.36 (s, 6H).

Step 5

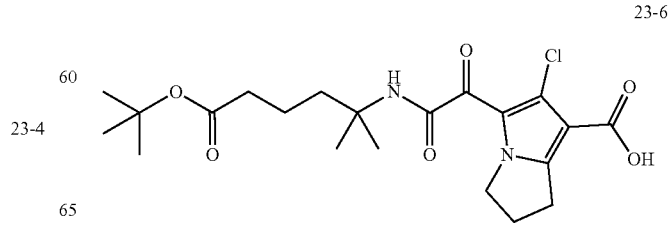

23-6

Compound 23-5 (480 mg, 1.06 mmol, 1 eq.) was dissolved in a mixture of tetrahydrofuran (5 mL), methanol (5 mL) and water (5 mL), and lithium hydroxide monohydrate (221.37 mg, 5.28 mmol, 5 eq.) was added. The reaction mixture was stirred at 50° C. for 1 h. LCMS showed that the reaction was completed. 2.0 mol/L aqueous potassium hydrogen sulfate solution was added to the reaction solution until pH=5, and the mixture was extracted with ethyl acetate (10 mL×2). The organic phases were combined, washed with saturated sodium chloride (10 mL×1), dried over anhydrous sodium sulfate, filtered and concentrated under reduced pressure to give compound 23-6. MS (ESI) m/z: 463.3 [M+Na]$^+$.

$^1$H NMR (400 MHz, CDCl$_3$) δ=4.19 (t, J=7.0 Hz, 2H), 3.22 (s, 1H), 3.01 (t, J=7.6 Hz, 2H), 2.38-2.36 (m, 2H), 2.18-2.09 (m, 2H), 1.63-1.60 (m, 2H), 1.51-1.49 (m, 2H), 1.30 (d, J=6.4 Hz, 15H).

Step 6

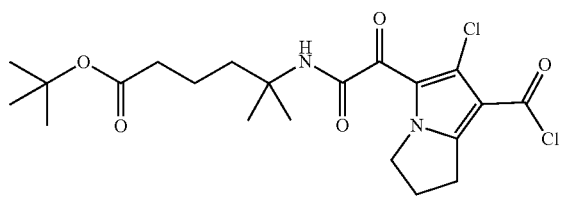

23-7

Compound 23-6 (100 mg, 226.80 μmol, 1 eq.) was dissolved in dichloromethane (5 mL), and oxalyl chloride (57.57 mg, 453.60 μmol, 39.71 μL, 2 eq.) and N,N-dimethylformamide (1.66 mg, 22.68 μmol, 1.75 μL, 0.1 eq.) were added at 0° C. After the addition was completed, the reaction system was heated to 26° C. and stirred for 0.5 h. A small amount of the reaction solution was added to 1 mL of methanol to quench the reaction. TLC (petroleum ether: ethyl acetate=3:1) showed that the starting materials were completely consumed and new spots were generated. The reaction solution was directly concentrated under reduced pressure to give compound 23-7.

Step 7

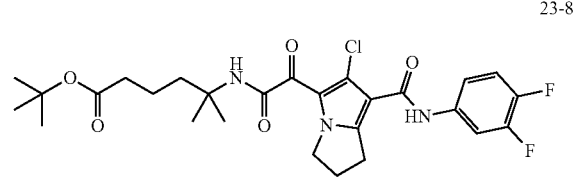 [SMILES: CC(C)(CCCC(=O)OC(C)(C)C)NC(=O)C(=O)c1c(Cl)c(C(=O)Nc2ccc(F)c(F)c2)c2n1CCC2]

23-8

Compound 1-9 (56.21 mg, 435.39 μmol, 2 eq.) was dissolved in dichloromethane (5 mL), and sodium bicarbonate (91.44 mg, 1.09 mmol, 42.33 μL, 5 eq.) was added. A mixture of compound 23-7 (100 mg, 217.69 mol, 1 eq.) and dichloromethane (5 mL) was added dropwise at 26° C. After the addition was completed, the reaction system was stirred at 26° C. for 0.5 h. LCMS showed that the reaction was completed. The reaction solution was added with water (10 mL) while being stirred, and let stand for liquid separation to obtain the dichloromethane phase. The aqueous phase was extracted with dichloromethane (10 mL×1), and the organic phases were combined, washed with saturated aqueous sodium chloride solution (10 mL×1), dried over anhydrous sodium sulfate, filtered and concentrated under reduced pressure to give compound 23-8. MS (ESI) m/z: 574.4 [M+Na]$^+$.

Step 8

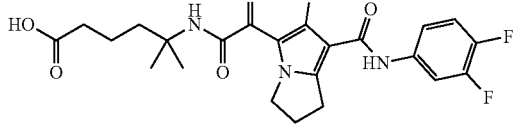

23

Compound 23-8 (150 mg, 271.73 μmol, 1 eq.) was dissolved in dichloromethane (5 mL), and trifluoroacetic acid (309.84 mg, 2.72 mmol, 201.19 μL, 10 eq.) was added at 26° C. After the addition was completed, the reaction system was stirred at 26° C. for 0.5 h. LCMS showed that the reaction was completed. The reaction solution was directly concentrated under reduced pressure, and the crude product was purified by prep-HPLC (column: Xtimate C18 150 mm×25 mm×5 μm; mobile phase: water (containing 0.225% formic acid)-acetonitrile; acetonitrile %: 47%-77%, 7 min) to give compound 23. MS (ESI) m/z: 518.3 [M+Na]$^+$.

$^1$H NMR (DMSO-d$_6$) δ=12.04 (br s, 1H), 9.93 (s, 1H), 8.30 (s, 1H), 7.87-7.82 (m, 1H), 7.43-7.40 (m, 2H), 4.28 (t, J=7.2 Hz, 2H), 3.08 (t, J=7.6 Hz, 2H), 2.47-2.45 (m, 2H), 2.19 (t, J=7.2 Hz, 2H), 1.68 (t, J=8.2 Hz, 2H), 1.56-1.52 (m, 2H), 1.32 (s, 6H).

Example 24

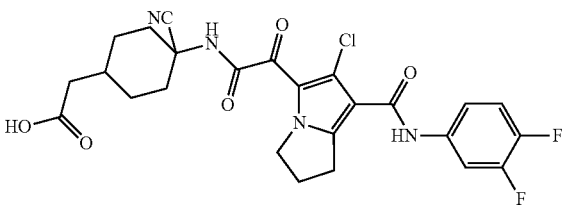

24

Synthetic Route:
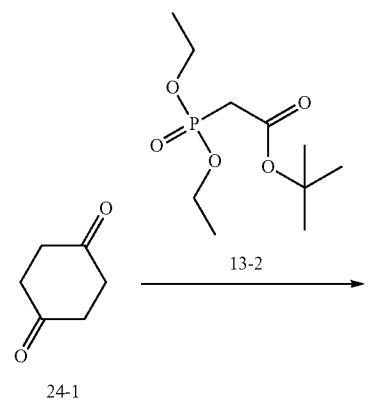
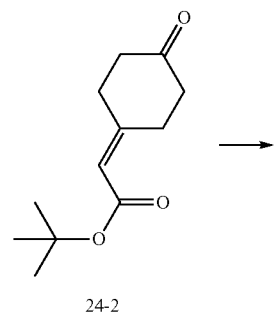
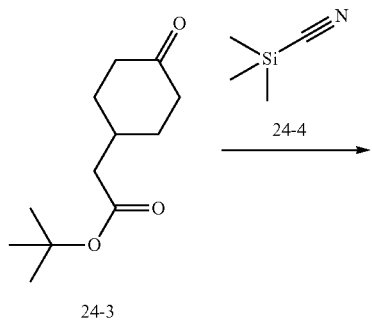
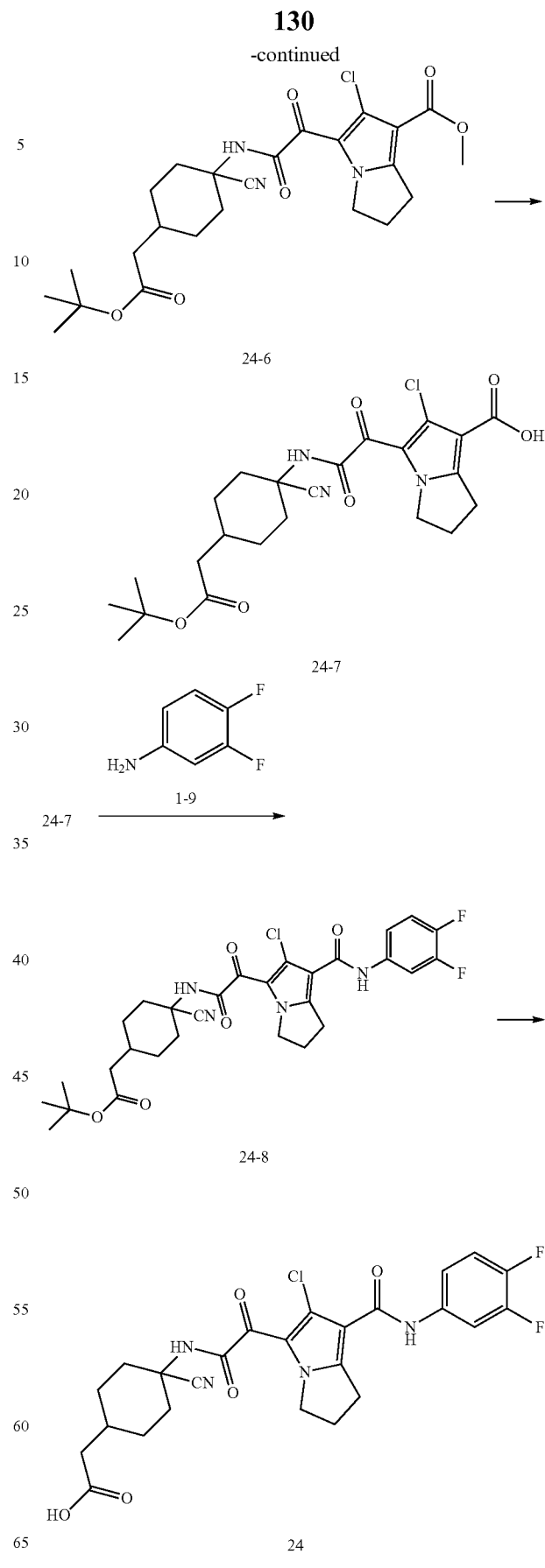

Step 1

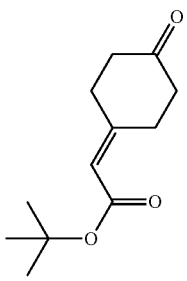

24-2

Compound 13-2 (25 g, 99.11 mmol, 1 eq.) was dissolved in tetrahydrofuran (100 mL), and then sodium hydride (5.95 g, 148.67 mmol, purity: 60%, 1.5 eq.) was added. The reaction system reacted at 0° C. for 1 h, and then was added with compound 24-1 (22.23 g, 198.22 mmol, 2 eq.) and reacted at 25° C. for 1 h. LCMS showed that compound 24-1 was completely consumed and compound 24-2 was produced. The reaction solution was poured into 500 mL of saturated ammonium chloride solution, and extracted with ethyl acetate (500 mL×3). The organic phase was dried over anhydrous sodium sulfate, filtered and concentrated under reduced pressure to give a crude product. The crude product was purified by column chromatography (100-200 mesh silica gel, petroleum ether:ethyl acetate=20:1 to 5:1, V/V) to give compound 24-2.

$^1$H NMR (400 MHz, CDCl$_3$) δ=5.77 (s, 1H), 3.17 (t, J=7.2 Hz, 2H), 2.63 (t, J=6.4 Hz, 2H), 2.52-2.47 (m, 4H), 1.49 (s, 9H).

Step 2

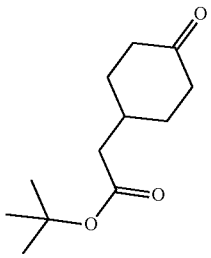

24-3

Compound 24-2 (6 g, 28.53 mmol, 1 eq.) was dissolved in ethanol (20 mL), and then wet palladium on carbon (0.2 g, 28.53 mmol, content: 10%, 1 eq.) was added. The reaction system reacted at 25° C. for 1 h under hydrogen atmosphere (15 psi). TLC (petroleum ether:ethyl acetate=3:1) showed that compound 24-2 was completely consumed. The reaction solution was filtered directly to give a crude product. The crude product was purified by column chromatography (100-200 mesh silica gel, petroleum ether:ethyl acetate=10:1 to 3:1, V/V) to give compound 24-3.

$^1$H NMR (400 MHz, CDCl$_3$) δ=3.45 (s, 1H), 2.40-2.37 (m, 4H), 2.23 (s, 3H), 2.07-2.06 (m, 3H), 1.47 (s, 9H).

Step 3

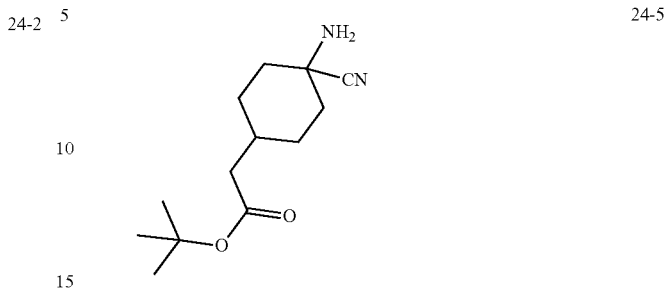

24-5

Titanium tetraisopropoxide (4.50 g, 15.83 mmol, 4.67 mL, 1.2 eq.) was dissolved in ammonia/methanol (7 M, 7.54 mL, 4 eq.), and then compound 24-3 (2.8 g, 13.19 mmol, 1 eq.) was added. The reaction system reacted at 25° C. for 2 h and then cooled to −5° C., added with compound 24-4 (1.37 g, 13.85 mmol, 1.73 mL, 1.05 eq.), and then reacted at 25° C. for 14 h. HPLC showed that compound 24-3 was completely consumed. The reaction solution was added with water (5 mL), stirred for 0.5 h and filtered. The filtrate was concentrated under reduced pressure to give a crude product. The crude product was purified by column chromatography (100-200 mesh silica gel, petroleum ether:ethyl acetate=3:1 to 1:1, V/V) to give compound 24-5.

$^1$H NMR (400 MHz, CDCl$_3$) δ=2.19-2.06 (m, 2H), 2.06-2.03 (m, 2H), 1.86-1.82 (m, 5H), 1.60-1.53 (m, 2H), 1.52 (s, 9H), 1.45-1.38 (m, 2H).

Step 4

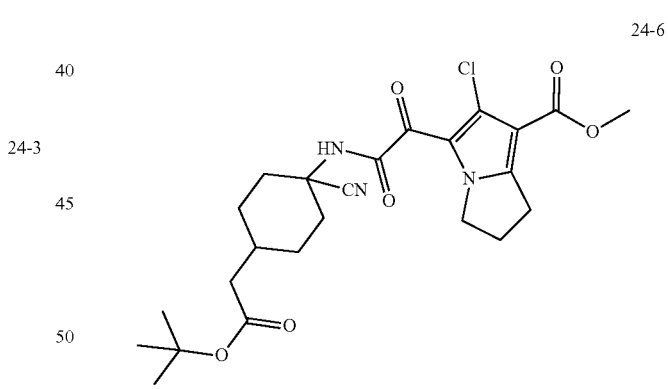

24-6

Compound 24-5 (1.23 g, 5.17 mmol, 1.5 eq.) and triethylamine (1.05 g, 10.34 mmol, 1.44 mL, 3 eq.) were dissolved in dichloromethane (5 mL), and then a solution of compound 11-7 (1 g, 3.45 mmol, 1 eq.) in dichloromethane (5 mL) was added at 0° C. under nitrogen atmosphere. The reaction system was heated to 30° C. and stirred for 1 h. TLC (petroleum ether:ethyl acetate=3:1) showed that compound 11-7 was completely consumed and new spots were produced. LCMS confirmed that compound 24-6 was produced. The reaction was quenched with water (30 mL), and then the reaction solution was extracted with dichloromethane (30 mL×3). The organic phase was dried over anhydrous sodium sulfate, filtered and concentrated under reduced pressure. The crude product was purified by column chromatography (100-200 mesh silica gel, petroleum ether:ethyl acetate=100:1 to 2:1, V/V) to give compound 24-6. MS(ESI) m/s: 436.0 [M+H-(t-Bu)]+.

Step 5

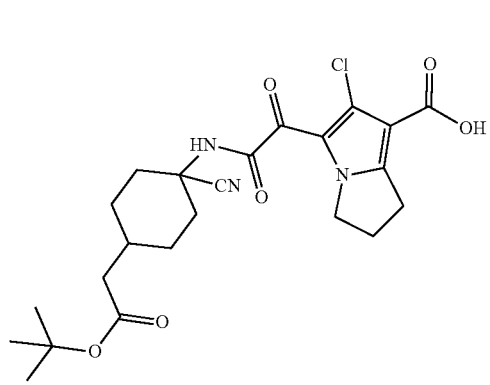

24-7

Compound 24-6 (1 g, 2.03 mmol, 1 eq.) was dissolved in a mixture of tetrahydrofuran (10 mL) and water (5 mL), and then lithium hydroxide monohydrate (255.87 mg, 6.10 mmol, 3 eq.) was added. The reaction system was stirred at 30° C. for 16 h. LCMS showed that compound 24-6 was completely consumed and compound 24-7 was produced. The reaction solution was adjusted to pH=3-5 with 1.0 mol/L diluted hydrochloric acid, and extracted with ethyl acetate (30 mL×3). The organic phase was dried over anhydrous sodium sulfate, filtered and concentrated under reduced pressure to give compound 24-7. MS(ESI) m/s: 476.1 [M−H]−.

$^1$H NMR (400 MHz, DMSO-$d_6$) δ=12.43 (br s, 1H), 9.40 (s, 1H), 4.27 (t, J=7.2 Hz, 2H), 3.06 (t, J=7.5 Hz, 2H), 2.45-2.40 (m, 4H), 2.15 (d, J=6.4 Hz, 2H), 1.91 (s, 1H), 1.79 (d, J=12.8 Hz, 2H), 1.64-1.58 (m, 2H), 1.41 (s, 9H), 1.31-1.23 (m, 2H).

Step 6

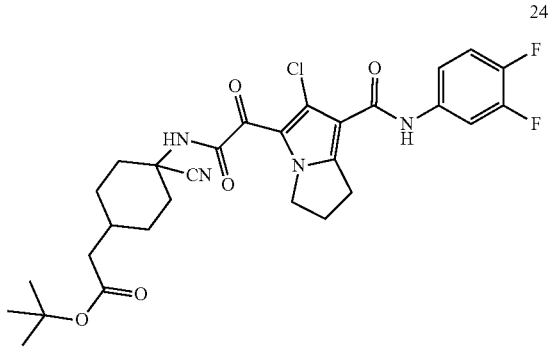

24-8

Compound 24-7 (0.4 g, 836.93 μmol, 1 eq.), triethylamine (127.03 mg, 1.26 mmol, 174.74 μL, 1.5 eq.) and O-(7-azabenzotriazol-1-yl)-N,N,N',N'-tetramethyluronium hexafluorophosphate (381.87 mg, 1.00 mmol, 1.2 eq.) were dissolved in N,N-dimethylformamide (5 mL). The reaction system was stirred at 25° C. for 0.5 h, and then added with compound 1-9 (324.16 mg, 2.51 mmol, 3 eq.). The reaction system was heated to 60° C. and stirred for 5 h. TLC (petroleum ether:ethyl acetate=3:1) showed that compound 24-7 was completely consumed and new spots were produced; LCMS showed that compound 24-8 was produced. The reaction was quenched with water (30 mL), and then the reaction solution was extracted with ethyl acetate (20 mL×3). The organic phase was dried over anhydrous sodium sulfate, filtered and concentrated under reduced pressure. The crude product was purified by column chromatography (100-200 mesh silica gel, petroleum ether:ethyl acetate=100:1 to 2:1, V/V) to give compound 24-8. MS(ESI) m/s: 587.1 [M−H]−.

Step 7

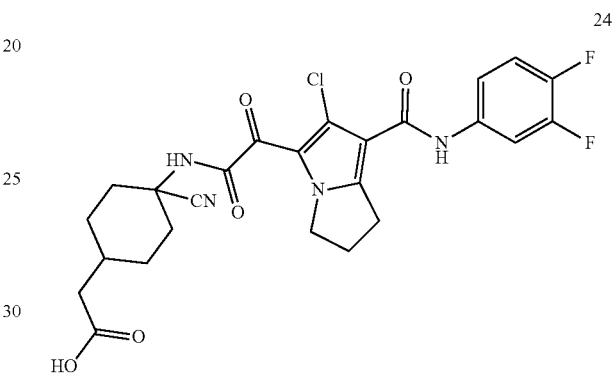

24

Compound 24-8 (0.3 g, 509.31 μmol, 1 eq.) was dissolved in dichloromethane (5 mL), and then trifluoroacetic acid (5 mL) was added. The reaction system was stirred at 30° C. for 1 h. LCMS and HPLC showed that the reaction was completed. The reaction solution was added with water (0.1 mL) to quench the reaction and then filtered. The filtrate was purified by prep-HPLC (neutral, column: Xtimate C18 150 mm×25 mm×5 μm; mobile phase: water (containing 10 mM ammonium bicarbonate)-acetonitrile; acetonitrile %: 10%-50%, 20 min) to give compound 24. MS(ESI) m/s: 531.1 [M−H]−.

$^1$H NMR (400 MHz, DMSO-$d_6$) δ=9.96 (s, 1H), 9.45 (br s, 1H), 7.86-7.81 (m, 1H), 7.45-7.39 (m, 2H), 4.30 (t, J=7.2 Hz, 2H), 3.09 (t, J=7.6 Hz, 2H), 2.53-2.52 (m, 2H), 2.46-2.41 (m, 2H), 2.15 (d, J=6.8 Hz, 2H), 1.83 (d, J=12.8 Hz, 2H), 1.75 (br s, 1H), 1.65-1.59 (m, 2H), 1.29-1.20 (m, 2H).

Example 25

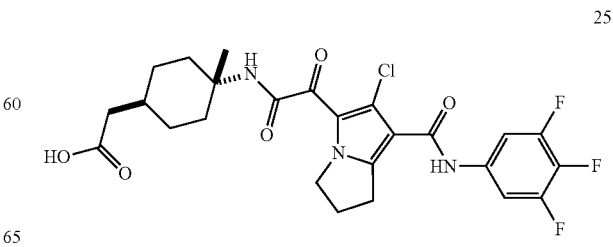

25

135

Synthetic Route:

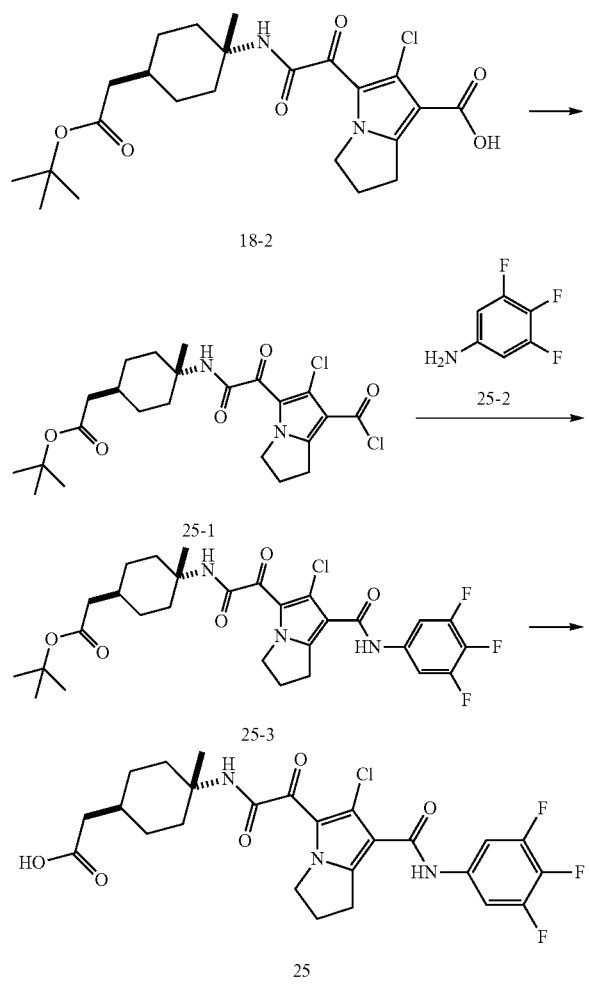

Step 1

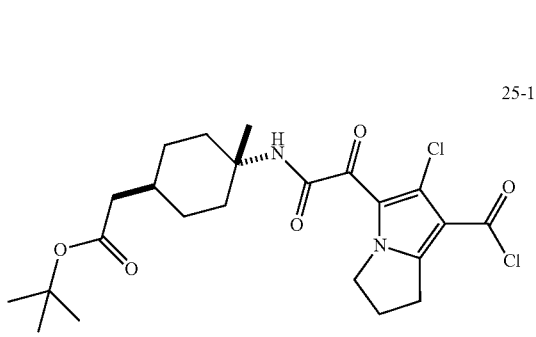 [SMILES: CC(C)(C)OC(=O)C[C@H]1CC[C@](C)(NC(=O)C(=O)c2c(Cl)c(C(=O)Cl)c3n2CCC3)CC1]

Compound 18-2 (500 mg, 1.07 mmol, 1 eq.) was dissolved in dichloromethane (20 mL), and oxalyl chloride (271.83 mg, 2.14 mmol, 187.47 µL, 2 eq.) and N,N-dimethylformamide (7.83 mg, 107.08 µmol, 8.24 µL, 0.1 eq.) were added dropwise under nitrogen atmosphere at 0° C. The reaction system was stirred at 25° C. for 1 h. Two drops of the reaction solution were taken and added with methanol to quench the reaction, and LCMS showed that the reaction was completed. The reaction solution was concentrated under reduced pressure to give compound 25-1.

136

Step 2

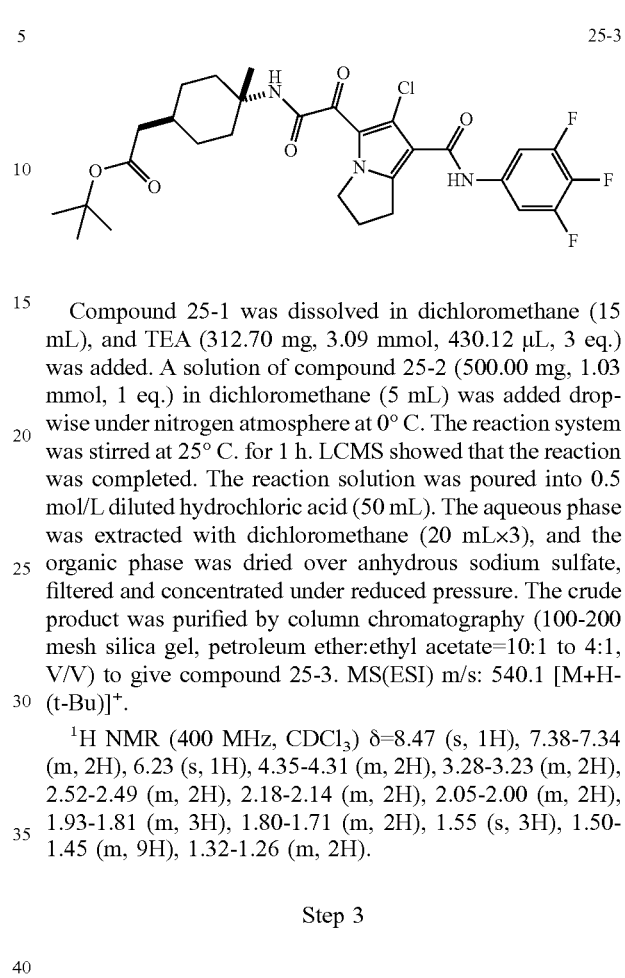

Compound 25-1 was dissolved in dichloromethane (15 mL), and TEA (312.70 mg, 3.09 mmol, 430.12 µL, 3 eq.) was added. A solution of compound 25-2 (500.00 mg, 1.03 mmol, 1 eq.) in dichloromethane (5 mL) was added dropwise under nitrogen atmosphere at 0° C. The reaction system was stirred at 25° C. for 1 h. LCMS showed that the reaction was completed. The reaction solution was poured into 0.5 mol/L diluted hydrochloric acid (50 mL). The aqueous phase was extracted with dichloromethane (20 mL×3), and the organic phase was dried over anhydrous sodium sulfate, filtered and concentrated under reduced pressure. The crude product was purified by column chromatography (100-200 mesh silica gel, petroleum ether:ethyl acetate=10:1 to 4:1, V/V) to give compound 25-3. MS(ESI) m/s: 540.1 [M+H-(t-Bu)]$^+$.

$^1$H NMR (400 MHz, CDCl$_3$) δ=8.47 (s, 1H), 7.38-7.34 (m, 2H), 6.23 (s, 1H), 4.35-4.31 (m, 2H), 3.28-3.23 (m, 2H), 2.52-2.49 (m, 2H), 2.18-2.14 (m, 2H), 2.05-2.00 (m, 2H), 1.93-1.81 (m, 3H), 1.80-1.71 (m, 2H), 1.55 (s, 3H), 1.50-1.45 (m, 9H), 1.32-1.26 (m, 2H).

Step 3

Compound 25-3 (100.00 mg, 167.78 µmol, 1 eq.) was dissolved in dichloromethane (1 mL), and trifluoroacetic acid (382.59 mg, 3.36 mmol, 248.44 µL, 20 eq.) was added. The reaction system was stirred at 25° C. for 1 h. LCMS and HPLC showed that the reaction was completed. The reaction solution was concentrated under reduced pressure. The crude product was purified by prep-HPLC (neutral system, column: Xtimate C18 150 mm×25 mm×5 µm; mobile phase: water (containing 10 mM ammonium bicarbonate)-acetonitrile; acetonitrile %: 10%-50%, 20 min) to give compound 25. MS(ESI) m/s: 540.2 [M+H]$^+$.

$^1$H NMR (400 MHz, DMSO-d$_6$) δ=9.99 (s, 1H), 8.29 (s, 1H), 7.65-7.57 (m, 2H), 4.30-4.26 (m, 2H), 3.09-3.05 (m, 2H), 2.47-2.43 (m, 2H), 2.16-2.12 (m, 2H), 1.85-1.80 (m, 2H), 1.75-1.61 (m, 5H), 1.35 (s, 3H), 1.21-1.16 (m, 2H).

Example 26

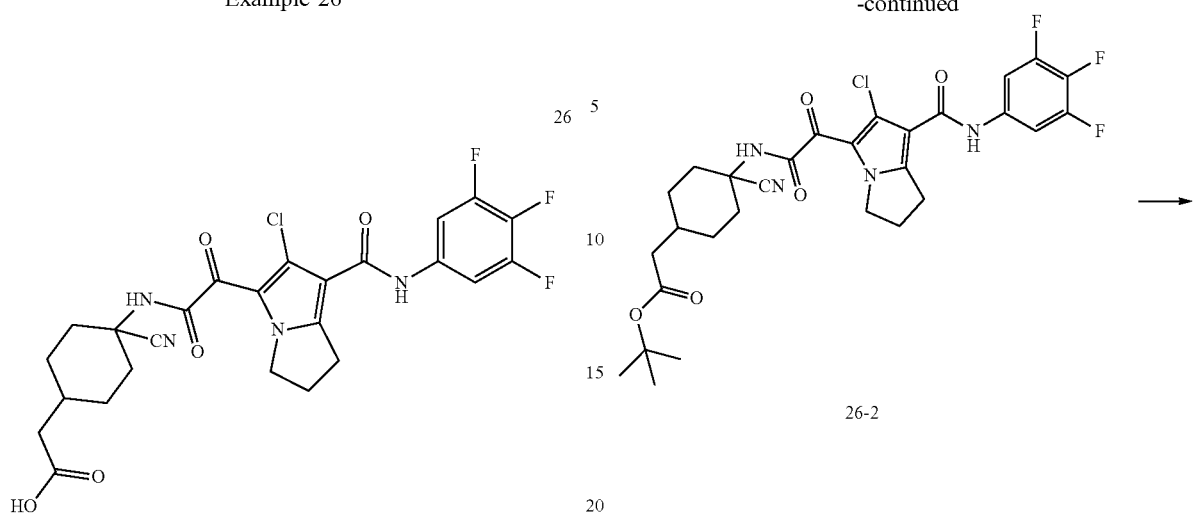

24-7

Synthetic Route:

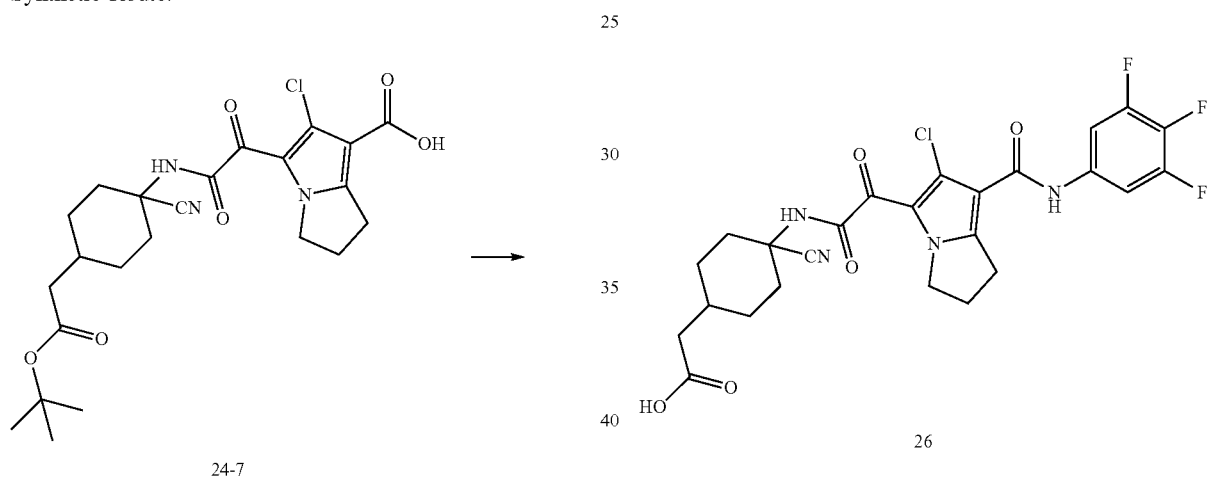

26-1

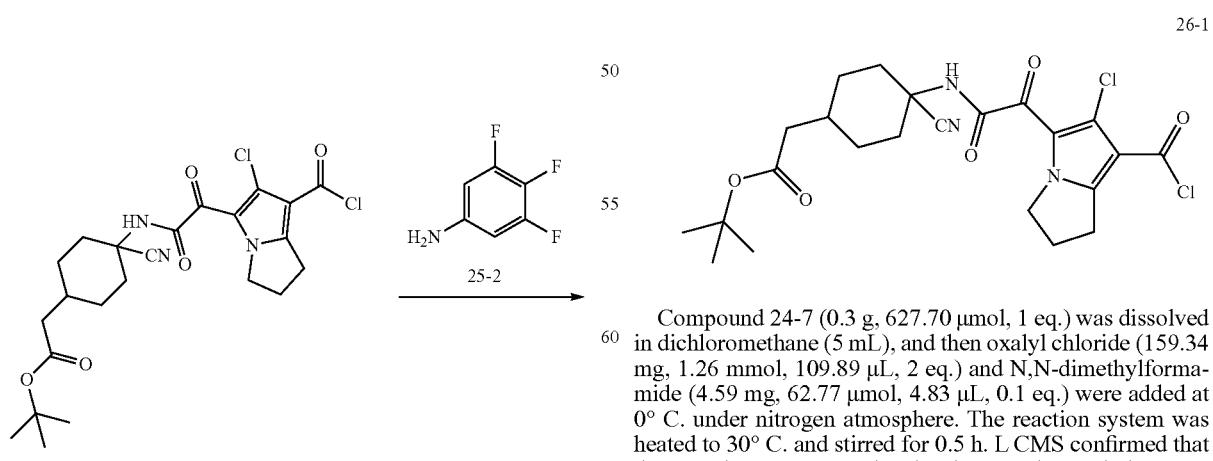

26-2

Step 1

Compound 24-7 (0.3 g, 627.70 μmol, 1 eq.) was dissolved in dichloromethane (5 mL), and then oxalyl chloride (159.34 mg, 1.26 mmol, 109.89 μL, 2 eq.) and N,N-dimethylformamide (4.59 mg, 62.77 μmol, 4.83 μL, 0.1 eq.) were added at 0° C. under nitrogen atmosphere. The reaction system was heated to 30° C. and stirred for 0.5 h. LCMS confirmed that the reaction was completed. The reaction solution was concentrated under reduced pressure to give compound 26-1, which was directly used in the next step.

Step 2

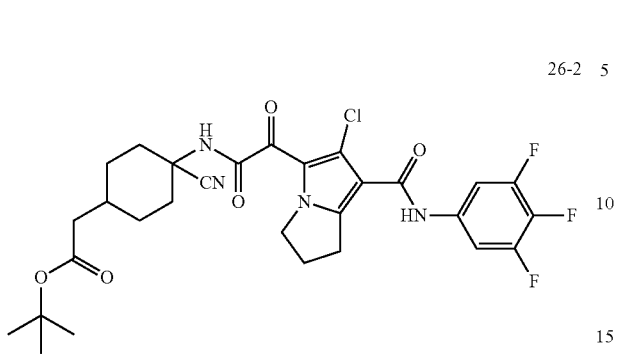

Compound 25-2 (133.35 mg, 906.56 μmol, 1.5 eq.) and triethylamine (183.47 mg, 1.81 mmol, 252.36 μL, 3 eq.) were dissolved in dichloromethane (5 mL), and then a solution of compound 26-1 (0.3 g, 604.37 μmol, 1 eq.) in dichloromethane (5 mL) was added at 0° C. under nitrogen atmosphere. The reaction system was heated to 30° C. and stirred for 1 h. LCMS and HPLC confirmed that the reaction was completed. The reaction solution was poured into water (20 mL), and extracted with dichloromethane (15 mL×3). The organic phase was dried over anhydrous sodium sulfate, filtered and concentrated under reduced pressure. The crude product was purified by prep-HPLC (HCl system, column: Xtimate C18 100 mm×30 mm×5 μm; mobile phase: water (containing 0.05% hydrochloric acid)-acetonitrile; acetonitrile %: 50%-75%, 10 min) to give compound 26-2. MS(ESI) m/s: 605.1 [M–H]⁻.

$^1$H NMR (400 MHz, DMSO-$d_6$) δ=10.07 (s, 1H), 9.46 (s, 1H), 7.64-7.59 (m, 2H), 4.30 (t, J=7.2 Hz, 2H), 3.09 (t, J=7.4 Hz, 2H), 2.53-2.51 (m, 2H), 2.47-2.44 (m, 1H), 2.42-2.41 (m, 2H), 2.15 (d, J=6.8 Hz, 2H), 1.80 (d, J=12.8 Hz, 2H), 1.65-1.56 (m, 2H), 1.41 (s, 9H), 1.32-1.23 (m, 2H).

Step 3

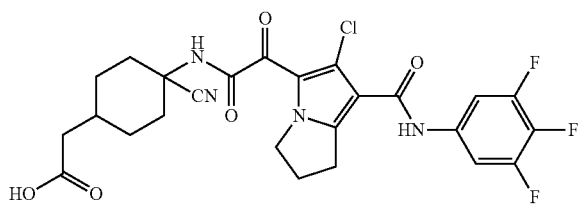

Compound 26-2 (15 mg, 24.71 μmol, 1 eq.) was dissolved in dichloromethane (2 mL), and then trifluoroacetic acid (2 mL) was added. The reaction system was stirred at 30° C. for 0.5 h. LCMS and HPLC confirmed that the reaction was completed. The reaction solution was concentrated under reduced pressure to give residue. The residue was purified by prep-HPLC (neutral, column: Xtimate C18 150 mm×25 mm×5 μm; mobile phase: water (containing 10 mM ammonium bicarbonate)-acetonitrile; acetonitrile %: 5%-50%, 20 min) to give compound 26. MS(ESI) m/s: 549.1 [M–H]⁻.

$^1$H NMR (400 MHz, DMSO-$d_6$) δ=10.06 (s, 1H), 9.46 (s, 1H), 7.64-7.60 (m, 2H), 4.30 (t, J=7.2 Hz, 2H), 3.09 (t, J=7.8 Hz, 2H), 2.52-2.51 (m, 2H), 2.45-2.41 (m, 2H), 2.17 (d, J=6.8 Hz, 2H), 1.83 (d, J=13.6 Hz, 2H), 1.75 (br s, 1H), 1.65-1.59 (m, 2H), 1.30-1.24 (m, 2H).

Example 27

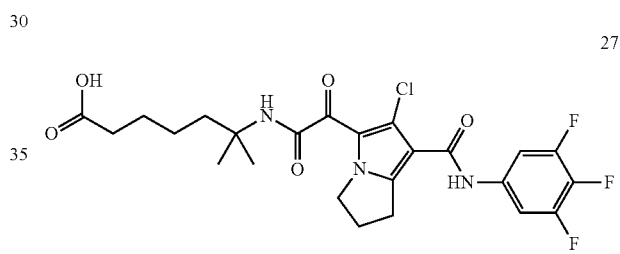

Synthetic Route:

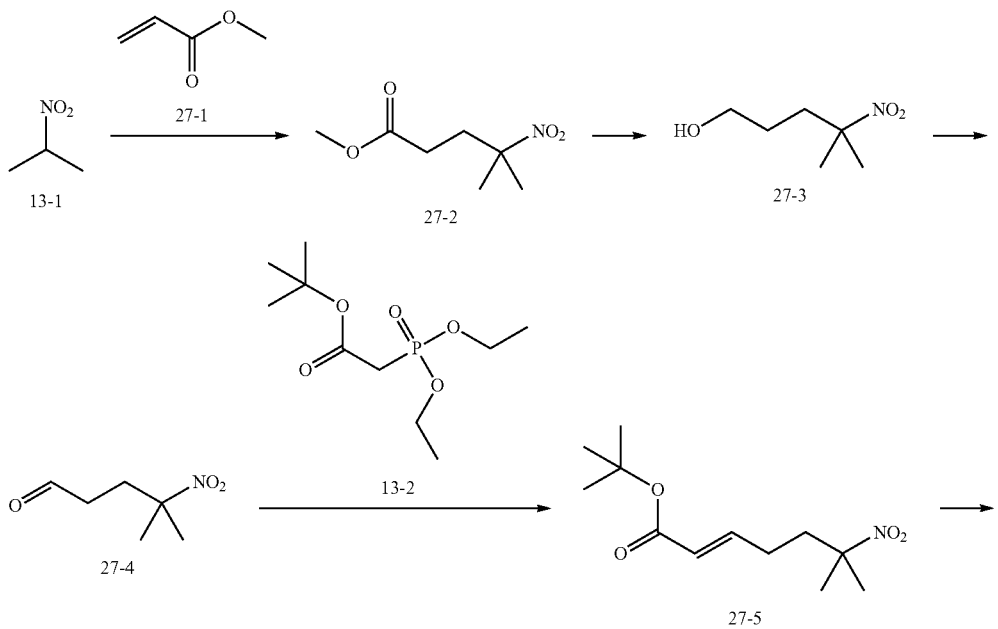

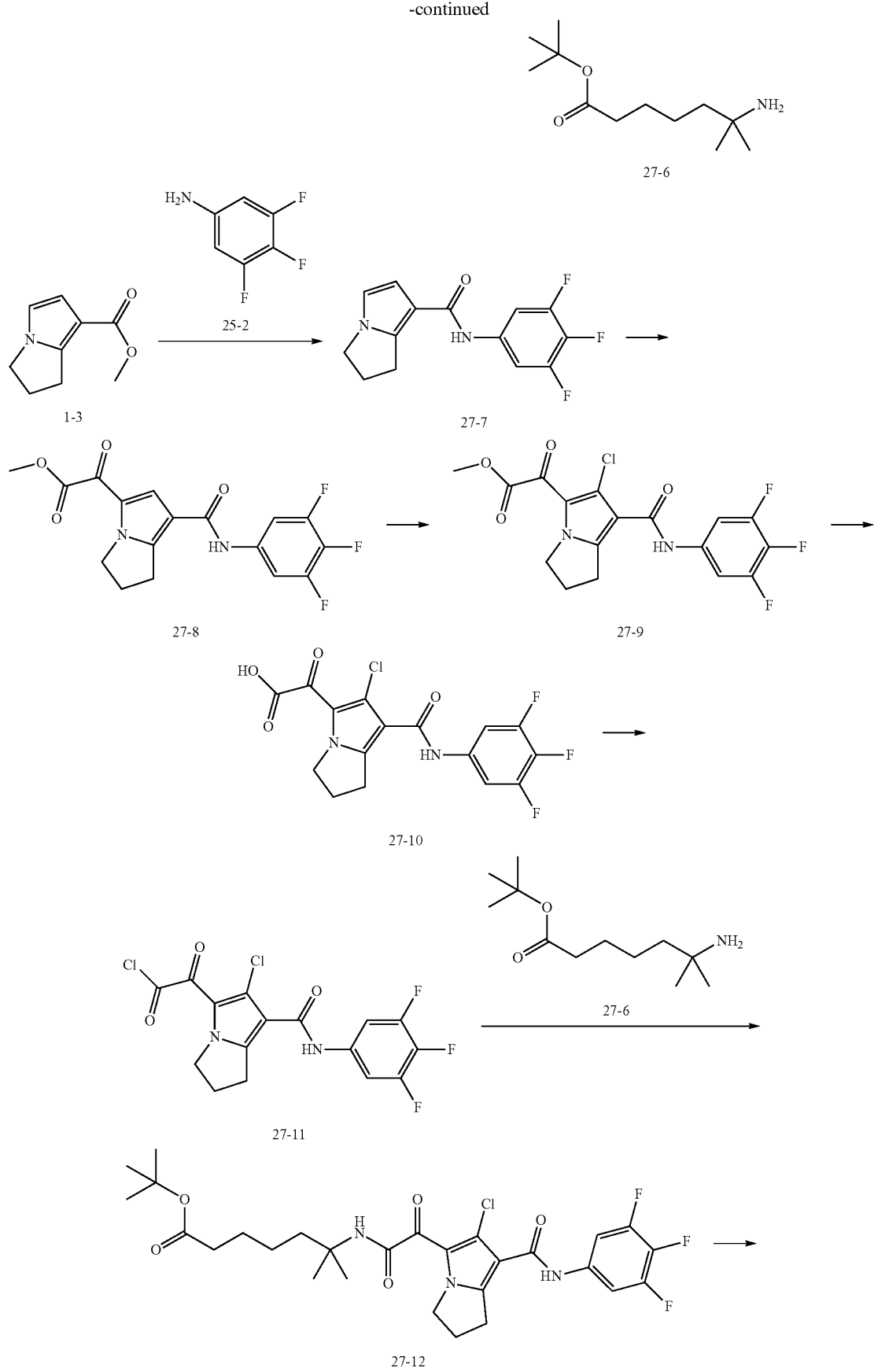

-continued

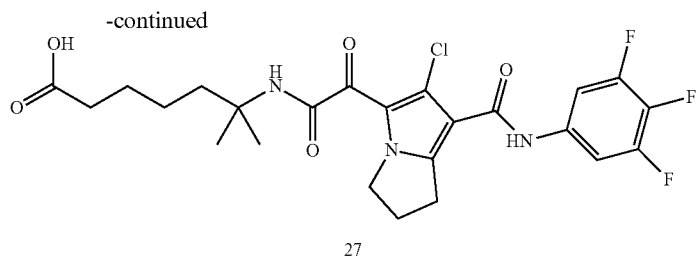

27

Step 1

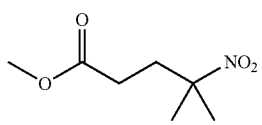
27-2

Compound 13-1 (20 g, 224.48 mmol, 20.16 mL, 1 eq.) was dissolved in dichloromethane (100 mL), and then compound 27-1 (23.19 g, 269.38 mmol, 24.26 mL, 1.2 eq.) and 1,8-diazabicyclo[5.4.0]undec-7-ene (68.35 g, 448.97 mmol, 67.67 mL, 2 eq.) were added. The reaction system was stirred at 45° C. for 12 h. TLC (petroleum ether:ethyl acetate=5:1) showed that compound 27-2 was produced. The reaction solution was poured into saturated ammonium chloride solution (100 mL), and extracted with dichloromethane (100 mL×3). The organic phase was dried over anhydrous sodium sulfate, filtered and concentrated under reduced pressure to give a crude compound. The crude compound was purified by column chromatography (100-200 mesh silica gel, gradient elution: petroleum ether:ethyl acetate=20:1 to 5:1, V/V) to give compound 27-2.

$^1$H NMR (400 MHz, CDCl$_3$) δ=3.69 (s, 3H), 2.35-2.32 (m, 2H), 2.29-2.26 (m, 2H), 1.60 (s, 6H).

Step 2

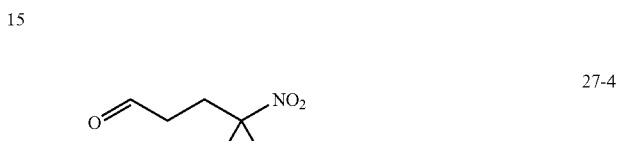
27-3

Under nitrogen atmosphere, compound 27-2 (18 g, 102.75 mmol, 1 eq.) was dissolved in tetrahydrofuran (1 L) in a dry flask, and lithium aluminium hydride (2.14 g, 56.51 mmol, 0.55 eq.) was slowly added at 0° C. The reaction system was slowly heated to 25° C. and stirred for 1 h. TLC (petroleum ether:ethyl acetate=3:1) showed that the reaction was completed. The reaction solution was slowly added with a saturated solution of potassium sodium tartrate (9 mL) dropwise while being stirred, and then filtered. The filtrate was directly concentrated under reduced pressure to give a crude product. The crude product was purified by column chromatography (100-200 mesh silica gel, gradient elution: petroleum ether:ethyl acetate=4:1, V/V) to give compound 27-3.

$^1$H NMR (400 MHz, CDCl$_3$) δ=3.68-3.63 (m, 2H), 2.04-1.97 (m, 2H), 1.59 (s, 6H), 1.55-1.51 (m, 2H).

Step 3

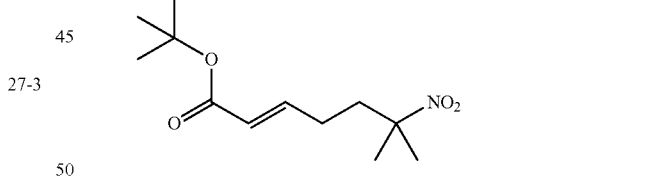
27-4

Compound 27-3 (2 g, 13.59 mmol, 1 eq.) was dissolved in dichloromethane (50 mL) in a dry flask, and pyridinium chlorochromate (4.39 g, 20.38 mmol, 1.5 eq.) was added at 0° C. under nitrogen atmosphere. The reaction system was stirred at 25° C. for 1 h. TLC (petroleum ether:ethyl acetate=3:1) showed that the reaction was completed. The reaction was quenched with water (20 mL), and then the reaction solution was extracted with dichloromethane (10 mL×2). The organic phase was dried over anhydrous sodium sulfate, filtered and concentrated under reduced pressure. The crude product was purified by column chromatography (100-200 mesh silica gel, gradient elution: petroleum ether:ethyl acetate=30:1 to 10:1) to give compound 27-4.

$^1$H NMR (400 MHz, CDCl$_3$) δ=9.78 (s, 1H), 2.52-2.49 (m, 2H), 2.25-2.23 (m, 2H), 1.60 (s, 6H).

Step 4

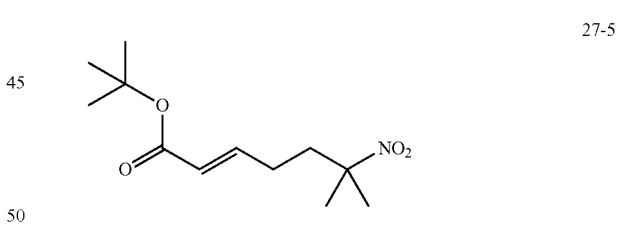
27-5

Compound 13-2 (2.68 g, 10.61 mmol, 2.2 eq.) was dissolved in tetrahydrofuran (15 mL) in a dry flask, and sodium hydride (578.69 mg, 14.47 mmol, purity: 60%, 3 eq.) was added at 0° C. under nitrogen atmosphere. After stirring for 30 min, a solution of compound 27-4 (700 mg, 4.82 mmol, 1 eq.) in tetrahydrofuran (5 mL) was added, and the reaction system was stirred at 25° C. for 16 h. TLC (petroleum ether:ethyl acetate=5:1) showed that the reaction was completed. The reaction solution was poured into diluted hydrochloric acid (0.5 mol/L, 20 mL). The aqueous phase was extracted with ethyl acetate (20 mL×3), and the organic phase was dried over anhydrous sodium sulfate, filtered and concentrated under reduced pressure. The crude product was purified by column chromatography (100-200 mesh silica gel, gradient elution: petroleum ether:ethyl acetate=30:1 to 10:1, V/V) to give compound 27-5.

¹H NMR (400 MHz, CDCl₃) δ=6.83-6.76 (m, 1H), 5.77 (d, J=15.6 Hz, 1H), 2.16-2.06 (m, 2H), 2.05-2.04 (m, 2H), 1.60 (s, 6H), 1.48 (s, 9H).

Step 5

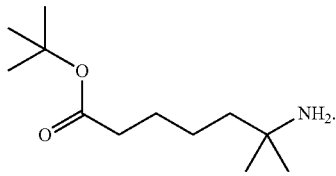

27-6

Under a slight stream of argon, palladium on carbon (150 mg, purity: 10%) was added into a hydrogenation flask, methanol (20 mL) was added slowly along the wall of the flask, and then compound 27-5 (800 mg, 3.29 mmol, 1 eq.) was added. After 3 hydrogen purges, the reaction system was stirred at 20° C. for 2 h under hydrogen atmosphere (50 psi). TLC (petroleum ether:ethyl acetate=5:1) showed that the reaction was completed. The reaction solution was directly filtered and concentrated under reduced pressure to give compound 27-6.

¹H NMR (400 MHz, CDCl₃) δ=2.22 (t, J=7.6 Hz, 2H), 1.60-1.57 (m, 2H), 1.44 (s, 9H), 1.37-1.28 (m, 4H), 1.10 (s, 6H).

Step 6

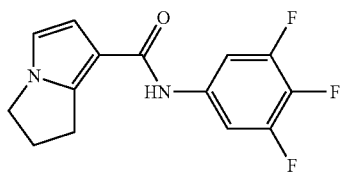

27-7

Compound 1-3 (20 g, 121.07 mmol, 1 eq.) and compound 25-2 (26.71 g, 181.61 mmol, 1.5 eq.) were dissolved in toluene (300 mL), and then lithium hexamethyldisilazide (1 mol/L, 242.15 mL, 2 eq.) was added at 0° C. under nitrogen atmosphere. The reaction system was heated to 25° C. and stirred for 16 h. TLC confirmed that compound 1-3 was completely consumed and new spots were produced. LCMS confirmed that compound 1-3 was completely consumed and compound 27-7 was produced. The reaction solution was poured into saturated ammonium chloride solution (500 mL) to quench the reaction, and extracted with ethyl acetate (200 mL×3). The organic phase was dried over anhydrous sodium sulfate, filtered and concentrated under reduced pressure. The crude product was purified by column chromatography (100-200 mesh silica gel, gradient elution: petroleum ether:ethyl acetate=100:1 to 1:1.5, V/V) to give compound 27-7. MS(ESI) m/s: 281.0 [M+H]⁺.

¹H NMR (400 MHz, CDCl₃) δ=7.44 (s, 1H), 7.37-7.28 (m, 2H), 6.61 (d, J=2.8 Hz, 1H), 6.45 (d, J=3.2 Hz, 1H), 3.99 (t, J=2.8 Hz, 2H), 3.13 (t, J=3.2 Hz, 2H), 2.62-2.55 (m, 2H).

Step 7

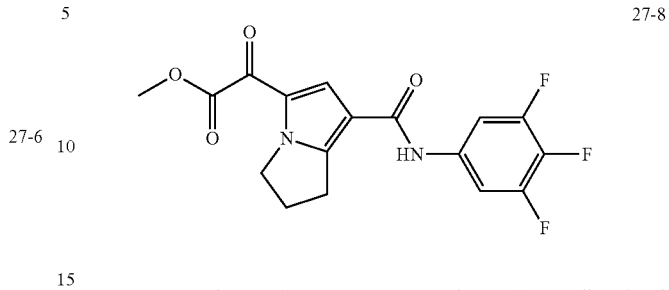

27-8

Compound 27-7 (31 g, 110.62 mmol, 1 eq.) was dissolved in dichloromethane (300 mL), and then methyl oxalyl chloride (27.10 g, 221.23 mmol, 20.38 mL, 2 eq.) was added at 0° C. under nitrogen atmosphere. The reaction system was stirred at 25° C. for 1.5 h. TLC (petroleum ether:ethyl acetate=3:1) confirmed that the reaction was completed. The reaction solution was poured into ice water (300 mL) to quench the reaction, and then extracted with ethyl acetate (100 mL×3). The organic phase was dried over anhydrous sodium sulfate, filtered and concentrated under reduced pressure. The crude product was purified by column chromatography (100-200 mesh silica gel, gradient elution: petroleum ether:ethyl acetate=100:1 to 2.5:1, V/V) to give compound 27-8. MS(ESI) m/s: 367.1 [M+H]⁺.

¹H NMR (400 MHz, CDCl₃) δ=9.92 (s, 1H), 7.80 (s, 1H), 7.43-7.32 (m, 2H), 4.37 (t, J=7.4 Hz, 2H), 3.91 (s, 3H), 3.19 (t, J=7.6 Hz, 2H), 2.65-2.57 (m, 2H).

Step 8

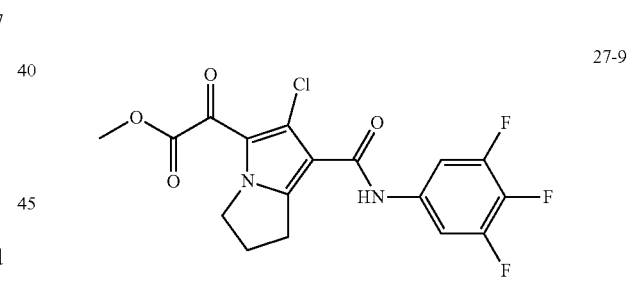

27-9

Compound 27-8 (11 g, 21.02 mmol, 1 eq.) was dissolved in acetic acid (110 mL), and then N-chlorosuccinimide (4.21 g, 31.53 mmol, 1.5 eq.) was added. The reaction system was stirred at 40° C. for 16 h. TLC showed that the compound was completely consumed. The reaction solution was poured into water (100 mL) to quench the reaction, and extracted with ethyl acetate (50 mL×3). The organic phase was washed with saturated sodium bicarbonate solution (50 mL×3), dried over anhydrous sodium sulfate, filtered and concentrated under reduced pressure successively. The crude product was purified by column chromatography (100-200 mesh silica gel, gradient elution: petroleum ether:ethyl acetate=100:1 to 4:1, V/V) to give compound 27-9. MS(ESI) m/s: 401.0 [M+H]⁺.

¹H NMR (400 MHz, CDCl₃) δ=8.29 (s, 1H), 7.36-7.30 (m, 2H), 4.40 (t, J=7.4 Hz, 2H), 3.98 (s, 3H), 3.26 (t, J=7.6 Hz, 2H), 2.61-2.51 (m, 2H).

Step 9

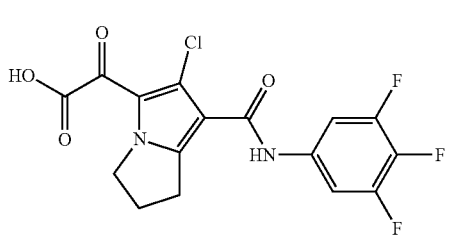

27-10

Compound 27-9 (8 g, 19.96 mmol, 1 eq.) was dissolved in a mixture of tetrahydrofuran (100 mL) and water (100 mL), and then lithium hydroxide monohydrate (2.51 g, 59.89 mmol, 3 eq.) was added. The reaction system was stirred at 25° C. for 16 h. LCMS confirmed that the compound was completely consumed. The reaction solution was poured into water (50 mL), extracted with ethyl acetate (50 mL×2), adjusted to pH=2 with 1.0 mol/L hydrochloric acid, and then extracted with ethyl acetate (50 mL×3). The organic phase was dried over anhydrous sodium sulfate, filtered and concentrated under reduced pressure to give compound 27-10. MS(ESI) m/s: 387.1 [M+H]$^+$.

$^1$H NMR (400 MHz, MeOH-d$_4$) δ=7.63-7.41 (m, 2H), 4.38 (t, J=7.6 Hz, 2H), 3.15 (t, J=7.6 Hz, 2H), 2.62-2.50 (m, 2H).

Step 10

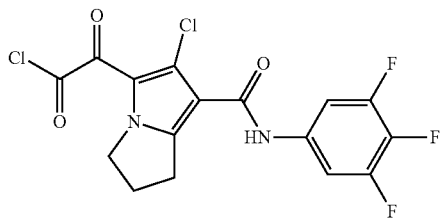

27-11

Compound 27-10 (150 mg, 387.89 μmol, 1 eq.) was dissolved in dichloromethane (10 mL) in a dry flask, and oxalyl chloride (98.47 mg, 775.78 μmol, 67.91 μL, 2 eq.) and N,N-dimethylformamide (2.84 mg, 38.79 μmol, 2.98 μL, 0.1 eq.) were added dropwise under nitrogen atmosphere at 0° C. The reaction system was stirred at 20° C. for 1 h. Two drops of the reaction solution were taken and added with methanol to quench the reaction, and then detected. TLC (petroleum ether:ethyl acetate=3:1) showed that the conversion of the starting materials was completed. The reaction solution was directly concentrated under reduced pressure to give compound 27-11.

Step 11

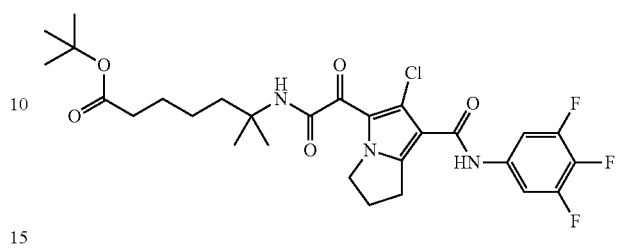

27-12

Compound 27-6 (87.69 mg, 407.25 μmol, 1.1 eq.) was dissolved in dichloromethane (5 mL) in a dry flask, and triethylamine (112.39 mg, 1.11 mmol, 154.59 μL, 3 eq.) was added. A solution of compound 27-11 (150 mg, 370.23 μmol, 1 eq.) in dichloromethane (5 mL) was added at 0° C. under nitrogen atmosphere. The reaction system was stirred at 20° C. for 2 h. LCMS showed that the reaction was completed. The reaction solution was poured into diluted hydrochloric acid (0.5 mol/L, 20 mL). The aqueous phase was extracted with dichloromethane (10 mL×2), and the organic phase was dried over anhydrous sodium sulfate, filtered and concentrated under reduced pressure to give compound 27-12. MS(ESI) m/s: 528.2 [M+H-(t-Bu)]$^+$.

Step 12

27

Compound 27-12 (150 mg, 256.84 μmol, 1 eq.) was dissolved in dichloromethane (1 mL) in a dry flask, and trifluoroacetic acid (585.69 mg, 5.14 mmol, 380.32 μL, 20 eq.) was added. The reaction system was stirred at 20° C. for 1 h. LCMS and HPLC showed that the reaction was completed. The reaction solution was directly concentrated. The crude product was purified by prep-HPLC (neutral system, column: Xtimate C18 150 mm×25 mm×5 μm; mobile phase: water (containing 0.04% ammonium hydroxide+10 mM ammonium bicarbonate)-acetonitrile; acetonitrile %: 28%-58%, 10.5 min) to give compound 27. MS(ESI) m/s: 528.1 [M+H]$^+$.

$^1$H NMR (400 MHz, DMSO-d$_6$) δ=10.02 (s, 1H), 8.25 (s, 1H), 7.64-7.60 (m, 2H), 4.28 (t, J=6.8 Hz, 2H), 3.08 (t, J=7.2 Hz, 2H), 2.50-2.46 (m, 2H), 2.20 (t, J=7.2 Hz, 2H), 1.68-1.64 (m, 2H), 1.50-1.46 (m, 2H), 1.35-1.28 (m, 8H).

Example 28

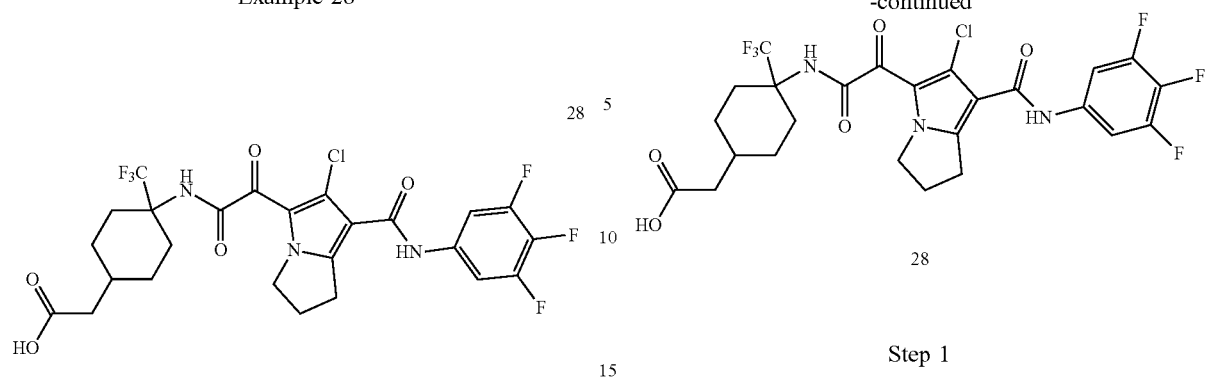

Synthetic Route:

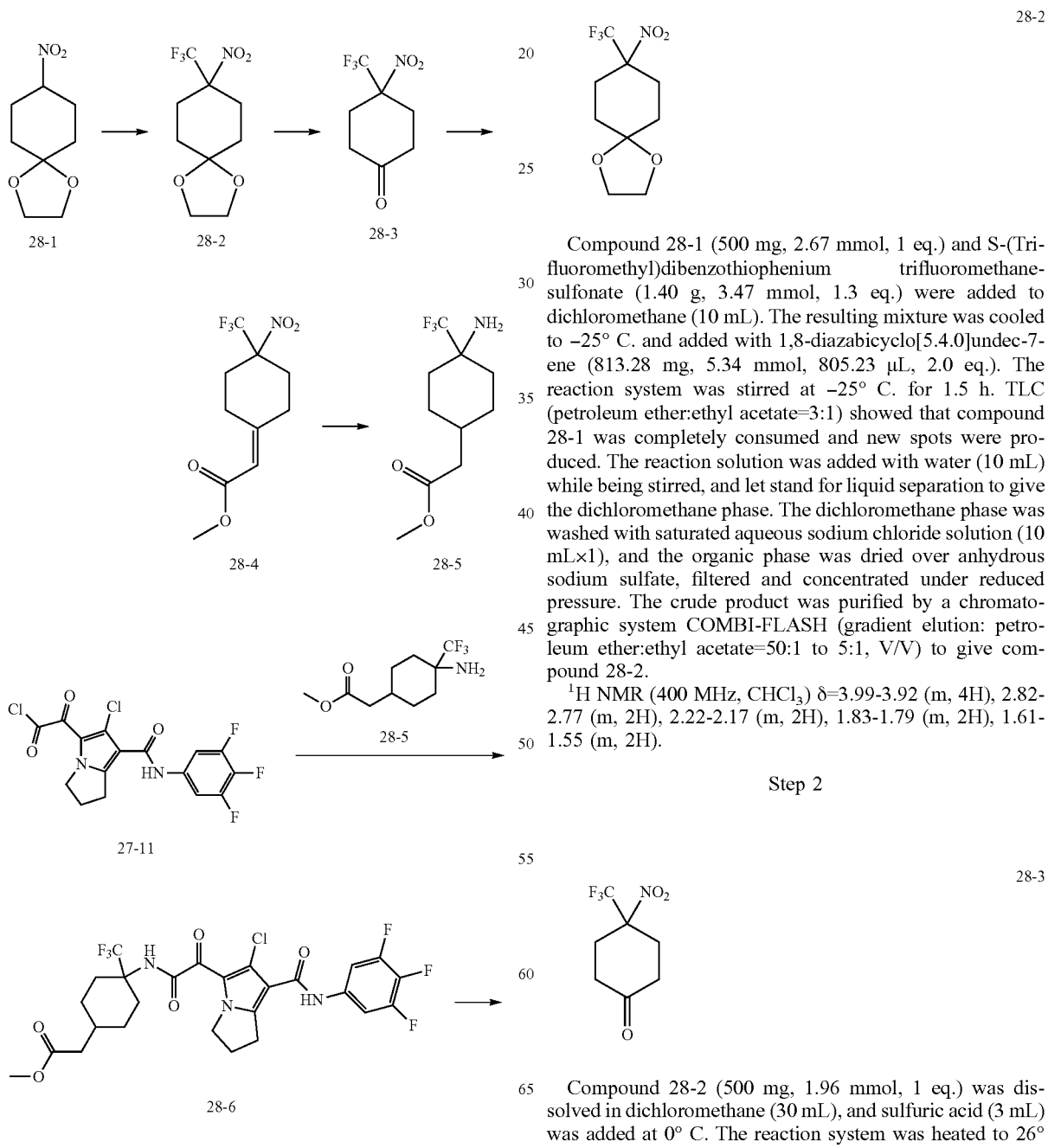

Step 1

Compound 28-1 (500 mg, 2.67 mmol, 1 eq.) and S-(Trifluoromethyl)dibenzothiophenium trifluoromethanesulfonate (1.40 g, 3.47 mmol, 1.3 eq.) were added to dichloromethane (10 mL). The resulting mixture was cooled to −25° C. and added with 1,8-diazabicyclo[5.4.0]undec-7-ene (813.28 mg, 5.34 mmol, 805.23 μL, 2.0 eq.). The reaction system was stirred at −25° C. for 1.5 h. TLC (petroleum ether:ethyl acetate=3:1) showed that compound 28-1 was completely consumed and new spots were produced. The reaction solution was added with water (10 mL) while being stirred, and let stand for liquid separation to give the dichloromethane phase. The dichloromethane phase was washed with saturated aqueous sodium chloride solution (10 mL×1), and the organic phase was dried over anhydrous sodium sulfate, filtered and concentrated under reduced pressure. The crude product was purified by a chromatographic system COMBI-FLASH (gradient elution: petroleum ether:ethyl acetate=50:1 to 5:1, V/V) to give compound 28-2.

$^1$H NMR (400 MHz, CHCl$_3$) δ=3.99-3.92 (m, 4H), 2.82-2.77 (m, 2H), 2.22-2.17 (m, 2H), 1.83-1.79 (m, 2H), 1.61-1.55 (m, 2H).

Step 2

Compound 28-2 (500 mg, 1.96 mmol, 1 eq.) was dissolved in dichloromethane (30 mL), and sulfuric acid (3 mL) was added at 0° C. The reaction system was heated to 26°

C. and stirred for 5 h. TLC (petroleum ether: ethyl acetate=3:1) showed that compound 28-2 was completely consumed and new spots were produced. The reaction solution was poured into ice water (30 mL), and saturated aqueous sodium carbonate solution was added slowly until pH=7. Then the resulting mixture was extracted with dichloromethane (20 mL×3). The organic phases were combined, washed with saturated aqueous sodium chloride solution (50 mL×1), dried over anhydrous sodium sulfate, filtered and concentrated under reduced pressure. The crude product was purified by a chromatographic system COMBI-FLASH (petroleum ether:ethyl acetate=50:1 to 3:1, V/V) to give compound 28-3.

$^1$H NMR (400 MHz, CHCl$_3$) δ=3.12-3.09 (m, 2H), 2.56-2.48 (m, 2H), 2.45-2.39 (m, 4H).

Step 3

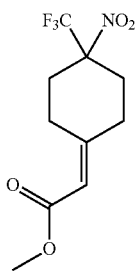

28-4

Compound 28-3 (270 mg, 1.28 mmol, 1 eq.) was dissolved in dichloromethane (5 mL), and triphenylmethyl methacrylate (427.56 mg, 1.28 mmol, 1 eq.) was added at 26° C. under nitrogen atmosphere. The reaction system was heated to 50° C. and stirred for 6 h. TLC (petroleum ether:ethyl acetate=3:1) showed that compound 28-3 was completely consumed and new spots were produced. The reaction solution was cooled to room temperature, added with water (10 mL), and then extracted with dichloromethane (10 mL×2). The organic phases were combined, washed with saturated aqueous sodium chloride solution (10 mL×1), dried over anhydrous sodium sulfate, filtered and concentrated under reduced pressure. The crude product was purified by a chromatographic system COMBI-FLASH (petroleum ether:ethyl acetate=50:1 to 5:1) to give compound 28-4.

$^1$H NMR (400 MHz, CHCl$_3$) δ=5.76 (s, 1H), 4.01-3.98 (m, 1H), 3.71 (s, 3H), 2.97-2.92 (m, 2H), 2.43-2.37 (m, 1H), 2.32-2.31 (m, 1H), 2.02-1.96 (m, 3H).

Step 4

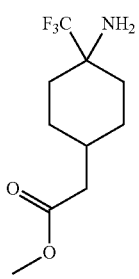

28-5

Compound 28-4 (250 mg, 935.63 μmol, 1 eq.) and methanol (10 mL) were added into a dry hydrogenation flask, and palladium on carbon (20 mg, 935.63 μmol, purity: 5%, 1 eq.) was added under hydrogen atmosphere. The reaction system was stirred at 60° C. for 16 h under hydrogen atmosphere (50 psi). LCMS showed that compound 28-4 was completely consumed. The reaction solution was filtered through celite to remove palladium on carbon, and the filtrate was concentrated under reduced pressure to give compound 28-5. MS (ESI) m/z: 239.7 [M+H]$^+$.

Step 5

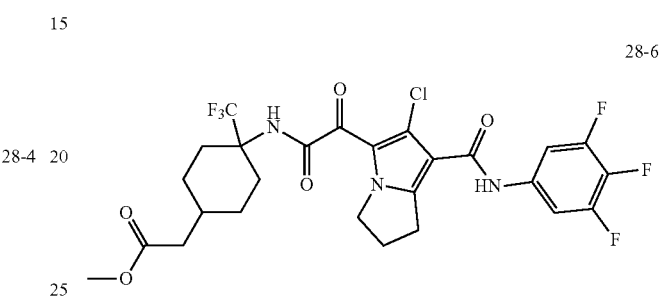

28-6

Compound 28-5 (67.90 mg, 283.84 μmol, 1 eq.) and sodium bicarbonate (143.07 mg, 1.70 mmol, 66.24 μL, 6 eq.) were added to dichloromethane (2 mL), and a mixture of compound 27-11 (115 mg, 283.84 μmol, 1 eq.) and dichloromethane (2 mL) was slowly added at 0° C. The reaction system was heated to 26° C. and stirred for 0.5 h. TLC (petroleum ether:ethyl acetate=2:1) showed that compound 27-11 was completely consumed. The reaction solution was added with water (10 mL), and then extracted with dichloromethane (5 mL×2). The organic phases were combined, washed with saturated aqueous sodium chloride solution (10 mL×1), dried over anhydrous sodium sulfate, filtered and concentrated under reduced pressure. The crude product was separated by a chromatographic system COMBI-FLASH (gradient elution: petroleum ether:ethyl acetate=50:1 to 3:1, V/V) to give compound 28-6. MS (ESI) m/z: 608.3 [M+H]$^+$.

$^1$H NMR (400 MHz, CHCl$_3$) δ=8.47 (s, 1H), 7.34 (dd, J=9.0, 6.4 Hz, 2H), 6.22-6.16 (m, 1H), 4.33 (t, J=7.2 Hz, 2H), 3.70-3.69 (m, 3H), 3.27 (t, J=7.6 Hz, 2H), 2.62-2.52 (m, 3H), 2.41 (d, J=7.2 Hz, 1H), 2.40-2.26 (m, 2H), 2.04-1.96 (m, 1H), 1.86-1.75 (m, 3H), 1.28-1.24 (m, 3H).

Step 6

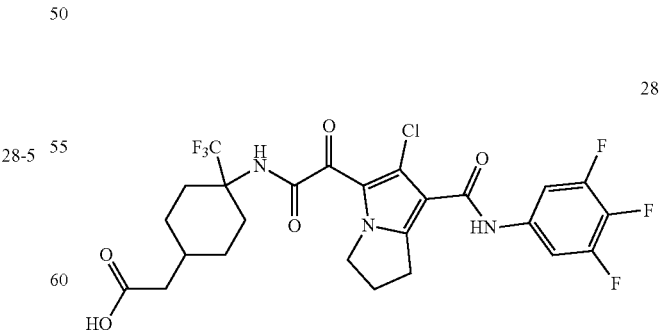

28

Compound 28-6 (60.00 mg, 98.70 μmol, 1 eq.) was dissolved in a mixture of tetrahydrofuran (1 mL), methanol (1 mL) and water (1 mL), and lithium hydroxide monohydrate (24.85 mg, 592.18 μmol, 6 eq.) was added at 40° C.

The reaction system was stirred at 40° C. for 0.5 h. LCMS showed that compound 28-6 was completely consumed. The reaction solution was added with 2 mol/L aqueous potassium hydrogen sulfate solution until pH=4, and then extracted with dichloromethane (10 mL×2). The organic phases were combined, washed with saturated aqueous sodium chloride solution, dried over anhydrous sodium sulfate, filtered and concentrated under reduced pressure. The residue was purified by prep-HPLC (formic acid system, column: Waters Xbridge 150 mm×18 mm×5 μm; mobile phase: water (containing 0.225% formic acid)-acetonitrile; acetonitrile %: 55%-85%, 7 min) to give compound 28. MS (ESI) m/z: 594.3 [M+H]$^+$.

$^1$H NMR (400 MHz, DMSO-d$_6$) δ=12.12 (s, 1H), 10.07 (d, J=8.2 Hz, 1H), 8.70 (d, J=16.2 Hz, 1H), 7.63 (dd, J=10.2, 6.2 Hz, 2H), 4.31 (t, J=7.2 Hz, 2H), 3.10 (t, J=7.6 Hz, 2H), 2.49-2.43 (m, 3H), 2.35-2.25 (m, 2H), 2.16-2.07 (m, 2H), 1.78-1.65 (m, 3H), 1.59-1.42 (m, 2H), 1.28-1.17 (m, 1H).

Examples 29 and 30

Synthetic Route:

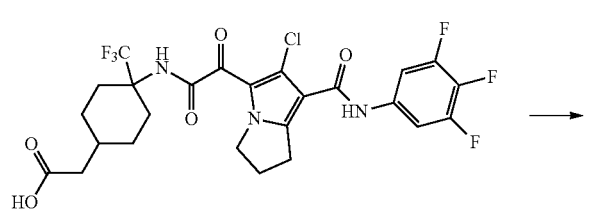

28

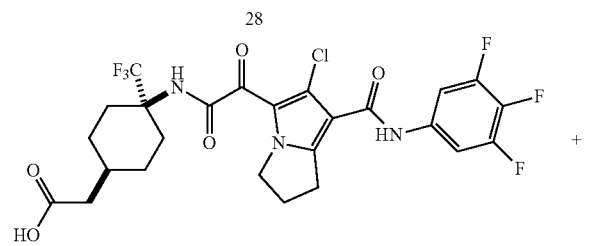

29

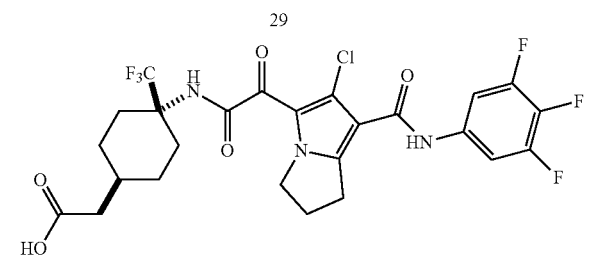

30

Compound 28 (15 mg, 25.26 μmol, 1 eq.) was separated by SFC (column: Phenomenex-Amylose-1 (250 mm×30 mm, 5 μm); mobile phase: 0.1% NH$_3$H$_2$O EtOH; B %: 35%-35%, min) to give compound 29 (retention time in SFC: 1.763 min) and compound 30 (retention time in SFC: 2.086 min). SFC analysis conditions: column: Agilent 1260 chiral column with DAD detector, with a specification of AD-3 50×3 mm I.D., 3 μm; mobile phase: A: carbon dioxide, B: ethanol (containing 0.05% diethanolamine); gradient: B changed from 5% to 40% in 2.5 min, kept at 40% for 0.35 min, and then kept flowing at 1.65 min; flow rate: 2.5 mL/min; column temperature: 40° C.

Compound 29 $^1$H NMR (DMSO-d$_6$) δ=10.14 (br s, 1H), 8.65 (br s, 1H), 7.68-7.62 (m, 2H), 4.35-4.33 (m, 2H), 3.13-3.09 (m, 2H), 2.37-2.31 (m, 2H), 2.09-2.03 (m, 2H), 1.70-1.62 (m, 3H), 1.59-1.48 (m, 2H), 1.27-1.21 (m, 4H).

Compound 30 $^1$H NMR (DMSO-d$_6$) δ=10.09 (s, 1H), 8.70 (s, 1H), 7.64 (dd, J=10.2, 6.27 Hz, 2H), 4.31 (t, J=7.2 Hz, 2H), 3.10 (t, J=7.2 Hz, 2H), 2.34-2.25 (m, 4H), 2.14-2.09 (m, 1H), 1.75-1.32 (m, 4H), 1.46 (br s, 2H), 1.24 (s, 2H).

Example 31

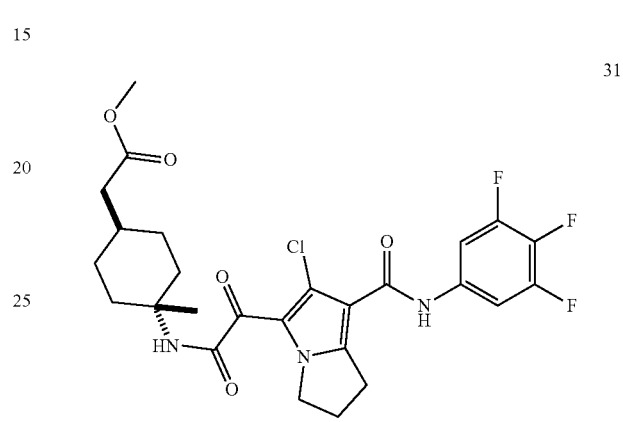

31

Synthetic Route:

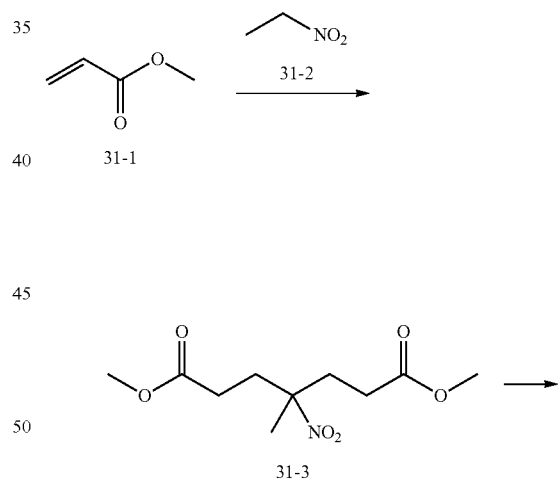

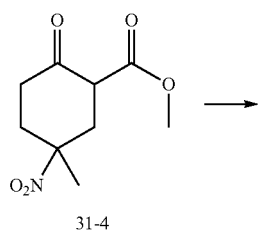

31-4

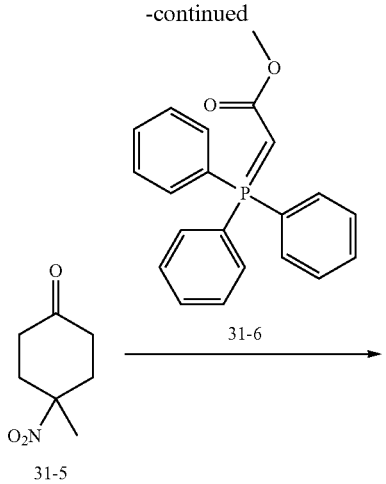

31-5

31-6

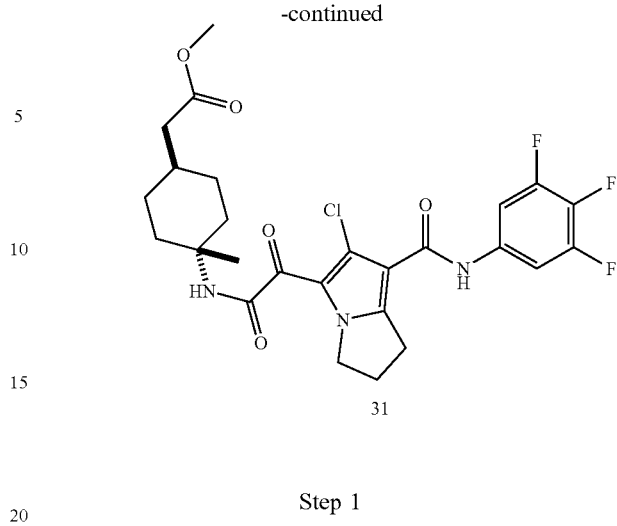

31

Step 1

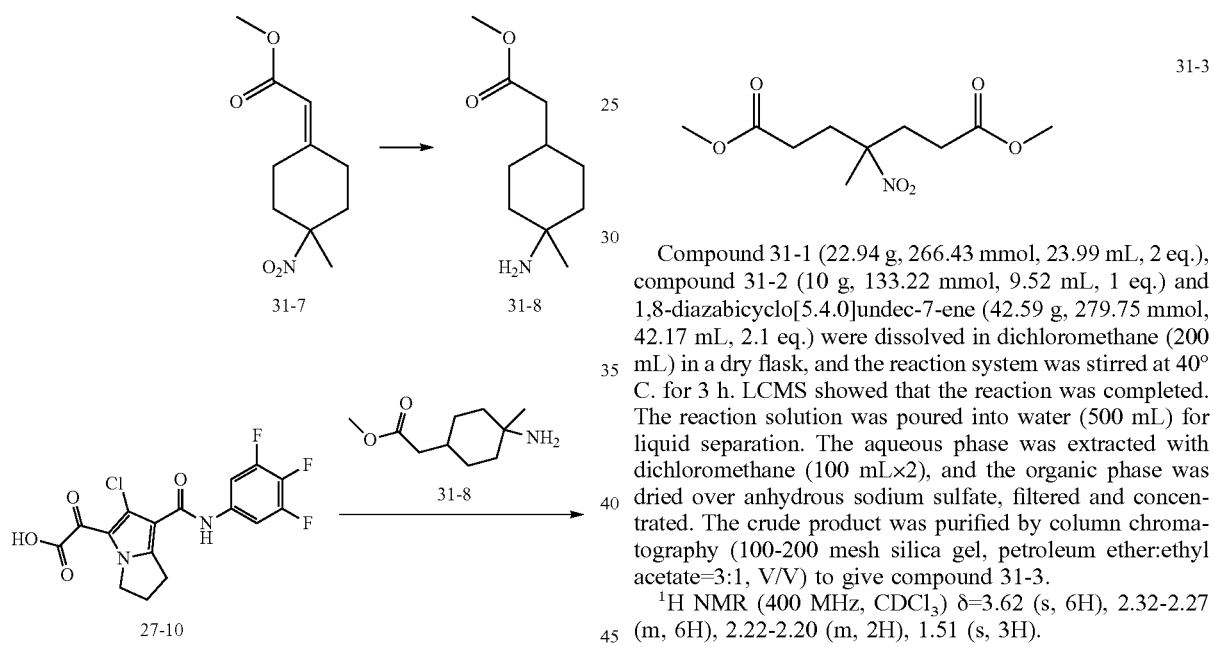

31-3

Compound 31-1 (22.94 g, 266.43 mmol, 23.99 mL, 2 eq.), compound 31-2 (10 g, 133.22 mmol, 9.52 mL, 1 eq.) and 1,8-diazabicyclo[5.4.0]undec-7-ene (42.59 g, 279.75 mmol, 42.17 mL, 2.1 eq.) were dissolved in dichloromethane (200 mL) in a dry flask, and the reaction system was stirred at 40° C. for 3 h. LCMS showed that the reaction was completed. The reaction solution was poured into water (500 mL) for liquid separation. The aqueous phase was extracted with dichloromethane (100 mL×2), and the organic phase was dried over anhydrous sodium sulfate, filtered and concentrated. The crude product was purified by column chromatography (100-200 mesh silica gel, petroleum ether:ethyl acetate=3:1, V/V) to give compound 31-3.

$^1$H NMR (400 MHz, CDCl$_3$) δ=3.62 (s, 6H), 2.32-2.27 (m, 6H), 2.22-2.20 (m, 2H), 1.51 (s, 3H).

Step 2

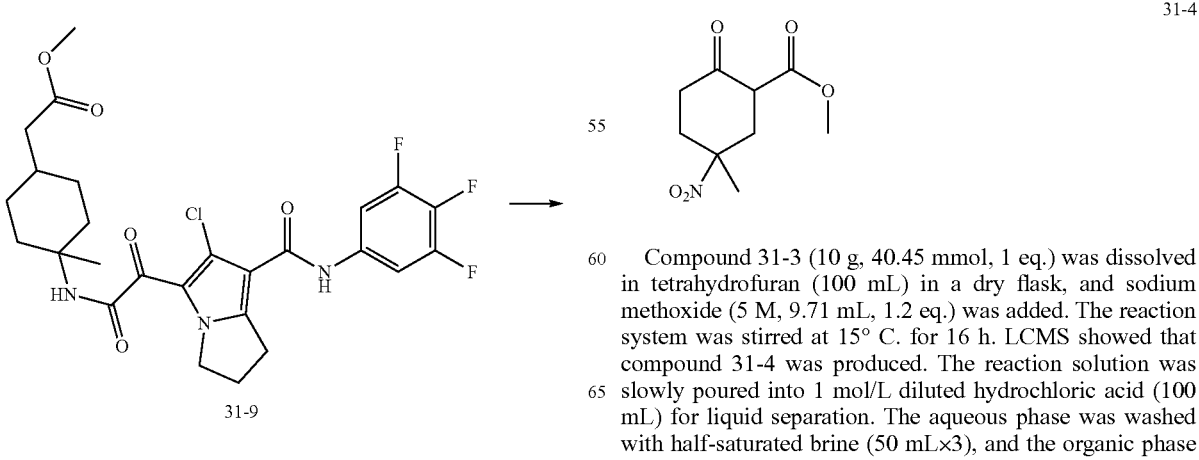

31-4

Compound 31-3 (10 g, 40.45 mmol, 1 eq.) was dissolved in tetrahydrofuran (100 mL) in a dry flask, and sodium methoxide (5 M, 9.71 mL, 1.2 eq.) was added. The reaction system was stirred at 15° C. for 16 h. LCMS showed that compound 31-4 was produced. The reaction solution was slowly poured into 1 mol/L diluted hydrochloric acid (100 mL) for liquid separation. The aqueous phase was washed with half-saturated brine (50 mL×3), and the organic phase was collected, dried over anhydrous sodium sulfate, filtered and concentrated under reduced pressure to give compound 31-4. MS (ESI) m/z: 216.1 [M+H]$^+$.

$^1$H NMR (400 MHz, CDCl$_3$) δ=12.12 (s, 1H), 4.11 (s, 3H), 3.36-3.24 (m, 1H), 2.54-2.45 (m, 2H), 2.40-2.35 (m, 2H), 2.19-1.54 (m, 1H), 1.26 (s, 3H).

Step 3

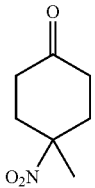

31-5

Compound 31-4 (4 g, 18.59 mmol, 1 eq.) was dissolved in a mixture of 2-methyltetrahydrofuran (20 mL) and water (20 mL) in a flask, and potassium hydroxide (3.13 g, 55.76 mmol, 3 eq.) was added. The reaction system was stirred at 85° C. for 16 h. TLC (petroleum ether:ethyl acetate=3:1) showed that the reaction was completed. The reaction solution was layered. The aqueous phase was extracted with ethyl acetate (10 mL×6), and the organic phase was dried over anhydrous sodium sulfate, filtered and concentrated. The crude product was purified by column chromatography (100-200 mesh silica gel, gradient elution: petroleum ether: ethyl acetate=20:1 to 3:1, V/V) to give compound 31-5.

$^1$H NMR (400 MHz, CDCl$_3$) δ=2.89-2.78 (m, 2H), 2.50-2.41 (m, 2H), 2.39-2.27 (m, 2H), 2.06-1.82 (m, 2H), 1.56 (s, 3H).

Step 4

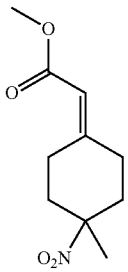

31-7

Compound 31-5 (11.4 g, 72.53 mmol, 1 eq.) was dissolved in toluene (100 mL) in a dry flask, and compound 31-6 (26.68 g, 79.79 mmol, 1.1 eq.) was added. The reaction system was stirred at 110° C. for 16 h under nitrogen atmosphere. LCMS showed that the reaction was completed. The reaction solution was poured into 0.5 mol/L diluted hydrochloric acid (50 mL). The aqueous phase was extracted with ethyl acetate (10 mL×3), and the organic phase was dried over anhydrous sodium sulfate, filtered and concentrated. The crude product was purified by column chromatography (100-200 mesh silica gel, gradient elution: petroleum ether:ethyl acetate=100:0 to 10:1, V/V) to give compound 31-7.

$^1$H NMR (400 MHz, CDCl$_3$) δ=5.70 (s, 1H), 3.68 (s, 3H), 3.51-3.48 (s, 1H), 2.68-2.63 (m, 2H), 2.35-2.04 (m, 3H), 1.77-1.60 (m, 2H), 1.59 (s, 3H).

Step 5

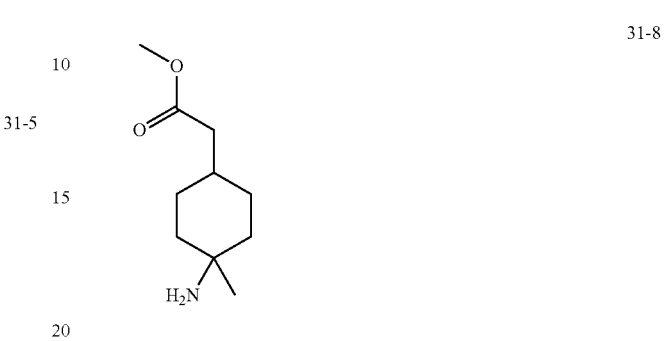

31-8

Raney nickel (7.00 g, 119.26 mmol, 3.63 eq.) was dissolved in methanol (60 mL), and then compound 31-7 (7 g, 32.83 mmol, 1 eq.) was added. The reaction system was stirred at 30° C. for 16 h under hydrogen atmosphere (30 psi). TLC (dichloromethane:methanol=10:1) showed that compound 31-7 was completely consumed. The reaction solution was filtered and concentrated under reduced pressure to give compound 31-8.

$^1$H NMR (400 MHz, MeOD-d$_4$) δ=3.65 (s, 3H), 2.29-2.22 (m, 2H), 1.73-1.67 (m, 2H), 1.56-1.51 (m, 4H), 1.39-1.38 (m, 1H), 1.35 (s, 3H), 1.19-1.14 (m, 2H).

Step 6

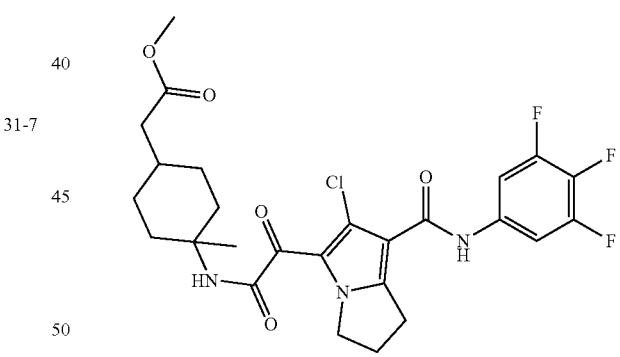

31-9

Compound 27-10 (0.5 g, 1.29 mmol, 1 eq.) was dissolved in N,N-dimethylformamide (10 mL), and then benzotriazol-1-yl-oxytripyrrolidinophosphonium hexafluorophosphate (1.08 g, 2.07 mmol, 1.6 eq.), 1-hydroxybenzotriazole (297.00 mg, 2.20 mmol, 1.7 eq.) and N,N-diisopropylethylamine (668.41 mg, 5.17 mmol, 900.82 μL, 4 eq.) were added. The resulting mixture was stirred at 20° C. for 0.5 h, and then added with compound 31-8 (287.44 mg, 1.55 mmol, 1.2 eq.). The reaction system was stirred at 40° C. for 15.5 h. LCMS and HPLC confirmed that the reaction was completed. The reaction solution was poured into water (50 mL) to quench the reaction, and then filtered. The filtrate was extracted with ethyl acetate (20 mL×2). The organic phase was dried over anhydrous sodium sulfate, filtered and concentrated under reduced pressure. The crude product was purified by column chromatography (gradient elution: petroleum ether:ethyl acetate=100:1 to 3:1, V/V). Then the crude product was separated by SFC (retention time=2.35 min) (column: DAICEL CHIRALPAKIC (250 mm×30 mm, 5 μm); mobile phase: Neu-MeOH; B %: 40%-40%, 10 min) to give compound 31-9. MS (ESI) m/z: 554.2 [M+H]$^+$.

Step 7

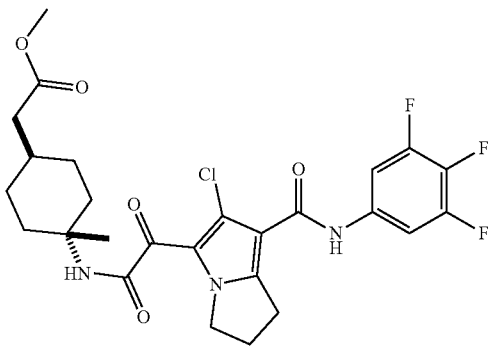

Compound 31-9 (0.1 g, 180.52 μmol, 1 eq.) was purified by prep-HPLC (neutral system, column: Xtimate C18 150 mm×25 mm×5 μm; mobile phase: water (containing 10 mM ammonium bicarbonate)-acetonitrile; acetonitrile %: 50%-80%, 10.5 min) to give compound 31. MS (ESI) m/z: 554.2 [M+H]$^+$.

$^1$H NMR (400 MHz, DMSO-d$_6$) δ=10.01 (s, 1H), 8.30 (s, 1H), 7.66-7.58 (m, 2H), 4.28 (t, J=7.6 Hz, 2H), 3.58 (s, 3H), 3.08 (t, J=7.6 Hz, 2H), 2.49-2.43 (m, 2H), 2.26 (d, J=7.0 Hz, 2H), 1.88-1.56 (m, 7H), 1.36 (s, 3H), 1.24-1.11 (m, 2H).

Experimental Example 1: qPCR Test in the HBV In Vitro Test

1. Experimental Objective:
To evaluate the inhibitory effect of the compound on HBV by detecting content of HBV DNA in HepG2.2.15 cells in a real-time qPCR test, with EC$_{50}$ of the compound as an indicator.
2. Experimental Materials:
2.1. Cell Line: HepG2.2.15 Cells
  HepG2.2.15 cell culture medium (DMEM/F12, Invitrogen-11330057; 10% serum, Invitrogen-10099141; 100 units/mL penicillin and 10 μg/mL streptomycin, Invitrogen-15140122; 1% non-essential amino acids, Invitrogen-11140076; 2 mM L-glutamine, Invitrogen-25030081; 300 μg/mL geneticin, Invitrogen-10131027)
2.2. Reagents:
  Pancreatin (Invitrogen-25300062)
  DPBS (Hyclone-SH30028.01B)
  DMSO (Sigma-D2650-100 ML)
  High-throughput DNA purification kit (QIAamp 96 DNA Blood Kit, Qiagen-51162)
  Quantitative faststart universal probe reagent (FastStart Universal Probe Master, Roche-04914058001)
2.3. Consumables and Instruments:
  96-well cell culture plate (Corning-3599)
  CO$_2$ incubator (HERA-CELL-240)
  Optical sealing film (ABI-4311971)
  Quantitative PCR 96-well plate (Applied Biosystems-4306737)
  Fluorescence quantitative PCR instrument (Applied Biosystems-7500 real time PCR system)
3. Experimental Steps and Methods:
3.1. HepG2.2.15 cells (4×10$^4$ cells/well) were inoculated into a 96-well plate and cultured at 37° C. in 5% CO$_2$ overnight.
3.2. On day 2, the compound was 3-fold diluted in gradient for a total of 8 dilution gradients. The compound at different concentrations was added into the culture wells in duplicate. The final concentration of DMSO in the culture medium was 1%. 1 μM GLS4 was used as a 100% inhibition control (the structure of GLS4 disclosed in WO2008154817A1 is as follows:

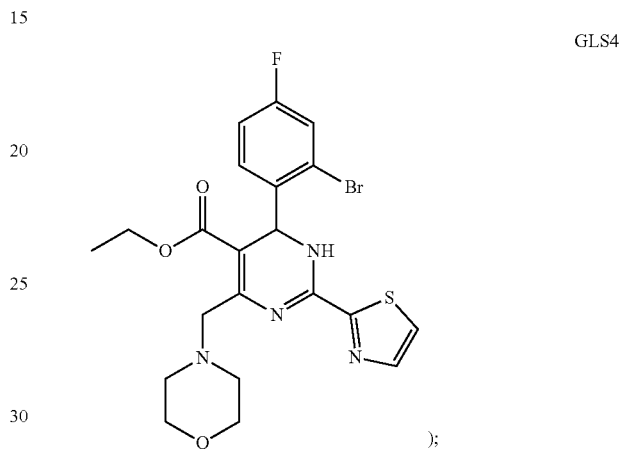

1% DMSO was used as a 0% inhibition control.
3.3. On day 5, the culture medium was replaced with a fresh culture medium containing the compound.
3.4. On day 8, the culture medium in the culture wells was collected, and the high-throughput DNA purification kit (Qiagen-51162) was used to extract DNA. For specific steps, refer to the product manual.
3.5 The preparation of the PCR reaction solution is shown in Table 1.

TABLE 1

Preparation of the PCR reaction solution

| Item | Volume required for 1 well (μL) | Volume required for 80 wells (μL) |
| --- | --- | --- |
| Quantitative faststart universal probe reagent | 12.5 | 1000 |
| Upstream primer (10 μmol) | 1 | 80 |
| Downstream primer (10 μmol) | 1 | 80 |
| Probe (10 μmol) | 0.5 | 40 |

```
Upstream primer sequence:
                            (SEQ ID NO: 1)
GTGTCTGCGGCGTTTTATCA Downstream primer sequence:
                            (SEQ ID NO: 2)
GACAAACGGGCAACATACCTT Probe sequence:
                            (SEQ ID NO: 3)
5' + FAM + CCTCTKCATCCTGCTGCTATGCCTCATC +
TAMRA -3'
```

3.6. Each well of the 96-well PCR plate was added with 15 μL of the reaction mixture, and then with 10 μL of sample DNA or HBV DNA standard.

3.7. The reaction conditions for PCR: heating at 95° C. for 10 min, degeneration at 95° C. for 15 s, and extension at 60° C. for 1 min, with a total of 40 cycles.

3.8. Data Analysis:

3.8.1. Calculation of the inhibition percentage: % Inh.=[1−(DNA copy number in the sample−DNA copy number in 1 μM GLS4)/(DNA copy number in the DMSO control−DNA copy number in 1 μM GLS4)]×100.

3.8.2. Calculation of $EC_{50}$: half maximal inhibitory concentration ($EC_{50}$) of the compound for HBV was calculated using GraphPad Prism software.

3.8.3. The experimental results are shown in Table 2.

TABLE 2

$EC_{50}$ results of the qPCR test

| Sample (title compound) | Half maximal inhibitory concentration ($EC_{50}$) of HBV |
|---|---|
| 1 | 35 nM |
| 2 | 3 nM |
| 3 | 5 nM |
| 4 | 580 nM |
| 5 | 7 nM |
| 6 | 110 nM |
| 7 | 30 nM |
| 8 | 9 nM |
| 9 | 41 nM |
| 10 | 2 nM |
| 11 | 4 nM |
| 12 | 5 nM |
| 13 | 19 nM |
| 14 | 70 nM |
| 15 | 37 nM |
| 16 | 41 nM |
| 17 | 7 nM |
| 18 | 11 nM |
| 19 | 20 nM |
| 20 | 11 nM |
| 21 | 3 nM |
| 22 | 14 nM |
| 23 | 27 nM |
| 24 | 299 nM |
| 25-3 | 4 nM |
| 25 | 4 nM |
| 26 | 174 nM |
| 27 | 12 nM |
| 28 | 2 nM |
| 29 | 3 nM |
| 30 | 1 nM |
| 31 | 5 nM. |

Experimental Example 2: Inhibition Test of the hERG Potassium Channel

1. Experimental Objective:

To assay the effect of the compound disclosed herein on hERG potassium channel by using automatic patch-clamp method.

2. Experimental Method 2.1. Cell Culture

The cells stably expressing the hERG potassium channel used in the experiment were CHO-hERE from Aviva Biosciences. CHO-hERG was cultured at 37° C. in 5% $CO_2$. CHO hERG culture medium is shown in Table 3.

TABLE 3

CHO hERG culture medium

| Reagent | Supplier | Volume (mL) |
|---|---|---|
| F12 culture medium | Invitrogen | 500 |
| Fetal bovine serum | Invitrogen | 50 |
| G418/Geneticin | Invitrogen | 1 |
| Hygromycin B | Invitrogen | 1 |

2.2. Preliminary Preparation for Cells

The CHO-hERG cells used in the experiment were cultured for at least two days, and the cell density reached 75% or more. Before the experiment, the cells were digested with TrypLE, and then the collected cells were resuspended in extracellular fluid.

2.3. Preparation of the Intracellular and Extracellular Fluids

The extracellular fluid needed to be prepared once a month. The intracellular fluid must be frozen in aliquots at −20° C. Compositions of the intracellular and extracellular fluids are shown in Table 4.

TABLE 4

Compositions of the intracellular and extracellular fluids

| Composition | Extracellular fluid (mM) | Intracellular fluid (mM) |
|---|---|---|
| NaCl | 145 | — |
| KCl | 4 | 120 |
| KOH | — | 31.25 |
| $CaCl_2$ | 2 | 5.374 |
| $MgCl_2$ | 1 | 1.75 |
| Glucose | 10 | — |
| $Na_2ATP$ | — | 4 |
| HEPES | 10 | 10 |
| EGTA | — | 10 |
| pH | pH was adjusted to 7.4 with sodium hydroxide | pH was adjusted to 7.4 with potassium hydroxide |
| Osmotic pressure | 295 mOsm | 285 mOsm |

2.4. Preparation of Compound

The test compound and its positive control amitriptyline were dissolved in DMSO to obtain a stock solution at a certain concentration. Then the stock solution was diluted for different gradients, and finally added to an extracellular fluid at a certain ratio to be diluted to a concentration for test. Precipitation was checked with the naked eye before the experiment. Finally, the concentration of DMSO in the solution to be tested and the positive control amitriptyline should not exceed 0.3%.

2.5. Voltage Stimulation Scheme

With a holding potential of −80 mv, a voltage stimulation of −50 my was applied for 80 ms to record the cell leakage current value; then hERG channel was opened by a depolarization to +20 my for 4800 ms and hERG tail current was elicited by a repolarization to −50 my for 5000 ms and recorded; and finally, the voltage was restored to the holding potential of −80 my and maintained for 3100 ms. The above voltage stimulation was repeated every 15000 ms.

2.6. QPatch$^{HTX}$ Whole-Cell Patch Clamp Recording

The hERG QPatch$^{HTX}$ experiment was performed at room temperature. Whole-cell scheme, voltage stimulation scheme and compound detection scheme were established on QPatch Assay Software 5.2 (Sophion Bioscience).

First, 30 repetitive set voltage stimulations were performed, of which the section on a current spectrum was the baseline section for subsequent analysis. Then 5 μL of extracellular fluid was added, and the voltage stimulation was repeated three times. Each compound at the action concentration was added in sequence with a volume of 5 μL, and the voltage stimulation was repeated three times. The cells were incubated for at least 5 min with the compound at each tested concentration. During the entire recording process, all indicators needed to meet the data analysis acceptance standard. If the standard was not met, the cell would not be included in the analysis range and the compound would be tested again. The above recording process was automatically operated by the Qpatch analysis software. The tested concentrations of the compounds were 0.24 μM, 1.20 μM, 6.00 μM and 30.00 μM, and each concentration was repeated for at least two cells.

2.7. Data Analysis

In each complete current recording, the inhibition percentage of each compound at the action concentration could be calculated based on the percentage of peak current in the negative control. The dose-effect relationship curve was obtained by fitting with the standard Hill Equation, and the specific equation is as follows:

$$I_{(C)} = I_b + (I_{fr} - I_b) \times c^n / (IC_{50}^n + c^n)$$

C is the tested concentration of the compound, n is the slope, and I is the current The curve fitting and inhibition rate calculation were all completed by Qpatch analysis software. If the inhibition rate exceeded 50% at the lowest concentration or the inhibition rate did not reach 50% at the highest concentration, the corresponding $IC_{50}$ of the compound was lower than the lowest concentration or greater than the highest concentration.

2.8. Test Results

The hERG $IC_{50}$ values of the compounds in the examples are shown in Table 5.

TABLE 5 hERG $IC_{50}$ values of the compounds in the examples

| Sample | hERG IC50 (μM) |
|---|---|
| Compound 18 | >40 |
| Compound 25 | >40. |

Experimental Example 3: Experiment on the Inhibition of Cytochrome P450 Isoenzymes Experimental objective: to determine the inhibitory effect of the test compound on the activity of human liver microsomal cytochrome P450 isoenzymes (CYP1A2, CYP2C9, CYP2C19, CYP2D6 and CYP3A4).

Experimental procedures: first, the test compound (10 mM) was diluted in gradient to prepare working solutions (100× final concentration) at concentrations of: 5, 1.5, 0.5, 0.15, 0.05, 0.015, and 0.005 mM, and working solutions of positive inhibitors for P450 isoenzymes (CYP1A2, CYP2C9, CYP2C19, CYP2D6, and CYP3A4) and the specific substrate mixtures thereof (5 in 1) were prepared simultaneously; human liver microsomes frozen in a −80° C. refrigerator were thawed on ice, and after all thawed, the human liver microsomes were diluted with PB to prepare a working solution at a specific concentration (0.253 mg/mL); 20 μL of the substrate mixture (20 μL of PB was added into the blank well) and 158 μL of the working solution of human liver microsomes were added into the reaction plate which was then placed on ice for use; then 2 μL of the test compound at each concentration (N=1) and a specific inhibitor (N=2) were added into the corresponding well, and the group without the inhibitor (test compound or the positive inhibitor) was added with a corresponding organic solvent as a control sample (the test compound control sample was 1:1 DMSO:MeOH; the positive control sample was 1:9 DMSO:MeOH); after pre-incubation under a 37° C. water bath for 10 min, 20 μL of a coenzyme factor (NADPH) solution was added into the reaction plate and incubated under a 37° C. water bath for 10 min, 400 μL of a cold acetonitrile solution (the internal standard was 200 ng/mL Tolbutamide and Labetalol) was added to terminate the reaction, and the reaction plate was placed on a shaker and shaken for 10 min; after centrifugation at 4,000 rpm for 20 min, 200 μL of the supernatant was collected and added to 100 μL of water to dilute the sample, and, finally, the plate was sealed, oscillated shaken evenly, and subjected to LC/MS/MS detection. The experimental results are shown in Table 6.

TABLE 6

Results of inhibitory effect of the test compound on the activity of human liver microsomal cytochrome P450 isoenzymes

| | $IC_{50}$ (μM) | | | | |
|---|---|---|---|---|---|
| Compound | CYP1A2 | CYP2C9 | CYP2C19 | CYP2D6 | CYP3A4-M |
| Compound 2 | >50 | >50 | >50 | >50 | >50 |
| Compound 17 | >50 | >50 | >50 | >50 | >50 |
| Compound 18 | >50 | >50 | >50 | >50 | >50 |
| Compound 25 | >50 | >50 | >50 | >50 | >50. |

Experimental Example 4: Experiment on Cytotoxicity

1. The compound was diluted with DMSO (dimethyl sulfoxide) in a 3-fold gradient for 9 concentrations, and added into a 96-well plate in duplicate. The compound concentration was 200-fold of the final test concentration.
2. The cells were rinsed with PBS (phosphate buffered saline) once, added with 0.25% trypsin and digested for about 2-5 min in a 37° C., 5% $CO_2$ incubator. Then the digestion was terminated with a cell culture medium and the cells were dispersed into single cells by pipetting with a pipettor.
3. The cell density was counted with a cell counter, and adjusted to the required density with the medium.
4. The cells were added into a 96-well plate that had been added with the compound. The final concentration of DMSO in each well was 0.5%. Wells containing 0.5% DMSO were used as non-toxic negative controls, and wells containing the cell culture medium were used as 100% cytotoxicity controls. Then the cell plate was incubated in a 37° C., 5% $CO_2$ cell incubator for 3 days.

5. The chemiluminescence signal (RLU, relative chemiluminescence unit) of each well in the cell plate was detected with the cell viability detection kit CellTiter-Glo using the multi-functional microplate reader Envision, with instructions on the kit followed.
6. The raw data (RLU) were substituted into the following formula to calculate the cell viability of each well (cell viability %):

Cell viability %=($RLU_{Sample}$−Average $RLU_{Mediumcontrol}$)/(Average$RLU_{Cellcontrol}$−Average$RLU_{Mediumcontrol}$)×100%

$RLU_{Sample}$: signal value of the sample well; Average $RLU_{Cell\ control}$: average signal value of the cell control well; Average $RLU_{Medium\ Control}$: average signal value of the medium control well.

7. Using the GraphPad Prism software, the cell viability data were nonlinearly fitted to draw a dose-response curve and the 50% cytotoxic concentration ($CC_{50}$) value of the compound was obtained. The results are shown in Table 7.

TABLE 7

Test results of 50% cytotoxic concentration ($CC_{50}$)

| Compound | $CC_{50}$ (μM) |
| --- | --- |
| Compound 18 | >50 |
| Compound 25 | >50. |

Experimental Example 5: Experiment on In Vitro Microsomal Stability

Metabolic Stability of the Compound in CD-1 Mice and Human Liver Microsomes

Experimental objective: to evaluate the metabolic stability of the test compound in CD-1 mice and human liver microsomes Experimental procedures: first, the test compound (10 mM) was subjected to a two-step dilution, where the compound was diluted to an intermediate concentration of 100 μM with 100% methanol, and the working solution was diluted to 10 μM with a potassium phosphate buffer; eight 96-well incubation plates were prepared, and named T0, T5, T10, T20, T30, T60, Blank and NCF60, respectively; the reaction time points corresponding to the first 6 incubation plates were 0, 5, 10, 20, 30 and 60 min, respectively; for the Blank plate, neither the test compound nor a control compound was added, and for the NCF60 plate, potassium phosphate buffer was used in an incubation of 60 min in place of a NADPH regeneration system solution; 10 μL of the test compound working solution and 80 μL of the microsome working solution (liver microsome protein concentration was 0.625 mg/mL) were added to the T0, T5, T10, T20, T30, T60 and NCF60 plates, while only the microsome working solution was added to the Blank plate, and all the incubation plates were then placed in a 37° C. water bath for pre-incubation for about 10 min; after the pre-incubation, 10 μL of a NADPH regeneration system working solution was added into each sample well of all the plates except the NCF60 plate and T0 plate to start the reaction, and 10 μL of potassium phosphate buffer was added to each well of the NCF60 plate; therefore, in the test compound or control compound samples, the final reaction concentrations of the compound, testosterone, diclofenac and propafenone were 1 μM, the concentration of the liver microsomes was 0.5 mg/mL, and the final concentrations of DMSO and acetonitrile in the reaction system were 0.01% (v/v) and 0.99% (v/v), respectively; after incubation for an appropriate time (such as 5, 10, 20, 30, and 60 min), 300 μL of a stop solution (acetonitrile solution containing 100 ng/mL tolbutamide and 100 ng/mL labetalol) was added to each sample well to stop the reaction; 300 μL of the stop solution and then 10 μL of the NADPH working solution were added to the T0 plate, all the sample plates were shaken and centrifuged in a centrifuge (3220×g) for 20 min, and then 100 μL of supernatant was taken from each well and diluted with 300 μL of pure water for liquid chromatography-tandem mass spectrometry analysis.

The experimental results are shown in Table 8.

TABLE 8

Metabolic stability results of the test compound in CD-1 mice and human liver microsomes

| Compound | Species | $T_{1/2}$ (min) | $CL_{int(mic)}$ (μL/min/mg) | $CL_{int(liver)}$ (mL/min/kg) |
| --- | --- | --- | --- | --- |
| 17 | CD-1 mice | >145 | <9.6 | <38.0 |
|  | Human | >145 | <9.6 | <8.6 |
| 18 | CD-1 mice | >145 | <9.6 | <38.0 |
|  | Human | >145 | <9.6 | <8.6 |
| 25 | CD-1 mice | >145 | <9.6 | <38.0 |
|  | Human | >145 | <9.6 | <8.6. |

Metabolic Stability of the Compound in Liver Microsomes of SD Rats, Beagle Dogs and Cynomolgus Monkeys Experimental objective: to evaluate the metabolic stability of test compounds 18 and 25 in liver microsomes of rats, beagle dogs and cynomolgus monkeys Experimental procedures: first, the test compound (10 mM) was subjected to a two-step dilution, where the compound was diluted to an intermediate concentration of 100 μM with 100% methanol, and the working solution was diluted to 10 μM with a potassium phosphate buffer; eight 96-well incubation plates were prepared, and named T0, T5, T10, T20, T30, T60, Blank and NCF60, respectively; the reaction time points corresponding to the first 6 incubation plates were 0, 5, 10, 20, 30 and 60 min, respectively; for the Blank plate, neither the test compound nor a control compound was added, and for the NCF60 plate, potassium phosphate buffer was used in an incubation of 60 min in place of a NADPH regeneration system solution; 10 μL of the test compound working solution and 80 μL of the microsome working solution (liver microsome protein concentration was 0.625 mg/mL) were added to the T0, T5, T10, T20, T30, T60 and NCF60 plates, while only the microsome working solution was added to the Blank plate, and all the incubation plates were then placed in a 37° C. water bath for pre-incubation for about 10 min; after the pre-incubation, 10 μL of a NADPH regeneration system working solution was added into each sample well of all the plates except the NCF60 plate and T0 plate to start the reaction, and 10 μL of potassium phosphate buffer was added to each well of the NCF60 plate; therefore, in the test compound or control compound samples, the final reaction concentrations of the compound, testosterone, diclofenac and propafenone were 1 μM, the concentration of the liver microsomes was 0.5 mg/mL, and the final concentrations of DMSO and acetonitrile in the reaction system were 0.01% (v/v) and 0.99% (v/v), respectively; after incubation for an appropriate time (such as 5, 10, 20, 30, and 60 min), 300 μL of a stop solution (acetonitrile solution containing 100 ng/mL tolbutamide and 100 ng/mL labetalol) was added to each sample well to stop the reaction; 300 μL of the stop solution and then 10 μL of the NADPH working solution were added to the T0 plate, all the sample plates were shaken and centrifuged in a centrifuge (3220×g) for 20 min, and then 100 μL of supernatant was taken from each well and diluted with 300 μL of pure water for liquid chromatography-tandem mass spectrometry analysis.

The experimental results are shown in Table 9.

TABLE 9

Metabolic stability results of the test compound in liver microsomes of SD rats, beagle dogs and cynomolgus monkeys

| Compound | Species | $T_{1/2}$ (min) | $CL_{int(mic)}$ (μL/min/mg protein) | $CL_{int(liver)}$ (mL/min/kg) |
|---|---|---|---|---|
| 18 | SD rats | >145 | <9.6 | <17.3 |
| 18 | Beagle dogs | >145 | <9.6 | <13.8 |
| 18 | Cynomolgus monkeys | >145 | <9.6 | <13.0 |
| 25 | SD rats | >145 | <9.6 | <17.3 |
| 25 | Beagle dogs | >145 | <9.6 | <13.8 |
| 25 | Cynomolgus monkeys | >145 | <9.6 | <13.0. |

Experimental Example 6: Pharmacokinetic Study

Pharmacokinetic study of the test compound in Balb/c mice by oral administration and intravenous injection:

The test compound was mixed with a solution containing dimethyl sulfoxide (10%), polyethylene glycol 400 (60%) and water (30%), and the mixture was vortexed and sonicated to prepare a 0.2 mg/mL clear solution, which was filtered through a millipore filter for later use. Balb/c female mice aged 7 to 10 weeks were intravenously injected with the candidate compound solution at a dose of 1 mg/kg.

The test compound was mixed with an aqueous solution containing 10% polyoxyethylene stearate, and the mixture was vortexed and sonicated to prepare a 0.3 mg/mL clear solution for later use. Balb/c female mice aged 7 to 10 weeks were orally administered with the candidate compound solution at a dose of 3 mg/kg.

Whole-blood was collected and plasma was prepared. Drug concentration was analyzed by LC-MS/MS and pharmacokinetic parameters were calculated with Phoenix WinNonlin software. The results are shown in Table 10.

Experimental Example 7: Experiment on the Liver-to-Blood Ratio in Mice

Experiment on the liver-to-blood ratio in Balb/c mice orally administered with the test compound Compound 18 was mixed with an aqueous solution containing 10% polyethylene glycol-15 hydroxystearate, and the mixture was vortexed and sonicated to prepare a 0.3 mg/mL uniform suspension for later use. Balb/c female mice aged 7 to 10 weeks were orally administered with the candidate compound solution at a dose of 3 mg/kg.

Whole blood at a certain time point was collected and plasma was prepared. Liver tissues at the corresponding time point were collected to prepare a tissue homogenate. Drug concentration was analyzed by LC-MS/MS and pharmacokinetic parameters were calculated with Phoenix WinNonlin software.

Compound 25 was mixed with an aqueous solution containing 10% polyethylene glycol-15 hydroxystearate, and the mixture was vortexed and sonicated to prepare a 0.3 mg/mL clear solution for later use. Balb/c female mice aged 7 to 10 weeks were orally administered with the candidate compound solution at a dose of 3 mg/kg.

Whole blood at a certain time point was collected and plasma was prepared. Liver tissues at the corresponding time point were collected to prepare a tissue homogenate. Drug concentration was analyzed by LC-MS/MS and pharmacokinetic parameters were calculated with Phoenix WinNonlin software. The results are shown in Table 11.

TABLE 11

Liver-to-blood ratio of the test compound

| Compound | 18 | | 25 | |
|---|---|---|---|---|
| Matrix | Plasma | Liver | Plasma | Liver |
| $AUC_{0-last}$ (nM · h) or (nmol/kg · h) | 3694 | 75412 | 3476 | 86036 |
| AUC Ratio (L/P) Liver/plasma exposure ratio | — | 20.4 | — | 24.7. |

Experimental Example 8: Experiment on In Vivo Efficacy

HDI/HBV Model

Experimental objective: to assay the efficacy of the compound against hepatitis B virus in mice through the HDI/HBV mouse model.

TABLE 10

Pharmacokinetic results of the test compound

| Dose | Pharmacokinetic parameters | Compound 18 | Compound 25 |
|---|---|---|---|
| IV (1 mg/kg) | Half-life $T_{1/2}$ (h) | 2.8 | 1.95 |
| | Clearance CL (mL/min/kg) | 50.1 | 20 |
| | Apparent volume of distribution $Vd_{ss}$ (L/kg) | 8.8 | 3.1 |
| | Area under the plasma concentration-time curve $AUC_{0-24\,h}$ (nM · h) | 617 | 1488 |
| PO (3 mpk) | Peak time $T_{max}$ (h) | 0.5 | 0.5 |
| | Peak concentration $C_{max}$ (nM) | 1460 | 1480 |
| | Area under the plasma concentration-time curve AUC (nM · h) | 5018 | 2274 |
| | Bioavailability F (%) | 271% | 51%. |

Preparation of compound: the solvent was an aqueous solution containing 10% polyethylene glycol-15 hydroxystearate; a certain amount of the test compounds 18 and 25 were separately dissolved in an aqueous solution containing 10% polyethylene glycol-15 hydroxystearate, and the mixtures were vortexed and sonicated to prepare uniform suspensions. The suspensions were stored at 4° C. for later use.

High pressure injection of the HBV plasmid DNA solution via the tail vein of mice: the day of plasmid injection was day 0, the day after injection was day 1, and so on. On day 0, all mice were injected with normal saline containing 10 μg of plasmid DNA via their tail veins at a dose of 8% of body weight, and the injection was completed within 5 s.

Administration: all mice were administered intragastrically twice a day (8/16 h interval) on day 1-6 and once on day 7. All mice were euthanized in the afternoon on day 7. The body weight of the mice, which was monitored every day, remained stable throughout the experiment.

Sample collection: blood was collected from the submandibular vein 4 h after the first administration in the morning on days 1, 3, and 5. All blood samples were collected in $K_2$-EDTA anticoagulation tubes, and centrifuged for 10 min at 4° C., 7000 g to prepare about 40 μL of plasma. All mice were euthanized by $CO_2$ four hours after administration in the morning on day 7. Blood was collected from the heart, and the plasma preparation method was the same as above. Two liver tissues were collected with 70-100 mg each, and quick-frozen by liquid nitrogen. After all samples were collected, they were stored in a −80° C. refrigerator for HBV DNA content detection.

Sample analysis: all plasma samples and liver samples were detected for HBV DNA by qPCR.

Figure 2:
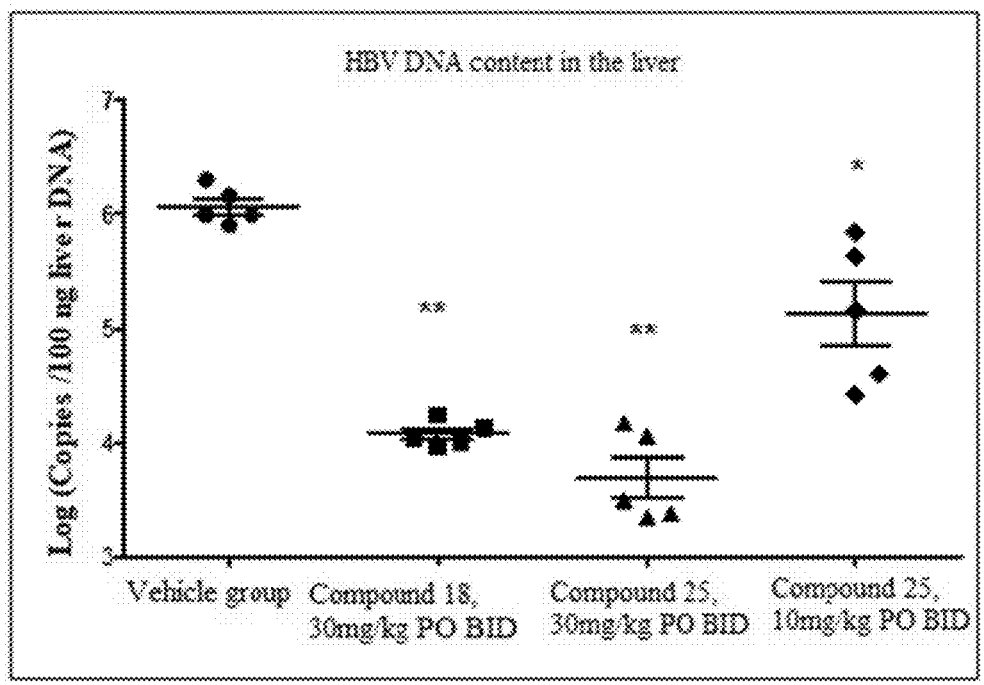
FIG. 2: HBV DNA levels in liver.

Experimental results: the experimental results are shown in Table 12, FIG. 1 and FIG. 2.

TABLE 12

| Test compounds | Dose | HBV-DNA reduction | |
| --- | --- | --- | --- |
| | | Plasma (day 5) Δ Log10 copies/μL | Liver (day 7) Δ Log10 copies/100 ng |
| 18 | 30 mg/kg | 2.84 | 1.99 |
| 25 | 30 mg/kg | 3.57 | 2.36 |
| 25 | 10 mg/kg | 2.0 | 0.94. |

The invention claimed is:
1. A compound of formula (II) or a pharmaceutically acceptable salt thereof,

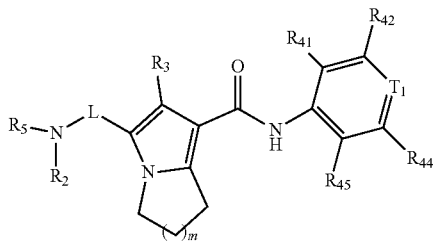

(II)

wherein,
m is 1;
L is selected from

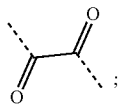

$T_1$ is selected from the group consisting of N and C ($R_{43}$);
$R_2$ is selected from the group consisting of H and $C_{1-6}$ alkyl, wherein the $C_{1-6}$ alkyl is optionally substituted by 1, 2, or 3 $R_b$;
$R_3$ is selected from the group consisting of Cl, F, Br, I, OH, $NH_2$, $C_{1-6}$ alkyl, and $C_{1-3}$ alkoxy, wherein the $C_{1-6}$ alkyl and the $C_{1-3}$ alkoxy are optionally substituted by 1, 2, or 3 $R_c$;
$R_{41}$, $R_{42}$, $R_{43}$, $R_{44}$, and $R_{45}$ are each independently selected from the group consisting of H, Cl, F, Br, I, OH, $NH_2$, CN, COOH, and $C_{1-3}$ alkyl, wherein the $C_{1-3}$ alkyl is optionally substituted by 1, 2, or 3 $R_d$;
$R_5$ is selected from the group consisting of $R_{51}$, $C_{3-10}$ cycloalkyl, and 3-6 membered heterocycloalkyl, wherein the $C_{3-10}$ cycloalkyl and the 3-6 membered heterocycloalkyl are optionally substituted by 1, 2, or 3 $R_1$;
$R_{51}$ is selected from the group consisting of $C_{1-7}$ alkyl and $C_{1-6}$ heteroalkyl, wherein the $C_{1-7}$ alkyl and the $C_{1-6}$ heteroalkyl are optionally substituted by 1, 2, or 3 $R_e$;
$R_1$ is each independently selected from the group consisting of H, Cl, F, Br, I, OH, $NH_2$, CN, COOH, $C_{1-6}$ alkyl, —COO—$C_{1-6}$ alkyl, and —$C_{1-3}$ alkyl-COO—$C_{1-6}$ alkyl, wherein the $C_{1-6}$ alkyl, the —COO—$C_{1-6}$ alkyl, and the —$C_{1-3}$ alkyl-COO—$C_{1-6}$ alkyl are optionally substituted by 1, 2, or 3 $R_a$;
$R_a$ is each independently selected from the group consisting of Cl, F, Br, I, $NH_2$, CN, COOH, $C_{1-3}$ alkyl, and $C_{1-3}$ alkoxy, wherein the $C_{1-3}$ is optionally substituted by 1, 2, or 3 R;
$R_b$ is each independently selected from the group consisting of Cl, F, Br, I, OH, $NH_2$, CN, and COOH;
$R_c$ is each independently selected from the group consisting of Cl, F, Br, I, OH, $NH_2$, CN, COOH, and $C_{1-3}$ alkyl, wherein the $C_{1-3}$ is optionally substituted by 1, 2, or 3 R;
$R_d$ is each independently selected from the group consisting of Cl, F, Br, I, OH, $NH_2$, CN, and COOH;
$R_e$ is each independently selected from the group consisting of Cl, F, Br, I, OH, $NH_2$, CN, and COOH;

R is each independently selected from the group consisting of Cl, F, Br, I, OH, $NH_2$, CN, and COOH; and
the $C_{1-6}$ heteroalkyl and the 3-6 membered heterocycloalkyl each contain 1, 2, 3, or 4 heteroatoms or heteroatom groups independently selected from the group consisting of —NH—, —O—, —S—, and N.

2. The compound or the pharmaceutically acceptable salt thereof according to claim 1, wherein $R_a$ is selected from the group consisting of Cl, F, Br, I, $NH_2$, CN, COOH, and —$OCH_3$; or $R_e$ is selected from the group consisting of Cl, F, Br, I, OH, $NH_2$, CN, and COOH.

3. The compound or the pharmaceutically acceptable salt thereof according to claim 1, wherein $R_1$ is each independently selected from the group consisting of H, Cl, F, Br, I, OH, $NH_2$, CN, COOH, $C_{1-3}$ alkyl, —COO—$C_{1-3}$ alkyl, and —$C_{1-3}$ alkyl-COO—$C_{1-3}$ alkyl, wherein the $C_{1-3}$ alkyl, the —COO—$C_{1-3}$ alkyl, and the —$C_{1-3}$ alkyl-COO—$C_{1-3}$ alkyl are optionally substituted by 1, 2, or 3 $R_a$.

4. The compound or the pharmaceutically acceptable salt thereof according to claim 3, wherein $R_1$ is each independently selected from the group consisting of H, Cl, F, Br, I, OH, $NH_2$, CN, COOH, $CH_3$, Et,

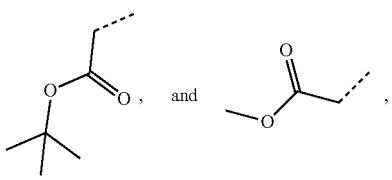

wherein the $CH_3$, the Et,

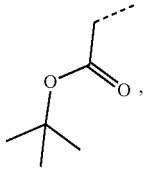

and the

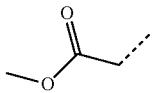

are optionally substituted by 1, 2, or 3 $R_a$.

5. The compound or the pharmaceutically acceptable salt thereof according to claim 4, wherein $R_1$ is each independently selected from the group consisting of H, Cl, F, Br, I, OH, $NH_2$, CN, COOH, $CH_3$, $CF_3$, Et, —$CH_2$—COOH, —$CH_2$—$OCH_3$, —$(CH_2)_2$—COOH,

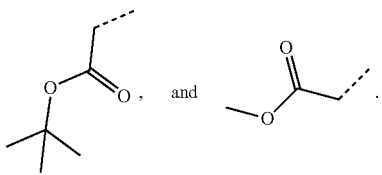

6. The compound or the pharmaceutically acceptable salt thereof according to claim 1, wherein $R_2$ is selected from the group consisting of H and $C_{1-3}$ alkyl, wherein the $C_{1-3}$ alkyl is optionally substituted by 1, 2, or 3 $R_b$.

7. The compound or the pharmaceutically acceptable salt thereof according to claim 1, wherein $R_3$ is selected from the group consisting of Cl, F, Br, I, OH, $NH_2$, and $C_{1-3}$ alkyl, wherein the $C_{1-3}$ alkyl is optionally substituted by 1, 2, or 3 $R_c$.

8. The compound or the pharmaceutically acceptable salt thereof according to claim 1, wherein $R_{41}$, $R_{42}$, $R_{43}$, $R_{44}$, and $R_{45}$ are each independently selected from the group consisting of H, Cl, F, Br, I, OH, $NH_2$, CN, and —COOH.

9. The compound or the pharmaceutically acceptable salt thereof according to claim 1, wherein $R_{51}$ is selected from the group consisting of $C_{1-7}$ alkyl and $C_{1-3}$ heteroalkyl, wherein the $C_{1-7}$ alkyl and the $C_{1-3}$ heteroalkyl are optionally substituted by 1, 2, or 3 $R_e$.

10. The compound or the pharmaceutically acceptable salt thereof according to claim 9, wherein $R_{51}$ is selected from the group consisting of methyl, ethyl, propyl, isopropyl,

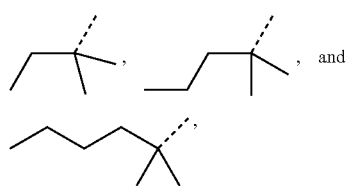

wherein the methyl, the ethyl, the propyl, the isopropyl, the

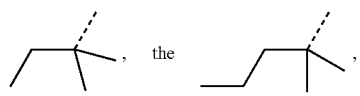

and the

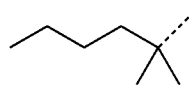

are optionally substituted by 1, 2, or 3 $R_e$.

11. The compound or the pharmaceutically acceptable salt thereof according to claim 1, wherein $R_5$ is selected from the group consisting of $R_{51}$, $C_{3-8}$ cycloalkyl, and 5-6 membered heterocycloalkyl, wherein the $C_{3-8}$ cycloalkyl and the 5-6 membered heterocycloalkyl are optionally substituted by 1, 2, or 3 $R_1$.

12. The compound or the pharmaceutically acceptable salt thereof according to claim 11, wherein $R_5$ is selected from the group consisting of $R_{51}$, cyclohexyl, tetrahydropyranyl, piperidinyl and bicyclo[2.2.2]octyl, wherein the cyclohexyl, the tetrahydropyranyl, the piperidinyl, and the bicyclo[2.2.2]octyl are optionally substituted by 1, 2, or 3 $R_1$.

13. The compound or the pharmaceutically acceptable salt thereof according to claim 12, wherein $R_5$ is selected from the group consisting of $R_{51}$,

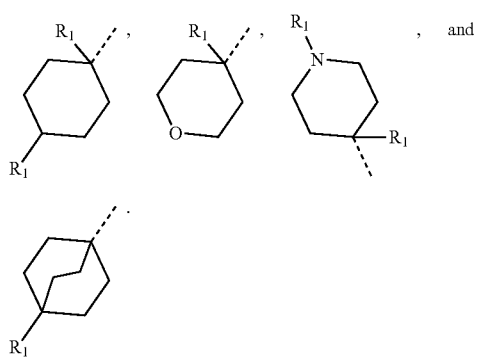

14. The compound or the pharmaceutically acceptable salt thereof according to claim 13, wherein $R_5$ is selected from the group consisting of

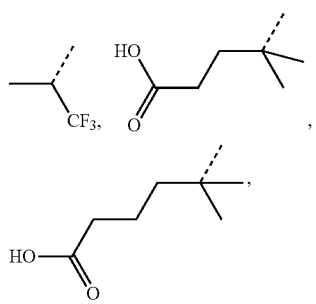

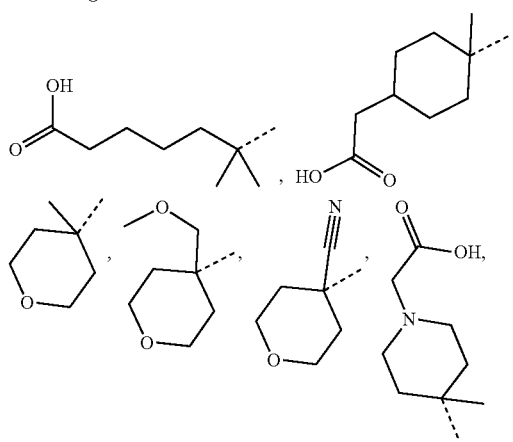

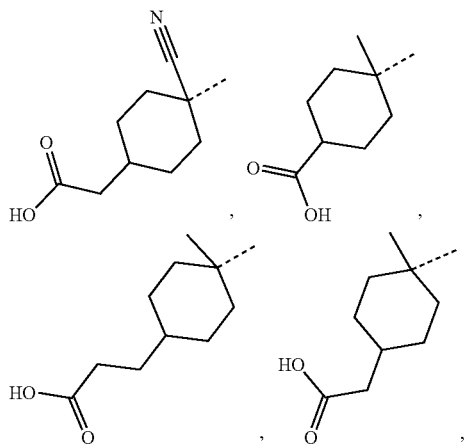

-continued

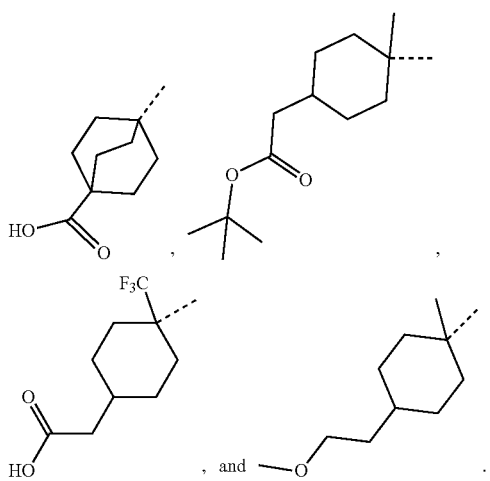

15. The compound or the pharmaceutically acceptable salt thereof according to claim 1, wherein structural unit

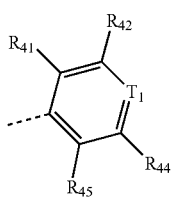

is selected from the group consisting of

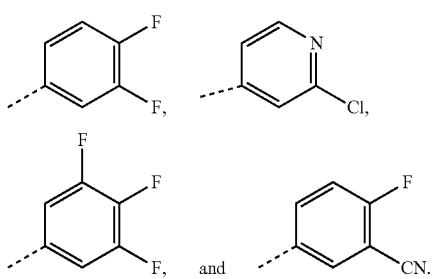

16. The compound or the pharmaceutically acceptable salt thereof according to claim 1, selected from the group consisting of

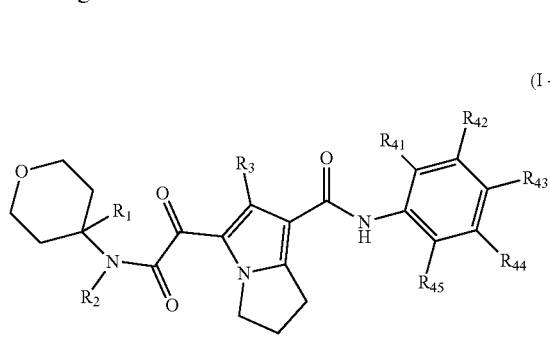

-continued

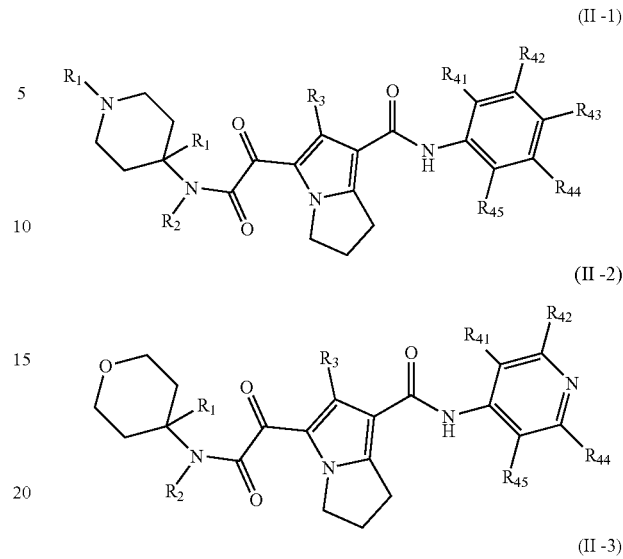

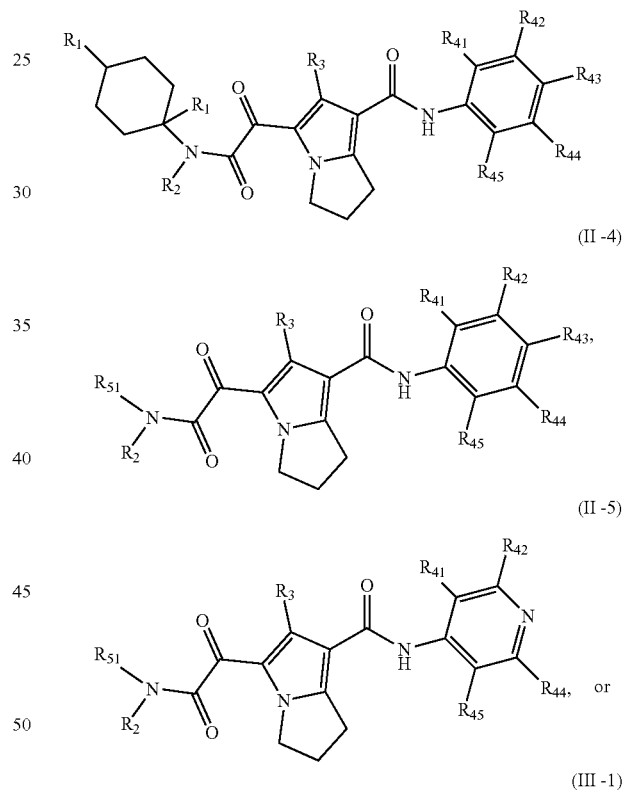

wherein each of $R_1$, $R_2$, $R_3$, $R_{41}$, $R_{42}$, $R_{43}$, $R_{44}$, $R_{45}$, and $R_{51}$ is as defined in claim 1.

17. A compound of the following formula, a stereoisomer thereof or a pharmaceutically acceptable salt thereof:

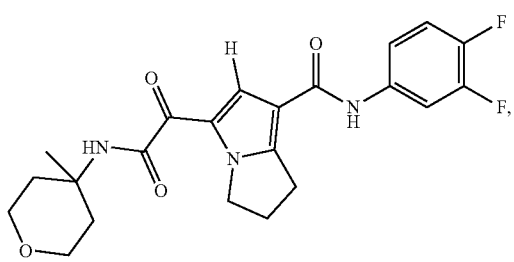
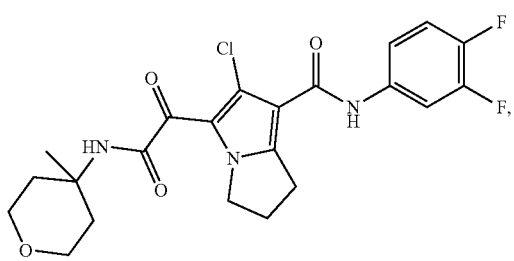
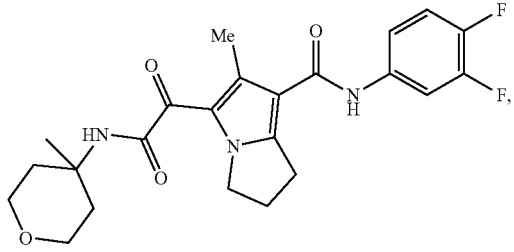
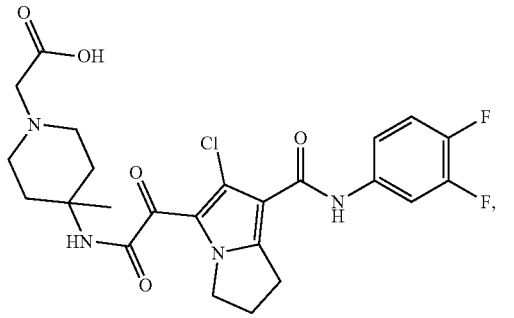
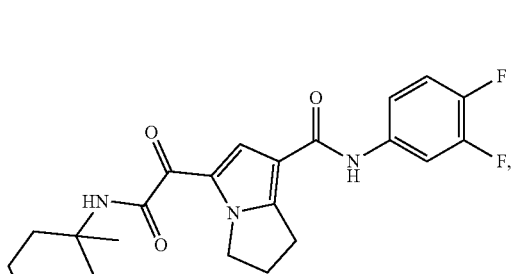
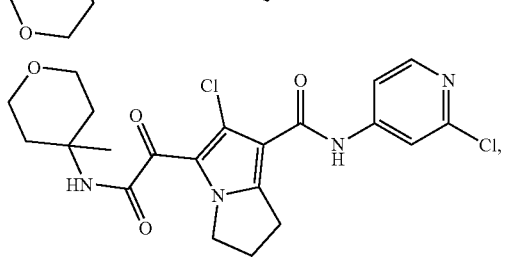
-continued
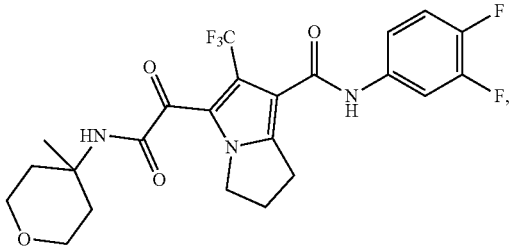
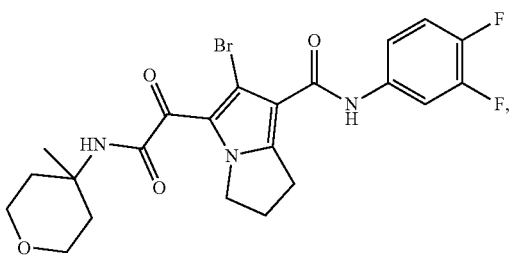
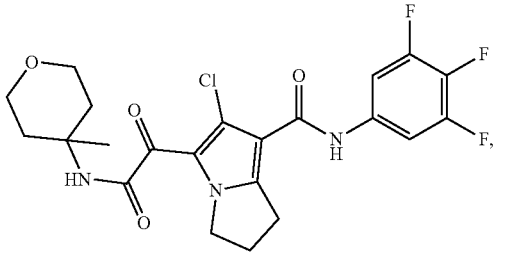
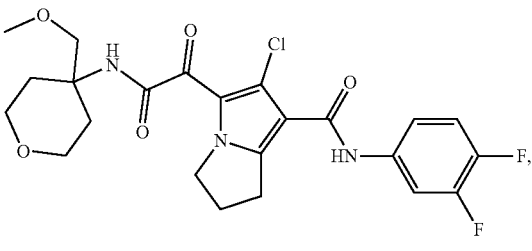
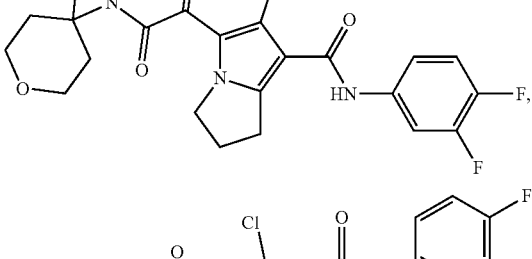
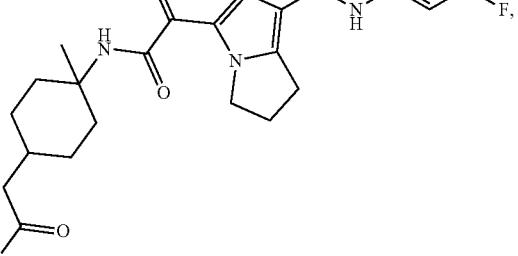

179
-continued
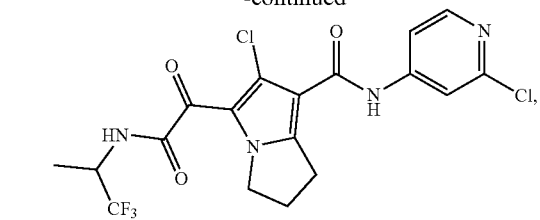
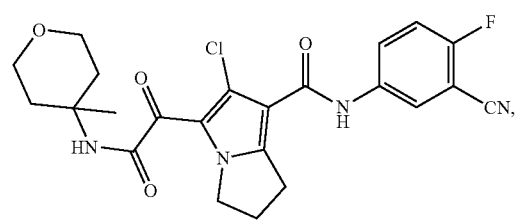
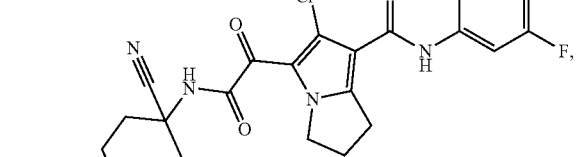
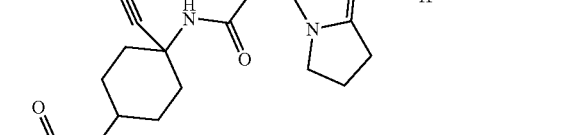
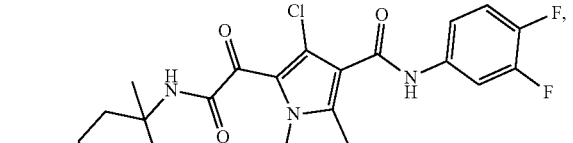
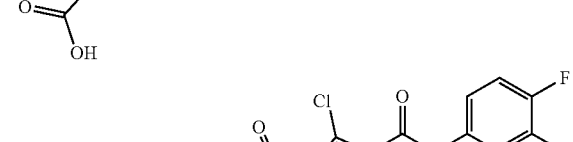
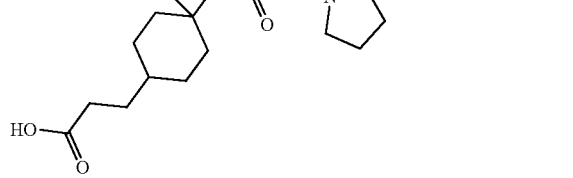
180
-continued
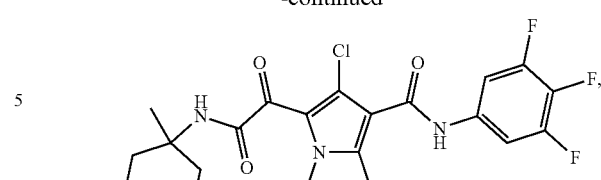
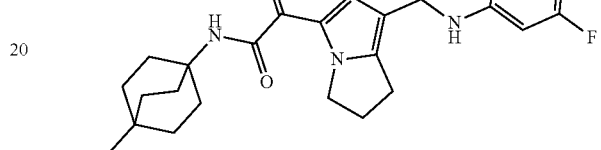
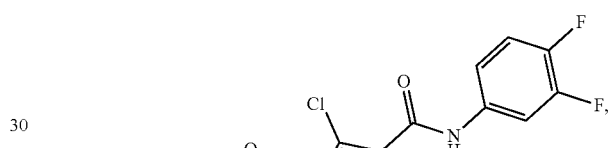
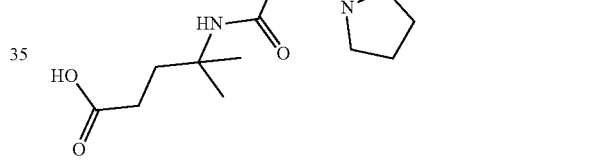
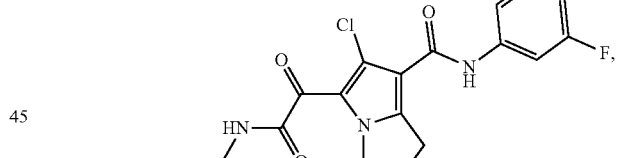
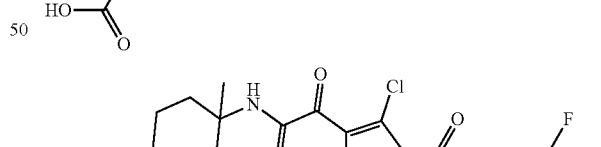
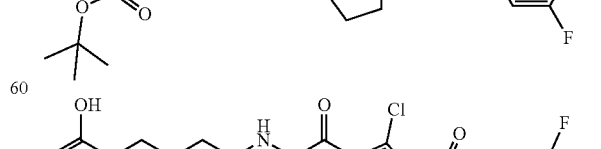

181
-continued
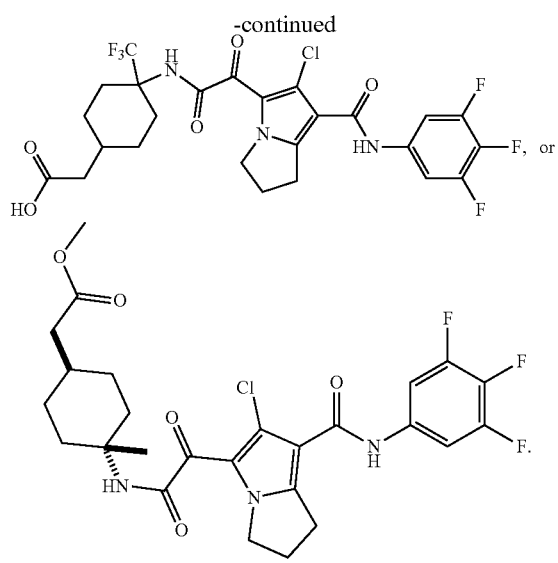
18. The compound, the stereoisomer thereof or the pharmaceutically acceptable salt thereof according to claim 17, selected from the group consisting of
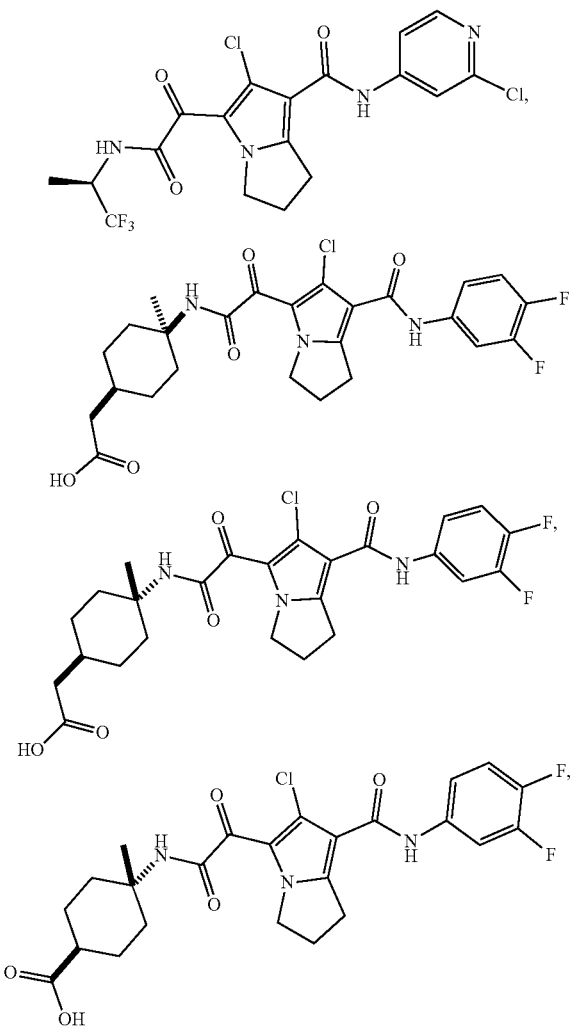
182
-continued
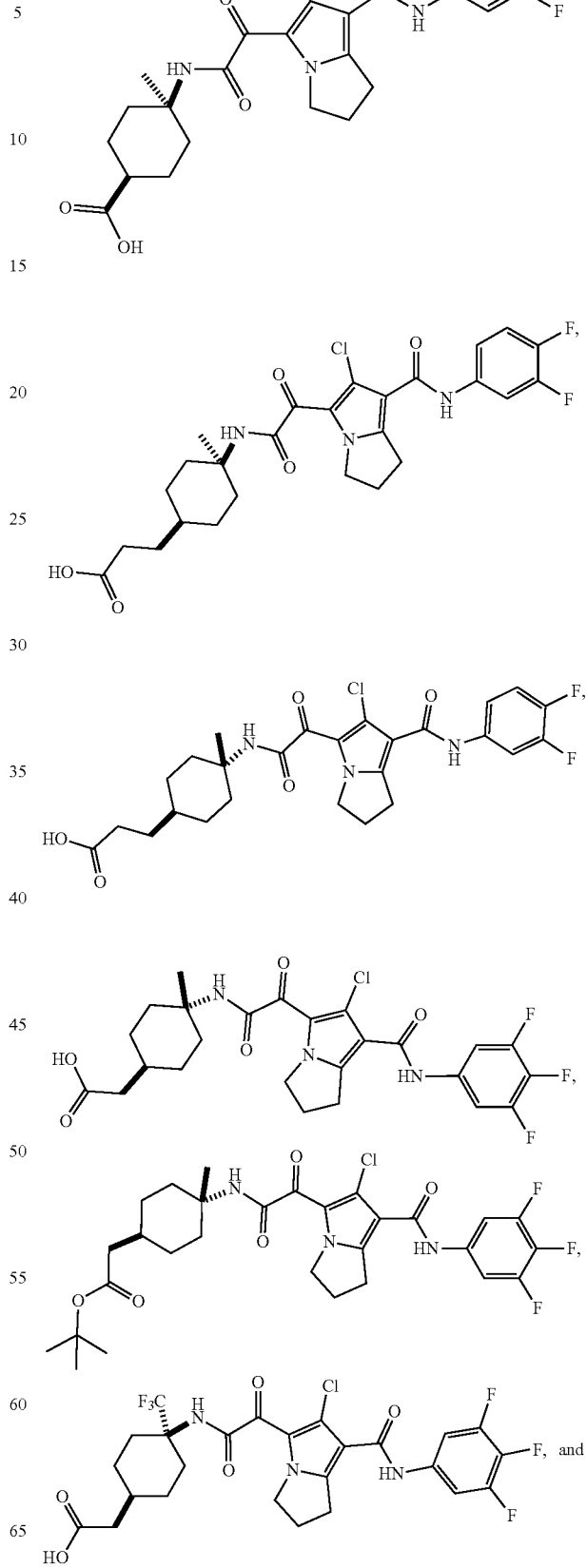

-continued

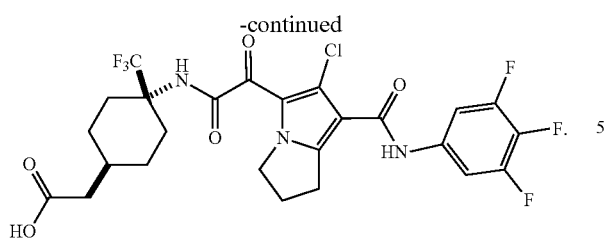

19. A pharmaceutical composition, comprising the compound, the stereoisomer thereof or the pharmaceutically acceptable salt thereof according to claim 1, and optionally further comprising a pharmaceutically acceptable carrier.

20. A method for treating related to HBV infection, comprising administering to a patient in need thereof a therapeutically effective amount of the compound, the stereoisomer thereof or the pharmaceutically acceptable salt thereof according to claim 1.

* * * * *

UNITED STATES PATENT AND TRADEMARK OFFICE
CERTIFICATE OF CORRECTION

PATENT NO. : 11,891,398 B2
APPLICATION NO. : 17/058308
DATED : February 6, 2024
INVENTOR(S) : Haiying He et al.

It is certified that error appears in the above-identified patent and that said Letters Patent is hereby corrected as shown below:

In the Claims

Column 171, Line 60, Claim 1, please delete "$R_e$" and insert therefore -- $R_c$ --;

Column 172, Line 10, Claim 2, please delete "$R_e$" and insert therefore -- $R_c$ --;

Column 175, Claim 14, please delete "  " and insert therefor -- 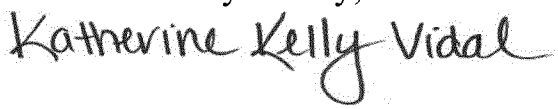 --.

Signed and Sealed this
Ninth Day of July, 2024

Katherine Kelly Vidal
*Director of the United States Patent and Trademark Office*